US010266899B2

(12) United States Patent
Parr et al.

(10) Patent No.: US 10,266,899 B2
(45) Date of Patent: Apr. 23, 2019

(54) ABERRANT MITOCHONDRIAL DNA, ASSOCIATED FUSION TRANSCRIPTS AND HYBRIDIZATION PROBES THEREFOR

(71) Applicant: MDNA LIFE SCIENCES INC., Wilmington, DE (US)

(72) Inventors: Ryan Parr, Thunder Bay (CA); Brian Reguly, Thunder Bay (CA); Gabriel Dakubo, Thunder Bay (CA); Jennifer Creed, Broomsfield, CO (US); Kerry Robinson, Thunder Bay (CA)

(73) Assignee: MDNA Life Sciences Inc., Wilmington, DE (US)

(*) Notice: Subject to any disclaimer, the term of this patent is extended or adjusted under 35 U.S.C. 154(b) by 0 days.

(21) Appl. No.: 14/627,755

(22) Filed: Feb. 20, 2015

(65) Prior Publication Data

US 2017/0152567 A1 Jun. 1, 2017

Related U.S. Application Data

(63) Continuation of application No. 12/935,181, filed as application No. PCT/CA2009/000351 on Mar. 27, 2009, now abandoned.

(60) Provisional application No. 61/040,616, filed on Mar. 28, 2008.

(51) Int. Cl.
*C12Q 1/6886* (2018.01)
*C07K 14/47* (2006.01)

(52) U.S. Cl.
CPC ........ *C12Q 1/6886* (2013.01); *C07K 14/4748* (2013.01); *C12Q 2600/158* (2013.01)

(58) Field of Classification Search
CPC ............ C12Q 1/6886; C12Q 2600/158; C07K 14/4748
See application file for complete search history.

(56) References Cited

U.S. PATENT DOCUMENTS

| | | | | |
|---|---|---|---|---|
| 3,817,837 | A | 6/1974 | Rubenstein et al. | |
| 3,850,752 | A | 11/1974 | Schuurs et al. | |
| 3,939,350 | A | 2/1976 | Kronick et al. | |
| 3,996,345 | A | 12/1976 | Ullman et al. | |
| 4,275,149 | A | 6/1981 | Litman et al. | |
| 4,277,437 | A | 7/1981 | Maggio | |
| 4,366,241 | A | 12/1982 | Tom et al. | |
| 5,807,522 | A | 9/1998 | Brown et al. | |
| 8,008,008 | B2 | 8/2011 | Parr et al. | |
| 2003/0162174 | A1* | 8/2003 | Sutherland ........... | C12Q 1/6853 435/6.12 |
| 2005/0255522 | A1 | 11/2005 | Seidman et al. | |
| 2007/0134678 | A1* | 6/2007 | Rees .................... | C12Q 1/6837 435/6.15 |
| 2014/0024025 | A1* | 1/2014 | Harbottle ............. | C12Q 1/6883 435/6.11 |

FOREIGN PATENT DOCUMENTS

| | | | |
|---|---|---|---|
| JP | 2005506057 | A | 3/2005 |
| WO | 2009039601 | A1 | 4/2009 |
| WO | 2010115261 | A1 | 10/2010 |

OTHER PUBLICATIONS

Yamagata et al reference (J Am Soc Nephrol 2002 vol. 13: pp. 1816-1823).*
Anderson et al. "Sequence and Organization of the Human Mitochondrial Genome", Nature; Apr. 1981, pp. 457-465, vol. 290.
Andrews et al., "Reanalysis and Revision of the Cambridge Reference Sequence for Human Mitochondrial DNA", Nature Genetics; Oct. 1999, p. 147, vol. 23(2).
Barron et al., "Mitochondrial Abnormalities in Ageing Macular Photoreceptors", Invest Ophthalmol Vis Sci; Nov. 2001, pp. 3016-3022, vol. 42(12).
Brandon et al., "Mitochondrial Mutations in Cancer", Oncogene (2006), pp. 4647-4662, vol. 25.
C. Gang et al., "Mitochondrial DNA Mutations and Related Human Diseases," Hereditas (Beijing) Nov. 29, 2007 pp. 1299-1308. (English Abstract).
Chabi, Beatrice et al., "Quantification of Mitochondrial DNA Deletion, Depletion, and Overreplication: Application to Diagnosis", Clinical Chemistry 49, No. 8, (2003), pp. 1309-1317.
Croteau et al., "Mitochondrial DNA Repair Pathways" Mutation Research (1999), pp. 137-148; vol. 434(3).
Dai et al., "Correlation of Cochlear Blood Supply With Mitochondrial DNA Common Deletion in Presbyacusis" Acta Otolaryngol, (2004), pp. 130-136, vol. 24(2).
Dai, Ji Gang et al., "Mitochondrial DNA 4977 BP deletion mutations in lung carcinoma", Indian Journal of Cancer; Jan.-Mar. 2006, vol. 43, Issue 1, pp. 20-25.
Database UniProt (online: http://ibis.internal.epo.org/exam/dbfetch.jsp?id=UNIPROT:Q8WCW0); retrieved from EBI accession No. UNIPROT:A6ZHA9; Database accession No. A6ZHA9; Aug. 21, 2007; Cytochrom c oxidase subunit 2; XP-002687300; 1 page.
Database UniProt (online: http://ibis.internal.epo.org/exam/dbfetch.jsp?id=UNIPROT:Q8WCW0); retrieved from EBI accession No. UNIPROT:Q8WCWO; Database accession No. Q8WCWO; Aug. 21, 2007; Cytochrom c oxidase subunit 2; XP-002687301; 3 pages.
Eguchi et al., "MLL Chimeric Protein Activation Renders Cells Vulnerable to Chromosomal Damage: An Explanation for the Very Short Latency of Infant Leukemia," Genes Chromosomes & Cancer (2006), pp. 754-760, vol. 45(8).
European Search Report; EP 10 76 1136; dated Nov. 16, 2012; Place of Search: Munich; 3 pages.
Gasparre "Disruptive Mitochondrial DNA Mutations in Complex I Subunits are Markers of Oncocytic Phenotype in Thyroid Tumors," Proceedings of the National Aceademy of Sciences, vol. 104, No. 21, May 22, 2007, pp. 9001-9006.

(Continued)

*Primary Examiner* — Catherine S Hibbert
(74) *Attorney, Agent, or Firm* — Jeffery B. Arnold; Holland & Knight LLP

(57) ABSTRACT

The present invention provides novel mitochondrial fusion transcripts and the parent mutated mtDNA molecules that are useful for predicting, diagnosing and/or monitoring cancer. Hybridization probes complementary thereto for use in the methods of the invention are also provided.

4 Claims, 150 Drawing Sheets

Specification includes a Sequence Listing.

(56) References Cited

OTHER PUBLICATIONS

Green et al., "Pharmacological Manipulation of Cell Death: Clinical Applications in Sight?" The Journal of Clinical Investigation; Oct. 2005, pp. 2610-2617, vol. 115(10).
Hayashi et al., "Introduction of Disease-Related Mitochondrial DNA Deletions Into Hela Cells Lacking Mitochondrial DNA Results in Mitochondrial Dysfunction", Proc. Natl. Acad. Sci. USA; Dec. 1991, pp. 10614-10618, vol. 88.
He, Langping et al., "Detection and quantification of mitochondrial DNA deletions in individual cells by real-time PCR", XP-002372964; Nucleic Acids Research, 2002, vol. 30, No. 14, e68; pp. 1-6.
International Search Report for International Application No. PCT/CA2010/000423; International Filing Date: Mar. 29, 2010; 5 pages.
Jakupciak et al., "Analysis of Potential Cancer Biomarkers in Mitochondrial DNA", Current Opinion in Molecular Therapeutics (2006), pp. 500-506, vol. 8(6).
Jessie, C. Benjamin et al., "Accumulation of mitochondrial DNA deletions in the malignant prostate of patients of different ages", XP-002524592; Experimental Gerontology 37 (2001) pp. 169-174.
Kazmierczak et al., "Description of a Novel Fusion Transcript Between HMGI-C, A Gene Encoding for a Member of the High Mobility Group Proteins, and the Mitochondrial Aldehyde Dehydrogenase Gene", Cancer Research; Dec. 15, 1995, pp. 6038-6039, vol. 55.
Krishnan et al., "What Causes Mitochondrial DNA Deletions in Human Cells?", Nature Genetics, pp. 275-279, vol. 40(3); Mar. 2008.
Lewis et al., "Detection of Damage to the Mitochondrial Genome in the Oncocytic Cells of Warthin's Tumour" Journal of Pathology, (2000), pp. 274-281, vol. 191(3).
Libura et al., Therapy-Related Acute Myeloid Leukemia-Like MLL Rearrangements Are Induced by Etoposide in Primary Human CD34+Cells and Remain Stable After Clonal Expansion, Blood Journal; Mar. 1, 2005, pp. 2124-2131, vol. 105(5).
Maitra, Anirban et al., "The Human MitoChip: A High-Throughput Sequencing Microarray for Mitochondrial Mutation Detection", downloaded from www.genome.org on Nov. 21, 2006, pp. 812-819.
Maki et al., Mitochondrial Genome Deletion Aids in the Identification of False-And-True-Negative Prostate Needle Core Biopsy Specimens, Am J Clin Pathol, (2008), pp. 57-66, vol. 129(1).
Meyer et al., "Diagnostic Tool for the Identification of MLL Rearrangements Including Unknown Partner Genes", Proc Natl Acad Sci USA; Jan. 11, 2005, pp. 449-454, vol. 102(2).
Mita, Shuji et al., "Recombination via flanking direct repeats is a major cause of large-scale deletions of human mitochondrial DNA", Nucleic Acids Research, vol. 18, No. 3, Received Oct. 4, 1989; Revised and Accepted Dec. 18, 1989; pp. 561-567.
Modica-Napolitano et al., "Mitochondria As Targets for Detection and Treatment of Cancer", Expert Rev MolMed, pp. 1-19, vol. 4; Apr. 11, 2002.
Morgens et al., "A Novel Soybean Mitochondrial Transcript Resulting From a DNA Rearrangement Involving the 5s rRNA Gene", Nucleic Acids Research (1984), pp. 5665-5684, vol. 12(14).
Müller-Höcker et al., "The Common 4977 Base Pair Deletion of Mitochondrial dNA Preferentially Accumulates in the Cardiac Conduction System of Patients With Kearns-Sayre Syndrome" Modern Pathology (1998), pp. 295-301, vol. 11(3).
Nakase et al., "Transcription and Translation of Deleted Mitochondrial Genomes in Kearns-Sayre Syndrome: Implications for Pathogenesis", Am J Hum Genet, (1990), pp. 418-427, vol. 46(3).
Parr et al., "Somatic Mitochondrial DNA Mutations in Prostate Cancer and Normal Appearing Adjacent Glands InComparison to Age-Matched Prostate Samples Without Malignant Histology"; Journal of Molecular Diagnostics; vol. 8,No. 3; Jul. 2006.
Parr, Ryan L., et al; "The Mitochondrial Genome: A Biosensor for Early Cancer Detection?"; Expert Opin. Med. Diagn.; vol. 1, No. 2; p. 169-182; 2007.
Petros et al "mtDNA mutations increase tumorigenicity in prostate cancer"; PNAS: 2005; vol. 102, No. 3; p. 719-724; Jan. 18, 2005.
Porteous et al., "Bioenergetic Consequences of Accumulating the Common 4977-Bp Mitochondrial DNA Deletion", Eur J Biochem (1998), pp. 192-201, vol. 257(1).
Ro et al., "Deleted 4977-Bp Mitochondrial DNA Mutation Is Associated With Sporadic Amyotrophic Lateral Sclerosis: A Hospital-Based Case-Control Study", Muscle Nerve; Dec. 2003, pp. 737-743, vol. 28(6).
Rupec, et al.; Isolation of a hypoxia-induced cDNA homology to the mammalian growth-related protein p23 ; Oncology Research; vol. 10, No. 2; p. 69-74; 1998.
Sherratt et al., "Mitochondrial DNA Defects: A Widening Clinical Spectrum of Disorders.", Clinical Science (Great Britain) (1997), pp. 225-235, vol. 92(3).
Supplemental European Search Report for Application No. EP09725638, Date of Completion of Search: Oct. 4, 2011; 3 pages.
Uchida, Takafumi et al., "Down-Regulation of Mitochondrial Gene Expression by the Anti-Tumor Arotinoid Mofarotene (Ro 40-8757)", Int. J. Cancer: 58, (1994) pp. 891-897.
Verma et al., "Application of mitochondrial genome information in cancer epidemiology", Clinica Chimica Acta, 2007, 383: pp. 41-50; available online at www.sciencedirect.com.
Written Opinion of the International Searching Authority for International Application No. PCT/CA2010/000423; International Filing Date: Mar. 29, 2010; 6 pages.
Zhu, Weizhu et al., "Large-scale mitochondrial DNA deletion mutations and nuclear genome instability in human breast cancer", Cancer Detection and Prevention 28, (2004), pp. 119-126.

* cited by examiner

Coordinates of the Curve

Test Result Variable(s): Probe 02

| Positive if Greater Than or Equal To[a] | Sensitivity | 1 - Specificity |
|---|---|---|
| .7568 | 1.000 | 1.000 |
| 2.1107 | .900 | 1.000 |
| 2.5160 | .900 | .889 |
| 2.6222 | .900 | .778 |
| 2.6862 | .900 | .667 |
| 2.7433 | .800 | .667 |
| 2.8012 | .800 | .556 |
| 2.8558 | .800 | .444 |
| 2.9369 | .800 | .333 |
| 2.9800 | .700 | .333 |
| 3.1676 | .600 | .333 |
| 3.4764 | .600 | .222 |
| 3.6129 | .600 | .111 |
| 3.7104 | .500 | .111 |
| 3.9727 | .400 | .111 |
| 4.8624 | .300 | .111 |
| 5.6516 | .300 | .000 |
| 5.9374 | .200 | .000 |
| 6.5163 | .100 | .000 |
| 7.8827 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 6C

Area Under the Curve

Test Result Variable(s): Probe 02

| Area | Std. Error[a] | Asymptotic Sig.[b] | Asymptotic 95% Confidence Interval | |
|---|---|---|---|---|
| | | | Lower Bound | Upper Bound |
| .733 | .121 | .086 | .497 | .970 |

a. Under the nonparametric assumption b. Null hypothesis: true area = 0.5

Coordinates of the Curve

Test Result Variable(s): Probe 03

| Positive if Greater Than or Equal To[a] | Sensitivity | 1 - Specificity |
|---|---|---|
| 1.7966 | 1.000 | 1.000 |
| 2.7983 | 1.000 | .889 |
| 2.8154 | .900 | .889 |
| 2.9284 | .900 | .778 |
| 3.0788 | .900 | .667 |
| 3.1540 | .900 | .556 |
| 3.4096 | .900 | .444 |
| 3.6685 | .900 | .333 |
| 3.6959 | .800 | .333 |
| 3.7094 | .800 | .222 |
| 3.8759 | .700 | .222 |
| 4.0813 | .600 | .222 |
| 4.3005 | .500 | .222 |
| 4.5109 | .500 | .111 |
| 4.7108 | .400 | .111 |
| 5.6001 | .300 | .111 |
| 6.4437 | .300 | .000 |
| 6.8705 | .200 | .000 |
| 7.6506 | .100 | .000 |
| 9.1160 | .000 | .000 |

a. The smallest cutoff value is the minimum observed test value minus 1, and the largest cutoff value is the maximum observed test value plus 1. All the other cutoff values are the averages of two consecutive ordered observed test values.

Fig.6G

Area Under the Curve

Test Result Variable(s): Probe 03

| Area | Std. Error[a] | Asymptotic Sig.[b] | Asymptotic 95% Confidence Interval | |
|---|---|---|---|---|
| | | | Lower Bound | Upper Bound |
| .789 | .110 | .034 | .572 | 1.005 |

a. Under the nonparametric assumption b. Null hypothesis: true area = 0.5

Coordinates of the Curve

Test Result Variable(s): Probe 08

| Positive if Greater Than or Equal To[a] | Sensitivity | 1 - Specificity |
|---|---|---|
| -24.2356 | 1.000 | 1.000 |
| -23.1238 | .900 | 1.000 |
| -22.5180 | .900 | .889 |
| -21.5598 | .900 | .778 |
| -17.4046 | .900 | .667 |
| -13.2542 | .900 | .556 |
| -12.7454 | .800 | .556 |
| -11.0063 | .800 | .444 |
| -8.4803 | .700 | .444 |
| -7.3886 | .700 | .333 |
| -6.7456 | .600 | .333 |
| -6.3510 | .600 | .222 |
| -6.0975 | .600 | .111 |
| -5.6176 | .500 | .111 |
| -4.5241 | .500 | .000 |
| -3.5933 | .400 | .000 |
| -3.1617 | .300 | .000 |
| -2.3596 | .200 | .000 |
| -1.3003 | .100 | .000 |
| .3178 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 6K

Area Under the Curve

Test Result Variable(s): Probe 08

| Area | Std. Error[a] | Asymptotic Sig.[b] | Asymptotic 95% Confidence Interval | |
|---|---|---|---|---|
| | | | Lower Bound | Upper Bound |
| .756 | .116 | .060 | .528 | .983 |

a. Under the nonparametric assumption b. Null hypothesis: true area = 0.5

Coordinates of the Curve

Test Result Variable(s): Probe 09

| Positive if Greater Than or Equal To[a] | Sensitivity | 1 - Specificity |
|---|---|---|
| -26.7218 | 1.000 | 1.000 |
| -25.3641 | .900 | 1.000 |
| -23.5151 | .800 | 1.000 |
| -21.8829 | .800 | .889 |
| -21.4187 | .800 | .778 |
| -20.4804 | .800 | .667 |
| -15.3686 | .800 | .556 |
| -10.5043 | .800 | .444 |
| -9.3795 | .800 | .333 |
| -8.4552 | .700 | .333 |
| -8.1579 | .700 | .222 |
| -7.7931 | .700 | .111 |
| -7.5555 | .600 | .111 |
| -7.0324 | .600 | .000 |
| -5.6631 | .500 | .000 |
| -4.6705 | .400 | .000 |
| -4.3237 | .300 | .000 |
| -3.2382 | .200 | .000 |
| -1.8956 | .100 | .000 |
| -.4350 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 6O

Area Under the Curve

Test Result Variable(s): Probe 09

| Area | Std. Error[a] | Asymptotic Sig.[b] | Asymptotic 95% Confidence Interval | |
|---|---|---|---|---|
| | | | Lower Bound | Upper Bound |
| .756 | .127 | .060 | .507 | 1.004 |

a. Under the nonparametric assumption b. Null hypothesis: true area = 0.5

Coordinates of the Curve

Test Result Variable(s): Probe 10

| Positive if Greater Than or Equal To[a] | Sensitivity | 1 - Specificity |
|---|---|---|
| -21.0353 | 1.000 | 1.000 |
| -19.9698 | 1.000 | .889 |
| -12.5697 | 1.000 | .778 |
| -5.2295 | 1.000 | .667 |
| -5.1624 | 1.000 | .556 |
| -4.8838 | 1.000 | .444 |
| -4.2646 | 1.000 | .333 |
| -3.8272 | .900 | .333 |
| -3.7343 | .800 | .333 |
| -3.6478 | .800 | .222 |
| -3.5841 | .700 | .222 |
| -3.4781 | .700 | .111 |
| -3.2304 | .600 | .111 |
| -2.9591 | .500 | .111 |
| -2.7091 | .400 | .111 |
| -2.1473 | .300 | .111 |
| -1.4695 | .200 | .111 |
| -1.1392 | .100 | .111 |
| -1.0450 | .100 | .000 |
| -.0097 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 6S

Area Under the Curve

Test Result Variable(s): Probe 10

| Area | Std. Error[a] | Asymptotic Sig.[b] | Asymptotic 95% Confidence Interval | |
|---|---|---|---|---|
| | | | Lower Bound | Upper Bound |
| .844 | .102 | .011 | .645 | 1.044 |

a. Under the nonparametric assumption b. Null hypothesis: true area = 0.5

Coordinates of the Curve

Test Result Variable(s): Probe 11

| Positive if Greater Than or Equal To[a] | Sensitivity | 1 - Specificity |
|---|---|---|
| .8199 | 1.000 | 1.000 |
| 1.8582 | .900 | 1.000 |
| 2.0162 | .900 | .889 |
| 2.2632 | .900 | .778 |
| 2.4301 | .900 | .667 |
| 2.6165 | .900 | .556 |
| 2.8041 | .900 | .444 |
| 2.8463 | .900 | .333 |
| 2.8543 | .800 | .333 |
| 2.9662 | .700 | .333 |
| 3.1753 | .700 | .222 |
| 3.3334 | .600 | .222 |
| 3.5634 | .500 | .222 |
| 3.7674 | .500 | .111 |
| 3.8907 | .400 | .111 |
| 4.3690 | .300 | .111 |
| 5.0928 | .200 | .111 |
| 5.6250 | .200 | .000 |
| 6.0840 | .100 | .000 |
| 7.3513 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 6W

Area Under the Curve

Test Result Variable(s): Probe 11

| Area | Std. Error[a] | Asymptotic Sig.[b] | Asymptotic 95% Confidence Interval | |
|---|---|---|---|---|
| | | | Lower Bound | Upper Bound |
| .756 | .120 | .060 | .520 | .991 |

a. Under the nonparametric assumption b. Null hypothesis: true area = 0.5

Coordinates of the Curve

Test Result Variable(s): Probe 12

| Positive if Greater Than or Equal To[a] | Sensitivity | 1 - Specificity |
|---|---|---|
| .9262 | 1.000 | 1.000 |
| 2.1243 | .900 | 1.000 |
| 2.3943 | .900 | .889 |
| 2.4824 | .900 | .778 |
| 2.5862 | .900 | .667 |
| 2.7316 | .900 | .556 |
| 2.7936 | .900 | .444 |
| 2.8907 | .900 | .333 |
| 2.9855 | .800 | .333 |
| 3.0347 | .700 | .333 |
| 3.2626 | .700 | .222 |
| 3.4645 | .600 | .222 |
| 3.7076 | .500 | .222 |
| 4.0397 | .400 | .222 |
| 4.2497 | .400 | .111 |
| 4.9044 | .300 | .111 |
| 5.5481 | .300 | .000 |
| 5.9577 | .200 | .000 |
| 6.8291 | .100 | .000 |
| 8.3796 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 6AA

Area Under the Curve

Test Result Variable(s): Probe 12

| Area | Std. Error[a] | Asymptotic Sig.[b] | Asymptotic 95% Confidence Interval | |
|---|---|---|---|---|
| | | | Lower Bound | Upper Bound |
| .756 | .119 | .060 | .522 | .989 |

a. Under the nonparametric assumption b. Null hypothesis: true area = 0.5

Fig. 6BB

Coordinates of the Curve

Test Result Variable(s): Probe 06

| Positive if Greater Than or Equal To[a] | Sensitivity | 1 - Specificity |
|---|---|---|
| -18.8885 | 1.000 | 1.000 |
| -13.5845 | 1.000 | .857 |
| -8.7622 | 1.000 | .714 |
| -8.2117 | 1.000 | .571 |
| -8.1245 | 1.000 | .429 |
| -7.4446 | .900 | .429 |
| -6.7388 | .800 | .429 |
| -6.5691 | .800 | .286 |
| -6.4475 | .700 | .286 |
| -6.2968 | .600 | .286 |
| -6.0956 | .500 | .286 |
| -5.7666 | .400 | .286 |
| -5.1640 | .400 | .143 |
| -4.7948 | .300 | .143 |
| -4.6092 | .200 | .143 |
| -4.2851 | .200 | .000 |
| -3.2263 | .100 | .000 |
| -1.3185 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 7C

Area Under the Curve

Test Result Variable(s): Probe 06

| Area | Std. Error[a] | Asymptotic Sig.[b] | Asymptotic 95% Confidence Interval | |
|---|---|---|---|---|
| | | | Lower Bound | Upper Bound |
| .771 | .129 | .064 | .518 | 1.025 |

a. Under the nonparametric assumption b. Null hypothesis: true area = 0.5

Coordinates of the Curve

Test Result Variable(s): Probe 08

| Positive if Greater Than or Equal To[a] | Sensitivity | 1 - Specificity |
|---|---|---|
| -23.3755 | 1.000 | 1.000 |
| -20.4163 | 1.000 | .857 |
| -18.1143 | 1.000 | .714 |
| -15.2935 | 1.000 | .571 |
| -11.4591 | 1.000 | .429 |
| -9.9810 | 1.000 | .286 |
| -9.8002 | .900 | .286 |
| -9.6166 | .900 | .143 |
| -9.2691 | .800 | .143 |
| -8.8850 | .700 | .143 |
| -8.4042 | .600 | .143 |
| -8.0223 | .500 | .143 |
| -7.3333 | .400 | .143 |
| -6.6295 | .300 | .143 |
| -5.7177 | .200 | .143 |
| -4.7619 | .100 | .143 |
| -4.4650 | .100 | .000 |
| -3.2895 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 7G

Area Under the Curve

Test Result Variable(s): Probe 08

| Area | Std. Error[a] | Asymptotic Sig.[b] | Asymptotic 95% Confidence Interval | |
|---|---|---|---|---|
| | | | Lower Bound | Upper Bound |
| .857 | .121 | .015 | .621 | 1.093 |

a. Under the nonparametric assumption b. Null hypothesis: true area = 0.5

Coordinates of the Curve

Test Result Variable(s): Probe 10

| Positive if Greater Than or Equal To[a] | Sensitivity | 1 - Specificity |
|---|---|---|
| -24.5800 | 1.000 | 1.000 |
| -23.0973 | 1.000 | .857 |
| -22.4697 | .900 | .857 |
| -20.4726 | .900 | .714 |
| -18.5350 | .900 | .571 |
| -18.1631 | .900 | .429 |
| -15.2328 | .900 | .286 |
| -10.6717 | .900 | .143 |
| -8.4815 | .800 | .143 |
| -7.7503 | .700 | .143 |
| -7.2397 | .700 | .000 |
| -7.0417 | .600 | .000 |
| -6.8161 | .500 | .000 |
| -6.4752 | .400 | .000 |
| -6.1770 | .300 | .000 |
| -5.0643 | .200 | .000 |
| -3.3700 | .100 | .000 |
| -1.7508 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 7K

Area Under the Curve

Test Result Variable(s): Probe 10

| Area | Std. Error[a] | Asymptotic Sig.[b] | Asymptotic 95% Confidence Interval | |
|---|---|---|---|---|
| | | | Lower Bound | Upper Bound |
| .886 | .089 | .008 | .712 | 1.060 |

a. Under the nonparametric assumption b. Null hypothesis: true area = 0.5

Coordinates of the Curve

Test Result Variable(s): Probe 20

| Positive if Greater Than or Equal To[a] | Sensitivity | 1 - Specificity |
|---|---|---|
| -.5169 | 1.000 | 1.000 |
| .9068 | .900 | 1.000 |
| 1.5912 | .900 | .857 |
| 1.8981 | .800 | .857 |
| 2.0188 | .800 | .714 |
| 2.1229 | .800 | .571 |
| 2.2297 | .800 | .429 |
| 2.3347 | .700 | .429 |
| 2.5071 | .700 | .286 |
| 2.6562 | .600 | .286 |
| 2.6809 | .600 | .143 |
| 2.7242 | .600 | .000 |
| 2.7672 | .500 | .000 |
| 2.8328 | .400 | .000 |
| 3.0151 | .300 | .000 |
| 3.3308 | .200 | .000 |
| 4.6060 | .100 | .000 |
| 6.7022 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 7O

Area Under the Curve

Test Result Variable(s): Probe 20

| Area | Std. Error[a] | Asymptotic Sig.[b] | Asymptotic 95% Confidence Interval | |
|---|---|---|---|---|
| | | | Lower Bound | Upper Bound |
| .743 | .125 | .097 | .498 | .988 |

a. Under the nonparametric assumption b. Null hypothesis: true area = 0.5

Coordinates of the Curve

Test Result Variable(s): Probe 06

| Positive if Less Than or Equal To[a] | Sensitivity | 1 - Specificity |
|---|---|---|
| -22.0392 | .000 | .000 |
| -20.9814 | .111 | .000 |
| -19.4099 | .222 | .000 |
| -17.6643 | .333 | .000 |
| -17.3445 | .444 | .000 |
| -13.0322 | .556 | .000 |
| -7.8187 | .667 | .000 |
| -6.7994 | .778 | .000 |
| -6.3994 | .889 | .000 |
| -5.9531 | .889 | .200 |
| -5.3975 | .889 | .400 |
| -4.8747 | 1.000 | .400 |
| -4.4546 | 1.000 | .600 |
| -3.8466 | 1.000 | .800 |
| -2.6149 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 8C

Area Under the Curve

Test Result Variable(s): Probe 06

| Area | Std. Error[a] | Asymptotic Sig.[b] | Asymptotic 95% Confidence Interval | |
|---|---|---|---|---|
| | | | Lower Bound | Upper Bound |
| .956 | .054 | .006 | .850 | 1.061 |

a. Under the nonparametric assumption b. Null hypothesis: true area = 0.5

Coordinates of the Curve

Test Result Variable(s): Probe 10

| Positive if Less Than or Equal To[a] | Sensitivity | 1 - Specificity |
|---|---|---|
| -18.8961 | .000 | .000 |
| -17.6643 | .111 | .000 |
| -12.5362 | .222 | .000 |
| -7.6318 | .333 | .000 |
| -7.1352 | .444 | .000 |
| -6.5045 | .556 | .000 |
| -6.2157 | .667 | .000 |
| -6.0322 | .667 | .200 |
| -5.7932 | .667 | .400 |
| -5.5472 | .778 | .400 |
| -5.4308 | .778 | .600 |
| -4.7572 | .889 | .600 |
| -3.9035 | 1.000 | .600 |
| -3.4191 | 1.000 | .800 |
| -2.1871 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 8G

Area Under the Curve

Test Result Variable(s): Probe 10

| Area | Std. Error[a] | Asymptotic Sig.[b] | Asymptotic 95% Confidence Interval | |
|---|---|---|---|---|
| | | | Lower Bound | Upper Bound |
| .822 | .115 | .053 | .597 | 1.047 |

a. Under the nonparametric assumption b. Null hypothesis: true area = 0.5

Coordinates of the Curve

Test Result Variable(s): Probe 11

| Positive if Greater Than or Equal To[a] | Sensitivity | 1 - Specificity |
|---|---|---|
| -.5371 | 1.000 | 1.000 |
| .6980 | 1.000 | .800 |
| 1.0810 | 1.000 | .600 |
| 1.2329 | .889 | .600 |
| 1.2424 | .889 | .400 |
| 1.3246 | .778 | .400 |
| 1.5257 | .778 | .200 |
| 1.6762 | .778 | .000 |
| 1.7214 | .667 | .000 |
| 1.9017 | .556 | .000 |
| 2.2043 | .444 | .000 |
| 2.3772 | .333 | .000 |
| 2.5673 | .222 | .000 |
| 2.8707 | .111 | .000 |
| 4.0156 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 8L

Area Under the Curve

Test Result Variable(s): Probe 11

| Area | Std. Error[a] | Asymptotic Sig.[b] | Asymptotic 95% Confidence Interval | |
|---|---|---|---|---|
| | | | Lower Bound | Upper Bound |
| .889 | .089 | .020 | .714 | 1.064 |

a. Under the nonparametric assumption b. Null hypothesis: true area = 0.5

Fig. 8M

Coordinates of the Curve

Test Result Variable(s): Probe 14

| Positive if Less Than or Equal To[a] | Sensitivity | 1 - Specificity |
|---|---|---|
| -22.0392 | .000 | .000 |
| -19.4676 | .111 | .000 |
| -17.6643 | .222 | .000 |
| -12.7717 | .333 | .000 |
| -7.9424 | .444 | .000 |
| -7.7602 | .556 | .000 |
| -7.2406 | .556 | .200 |
| -6.2127 | .667 | .200 |
| -5.5389 | .667 | .400 |
| -5.3642 | .778 | .400 |
| -4.9118 | .889 | .400 |
| -4.4384 | .889 | .600 |
| -4.0421 | 1.000 | .600 |
| -3.5533 | 1.000 | .800 |
| -2.4171 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 8P

Area Under the Curve

Test Result Variable(s): Probe 14

| Area | Std. Error[a] | Asymptotic Sig.[b] | Asymptotic 95% Confidence Interval | |
|---|---|---|---|---|
| | | | Lower Bound | Upper Bound |
| .822 | .116 | .053 | .596 | 1.049 |

a. Under the nonparametric assumption b. Null hypothesis: true area = 0.5

Fig. 8Q

Coordinates of the Curve

Test Result Variable(s): Probe 15

| Positive if Less Than or Equal To[a] | Sensitivity | 1 - Specificity |
|---|---|---|
| -20.1142 | .000 | .000 |
| -14.2809 | .111 | .000 |
| -9.1717 | .222 | .000 |
| -8.7108 | .333 | .000 |
| -8.1027 | .444 | .000 |
| -7.4967 | .556 | .000 |
| -7.3107 | .667 | .000 |
| -7.1709 | .667 | .200 |
| -6.5789 | .667 | .400 |
| -5.6633 | .778 | .400 |
| -5.0574 | .889 | .400 |
| -4.9067 | .889 | .600 |
| -4.6344 | .889 | .800 |
| -4.3629 | .889 | 1.000 |
| -3.3582 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 8T

Area Under the Curve

Test Result Variable(s): Probe 15

| Area | Std. Error[a] | Asymptotic Sig.[b] | Asymptotic 95% Confidence Interval | |
|---|---|---|---|---|
| | | | Lower Bound | Upper Bound |
| .800 | .123 | .072 | .559 | 1.041 |

a. Under the nonparametric assumption b. Null hypothesis: true area = 0.5

Fig. 8U

Coordinates of the Curve

Test Result Variable(s): Probe 16

| Positive if Less Than or Equal To[a] | Sensitivity | 1 - Specificity |
|---|---|---|
| -23.0959 | .000 | .000 |
| -21.5675 | .111 | .000 |
| -20.9814 | .222 | .000 |
| -20.8346 | .333 | .000 |
| -20.5630 | .333 | .200 |
| -20.3762 | .444 | .200 |
| -19.7431 | .556 | .200 |
| -18.2733 | .667 | .200 |
| -14.4760 | .778 | .200 |
| -10.5963 | .889 | .200 |
| -8.3543 | 1.000 | .200 |
| -6.6018 | 1.000 | .400 |
| -5.3915 | 1.000 | .600 |
| -4.5308 | 1.000 | .800 |
| -3.4469 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 8W

Area Under the Curve

Test Result Variable(s): Probe 16

| Area | Std. Error[a] | Asymptotic Sig.[b] | Asymptotic 95% Confidence Interval | |
|---|---|---|---|---|
| | | | Lower Bound | Upper Bound |
| .867 | .126 | .028 | .619 | 1.115 |

a. Under the nonparametric assumption b. Null hypothesis: true area = 0.5

Coordinates of the Curve

Test Result Variable(s): Probe 20

| Positive if Greater Than or Equal To[a] | Sensitivity | 1 - Specificity |
|---|---|---|
| 1.0284 | 1.000 | 1.000 |
| 2.2833 | 1.000 | .800 |
| 2.6520 | 1.000 | .600 |
| 2.9137 | 1.000 | .400 |
| 3.0975 | .889 | .400 |
| 3.1367 | .778 | .400 |
| 3.1915 | .667 | .400 |
| 3.2910 | .667 | .200 |
| 3.5084 | .556 | .200 |
| 3.8538 | .556 | .000 |
| 4.0448 | .444 | .000 |
| 4.2349 | .333 | .000 |
| 4.5324 | .222 | .000 |
| 4.7853 | .111 | .000 |
| 5.9158 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 8AA

Area Under the Curve

Test Result Variable(s): Probe 20

| Area | Std. Error[a] | Asymptotic Sig.[b] | Asymptotic 95% Confidence Interval | |
|---|---|---|---|---|
| | | | Lower Bound | Upper Bound |
| .844 | .112 | .039 | .625 | 1.064 |

a. Under the nonparametric assumption b. Null hypothesis: true area = 0.5

Fig. 8BB

Coordinates of the Curve

Test Result Variable(s): Probe 1

| Positive if Greater Than or Equal To[a] | Sensitivity | 1 - Specificity |
|---|---|---|
| -15.4761 | 1.000 | 1.000 |
| -13.5649 | 1.000 | .900 |
| -12.2015 | 1.000 | .800 |
| -11.7327 | 1.000 | .700 |
| -11.6981 | 1.000 | .600 |
| -11.6511 | 1.000 | .500 |
| -11.5103 | 1.000 | .400 |
| -11.3723 | 1.000 | .300 |
| -11.2832 | .900 | .300 |
| -11.1503 | .900 | .200 |
| -11.0681 | .800 | .200 |
| -11.0514 | .700 | .200 |
| -11.0285 | .700 | .100 |
| -10.9575 | .600 | .100 |
| -10.8113 | .500 | .100 |
| -10.5685 | .500 | .000 |
| -9.7680 | .400 | .000 |
| -9.0247 | .300 | .000 |
| -8.7768 | .200 | .000 |
| -8.3329 | .100 | .000 |
| -7.0448 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9B

Area Under the Curve

Test Result Variable(s): Probe 1

| Area | Std. Error[a] | Asymptotic Sig.[b] | Asymptotic 95% Confidence Interval | |
|---|---|---|---|---|
| | | | Lower Bound | Upper Bound |
| .910 | .065 | .002 | .783 | 1.037 |

a. Under the nonparametric assumption b. Null hypothesis: true area = 0.5

Fig. 9E

Coordinates of the Curve

Test Result Variable(s): Probe 2

| Positive if Greater Than or Equal To[a] | Sensitivity | 1 - Specificity |
|---|---|---|
| -2.5142 | 1.000 | 1.000 |
| -1.4962 | 1.000 | .900 |
| -1.4577 | 1.000 | .800 |
| -1.3167 | 1.000 | .700 |
| -1.1509 | 1.000 | .600 |
| -1.0633 | 1.000 | .500 |
| -1.0013 | 1.000 | .400 |
| -.9511 | .900 | .400 |
| -.8981 | .900 | .300 |
| -.8244 | .900 | .200 |
| -.7437 | .900 | .100 |
| -.6962 | .900 | .000 |
| -.5223 | .800 | .000 |
| -.2498 | .700 | .000 |
| -.0539 | .600 | .000 |
| .0701 | .500 | .000 |
| .1717 | .400 | .000 |
| .3552 | .300 | .000 |
| .5236 | .200 | .000 |
| .6224 | .100 | .000 |
| 1.6797 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9G

Area Under the Curve

Test Result Variable(s): Probe 2

| Area | Std. Error[a] | Asymptotic Sig.[b] | Asymptotic 95% Confidence Interval | |
|---|---|---|---|---|
| | | | Lower Bound | Upper Bound |
| .960 | .044 | .001 | .875 | 1.045 |

a. Under the nonparametric assumption b. Null hypothesis: true area = 0.5

Coordinates of the Curve

Test Result Variable(s): Probe 3

| Positive if Greater Than or Equal To[a] | Sensitivity | 1 - Specificity |
|---|---|---|
| -2.7188 | 1.000 | 1.000 |
| -1.6268 | 1.000 | .900 |
| -1.4628 | 1.000 | .800 |
| -1.3513 | 1.000 | .700 |
| -1.2780 | 1.000 | .600 |
| -1.2393 | 1.000 | .500 |
| -1.1402 | 1.000 | .400 |
| -1.0353 | 1.000 | .300 |
| -1.0098 | 1.000 | .200 |
| -.8590 | 1.000 | .100 |
| -.6754 | 1.000 | .000 |
| -.6215 | .900 | .000 |
| -.3833 | .800 | .000 |
| -.1380 | .700 | .000 |
| -.0985 | .600 | .000 |
| -.0043 | .500 | .000 |
| .0854 | .400 | .000 |
| .1595 | .300 | .000 |
| .2471 | .200 | .000 |
| .5721 | .100 | .000 |
| 1.8621 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9L

Area Under the Curve

Test Result Variable(s): Probe 3

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .000 | 1.000 | 1.000 |

a. Under the nonparametric assumption b. Null hypothesis: true area = 0.5

Fig. 9O

Coordinates of the Curve

Test Result Variable(s): Probe 6

| Positive if Greater Than or Equal To[a] | Sensitivity | 1 - Specificity |
|---|---|---|
| -12.2484 | 1.000 | 1.000 |
| -10.8974 | 1.000 | .900 |
| -10.3622 | 1.000 | .800 |
| -10.1290 | 1.000 | .700 |
| -10.0593 | 1.000 | .600 |
| -9.9364 | .900 | .600 |
| -9.8080 | .900 | .500 |
| -9.7497 | .900 | .400 |
| -9.6479 | .900 | .300 |
| -9.5650 | .800 | .300 |
| -9.3142 | .700 | .300 |
| -9.0593 | .700 | .200 |
| -9.0419 | .700 | .100 |
| -9.0155 | .600 | .100 |
| -8.9061 | .500 | .100 |
| -8.6798 | .500 | .000 |
| -8.3909 | .400 | .000 |
| -8.1522 | .300 | .000 |
| -7.5330 | .200 | .000 |
| -6.8311 | .100 | .000 |
| -5.6551 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9Q

Area Under the Curve

Test Result Variable(s): Probe 6

| Area | Std. Error[a] | Asymptotic Sig.[b] | Asymptotic 95% Confidence Interval | |
|---|---|---|---|---|
| | | | Lower Bound | Upper Bound |
| .860 | .083 | .007 | .698 | 1.022 |

a. Under the nonparametric assumption b. Null hypothesis: true area = 0.5

Coordinates of the Curve

Test Result Variable(s): Probe 11

| Positive if Greater Than or Equal To[a] | Sensitivity | 1 - Specificity |
|---|---|---|
| -3.0352 | 1.000 | 1.000 |
| -2.0097 | 1.000 | .900 |
| -1.9698 | 1.000 | .800 |
| -1.8754 | 1.000 | .700 |
| -1.7312 | 1.000 | .600 |
| -1.6369 | 1.000 | .500 |
| -1.5908 | 1.000 | .400 |
| -1.5241 | 1.000 | .300 |
| -1.4464 | 1.000 | .200 |
| -1.3794 | 1.000 | .100 |
| -1.3341 | .900 | .100 |
| -1.2849 | .900 | .000 |
| -1.1592 | .800 | .000 |
| -1.0137 | .700 | .000 |
| -.8767 | .600 | .000 |
| -.7930 | .500 | .000 |
| -.6813 | .400 | .000 |
| -.5192 | .300 | .000 |
| -.4421 | .200 | .000 |
| -.2957 | .100 | .000 |
| .8346 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9V

Area Under the Curve

Test Result Variable(s): Probe 11

| Area | Std. Error[a] | Asymptotic Sig.[b] | Asymptotic 95% Confidence Interval | |
|---|---|---|---|---|
| | | | Lower Bound | Upper Bound |
| .990 | .016 | .000 | .958 | 1.022 |

a. Under the nonparametric assumption b. Null hypothesis: true area = 0.5

Fig. 9Y

Coordinates of the Curve

Test Result Variable(s): Probe 12

| Positive if Greater Than or Equal To[a] | Sensitivity | 1 - Specificity |
|---|---|---|
| -26.9813 | 1.000 | 1.000 |
| -14.2108 | 1.000 | .900 |
| -2.3502 | 1.000 | .800 |
| -2.1570 | 1.000 | .700 |
| -2.0120 | 1.000 | .600 |
| -1.9490 | 1.000 | .500 |
| -1.9071 | 1.000 | .400 |
| -1.8435 | .900 | .400 |
| -1.7488 | .900 | .300 |
| -1.6219 | .900 | .200 |
| -1.4090 | .900 | .100 |
| -1.2379 | .900 | .000 |
| -.9801 | .800 | .000 |
| -.7077 | .700 | .000 |
| -.6048 | .600 | .000 |
| -.4856 | .500 | .000 |
| -.4097 | .400 | .000 |
| -.1985 | .300 | .000 |
| .0613 | .200 | .000 |
| .1524 | .100 | .000 |
| 1.1833 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9AA

ROC Curve

Area Under the Curve

Test Result Variable(s): Probe 12

| Area | Std. Error[a] | Asymptotic Sig.[b] | Asymptotic 95% Confidence Interval | |
|---|---|---|---|---|
| | | | Lower Bound | Upper Bound |
| .960 | .044 | .001 | .875 | 1.045 |

a. Under the nonparametric assumption b. Null hypothesis: true area = 0.5

Fig. 9DD

Coordinates of the Curve

Test Result Variable(s): Probe 15

| Positive if Greater Than or Equal To[a] | Sensitivity | 1 - Specificity |
|---|---|---|
| -10.8536 | 1.000 | 1.000 |
| -9.7839 | 1.000 | .900 |
| -9.6603 | 1.000 | .800 |
| -9.4725 | 1.000 | .700 |
| -9.3188 | 1.000 | .600 |
| -9.2553 | .900 | .600 |
| -9.1992 | .800 | .600 |
| -9.1050 | .800 | .500 |
| -9.0054 | .800 | .400 |
| -8.9524 | .700 | .400 |
| -8.8066 | .700 | .300 |
| -8.6926 | .700 | .200 |
| -8.6143 | .600 | .200 |
| -8.3481 | .600 | .100 |
| -8.0930 | .500 | .100 |
| -7.7916 | .400 | .100 |
| -7.2842 | .400 | .000 |
| -6.7136 | .300 | .000 |
| -5.9261 | .200 | .000 |
| -5.3645 | .100 | .000 |
| -4.2896 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9FF

Area Under the Curve

Test Result Variable(s): Probe 15

| Area | Std. Error[a] | Asymptotic Sig.[b] | Asymptotic 95% Confidence Interval | |
|---|---|---|---|---|
| | | | Lower Bound | Upper Bound |
| .800 | .099 | .023 | .605 | .995 |

a. Under the nonparametric assumption b. Null hypothesis: true area = 0.5

Fig. 9II

Coordinates of the Curve

Test Result Variable(s): Probe 20

| Positive if Greater Than or Equal To[a] | Sensitivity | 1 - Specificity |
|---|---|---|
| -2.2352 | 1.000 | 1.000 |
| -1.2122 | 1.000 | .900 |
| -1.1256 | 1.000 | .800 |
| -1.0534 | 1.000 | .700 |
| -1.0376 | 1.000 | .600 |
| -1.0051 | 1.000 | .500 |
| -.9534 | 1.000 | .400 |
| -.8448 | 1.000 | .300 |
| -.7367 | 1.000 | .200 |
| -.6881 | 1.000 | .100 |
| -.6521 | 1.000 | .000 |
| -.5198 | .900 | .000 |
| -.3915 | .800 | .000 |
| -.2781 | .700 | .000 |
| -.1688 | .600 | .000 |
| -.1252 | .500 | .000 |
| -.0292 | .400 | .000 |
| .1935 | .300 | .000 |
| .3859 | .200 | .000 |
| .5209 | .100 | .000 |
| 1.6286 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 9KK

Area Under the Curve

Test Result Variable(s): Probe 20

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .000 | 1.000 | 1.000 |

a. Under the nonparametric assumption b. Null hypothesis: true area = 0.5

Fig. 9NN

Transcript 2

Descriptives

Log2Pr-Log2HK

| | N | Mean | Std. Deviation | Std. Error | 95% Confidence Interval for Mean | | Minimum | Maximum |
|---|---|---|---|---|---|---|---|---|
| | | | | | Lower Bound | Upper Bound | | |
| Benign | 8 | 2.8505 | .92066 | .32550 | 2.0808 | 3.6202 | 1.64 | 4.72 |
| Non-Seminoma | 5 | 2.9789 | 1.44319 | .64542 | 1.1869 | 4.7708 | .74 | 4.69 |
| Seminoma | 4 | .7720 | .88991 | .44496 | -.6440 | 2.1881 | -.47 | 1.49 |
| Total | 17 | 2.3992 | 1.38160 | .33509 | 1.6889 | 3.1096 | -.47 | 4.72 |

Fig. 10B

Multiple Comparisons

Dependent Variable: Log2Pr-Log2HK
Tukey HSD

| (I) Secondary Diagnosis | (J) Secondary Diagnosis | Mean Difference (I-J) | Std. Error | Sig. | 95% Confidence Interval | |
|---|---|---|---|---|---|---|
| | | | | | Lower Bound | Upper Bound |
| Benign | Non-Seminoma | -.12836 | .62153 | .977 | -1.7551 | 1.4983 |
| | Seminoma | 2.07851* | .66763 | .020 | .3311 | 3.8259 |
| Non-Seminoma | Benign | .12836 | .62153 | .977 | -1.4983 | 1.7551 |
| | Seminoma | 2.20686* | .73135 | .024 | .2927 | 4.1210 |
| Seminoma | Benign | -2.07851* | .66763 | .020 | -3.8259 | -.3311 |
| | Non-Seminoma | -2.20686* | .73135 | .024 | -4.1210 | -.2927 |

*. The mean difference is significant at the .05 level.

Fig. 10C

Benign to Seminoma

Coordinates of the Curve

Test Result Variable(s): Log2Pr-Log2HK

| Positive if Less Than or Equal To[a] | Sensitivity | 1 - Specificity |
|---|---|---|
| -1.4662 | .000 | .000 |
| .1280 | .250 | .000 |
| 1.0328 | .500 | .000 |
| 1.4161 | .750 | .000 |
| 1.5621 | 1.000 | .000 |
| 1.7712 | 1.000 | .125 |
| 2.3297 | 1.000 | .250 |
| 2.7718 | 1.000 | .375 |
| 2.8684 | 1.000 | .500 |
| 2.9759 | 1.000 | .625 |
| 3.0282 | 1.000 | .750 |
| 3.8831 | 1.000 | .875 |
| 5.7161 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 10F

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .007 | 1.000 | 1.000 |

a. Under the nonparametric assumption b. Null hypothesis: true area = 0.5

Fig. 10G

Non-Seminoma to Seminoma

Coordinates of the Curve

Test Result Variable(s): Log2Pr-Log2HK

| Positive if Less Than or Equal To[a] | Sensitivity | 1 - Specificity |
|---|---|---|
| -1.4662 | .000 | .000 |
| .1280 | .250 | .000 |
| .7309 | .500 | .000 |
| 1.0415 | .500 | .200 |
| 1.4161 | .750 | .200 |
| 2.1006 | 1.000 | .200 |
| 3.0434 | 1.000 | .400 |
| 3.3757 | 1.000 | .600 |
| 4.0340 | 1.000 | .800 |
| 5.6909 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 10J

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .900 | .112 | .050 | .681 | 1.119 |

a. Under the nonparametric assumption b. Null hypothesis: true area = 0.5

Fig. 10K

Transcript 3

Descriptives

Log2Pr-Log2HK

| | N | Mean | Std. Deviation | Std. Error | 95% Confidence Interval for Mean | | Minimum | Maximum |
|---|---|---|---|---|---|---|---|---|
| | | | | | Lower Bound | Upper Bound | | |
| Benign | 8 | 2.6917 | 1.04169 | .36829 | 1.8208 | 3.5625 | 1.33 | 4.79 |
| Non-Seminoma | 5 | 2.9100 | 1.41243 | .63166 | 1.1562 | 4.6638 | .78 | 4.28 |
| Seminoma | 4 | .5670 | .67029 | .33515 | -.4996 | 1.6336 | -.07 | 1.36 |
| Total | 17 | 2.2560 | 1.41401 | .34295 | 1.5289 | 2.9830 | -.07 | 4.79 |

Fig. 11B

Benign to Seminoma

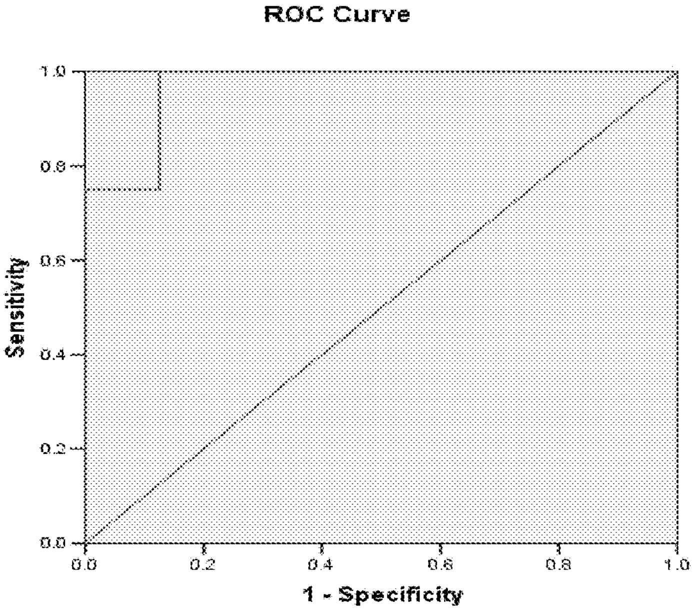

Fig. 11D

Coordinates of the Curve

Test Result Variable(s): Log2Pr-Log2HK

| Positive if Less Than or Equal To[a] | Sensitivity | 1 - Specificity |
|---|---|---|
| -1.0665 | .000 | .000 |
| .0167 | .250 | .000 |
| .4848 | .500 | .000 |
| 1.0981 | .750 | .000 |
| 1.3457 | .750 | .125 |
| 1.5359 | 1.000 | .125 |
| 2.1229 | 1.000 | .250 |
| 2.5712 | 1.000 | .375 |
| 2.6177 | 1.000 | .500 |
| 2.6580 | 1.000 | .625 |
| 2.9661 | 1.000 | .750 |
| 4.0208 | 1.000 | .875 |
| 5.7935 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 11E

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .969 | .047 | .011 | .876 | 1.061 |

a. Under the nonparametric assumption b. Null hypothesis: true area = 0.5

Fig. 11F

Non-Seminoma to Seminoma

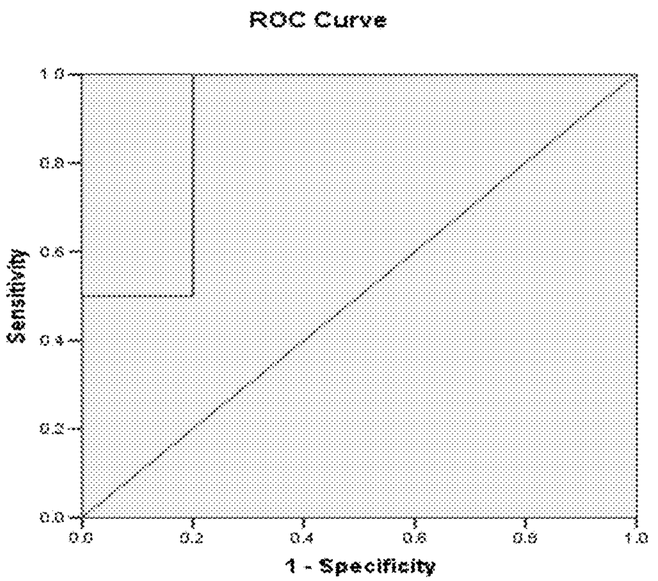

Fig. 11G

Coordinates of the Curve

Test Result Variable(s): Log2Pr-Log2HK

| Positive if Less Than or Equal To[a] | Sensitivity | 1 - Specificity |
|---|---|---|
| -1.0665 | .000 | .000 |
| .0167 | .250 | .000 |
| .4403 | .500 | .000 |
| .8251 | .500 | .200 |
| 1.1173 | .750 | .200 |
| 1.8181 | 1.000 | .200 |
| 2.7884 | 1.000 | .400 |
| 3.6099 | 1.000 | .600 |
| 4.0963 | 1.000 | .800 |
| 5.2783 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 11H

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .900 | .112 | .050 | .681 | 1.119 |

a. Under the nonparametric assumption b. Null hypothesis: true area = 0.5

Fig. 11I

Transcript 4

Independent Samples Test

| | | Levene's Test for Equality of Variances | | t-test for Equality of Means | | | | | | |
|---|---|---|---|---|---|---|---|---|---|---|
| | | | | | | | | | 95% Confidence Interval of the Difference | |
| | | F | Sig. | t | df | Sig. (2-tailed) | Mean Difference | Std. Error Difference | Lower | Upper |
| Log2Pr-Log2HK | Equal variances assumed | .424 | .525 | 2.337 | 15 | .034 | 2.79398 | 1.19570 | .24540 | 5.34256 |
| | Equal variances not assumed | | | 2.425 | 12.142 | .032 | 2.79398 | 1.15230 | .28660 | 5.30136 |

Fig. 12B

Coordinates of the Curve

Test Result Variable(s): Log2Pr-Log2HK

| Positive if Less Than or Equal To[a] | Sensitivity | 1 - Specificity |
|---|---|---|
| -19.1032 | .000 | .000 |
| -14.8271 | .111 | .000 |
| -11.1973 | .222 | .000 |
| -10.7498 | .333 | .000 |
| -10.6312 | .444 | .000 |
| -10.2319 | .556 | .000 |
| -9.7628 | .667 | .000 |
| -9.4346 | .667 | .125 |
| -9.1925 | .667 | .250 |
| -8.9503 | .778 | .250 |
| -8.6923 | .778 | .375 |
| -8.6324 | .778 | .500 |
| -8.5458 | .778 | .625 |
| -7.9611 | .889 | .625 |
| -7.4208 | 1.000 | .625 |
| -6.6410 | 1.000 | .750 |
| -5.6799 | 1.000 | .875 |
| -4.4918 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 12D

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .833 | .102 | .021 | .633 | 1.033 |

a. Under the nonparametric assumption b. Null hypothesis: true area = 0.5

Fig. 12E

Transcript 11

Multiple Comparisons

Dependent Variable: Log2Pr-Log2HK
Tukey HSD

| (I) Secondary Diagnosis | (J) Secondary Diagnosis | Mean Difference (I-J) | Std. Error | Sig. | 95% Confidence Interval | |
|---|---|---|---|---|---|---|
| | | | | | Lower Bound | Upper Bound |
| Benign | Non-Seminoma | -.17586 | .59248 | .953 | -1.7265 | 1.3748 |
| | Seminoma | 2.05715* | .63643 | .016 | .3914 | 3.7229 |
| Non-Seminoma | Benign | .17586 | .59248 | .953 | -1.3748 | 1.7265 |
| | Seminoma | 2.23301* | .69717 | .016 | .4083 | 4.0577 |
| Seminoma | Benign | -2.05715* | .63643 | .016 | -3.7229 | -.3914 |
| | Non-Seminoma | -2.23301* | .69717 | .016 | -4.0577 | -.4083 |

*. The mean difference is significant at the .05 level.

Fig. 13B

Benign to Seminoma

Coordinates of the Curve

Test Result Variable(s): Log2Pr-Log2HK

| Positive if Less Than or Equal To[a] | Sensitivity | 1 - Specificity |
|---|---|---|
| -1.7974 | .000 | .000 |
| -.6304 | .250 | .000 |
| -.1127 | .500 | .000 |
| .2892 | .750 | .000 |
| .7320 | 1.000 | .000 |
| 1.1910 | 1.000 | .125 |
| 1.3755 | 1.000 | .250 |
| 1.5677 | 1.000 | .375 |
| 1.6627 | 1.000 | .500 |
| 1.7308 | 1.000 | .625 |
| 1.8766 | 1.000 | .750 |
| 3.0567 | 1.000 | .875 |
| 5.1393 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 13E

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .007 | 1.000 | 1.000 |

a. Under the nonparametric assumption b. Null hypothesis: true area = 0.5

Fig. 13F

Non-Seminoma to Seminoma

Coordinates of the Curve

Test Result Variable(s): Log2Pr-Log2HK

| Positive if Less Than or Equal To[a] | Sensitivity | 1 - Specificity |
|---|---|---|
| -1.7974 | .000 | .000 |
| -.6304 | .250 | .000 |
| -.3218 | .500 | .000 |
| .0290 | .500 | .200 |
| .2892 | .750 | .200 |
| .9884 | 1.000 | .200 |
| 2.1680 | 1.000 | .400 |
| 2.7276 | 1.000 | .600 |
| 3.0782 | 1.000 | .800 |
| 4.4005 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 13H

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .900 | .112 | .050 | .681 | 1.119 |

a. Under the nonparametric assumption b. Null hypothesis: true area = 0.5

Fig. 13I

Transcript 12

Multiple Comparisons

Dependent Variable: Log2Pr-Log2HK
Tukey HSD

| (I) Secondary Diagnosis | (J) Secondary Diagnosis | Mean Difference (I-J) | Std. Error | Sig. | 95% Confidence Interval | |
|---|---|---|---|---|---|---|
| | | | | | Lower Bound | Upper Bound |
| Benign | Non-Seminoma | -.25989 | .62543 | .910 | -1.8968 | 1.3770 |
| | Seminoma | 1.71757 | .67182 | .056 | -.0408 | 3.4759 |
| Non-Seminoma | Benign | .25989 | .62543 | .910 | -1.3770 | 1.8968 |
| | Seminoma | 1.97745* | .73594 | .044 | .0513 | 3.9036 |
| Seminoma | Benign | -1.71757 | .67182 | .056 | -3.4759 | .0408 |
| | Non-Seminoma | -1.97745* | .73594 | .044 | -3.9036 | -.0513 |

*. The mean difference is significant at the .05 level.

Fig. 14B

Benign to Seminoma

Coordinates of the Curve

Test Result Variable(s): Log2Pr-Log2HK

| Positive if Less Than or Equal To[a] | Sensitivity | 1 - Specificity |
|---|---|---|
| -1.1036 | .000 | .000 |
| .2116 | .250 | .000 |
| .6444 | .500 | .000 |
| .8799 | .750 | .000 |
| 1.2345 | .750 | .125 |
| 1.5361 | 1.000 | .125 |
| 1.8719 | 1.000 | .250 |
| 2.1521 | 1.000 | .375 |
| 2.1746 | 1.000 | .500 |
| 2.4309 | 1.000 | .625 |
| 2.7874 | 1.000 | .750 |
| 3.6445 | 1.000 | .875 |
| 5.3880 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 14E

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .969 | .047 | .011 | .876 | 1.061 |

a. Under the nonparametric assumption b. Null hypothesis: true area = 0.5

Fig. 14F

Non-Seminoma to Seminoma

Coordinates of the Curve

Test Result Variable(s): Log2Pr-Log2HK

| Positive if Less Than or Equal To[a] | Sensitivity | 1 - Specificity |
|---|---|---|
| -1.1036 | .000 | .000 |
| .2116 | .250 | .000 |
| .5766 | .500 | .000 |
| .6942 | .500 | .200 |
| 1.1167 | .750 | .200 |
| 1.6039 | 1.000 | .200 |
| 2.3812 | 1.000 | .400 |
| 3.2778 | 1.000 | .600 |
| 3.9096 | 1.000 | .800 |
| 5.2895 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 14H

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .900 | .112 | .050 | .681 | 1.119 |

a. Under the nonparametric assumption b. Null hypothesis: true area = 0.5

Fig. 14I

Transcript 13

Benign to Malignant

Independent Samples Test

| | | Levene's Test for Equality of Variances | | t-test for Equality of Means | | | | | | |
|---|---|---|---|---|---|---|---|---|---|---|
| | | | | | | | | | 95% Confidence Interval of the Difference | |
| | | F | Sig. | t | df | Sig. (2-tailed) | Mean Difference | Std. Error Difference | Lower | Upper |
| Log2Pr-Log2HK | Equal variances assumed | 3.445 | .083 | 2.638 | 15 | .019 | 7.12469 | 2.70079 | 1.36810 | 12.88129 |
| | Equal variances not assumed | | | 2.682 | 14.703 | .017 | 7.12469 | 2.65646 | 1.45261 | 12.79678 |

Fig. 15B

Coordinates of the Curve

Test Result Variable(s): Log2Pr-Log2HK

| Positive if Greater Than or Equal To[a] | Sensitivity | 1 - Specificity |
|---|---|---|
| -24.4381 | 1.000 | 1.000 |
| -23.0168 | 1.000 | .889 |
| -22.2756 | 1.000 | .778 |
| -21.6134 | 1.000 | .667 |
| -20.8467 | 1.000 | .556 |
| -19.2627 | .875 | .556 |
| -15.8501 | .875 | .444 |
| -11.7732 | .875 | .333 |
| -9.8751 | .875 | .222 |
| -9.6932 | .750 | .222 |
| -9.3712 | .625 | .222 |
| -8.9122 | .625 | .111 |
| -8.5527 | .625 | .000 |
| -8.2104 | .500 | .000 |
| -7.7549 | .375 | .000 |
| -7.0316 | .250 | .000 |
| -5.7275 | .125 | .000 |
| -3.9187 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 15C

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .875 | .086 | .009 | .706 | 1.044 |

a. Under the nonparametric assumption b. Null hypothesis: true area = 0.5

Multiple Comparisons

Dependent Variable: Log2Pr-Log2HK
Tukey HSD

| (I) Secondary Diagnosis | (J) Secondary Diagnosis | Mean Difference (I-J) | Std. Error | Sig. | 95% Confidence Interval | |
|---|---|---|---|---|---|---|
| | | | | | Lower Bound | Upper Bound |
| Benign | Non-Seminoma | 12.07137* | 2.08974 | .000 | 6.6019 | 17.5408 |
| | Seminoma | .94135 | 2.24474 | .908 | -4.9338 | 6.8165 |
| Non-Seminoma | Benign | -12.07137* | 2.08974 | .000 | -17.5408 | -6.6019 |
| | Seminoma | -11.13002* | 2.45899 | .001 | -17.5659 | -4.6941 |
| Seminoma | Benign | -.94135 | 2.24474 | .908 | -6.8165 | 4.9338 |
| | Non-Seminoma | 11.13002* | 2.45899 | .001 | 4.6941 | 17.5659 |

*. The mean difference is significant at the .05 level.

Fig. 15G

Non-Seminoma to Seminoma

Coordinates of the Curve

Test Result Variable(s): Log2Pr-Log2HK

| Positive if Greater Than or Equal To[a] | Sensitivity | 1 - Specificity |
|---|---|---|
| -24.4381 | 1.000 | 1.000 |
| -23.0168 | 1.000 | .800 |
| -22.2756 | 1.000 | .600 |
| -21.6134 | 1.000 | .400 |
| -19.6872 | 1.000 | .200 |
| -15.8501 | 1.000 | .000 |
| -11.7732 | .750 | .000 |
| -9.5531 | .500 | .000 |
| -8.9122 | .250 | .000 |
| -7.6678 | .000 | .000 |

a. The smallest cutoff value is the minimum observed test value minus 1, and the largest cutoff value is the maximum observed test value plus 1. All the other cutoff values are the averages of two consecutive ordered observed test values.

Fig.15I

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .014 | 1.000 | 1.000 |

a. Under the nonparametric assumption b. Null hypothesis: true area = 0.5

Fig. 15J

Benign to Non-Seminoma

Coordinates of the Curve

Test Result Variable(s): Log2Pr-Log2HK

| Positive if Less Than or Equal To[a] | Sensitivity | 1 - Specificity |
|---|---|---|
| -24.4381 | .000 | .000 |
| -23.0168 | .200 | .000 |
| -22.2756 | .400 | .000 |
| -21.6134 | .600 | .000 |
| -20.8467 | .800 | .000 |
| -19.2627 | .800 | .125 |
| -13.9519 | 1.000 | .125 |
| -9.6932 | 1.000 | .250 |
| -9.0117 | 1.000 | .375 |
| -8.2104 | 1.000 | .500 |
| -7.7549 | 1.000 | .625 |
| -7.0316 | 1.000 | .750 |
| -5.7275 | 1.000 | .875 |
| -3.9187 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 15L

Case Processing Summary

| Diagnosis | Valid N (listwise) |
|---|---|
| Positive[a] | 5 |
| Negative | 8 |
| Missing | 4 |

Smaller values of the test result variable(s) indicate stronger evidence for a positive actual state.

a. The positive actual state is Seminoma.

Fig. 15M

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .975 | .039 | .005 | .899 | 1.051 |

a. Under the nonparametric assumption b. Null hypothesis: true area = 0.5

Fig. 15N

Transcript 15

Benign to Malignant

Independent Samples Test

| | | Levene's Test for Equality of Variances | | t-test for Equality of Means | | | | | | |
|---|---|---|---|---|---|---|---|---|---|---|
| | | | | | | | | | 95% Confidence Interval of the Difference | |
| | | F | Sig. | t | df | Sig. (2-tailed) | Mean Difference | Std. Error Difference | Lower | Upper |
| Log2Pr-Log2HK | Equal variances assumed | 1.272 | .277 | 1.995 | 15 | .065 | 3.02635 | 1.51727 | -.20763 | 6.26033 |
| | Equal variances not assumed | | | 2.084 | 10.974 | .061 | 3.02635 | 1.45201 | -.17044 | 6.22313 |

Fig. 16B

Coordinates of the Curve

Test Result Variable(s): Log2Pr-Log2HK

| Positive if Greater Than or Equal To[a] | Sensitivity | 1 - Specificity |
|---|---|---|
| -19.1032 | 1.000 | 1.000 |
| -13.3553 | 1.000 | .889 |
| -7.9658 | 1.000 | .778 |
| -7.2682 | .875 | .778 |
| -7.1398 | .875 | .667 |
| -6.9179 | .875 | .556 |
| -6.5654 | .875 | .444 |
| -6.1847 | .875 | .333 |
| -5.9128 | .750 | .333 |
| -5.7090 | .750 | .222 |
| -5.4916 | .750 | .111 |
| -5.3213 | .625 | .111 |
| -5.1819 | .500 | .111 |
| -4.9299 | .500 | .000 |
| -4.7011 | .375 | .000 |
| -4.0399 | .250 | .000 |
| -2.6039 | .125 | .000 |
| -.7752 | .000 | .000 |

a. The smallest cutoff value is the minimum observed test value minus 1, and the largest cutoff value is the maximum observed test value plus 1. All the other cutoff values are the averages of two consecutive ordered observed test values.

Fig. 16D

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .833 | .106 | .021 | .626 | 1.040 |

a. Under the nonparametric assumption b. Null hypothesis: true area = 0.5

Fig. 16E

Transcript 16

Benign to Malignant

Independent Samples Test

| | | Levene's Test for Equality of Variances | | t-test for Equality of Means | | | | | | |
|---|---|---|---|---|---|---|---|---|---|---|
| | | | | | | | | | 95% Confidence Interval of the Difference | |
| | | F | Sig. | t | df | Sig. (2-tailed) | Mean Difference | Std. Error Difference | Lower | Upper |
| Log2Pr-Log2HK | Equal variances assumed | .149 | .705 | 2.285 | 15 | .037 | 1.98991 | .87082 | .13381 | 3.84602 |
| | Equal variances not assumed | | | 2.265 | 13.995 | .040 | 1.98991 | .87870 | .10522 | 3.87461 |

Fig. 17B

Coordinates of the Curve

Test Result Variable(s): Log2Pr-Log2HK

| Positive if Less Than or Equal To[a] | Sensitivity | 1 - Specificity |
|---|---|---|
| -10.1467 | .000 | .000 |
| -8.9916 | .111 | .000 |
| -8.6680 | .222 | .000 |
| -8.4482 | .222 | .125 |
| -8.1689 | .333 | .125 |
| -7.8794 | .444 | .125 |
| -7.7537 | .556 | .125 |
| -7.4470 | .667 | .125 |
| -7.1508 | .778 | .125 |
| -6.9861 | .778 | .250 |
| -6.4480 | .889 | .250 |
| -5.8459 | .889 | .375 |
| -5.3490 | .889 | .500 |
| -5.0125 | .889 | .625 |
| -4.8989 | .889 | .750 |
| -4.1432 | .889 | .875 |
| -2.6805 | 1.000 | .875 |
| -.8743 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 17D

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .806 | .118 | .034 | .573 | 1.038 |

a. Under the nonparametric assumption b. Null hypothesis: true area = 0.5

Fig. 17E

Multiple Comparisons

Dependent Variable: Log2Pr-Log2HK
Tukey HSD

| (I) Secondary Diagnosis | (J) Secondary Diagnosis | Mean Difference (I-J) | Std. Error | Sig. | 95% Confidence Interval | |
|---|---|---|---|---|---|---|
| | | | | | Lower Bound | Upper Bound |
| Benign | Non-Seminoma | 1.14089 | .96443 | .482 | -1.3833 | 3.6651 |
| | Seminoma | 3.05119* | 1.03596 | .027 | .3398 | 5.7626 |
| Non-Seminoma | Benign | -1.14089 | .96443 | .482 | -3.6651 | 1.3833 |
| | Seminoma | 1.91029 | 1.13484 | .246 | -1.0599 | 4.8805 |
| Seminoma | Benign | -3.05119* | 1.03596 | .027 | -5.7626 | -.3398 |
| | Non-Seminoma | -1.91029 | 1.13484 | .246 | -4.8805 | 1.0599 |

*. The mean difference is significant at the .05 level.

Fig. 17F

Benign to Seminoma

Coordinates of the Curve

Test Result Variable(s): Log2Pr-Log2HK

| Positive if Less Than or Equal To[a] | Sensitivity | 1 - Specificity |
|---|---|---|
| -10.1467 | .000 | .000 |
| -8.9916 | .250 | .000 |
| -8.6680 | .500 | .000 |
| -8.4482 | .500 | .125 |
| -8.1075 | .750 | .125 |
| -7.4575 | 1.000 | .125 |
| -6.5589 | 1.000 | .250 |
| -5.8459 | 1.000 | .375 |
| -5.3490 | 1.000 | .500 |
| -5.0125 | 1.000 | .625 |
| -4.8989 | 1.000 | .750 |
| -3.3371 | 1.000 | .875 |
| -.8743 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 17I

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| .938 | .072 | .017 | .796 | 1.079 |

a. Under the nonparametric assumption b. Null hypothesis: true area = 0.5

Fig. 17J

Multiple Comparisons

Dependent Variable: Log2Pr-Log2HK
Tukey HSD

| (I) Secondary Diagnosis | (J) Secondary Diagnosis | Mean Difference (I-J) | Std. Error | Sig. | 95% Confidence Interval | |
|---|---|---|---|---|---|---|
| | | | | | Lower Bound | Upper Bound |
| Benign | Non-Seminoma | -.32805 | .59050 | .845 | -1.8735 | 1.2174 |
| | Seminoma | 2.38275* | .63429 | .006 | .7226 | 4.0429 |
| Non-Seminoma | Benign | .32805 | .59050 | .845 | -1.2174 | 1.8735 |
| | Seminoma | 2.71080* | .69484 | .004 | .8922 | 4.5294 |
| Seminoma | Benign | -2.38275* | .63429 | .006 | -4.0429 | -.7226 |
| | Non-Seminoma | -2.71080* | .69484 | .004 | -4.5294 | -.8922 |

*. The mean difference is significant at the .05 level.

Fig. 18B

Benign to Seminoma

Coordinates of the Curve

Test Result Variable(s): Log2Pr-Log2HK

| Positive if Less Than or Equal To[a] | Sensitivity | 1 - Specificity |
|---|---|---|
| -.8670 | .000 | .000 |
| .4000 | .250 | .000 |
| .9279 | .500 | .000 |
| 1.3158 | .750 | .000 |
| 1.8364 | 1.000 | .000 |
| 2.3956 | 1.000 | .125 |
| 2.6632 | 1.000 | .250 |
| 2.7784 | 1.000 | .375 |
| 2.8058 | 1.000 | .500 |
| 2.9821 | 1.000 | .625 |
| 3.5019 | 1.000 | .750 |
| 4.8065 | 1.000 | .875 |
| 6.7531 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 18E

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .007 | 1.000 | 1.000 |

a. Under the nonparametric assumption b. Null hypothesis: true area = 0.5

Fig. 18F

Non-Seminoma to Seminoma

Coordinates of the Curve

Test Result Variable(s): Log2Pr-Log2HK

| Positive if Less Than or Equal To[a] | Sensitivity | 1 - Specificity |
|---|---|---|
| -.8670 | .000 | .000 |
| .4000 | .250 | .000 |
| .9279 | .500 | .000 |
| 1.3158 | .750 | .000 |
| 1.6065 | 1.000 | .000 |
| 2.4411 | 1.000 | .200 |
| 3.6145 | 1.000 | .400 |
| 4.2275 | 1.000 | .600 |
| 4.4220 | 1.000 | .800 |
| 5.5063 | 1.000 | 1.000 |

a. The smallest cutoff value is the minimum observed test value minus 1, and the largest cutoff value is the maximum observed test value plus 1. All the other cutoff values are the averages of two consecutive ordered observed test values.

Fig. 18H

Area Under the Curve

Test Result Variable(s): Log2Pr-Log2HK

| Area | Std. Error[a] | Asymptotic Sig.[b] | Asymptotic 95% Confidence Interval | |
|---|---|---|---|---|
| | | | Lower Bound | Upper Bound |
| 1.000 | .000 | .014 | 1.000 | 1.000 |

a. Under the nonparametric assumption b. Null hypothesis: true area = 0.5

Fig. 18I

SEQUENCE LISTING

<160> NUMBER OF SEQ ID NOS: 56

<210> SEQ ID NO 1
<211> LENGTH: 16568
<212> TYPE: DNA
<213> ORGANISM: Human

<400> SEQUENCE: 1
gatcacaggt ctatcaccct attaaccact cacgggagct ctccatgcat ttggtatttt 60
cgtctggggg gtatgcacgc gatagcattg cgagacgctg gagccggagc accctatgtc 120
gcagtatctg tctttgattc ctgcctcatc ctattattta tcgcacctac gttcaatatt 180
acaggcgaac atacttacta aagtgtgtta attaattaat gcttgtagga cataataata 240
acaattgaat gtctgcacag ccactttcca cacagacatc ataacaaaaa atttccacca 300 aacccccccct cccccgcttc tggccacagc acttaaacac atctctgcca aaccccaaaa 360
acaaagaacc ctaacaccag cctaaccaga tttcaaattt tatcttttgg cggtatgcac 420
ttttaacagt caccccccaa ctaacacatt attttcccct cccactccca tactactaat 480
ctcatcaata caacccccgc ccatcctacc cagcacacac acaccgctgc taaccccata 540
ccccgaacca accaaacccc aaagacaccc cccacagttt atgtagctta cctcctcaaa 600
gcaatacact gaaaatgttt agacgggctc acatcacccc ataaacaaat aggtttggtc 660
ctagcctttc tattagctct tagtaagatt acacatgcaa gcatccccgt tccagtgagt 720
tcaccctcta aatcaccacg atcaaaagga acaagcatca agcacgcagc aatgcagctc 780
aaaacgctta gcctagccac acccccacgg gaaacagcag tgattaacct ttagcaataa 840
acgaaagttt aactaagcta tactaacccc agggttggtc aatttcgtgc cagccaccgc 900
ggtcacacga ttaacccaag tcaatagaag ccggcgtaaa gagtgtttta gatcaccccc 960
tccccaataa agctaaaact cacctgagtt gtaaaaaact ccagttgaca caaaatagac 1020
tacgaaagtg gctttaacat atctgaacac acaatagcta agacccaaac tgggattaga 1080
taccccacta tgcttagccc taaacctcaa cagttaaatc aacaaaactg ctcgccagaa 1140
cactacgagc cacagcttaa aactcaaagg acctggcggt gcttcatatc cctctagagg 1200
agcctgttct gtaatcgata aaccccgatc aacctcacca cctcttgctc agcctatata 1260
ccgccatctt cagcaaaccc tgatgaaggc tacaaagtaa gcgcaagtac ccacgtaaag 1320
acgttaggtc aaggtgtagc ccatgaggtg gcaagaaatg ggctacattt tctaccccag 1380
aaaactacga tagcccttat gaaacttaag ggtcgaaggt ggatttagca gtaaactaag 1440
agtagagtgc ttagttgaac agggccctga agcgcgtaca caccgcccgt caccctcctc 1500
aagtatactt caaaggacat ttaactaaaa cccctacgca tttatataga ggagacaagt 1560

-continued

```
cgtaacatgg taagtgtact ggaaagtgca cttggacgaa ccagagtgta gcttaacaca   1620
aagcacccaa cttacactta ggagatttca acttaacttg accgctctga gctaaaccta   1680
gccccaaacc cactccacct tactaccaga caaccttagc caaaccattt acccaaataa   1740
agtataggcg atagaaattg aaacctggcg caatagatat agtaccgcaa gggaaagatg   1800
aaaaattata accaagcata atatagcaag gactaacccc tataccttct gcataatgaa   1860
ttaactagaa ataactttgc aaggagagcc aaagctaaga cccccgaaac cagacgagct   1920
acctaagaac agctaaaaga gcacacccgt ctatgtagca aaatagtggg aagatttata   1980
ggtagaggcg acaaacctac cgagcctggt gatagctggt tgtccaagat agaatcttag   2040
ttcaacttta aatttgccca cagaaccctc taaatcccct tgtaaattta actgttagtc   2100
caaagaggaa cagctctttg gacactagga aaaaaccttg tagagagagt aaaaaattta   2160
acacccatag taggcctaaa agcagccacc aattaagaaa gcgttcaagc tcaacaccca   2220
ctacctaaaa aatcccaaac atataactga actcctcaca cccaattgga ccaatctatc   2280
accctataga agaactaatg ttagtataag taacatgaaa acattctcct ccgcataagc   2340
ctgcgtcaga ttaaaacact gaactgacaa ttaacagccc aatatctaca atcaaccaac   2400
aagtcattat taccctcact gtcaacccaa cacaggcatg ctcataagga aaggttaaaa   2460
aaagtaaaag gaactcggca aatcttaccc cgcctgttta ccaaaaacat cacctctagc   2520
atcaccagta ttagaggcac cgcctgccca gtgacacatg tttaacggcc gcggtaccct   2580
aaccgtgcaa aggtagcata atcacttgtt ccttaaatag ggacctgtat gaatggctcc   2640
acgagggttc agctgtctct tacttttaac cagtgaaatt gacctgcccg tgaagaggcg   2700
ggcataacac agcaagacga gaagacccta tggagcttta atttattaat gcaaacagta   2760
cctaacaaac ccacaggtcc taaactacca aacctgcatt aaaaatttcg gttggggcga   2820
cctcggagca gaacccaacc tccgagcagt acatgctaag acttcaccag tcaaagcgaa   2880
ctactatact caattgatcc aataacttga ccaacggaac aagttaccct agggataaca   2940
gcgcaatcct attctagagt ccatatcaac aatagggttt acgacctcga tgttggatca   3000
ggacatcccg atggtgcagc cgctattaaa ggttcgtttg ttcaacgatt aaagtcctac   3060
gtgatctgag ttcagaccgg agtaatccag gtcggtttct atctacttca aattcctccc   3120
tgtacgaaag gacaagagaa ataaggccta cttcacaaag cgccttcccc cgtaaatgat   3180
atcatctcaa cttagtatta tacccacacc cacccaagaa cagggtttgt taagatggca   3240
gagcccggta atcgcataaa acttaaaact ttacagtcag aggttcaatt cctcttctta   3300
acaacatacc catggccaac ctcctactcc tcattgtacc cattctaatc gcaatggcat   3360
tcctaatgct taccgaacga aaaattctag gctatataca actacgcaaa ggccccaacg   3420
ttgtaggccc ctacgggcta ctacaaccct tcgctgacgc cataaaactc ttcaccaaag   3480
agcccctaaa acccgccaca tctaccatca ccctctacat caccgccccg accttagctc   3540
tcaccatcgc tcttctacta tgaacccccc tccccatacc caaccccctg gtcaacctca   3600
acctaggcct cctatttatt ctagccacct ctagcctagc cgtttactca atcctctgat   3660
cagggtgagc atcaaactca aactacgccc tgatcggcgc actgcgagca gtagcccaaa   3720
caatctcata tgaagtcacc ctagccatca ttctactatc aacattacta ataagtggct   3780
cctttaacct ctccaccctt atcacaacac aagaacacct ctgattactc ctgccatcat   3840
gacccttggc cataatatga tttatctcca cactagcaga gaccaaccga accccccttcg   3900
accttgccga aggggagtcc gaactagtct caggcttcaa catcgaatac gccgcaggcc   3960
```

-continued

```
ccttcgccct attcttcata gccgaataca caaacattat tataataaac accctcacca   4020
ctacaatctt cctaggaaca acatatgacg cactctcccc tgaactctac acaacatatt   4080
ttgtcaccaa gaccctactt ctaacctccc tgttcttatg aattcgaaca gcataccccc   4140
gattccgcta cgaccaactc atacacctcc tatgaaaaaa cttcctacca ctcaccctag   4200
cattacttat atgatatgtc tccataccca ttacaatctc cagcattccc cctcaaacct   4260
aagaaatatg tctgataaaa gagttacttt gatagagtaa ataataggag cttaaacccc   4320
cttatttcta ggactatgag aatcgaaccc atccctgaga atccaaaatt ctccgtgcca   4380
cctatcacac cccatcctaa agtaaggtca gctaaataag ctatcgggcc cataccccga   4440
aaatgttggt tatacccttc ccgtactaat taatcccctg gcccaacccg tcatctactc   4500
taccatcttt gcaggcacac tcatcacagc gctaagctcg cactgatttt ttacctgagt   4560
aggcctagaa ataaacatgc tagcttttat tccagttcta accaaaaaaa taaaccctcg   4620
ttccacagaa gctgccatca agtatttcct cacgcaagca accgcatcca taatccttct   4680
aatagctatc ctcttcaaca atatactctc cggacaatga accataacca atactaccaa   4740
tcaatactca tcattaataa tcataatagc tatagcaata aaactaggaa tagccccctt   4800
tcacttctga gtcccagagg ttacccaagg cacccctctg acatccggcc tgcttcttct   4860
cacatgacaa aaactagccc ccatctcaat catataccaa atctctccct cactaaacgt   4920
aagccttctc ctcactctct caatcttatc catcatagca ggcagttgag gtggattaaa   4980
ccaaacccag ctacgcaaaa tcttagcata ctcctcaatt acccacatag gatgaataat   5040
agcagttcta ccgtacaacc ctaacataac cattcttaat ttaactattt atattatcct   5100
aactactacc gcattcctac tactcaactt aaactccagc accacgaccc tactactatc   5160
tcgcacctga aacaagctaa catgactaac acccttaatt ccatccaccc tcctctccct   5220
aggaggcctg cccccgctaa ccggcttttt gcccaaatgg gccattatcg aagaattcac   5280
aaaaaacaat agcctcatca tccccaccat catagccacc atcaccctcc ttaacctcta   5340
cttctaccta cgcctaatct actccacctc aatcacacta ctccccatat ctaacaacgt   5400
aaaaataaaa tgacagtttg aacatacaaa acccacccca ttcctcccca cactcatcgc   5460
ccttaccacg ctactcctac ctatctcccc ttttatacta ataatcttat agaaatttag   5520
gttaaataca gaccaagagc cttcaaagcc ctcagtaagt tgcaatactt aatttctgta   5580
acagctaagg actgcaaaac cccactctgc atcaactgaa cgcaaatcag ccactttaat   5640
taagctaagc ccttactaga ccaatgggac ttaaacccac aaacacttag ttaacagcta   5700
agcaccctaa tcaactggct tcaatctact tctcccgccg ccgggaaaaa aggcgggaga   5760
agccccggca ggtttgaagc tgcttcttcg aatttgcaat tcaatatgaa aatcacctcg   5820
gagctggtaa aaagaggcct aacccctgtc tttagattta cagtccaatg cttcactcag   5880
ccattttacc tcacccccac tgatgttcgc cgaccgttga ctattctcta caaaccacaa   5940
agacattgga acactatacc tattattcgg cgcatgagct ggagtcctag gcacagctct   6000
aagcctcctt attcgagccg agctgggcca gccaggcaac cttctaggta acgaccacat   6060
ctacaacgtt atcgtcacag cccatgcatt tgtaataatc ttcttcatag taatacccat   6120
cataatcgga ggctttggca actgactagt tcccctaata atcggtgccc ccgatatggc   6180
gtttccccgc ataaacaaca taagcttctg actcttacct ccctctctcc tactcctgct   6240
cgcatctgct atagtggagg ccggagcagg aacaggttga acagtctacc ctcccttagc   6300
```

-continued

```
agggaactac tcccaccctg gagcctccgt agacctaacc atcttctcct tacacctagc   6360
aggtgtctcc tctatcttag gggccatcaa tttcatcaca acaattatca atataaaacc   6420
ccctgccata acccaatacc aaacgcccct cttcgtctga tccgtcctaa tcacagcagt   6480
cctacttctc ctatctctcc cagtcctagc tgctggcatc actatactac taacagaccg   6540
caacctcaac accaccttct tcgaccccgc cggaggagga gaccccattc tataccaaca   6600
cctattctga tttttcggtc accctgaagt ttatattctt atcctaccag gcttcggaat   6660
aatctcccat attgtaactt actactccgg aaaaaaagaa ccatttggat acataggtat   6720
ggtctgagct atgatatcaa ttggcttcct agggtttatc gtgtgagcac accatatatt   6780
tacagtagga atagacgtag acacacgagc atatttcacc tccgctacca taatcatcgc   6840
tatccccacc ggcgtcaaag tatttagctg actcgccaca ctccacggaa gcaatatgaa   6900
atgatctgct gcagtgctct gagccctagg attcatcttt cttttcaccg taggtggcct   6960
gactggcatt gtattagcaa actcatcact agacatcgta ctacacgaca cgtactacgt   7020
tgtagcccac ttccactatg tcctatcaat aggagctgta tttgccatca taggaggctt   7080
cattcactga tttcccctat tctcaggcta caccctagac caaacctacg ccaaaatcca   7140
tttcactatc atattcatcg gcgtaaatct aactttcttc ccacaacact ttctcggcct   7200
atccggaatg ccccgacgtt actcggacta ccccgatgca tacaccacat gaaacatcct   7260
atcatctgta ggctcattca tttctctaac agcagtaata ttaataattt tcatgatttg   7320
agaagccttc gcttcgaagc gaaaagtcct aatagtagaa gaaccctcca taaacctgga   7380
gtgactatat ggatgccccc caccctacca cacattcgaa gaacccgtat acataaaatc   7440
tagacaaaaa aggaaggaat cgaacccccc aaagctggtt tcaagccaac cccatggcct   7500
ccatgacttt ttcaaaaagg tattagaaaa accatttcat aactttgtca aagttaaatt   7560
ataggctaaa tcctatatat cttaatggca catgcagcgc aagtaggtct acaagacgct   7620
acttccccta tcatagaaga gcttatcacc tttcatgatc acgccctcat aatcattttc   7680
cttatctgct tcctagtcct gtatgccctt ttcctaacac tcacaacaaa actaactaat   7740
actaacatct cagacgctca ggaaatagaa accgtctgaa ctatcctgcc cgccatcatc   7800
ctagtcctca tcgccctccc atccctacgc atcctttaca taacagacga ggtcaacgat   7860
ccctccctta ccatcaaatc aattggccac caatggtact gaacctacga gtacaccgac   7920
tacggcggac taatcttcaa ctcctacata cttcccccat tattcctaga accaggcgac   7980
ctgcgactcc ttgacgttga caatcgagta gtactcccga ttgaagcccc cattcgtata   8040
ataattacat cacaagacgt cttgcactca tgagctgtcc ccacattagg cttaaaaaca   8100
gatgcaattc ccggacgtct aaaccaaacc actttcaccg ctacacgacc gggggtatac   8160
tacggtcaat gctctgaaat ctgtggagca aaccacagtt tcatgcccat cgtcctagaa   8220
ttaattcccc taaaaatctt tgaaataggg cccgtattta ccctatagca ccccctctac   8280
cccctctaga gcccactgta aagctaactt agcattaacc ttttaagtta aagattaaga   8340
gaaccaacac ctctttacag tgaaatgccc caactaaata ctaccgtatg gcccaccata   8400
attaccccca tactccttac actattcctc atcacccaac taaaaatatt aaacacaaac   8460
taccacctac ctccctcacc aaagcccata aaaataaaaa attataacaa accctgagaa   8520
ccaaaatgaa cgaaaatctg ttcgcttcat tcattgcccc cacaatccta ggcctacccg   8580
ccgcagtact gatcattcta tttccccctc tattgatccc cacctccaaa tatctcatca   8640
acaaccgact aatcaccacc caacaatgac taatcaaact aacctcaaaa caaatgataa   8700
```

-continued

```
ccatacacaa cactaaagga cgaacctgat ctcttatact agtatcctta atcattttta   8760
ttgccacaac taacctcctc ggactcctgc ctcactcatt tacaccaacc acccaactat   8820
ctataaacct agccatggcc atccccttat gagcgggcac agtgattata ggctttcgct   8880
ctaagattaa aaatgcccta gcccacttct taccacaagg cacacctaca ccccttatcc   8940
ccatactagt tattatcgaa accatcagcc tactcattca accaatagcc ctggccgtac   9000
gcctaaccgc taacattact gcaggccacc tactcatgca cctaattgga agcgccaccc   9060
tagcaatatc aaccattaac cttccctcta cacttatcat cttcacaatt ctaattctac   9120
tgactatcct agaaatcgct gtcgccttaa tccaagccta cgttttcaca cttctagtaa   9180
gcctctacct gcacgacaac acataatgac ccaccaatca catgcctatc atatagtaaa   9240
acccagccca tgacccctaa caggggccct ctcagccctc ctaatgacct ccggcctagc   9300
catgtgattt cacttccact ccataacgct cctcatacta ggcctactaa ccaacacact   9360
aaccatatac caatgatggc gcgatgtaac acgagaaagc acataccaag gccaccacac   9420
accacctgtc caaaaaggcc ttcgatacgg gataatccta tttattacct cagaagtttt   9480
tttcttcgca ggatttttct gagcctttta ccactccagc ctagccccta ccccccaatt   9540
aggagggcac tggcccccaa caggcatcac cccgctaaat cccctagaag tcccactcct   9600
aaacacatcc gtattactcg catcaggagt atcaatcacc tgagctcacc atagtctaat   9660
agaaaacaac cgaaaccaaa taattcaagc actgcttatt acaattttac tgggtctcta   9720
ttttaccctc ctacaagcct cagagtactt cgagtctccc ttcaccattt ccgacggcat   9780
ctacggctca acattttttg tagccacagg cttccacgga cttcacgtca ttattggctc   9840
aactttcctc actatctgct tcatccgcca actaatattt cactttacat ccaaacatca   9900
ctttggcttc gaagccgccg cctgatactg gcattttgta gatgtggttt gactatttct   9960
gtatgtctcc atctattgat gagggtctta ctcttttagt ataaatagta ccgttaactt  10020
ccaattaact agttttgaca acattcaaaa aagagtaata aacttcgcct taattttaat  10080
aatcaacacc ctcctagcct tactactaat aattattaca ttttgactac cacaactcaa  10140
cggctacata gaaaaatcca ccccttacga gtgcggcttc gaccctatat cccccgcccg  10200
cgtccctttc tccataaaat tcttcttagt agctattacc ttcttattat ttgatctaga  10260
aattgccctc cttttacccc taccatgagc cctacaaaca actaacctgc cactaatagt  10320
tatgtcatcc ctcttattaa tcatcatcct agccctaagt ctggcctatg agtgactaca  10380
aaaaggatta gactgaaccg aattggtata tagtttaaac aaaacgaatg atttcgactc  10440
attaaattat gataatcata tttaccaaat gcccctcatt tacataaata ttatactagc  10500
atttaccatc tcacttctag gaatactagt atatcgctca cacctcatat cctccctact  10560
atgcctagaa ggaataatac tatcgctgtt cattatagct actctcataa ccctcaacac  10620
ccactccctc ttagccaata ttgtgcctat tgccatacta gtctttgccg cctgcgaagc  10680
agcggtgggc ctagccctac tagtctcaat ctccaacaca tatggcctag actacgtaca  10740
taacctaaac ctactccaat gctaaaacta atcgtcccaa caattatatt actaccactg  10800
acatgacttt ccaaaaaaca cataatttga atcaacacaa ccacccacag cctaattatt  10860
agcatcatcc ctctactatt ttttaaccaa atcaacaaca acctatttag ctgttcccca  10920
accttttcct ccgacccccc aacaaccccc ctcctaatac taactacctg actcctaccc  10980
ctcacaatca tggcaagcca acgccactta tccagtgaac cactatcacg aaaaaaactc  11040
```

-continued

```
taccctctca tactaatctc cctacaaatc tccttaatta taacattcac agccacagaa  11100
ctaatcatat tttatatctt cttcgaaacc acacttatcc ccaccttggc tatcatcacc  11160
cgatgaggca accagccaga acgcctgaac gcaggcacat acttcctatt ctacaccta  11220
gtaggctccc ttcccctact catcgcacta atttacactc acaacaccct aggctcacta  11280
aacattctac tactcactct cactgcccaa gaactatcaa actcctgagc caacaactta  11340
atatgactag cttacacaat agcttttata gtaaagatac ctctttacgg actccactta  11400
tgactcccta aagcccatgt cgaagccccc atcgctgggt caatagtact tgccgcagta  11460
ctcttaaaac taggcggcta tggtataata cgcctcacac tcattctcaa ccccctgaca  11520
aaacacatag cctacccctt ccttgtacta tccctatgag gcataattat aacaagctcc  11580
atctgcctac gacaaacaga cctaaaatcg ctcattgcat actcttcaat cagccacata  11640
gccctcgtag taacagccat tctcatccaa acccccctgaa gcttcaccgg cgcagtcatt  11700
ctcataatcg cccacgggct tacatcctca ttactattct gcctagcaaa ctcaaactac  11760
gaacgcactc acagtcgcat cataatcctc tctcaaggac ttcaaactct actcccacta  11820
atagcttttt gatgacttct agcaagcctc gctaacctcg ccttaccccc cactattaac  11880
ctactgggag aactctctgt gctagtaacc acgttctcct gatcaaatat cactctccta  11940
cttacaggac tcaacatact agtcacagcc ctatactccc tctacatatt taccacaaca  12000
caatggggct cactcaccca ccacattaac aacataaaac cctcattcac acgagaaaac  12060
accctcatgt tcatacacct atcccccatt ctcctcctat ccctcaaccc cgacatcatt  12120
accgggtttt cctcttgtaa atatagttta accaaaacat cagattgtga atctgacaac  12180
agaggcttac gacccettat ttaccgagaa agctcacaag aactgctaac tcatgccccc  12240
atgtctaaca acatggcttt ctcaactttt aaaggataac agctatccat tggtcttagg  12300
ccccaaaaat tttggtgcaa ctccaaataa aagtaataac catgcacact actataacca  12360
ccctaaccct gacttcccta attcccccca tccttaccac cctcgttaac cctaacaaaa  12420
aaaactcata cccccattat gtaaaatcca ttgtcgcatc cacctttatt atcagtctct  12480
tccccacaac aatattcatg tgcctagacc aagaagttat tatctcgaac tgacactgag  12540
ccacaaccca aacaacccag ctctccctaa gcttcaaact agactacttc tccataatat  12600
tcatccctgt agcattgttc gttacatggt ccatcataga attctcactg tgatatataa  12660
actcagaccc aaacattaat cagttcttca aatatctact catcttccta attaccatac  12720
taatcttagt taccgctaac aacctattcc aactgttcat cggctgagag ggcgtaggaa  12780
ttatatcctt cttgctcatc agttgatgat acgcccgagc agatgccaac acagcagcca  12840
ttcaagcaat cctatacaac cgtatcggcg atatcggttt catcctcgcc ttagcatgat  12900
ttatcctaca ctccaactca tgagacccac aacaaatagc ccttctaaac gctaatccaa  12960
gcctcacccc actactaggc ctcctcctag cagcagcagg caaatcagcc caattaggtc  13020
tccacccctg actcccctca gccatagaag gccccacccc agtctcagcc ctactccact  13080
caagcactat agttgtagca ggaatcttct tactcatccg cttccacccc ctagcagaaa  13140
atagcccact aatccaaact ctaacactat gcttaggcgc tatcaccact ctgttcgcag  13200
cagtctgcgc ccttacacaa aatgacatca aaaaaatcgt agccttctcc acttcaagtc  13260
aactaggact cataatagtt acaatcggca tcaaccaacc acacctagca ttcctgcaca  13320
tctgtaccca cgccttcttc aaagccatac tatttatgtg ctccgggtcc atcatccaca  13380
accttaacaa tgaacaagat attcgaaaaa taggaggact actcaaaacc atacctctca  13440
```

cttcaacctc cctcaccatt ggcagcctag cattagcagg aatacctttc ctcacaggtt 13500
tctactccaa agaccacatc atcgaaaccg caaacatatc atacacaaac gcctgagccc 13560
tatctattac tctcatcgct acctccctga caagcgccta tagcactcga ataattcttc 13620
tcaccctaac aggtcaacct cgcttcccca cccttactaa cattaacgaa aataacccca 13680
ccctactaaa ccccattaaa cgcctggcag ccggaagcct attcgcagga tttctcatta 13740
ctaacaacat ttcccccgca tccccccttcc aaacaacaat cccccctctac ctaaaactca 13800
cagccctcgc tgtcactttc ctaggacttc taacagccct agacctcaac tacctaacca 13860
acaaacttaa aataaaatcc ccactatgca cattttattt ctccaacata ctcggattct 13920
accctagcat cacacaccgc acaatcccct atctaggcct tcttacgagc caaaacctgc 13980
ccctactcct cctagaccta acctgactag aaaagctatt acctaaaaca atttcacagc 14040
accaaatctc cacctccatc atcacctcaa cccaaaaagg cataattaaa ctttacttcc 14100
tctctttctt cttcccactc atcctaaccc tactcctaat cacataacct attcccccga 14160
gcaatctcaa ttacaatata tacaccaaca aacaatgttc aaccagtaac tactactaat 14220
caacgcccat aatcatacaa agcccccgca ccaataggat cctcccgaat caaccctgac 14280
ccctctcctt cataaattat tcagcttcct acactattaa agtttaccac aaccaccacc 14340
ccatcatact ctttcaccca cagcaccaat cctacctcca tcgctaaccc cactaaaaca 14400
ctcaccaaga cctcaacccc tgacccccat gcctcaggat actcctcaat agccatcgct 14460
gtagtatatc caaagacaac catcattccc cctaaataaa ttaaaaaaac tattaaaccc 14520
atataacctc ccccaaaatt cagaataata acacacccga ccacaccgct aacaatcaat 14580
actaaacccc cataaatagg agaaggctta gaagaaaacc ccacaaaccc cattactaaa 14640
cccacactca acagaaacaa agcatacatc attattctcg cacggactac aaccacgacc 14700
aatgatatga aaaaccatcg ttgtatttca actacaagaa caccaatgac cccaatacgc 14760
aaaactaacc ccctaataaa attaattaac cactcattca tcgacctccc caccccatcc 14820
aacatctccg catgatgaaa cttcggctca ctccttggcg cctgcctgat cctccaaatc 14880
accacaggac tattcctagc catgcactac tcaccagacg cctcaaccgc cttttcatca 14940
atcgcccaca tcactcgaga cgtaaattat ggctgaatca tccgctacct tcacgccaat 15000
ggcgcctcaa tattctttat ctgcctcttc ctacacatcg ggcgaggcct atattacgga 15060
tcatttctct actcagaaac ctgaaacatc ggcattatcc tcctgcttgc aactatagca 15120
acagccttca taggctatgt cctcccgtga ggccaaatat cattctgagg ggccacagta 15180
attacaaact tactatccgc catcccatac attgggacag acctagttca atgaatctga 15240
ggaggctact cagtagacag tcccaccctc acacgattct ttacctttca cttcatcttg 15300
cccttcatta ttgcagccct agcaacactc cacctcctat tcttgcacga aacgggatca 15360
aacaaccccc taggaatcac ctcccattcc gataaaatca ccttccaccc ttactacaca 15420
atcaaagacg ccctcggctt acttctcttc cttctctcct taatgacatt aacactattc 15480
tcaccagacc tcctaggcga cccagacaat tataccctag ccaacccctt aaacacccct 15540
ccccacatca agcccgaatg atatttccta ttcgcctaca caattctccg atccgtccct 15600
aacaaactag gaggcgtcct tgccctatta ctatccatcc tcatcctagc aataatcccc 15660
atcctccata tatccaaaca acaaagcata atatttcgcc cactaagcca atcactttat 15720
tgactcctag ccgcagacct cctcattcta acctgaatcg gaggacaacc agtaagctac 15780 cctttttacca tcattggaca agtagcatcc gtactatact tcacaacaat cctaatccta 15840
ataccaacta tctccctaat tgaaaacaaa atactcaaat gggcctgtcc ttgtagtata 15900
aactaataca ccagtcttgt aaaccggaga tgaaaacctt tttccaagga caaatcagag 15960
aaaaagtctt taactccacc attagcaccc aaagctaaga ttctaattta aactattctc 16020
tgttctttca tggggaagca gatttgggta ccacccaagt attgactcac ccatcaacaa 16080
ccgctatgta tttcgtacat tactgccagc caccatgaat attgtacggt accataaata 16140
cttgaccacc tgtagtacat aaaaacccaa tccacatcaa aaccccctcc ccatgcttac 16200
aagcaagtac agcaatcaac cctcaactat cacacatcaa ctgcaactcc aaagccaccc 16260
ctcacccact aggataccaa caaacctacc cacccttaac agtacatagt acataaagcc 16320
atttaccgta catagcacat tacagtcaaa tcccttctcg tccccatgga tgacccccct 16380
cagatagggg tcccttgacc accatcctcc gtgaaatcaa tatcccgcac aagagtgcta 16440
ctctcctcgc tccgggccca taacacttgg gggtagctaa agtgaactgt atccgacatc 16500
tggttcctac ttcagggtca taaagcctaa atagcccaca cgttcccctt aaataagaca 16560
tcacgatg 16568

<210> SEQ ID NO 2
<211> LENGTH: 783
<212> TYPE: DNA
<213> ORGANISM: Artificial
<220> FEATURE:
<223> OTHER INFORMATION: cDNA

<400> SEQUENCE: 2
atggcccacc ataattaccc ccatactcct tacactattc ctcatcaccc aactaaaaat 60
attaaacaca aactaccacc tacctccctc accattggca gcctagcatt agcaggaata 120
cctttcctca caggtttcta ctccaaagac cacatcatcg aaaccgcaaa catatcatac 180
acaaacgcct gagccctatc tattactctc atcgctacct ccctgacaag cgcctatagc 240
actcgaataa ttcttctcac cctaacaggt caacctcgct tccccaccct tactaacatt 300
aacgaaaata accccaccct actaaacccc attaaacgcc tggcagccgg aagcctattc 360
gcaggatttc tcattactaa caacatttcc cccgcatccc ccttccaaac aacaatcccc 420
ctctacctaa aactcacagc cctcgctgtc actttcctag gacttctaac agccctagac 480
ctcaactacc taaccaacaa acttaaaata aaatccccac tatgcacatt ttatttctcc 540
aacatactcg gattctaccc tagcatcaca caccgcacaa tcccctatct aggccttctt 600
acgagccaaa acctgcccct actcctccta gacctaacct gactagaaaa gctattacct 660
aaaacaattt cacagcacca aatctccacc tccatcatca cctcaaccca aaaaggcata 720
attaaacttt acttcctctc tttcttcttc ccactcatcc taaccctact cctaatcaca 780
taa 783

<210> SEQ ID NO 3
<211> LENGTH: 300
<212> TYPE: DNA
<213> ORGANISM: Artificial
<220> FEATURE:
<223> OTHER INFORMATION: cDNA

<400> SEQUENCE: 3
atgcccctca tttacataaa tattatacta gcatttacca tctcacttct aggaatacta 60
gtatatcgct cacacctcat atcctcccta ctatgcctag aaggaataat actatcgctg 120

```
ttcattatag ctactctcat aaccctcaac acccactccc tcttagccaa tattgtgcct    180

attgccatac tagtctttgc cgcctgcgaa gcagcggtgg gcctagccct actagtctca    240

atctccaaca catatggcct agactacgta cataacctaa ccctactcct aatcacataa    300
```

<210> SEQ ID NO 4
<211> LENGTH: 781
<212> TYPE: DNA
<213> ORGANISM: Artificial
<220> FEATURE:
<223> OTHER INFORMATION: cDNA

<400> SEQUENCE: 4

```
atggcacatg cagcgcaagt aggtctacaa gacgctactt cccctatcat agaagagctt     60

atcacctttc atgatcacgc cctcataatc attttcctta tctgcttcct agtcctgtat    120

gcccttttcc taacactcac aacaaaacta actaatacta acatctcaga cgctcaggaa    180

atagaaaccg tctgaactat cctgcccgcc atcatcctag tcctcatcgc cctcccatcc    240

ctacgcatcc tttacataac agacgaggtc aacgatccct ccccttaccat caaatcaatt    300

ggccaccaat ggtactgaac ctacgagtac accgactacg gcggactaat cttcaactcc    360

tacatacttc ccccattatt cctagaacca ggcgacccag acaattatac cctagccaac    420

cccttaaaca cccctcccca catcaagccc gaatgatatt tcctattcgc ctacacaatt    480

ctccgatccg tccctaacaa actaggaggc gtccttgccc tattactatc catcctcatc    540

ctagcaataa tccccatcct ccatatatcc aaacaacaaa gcataatatt tcgcccacta    600

agccaatcac tttattgact cctagccgca gacctcctca ttctaacctg aatcggagga    660

caaccagtaa gctacccttt taccatcatt ggacaagtag catccgtact atacttcaca    720

acaatcctaa tcctaatacc aactatctcc ctaattgaaa acaaaatact caaatgggcc    780

t                                                                     781
```

<210> SEQ ID NO 5
<211> LENGTH: 565
<212> TYPE: DNA
<213> ORGANISM: Artificial
<220> FEATURE:
<223> OTHER INFORMATION: cDNA

<400> SEQUENCE: 5

```
atggcacatg cagcgcaagt aggtctacaa gacgctactt cccctatcat agaagagctt     60

atcacctttc atgatcacgc cctcataatc attttcctta tctgcttcct agtcctgtat    120

gcccttttcc taacactcac aacaaaacta actaatacta acatctcaga cgctcaggaa    180

atagaaaccg tctgaactat cctgcccgcc atcatcctag tcctcatcgc cctcccatcc    240

ctacgcatcc tttacataac agacgaggtc aacgatccct ccccttaccat caaatcaatt    300

ggccaccaat ggtactgaac ctacgagtac accgactacg gcggactaat cttcaactcc    360

tacatacttc ccccattatt cctagaacca ggcgacctgc gactcctagc cgcagacctc    420

ctcattctaa cctgaatcgg aggacaacca gtaagctacc cttttaccat cattggacaa    480

gtagcatccg tactatactt cacaacaatc ctaatcctaa taccaactat ctccctaatt    540

gaaaacaaaa tactcaaatg ggcct                                           565
```

<210> SEQ ID NO 6
<211> LENGTH: 1174
<212> TYPE: DNA

<213> ORGANISM: Artificial
<220> FEATURE:
<223> OTHER INFORMATION: cDNA

<400> SEQUENCE: 6

```
atggcacatg cagcgcaagt aggtctacaa gacgctactt cccctatcat agaagagctt     60

atcacctttc atgatcacgc cctcataatc attttcctta tctgcttcct agtcctgtat    120

gcccttttcc taacactcac aacaaaacta actaatacta acatctcaga cgctcaggaa    180

atagaaaccg tctgaactat cctgcccgcc atcatcctag tcctcatcgc cctcccatcc    240

ctacgcatcc tttacataac agacgaggtc aacgatccct cccttaccat caaatcaatt    300

ggccaccaat ggtactgaac ctacgagtac accgactacg gcggactaat cttcaactcc    360

tacatacttc cccccattatt cctagaacca ggcgacctgc gactccttga cgttgacaat    420

cgagtagtac tcccgattga agcccccatt cgtataataa ttacatcaca agacgtcttg    480

cactcatgag ctgtccccac attaggctta aaaacagatg caattcccgg acgtctaaac    540

caaaccactt tcaccgctac acgaccgggg gtatactacg gtcaatgctc tgaaatctgt    600

ggagcaaacc acagtttcat gcccatattc ttgcacgaaa cgggatcaaa caacccccta    660

ggaatcacct cccattccga taaaatcacc ttccaccctt actacacaat caaagacgcc    720

ctcggcttac ttctcttcct tctctcctta atgacattaa cactattctc accagacctc    780

ctaggcgacc cagacaatta taccctagcc aaccccttaa acacccctcc ccacatcaag    840

cccgaatgat atttcctatt cgcctacaca attctccgat ccgtccctaa caaactagga    900

ggcgtccttg ccctattact atccatcctc atcctagcaa taatccccat cctccatata    960

tccaaacaac aaagcataat atttcgccca ctaagccaat cactttattg actcctagcc   1020

gcagacctcc tcattctaac ctgaatcgga ggacaaccag taagctaccc ttttaccatc   1080

attggacaag tagcatccgt actatacttc acaacaatcc taatcctaat accaactatc   1140

tccctaattg aaaacaaaat actcaaatgg gcct                               1174
```

<210> SEQ ID NO 7
<211> LENGTH: 1294
<212> TYPE: DNA
<213> ORGANISM: Artificial
<220> FEATURE:
<223> OTHER INFORMATION: cDNA

<400> SEQUENCE: 7

```
atgaacgaaa atctgttcgc ttcattcatt gcccccacaa tcctaggcct acccgccgca     60

gtactgatca ttctatttcc ccctctattg atccccacct ccaaatatct catcaacaac    120

cgactaatca ccacccaaca atgactaatc aaactaacct caaaacaaat gataaccata    180

cacaacacta aaggacgaac ctgatctctt atactagtat ccttaatcat ttttattgcc    240

acaactaacc tcctcggact cctgcctcac tcatttacac caaccaccca actatctata    300

aacctagcca tgcactactc accagacgcc tcaaccgcct tttcatcaat cgcccacatc    360

actcgagacg taaattatgg ctgaatcatc cgctaccttc acgccaatgg cgcctcaata    420

ttctttatct gcctcttcct acacatcggg cgaggcctat attacggatc atttctctac    480

tcagaaacct gaaacatcgg cattatcctc ctgcttgcaa ctatagcaac agccttcata    540

ggctatgtcc tcccgtgagg ccaaatatca ttctgagggg ccacagtaat tacaaactta    600

ctatccgcca tcccatacat tgggacagac ctagttcaat gaatctgagg aggctactca    660

gtagacagtc ccaccctcac acgattcttt acctttcact tcatcttgcc cttcattatt    720
```

gcagccctag caacactcca cctcctattc ttgcacgaaa cgggatcaaa caacccccta 780
ggaatcacct cccattccga taaaatcacc ttccaccctt actacacaat caaagacgcc 840
ctcggcttac ttctcttcct tctctcctta atgacattaa cactattctc accagacctc 900
ctaggcgacc cagacaatta taccctagcc aaccccttaa acacccctcc ccacatcaag 960
cccgaatgat atttcctatt cgcctacaca attctccgat ccgtccctaa caaactagga 1020
ggcgtccttg ccctattact atccatcctc atcctagcaa taatccccat cctccatata 1080
tccaaacaac aaagcataat atttcgccca ctaagccaat cactttattg actcctagcc 1140
gcagacctcc tcattctaac ctgaatcgga ggacaaccag taagctaccc ttttaccatc 1200
attggacaag tagcatccgt actatacttc acaacaatcc taatcctaat accaactatc 1260
tccctaattg aaaacaaaat actcaaatgg gcct 1294

<210> SEQ ID NO 8
<211> LENGTH: 1228
<212> TYPE: DNA
<213> ORGANISM: Artificial
<220> FEATURE:
<223> OTHER INFORMATION: cDNA

<400> SEQUENCE: 8
atgcccctca tttacataaa tattatacta gcatttacca tctcacttct aggaatacta 60
gtatatcgct cacacctcat atcctcccta ctatgcctag aaggaataat actatcgctg 120
ttcattatag ctactctcat aaccctcaac acccactccc tcttagccaa tattgtgcct 180
attgccatac tagtctttgg cgcctgcctg atcctccaaa tcaccacagg actattccta 240
gccatgcact actcaccaga cgcctcaacc gccttttcat caatcgccca catcactcga 300
gacgtaaatt atggctgaat catccgctac cttcacgcca atggcgcctc aatattcttt 360
atctgcctct tcctacacat cgggcgaggc ctatattacg gatcatttct ctactcagaa 420
acctgaaaca tcggcattat cctcctgctt gcaactatag caacagcctt cataggctat 480
gtcctcccgt gaggccaaat atcattctga ggggccacag taattacaaa cttactatcc 540
gccatcccat acattgggac agacctagtt caatgaatct gaggaggcta ctcagtagac 600
agtcccaccc tcacacgatt ctttaccttt cacttcatct tgcccttcat tattgcagcc 660
ctagcaacac tccacctcct attcttgcac gaaacgggat caaacaaccc cctaggaatc 720
acctcccatt ccgataaaat caccttccac ccttactaca caatcaaaga cgccctcggc 780
ttacttctct tccttctctc cttaatgaca ttaacactat tctcaccaga cctcctaggc 840
gacccagaca attataccct agccaacccc ttaaacaccc ctccccacat caagcccgaa 900
tgatatttcc tattcgccta cacaattctc cgatccgtcc ctaacaaact aggaggcgtc 960
cttgccctat tactatccat cctcatccta gcaataatcc ccatcctcca tatatccaaa 1020
caacaaagca taatatttcg cccactaagc caatcacttt attgactcct agccgcagac 1080
ctcctcattc taacctgaat cggaggacaa ccagtaagct acccttttac catcattgga 1140
caagtagcat ccgtactata cttcacaaca atcctaatcc taataccaac tatctcccta 1200
attgaaaaca aaatactcaa atgggcct 1228

<210> SEQ ID NO 9
<211> LENGTH: 522
<212> TYPE: DNA
<213> ORGANISM: Artificial
<220> FEATURE:

<223> OTHER INFORMATION: cDNA

<400> SEQUENCE: 9
atgttcgccg accgttgact attctctaca aaccacaaag acattggaac actataccta 60
ttattcggcg catgagctgg agtcctaggc acagctctaa gcctccttat tcgagccgag 120
ctgggccagc caggcaacct tctaggtaac gaccacatct acaacgttat cgtcacagcc 180
ctcgctgtca ctttcctagg acttctaaca gccctagacc tcaactacct aaccaacaaa 240
cttaaaataa aatccccact atgcacattt tatttctcca acatactcgg attctaccct 300
agcatcacac accgcacaat cccctatcta ggccttctta cgagccaaaa cctgccccta 360
ctcctcctag acctaacctg actagaaaag ctattaccta aaacaatttc acagcaccaa 420
atctccacct ccatcatcac ctcaacccaa aaaggcataa ttaaacttta cttcctctct 480
ttcttcttcc cactcatcct aaccctactc ctaatcacat aa 522

<210> SEQ ID NO 10
<211> LENGTH: 582
<212> TYPE: DNA
<213> ORGANISM: Artificial
<220> FEATURE:
<223> OTHER INFORMATION: cDNA

<400> SEQUENCE: 10
atgttcgccg accgttgact attctctaca aaccacaaag acattggaac actataccta 60
ttattcggcg catgagctgg agtcctaggc acagctctaa gcctccttat tcgagccgag 120
ctgggccagc caggcaacct tctaggtaac gaccacatct acaacgttat cgtcacagcc 180
catgcatttg taataatctt cttcatagta atacccatca taatcggagg ctttggcaac 240
tgactagttc ccctaataat cggtgccccc gatatggcgt ttccccgcat aaacaacata 300
agcttctgac tcttacctcc ctctctccta ctcctgctcg catctgctat agtggaggcc 360
ggagcaggaa caggttgaac agtctaccct ccccttagcag ggaactactc ccaccctgga 420
gccctcctag acctaacctg actagaaaag ctattaccta aaacaatttc acagcaccaa 480
atctccacct ccatcatcac ctcaacccaa aaaggcataa ttaaacttta cttcctctct 540
ttcttcttcc cactcatcct aaccctactc ctaatcacat aa 582

<210> SEQ ID NO 11
<211> LENGTH: 2208
<212> TYPE: DNA
<213> ORGANISM: Artificial
<220> FEATURE:
<223> OTHER INFORMATION: cDNA

<400> SEQUENCE: 11
atgttcgccg accgttgact attctctaca aaccacaaag acattggaac actataccta 60
ttattcggcg catgagctgg agtcctaggc acagctctaa gcctccttat tcgagccgag 120
ctgggccagc caggcaacct tctaggtaac gaccacatct acaacgttat cgtcacagcc 180
catgcatttg taataatctt cttcatagta atacccatca taatcggagg ctttggcaac 240
tgactagttc ccctaataat cggtgccccc gatatggcgt ttccccgcat aaacaacata 300
agcttctgac tcttacctcc ctctctccta ctcctgctcg catctgctat agtggaggcc 360
ggagcaggaa caggttgaac agtctaccct ccccttagcag ggaactactc ccaccctgga 420
gcctccgtag acctaaccat cttctcctta cacctagcag gtgtctcctc tatcttaggg 480
gccatcaatt tcatcacaac aattatcaat ataaaacccc ctgccataac ccaataccaa 540
acgcccctct tcgtctgatc cgtcctaatc acagcagtcc tacttctcct atctctccca 600
gtcctagctg ctggcatcac tatactacta acagaccgca acctcaacac caccttcttc 660
gaccccgccg gaggaggaga ccccattcta taccaacacc tattctgatt tttcggtcac 720
cctgaagttt atattcttat cctaccaggc ttcggaataa tctcccatat tgtaacttac 780
tactccggaa aaaaagaacc atttggatac ataggtatgg tctgagctat gatatcaatt 840
ggcttcctag ggtttatcgt gtgagcacac catatattta cagtaggaat agacgtagac 900
acacgagcat atttcacctc cgctaccata atcatcgcta tccccaccgg cgtcaaagta 960
tttagctgac tcgccacact ccacggaagc aatatgaaat gatctgctgc agtgctctga 1020
gccctaggat tcatctttct tttcaccgta ggtggcctga ctggcattgt attagcaaac 1080
tcatcactag acatcgtact acacgacacg tactacgttg tagcccactt ccactatgtc 1140
ctatcaatag gagctgtatt tgccatcata ggaggcttca ttcactgatt tcccctattc 1200
tcaggctaca ccctagacca aacctacgcc aaaatccatt tcactatcat attcatcggc 1260
gtaaatctaa ctttcttccc acaacacttt ctcggcctat ccggaatgcc ccgacgttac 1320
tcggactacc ccgatgcata caccacatga aacatcctat catctgtagg ctcattcatt 1380
tctctaacag cagtaatatt aataatttc atgatttgag aagccttcgc ttcgaagcga 1440
aaagtcctaa tagtagaaga accctccata aacctggagt gactatatgg atgcccccca 1500
ccctaccaca cattcgaaga acccgtatac ataaaagcag gaataccttt cctcacaggt 1560
ttctactcca aagaccacat catcgaaacc gcaaacatat catacacaaa cgcctgagcc 1620
ctatctatta ctctcatcgc tacctccctg acaagcgcct atagcactcg aataattctt 1680
ctcaccctaa caggtcaacc tcgcttcccc acccttacta acattaacga aaataacccc 1740
accctactaa accccattaa acgcctggca gccggaagcc tattcgcagg atttctcatt 1800
actaacaaca tttcccccgc atcccccttc caaacaacaa tccccctcta cctaaaactc 1860
acagccctcg ctgtcacttt cctaggactt ctaacagccc tagacctcaa ctacctaacc 1920
aacaaactta aaataaaatc cccactatgc acattttatt tctccaacat actcggattc 1980
taccctagca tcacacaccg cacaatcccc tatctaggcc ttcttacgag ccaaaacctg 2040
cccctactcc tcctagacct aacctgacta gaaaagctat tacctaaaac aatttcacag 2100
caccaaatct ccacctccat catcacctca acccaaaaag gcataattaa actttacttc 2160
ctctctttct tcttcccact catcctaacc ctactcctaa tcacataa 2208

<210> SEQ ID NO 12
<211> LENGTH: 807
<212> TYPE: DNA
<213> ORGANISM: Artificial
<220> FEATURE:
<223> OTHER INFORMATION: cDNA

<400> SEQUENCE: 12
atggcacatg cagcgcaagt aggtctacaa gacgctactt cccctatcat agaagagctt 60
atcacctttc atgatcacgc cctcataatc attttcctta tctgcttcct agtcctgtat 120
gcccttttcc taacactcac aacaaaacta actaatacta acatctcaga cgctcaggaa 180
atagaaaccg caaacatatc atacacaaac gcctgagccc tatctattac tctcatcgct 240
acctccctga caagcgccta tagcactcga ataattcttc tcaccctaac aggtcaacct 300
cgcttcccca cccttactaa cattaacgaa aataacccca ccctactaaa ccccattaaa 360

-continued

```
cgcctggcag ccggaagcct attcgcagga tttctcatta ctaacaacat ttcccccgca    420

tccccccttcc aaacaacaat ccccctctac ctaaaactca cagccctcgc tgtcactttc    480

ctaggacttc taacagccct agacctcaac tacctaacca acaaacttaa aataaaatcc    540

ccactatgca cattttattt ctccaacata ctcggattct accctagcat cacacaccgc    600

acaatcccct atctaggcct tcttacgagc caaaacctgc ccctactcct cctagaccta    660

acctgactag aaaagctatt acctaaaaca atttcacagc accaaatctc cacctccatc    720

atcacctcaa cccaaaaagg cataattaaa ctttacttcc tctctttctt cttcccactc    780

atcctaaccc tactcctaat cacataa                                        807
```

<210> SEQ ID NO 13
<211> LENGTH: 786
<212> TYPE: DNA
<213> ORGANISM: Artificial
<220> FEATURE:
<223> OTHER INFORMATION: cDNA

<400> SEQUENCE: 13

```
atggcacatg cagcgcaagt aggtctacaa gacgctactt cccctatcat agaagagctt     60

atcacctttc atgatcacgc cctcataatc attttcctta tctgcttcct agtcctgtat    120

gcccttttcc taacactcac aacaaaacta actaatacta acatctcaga cgctcaggaa    180

atagaaaccg tctgaactat cctgcccgcc atcatcctag tcctcatcgc cctcccatcc    240

ctacgcatcc tttacataac agacgaggtc aacgatccct cccttaccat caaatcaatt    300

ggccaccaat ggtactgaac ctacgagtac accgactacg gcggactaat cttcaactcc    360

tacatacttc ccccattatt cctagaacca ggcgacctgc gactccttga cgttgacaat    420

cgagtagtac tcccgattga agcccccatt cgtataataa ttacatcaca agacgtcttg    480

cactcatgag ctgtccccac attaggctta aaaacagatg caattcccgg acgtctaaac    540

caaaccactt tcaccgctac acgaccgggg gtatactacg gtcaatgctc tgaaatctgt    600

ggagcaaacc acagtttcat gcccatcgtc ctagacctaa cctgactaga aaagctatta    660

cctaaaacaa tttcacagca ccaaatctcc acctccatca tcacctcaac ccaaaaaggc    720

ataattaaac tttacttcct ctctttcttc ttcccactca tcctaaccct actcctaatc    780

acataa                                                               786
```

<210> SEQ ID NO 14
<211> LENGTH: 1905
<212> TYPE: DNA
<213> ORGANISM: Artificial
<220> FEATURE:
<223> OTHER INFORMATION: cDNA

<400> SEQUENCE: 14

```
atgaacgaaa atctgttcgc ttcattcatt gcccccacaa tcctaggcct acccgccgca     60

gtactgatca ttctatttcc ccctctattg atccccacct ccaaatatct catcaacaac    120

cgactaatca ccacccaaca atgactaatc aaactaacct caaaacaaat gataaccata    180

cacaacacta aaggacgaac ctgatctctt atactagtat ccttaatcat ttttattgcc    240

acaactaacc tcctcggact cctgcctcac tcatttacac caaccaccca actatctata    300

aacctagcca tggccatccc cttatgagcg ggcacagtga ttataggctt tcgctctaag    360

attaaaaatg ccctagccca cttcttacca caaggcacac ctacacccct tatccccata    420

ctagttatta tcgaaaccat cagcctactc attcaaccaa tagccctggc cgtacgccta    480
```

accgctaaca ttactgcagg ccacctactc atgcacctaa ttggaagcgc caccctagca 540
atatcaacca ttaaccttcc ctctacactt atcatcttca caattctaat tctactgact 600
atcctagaaa tcgctgtcgc cttaatccaa gcctacgttt tcacacttct agtaagcctc 660
tacctacact ccaactcatg agacccacaa caaatagccc ttctaaacgc taatccaagc 720
ctcaccccac tactaggcct cctcctagca gcagcaggca aatcagccca attaggtctc 780
cacccctgac tcccctcagc catagaaggc ccccaccccag tctcagccct actccactca 840
agcactatag ttgtagcagg aatcttctta ctcatccgct tccacccccct agcagaaaat 900 agcccactaa tccaaactct aacactatgc ttaggcgcta tcaccactct gttcgcagca 960
gtctgcgccc ttacacaaaa tgacatcaaa aaaatcgtag ccttctccac ttcaagtcaa 1020
ctaggactca taatagttac aatcggcatc aaccaaccac acctagcatt cctgcacatc 1080
tgtacccacg ccttcttcaa agccatacta tttatgtgct ccgggtccat catccacaac 1140
cttaacaatg aacaagatat tcgaaaaata ggaggactac tcaaaaccat acctctcact 1200
tcaacctccc tcaccattgg cagcctagca ttagcaggaa tacctttcct cacaggtttc 1260
tactccaaag accacatcat cgaaaccgca aacatatcat acacaaacgc ctgagcccta 1320
tctattactc tcatcgctac ctccctgaca agcgcctata gcactcgaat aattcttctc 1380
accctaacag gtcaacctcg cttccccacc cttactaaca ttaacgaaaa taaccccacc 1440
ctactaaacc ccattaaacg cctggcagcc ggaagcctat tcgcaggatt tctcattact 1500
aacaacattt cccccgcatc cccttccaa acaacaatcc ccctctacct aaaactcaca 1560
gccctcgctg tcactttcct aggacttcta acagccctag acctcaacta cctaaccaac 1620
aaacttaaaa taaaatcccc actatgcaca ttttatttct ccaacatact cggattctac 1680
cctagcatca cacaccgcac aatcccctat ctaggccttc ttacgagcca aaacctgccc 1740
ctactcctcc tagacctaac ctgactagaa aagctattac ctaaaacaat ttcacagcac 1800
caaatctcca cctccatcat cacctcaacc caaaaaggca taattaaact ttacttcctc 1860
tctttcttct tcccactcat cctaacccta ctcctaatca cataa 1905

<210> SEQ ID NO 15
<211> LENGTH: 1545
<212> TYPE: DNA
<213> ORGANISM: Artificial
<220> FEATURE:
<223> OTHER INFORMATION: cDNA

<400> SEQUENCE: 15
atgacccacc aatcacatgc ctatcatata gtaaaaccca gcccatgacc cctaacaggg 60
gccctctcag ccctcctaat gacctccggc ctagccatgt gatttcactt ccactccata 120
acgctcctca tactaggcct actaaccaac acactaacca tataccaatg atggcgcgat 180
gtaacacgag aaagcacata ccaaggccac cacacaccac ctgtccaaaa aggccttcga 240
tacgggataa tcctatttat tacctcagaa gttttttttct tcgcaggatt tttctgagcc 300
ttttaccact ccagcctagc ccctaccccc caattaggag ggcactggcc cccaacaggc 360
atcaccccac tactaggcct cctcctagca gcagcaggca aatcagccca attaggtctc 420
cacccctgac tcccctcagc catagaaggc ccccaccccag tctcagccct actccactca 480
agcactatag ttgtagcagg aatcttctta ctcatccgct tccacccccct agcagaaaat 540 agcccactaa tccaaactct aacactatgc ttaggcgcta tcaccactct gttcgcagca 600

-continued

```
gtctgcgccc ttacacaaaa tgacatcaaa aaaatcgtag ccttctccac ttcaagtcaa     660
ctaggactca taatagttac aatcggcatc aaccaaccac acctagcatt cctgcacatc     720
tgtacccacg ccttcttcaa agccatacta tttatgtgct ccgggtccat catccacaac     780
cttaacaatg aacaagatat tcgaaaaata ggaggactac tcaaaaccat acctctcact     840
tcaacctccc tcaccattgg cagcctagca ttagcaggaa tacctttcct cacaggtttc     900
tactccaaag accacatcat cgaaaccgca aacatatcat acacaaacgc ctgagcccta     960
tctattactc tcatcgctac ctccctgaca agcgcctata gcactcgaat aattcttctc    1020
accctaacag gtcaacctcg cttccccacc cttactaaca ttaacgaaaa taaccccacc    1080
ctactaaacc ccattaaacg cctggcagcc ggaagcctat tcgcaggatt tctcattact    1140
aacaacattt cccccgcatc cccccttcaa acaacaatcc ccctctacct aaaactcaca    1200
gccctcgctg tcactttcct aggacttcta acagccctag acctcaacta cctaaccaac    1260
aaacttaaaa taaaatcccc actatgcaca ttttatttct ccaacatact cggattctac    1320
cctagcatca cacaccgcac aatcccctat ctaggccttc ttacgagcca aaacctgccc    1380
ctactcctcc tagacctaac ctgactagaa aagctattac ctaaaacaat ttcacagcac    1440
caaatctcca cctccatcat cacctcaacc caaaaaggca taattaaact ttacttcctc    1500
tctttcttct tcccactcat cctaacccta ctcctaatca cataa                    1545
```

<210> SEQ ID NO 16
<211> LENGTH: 1629
<212> TYPE: DNA
<213> ORGANISM: Artificial
<220> FEATURE:
<223> OTHER INFORMATION: cDNA

<400> SEQUENCE: 16

```
ataaacttcg ccttaatttt aataatcaac accctcctag ccttactact aataattatt      60
acattttgac taccacaact caacggctac atagaaaaat ccacccctta cgagtgcggc     120
ttcgacccta tatcccccgc ccgcgtccct ttctccataa aattcttctt agtagctatt     180
accttcttat tatttgatct agaaattgcc ctccttttac ccctaccatg agccctacaa     240
acaactaacc tgccactaat agttatgtca tccctcttat taatcatcat cctagcccta     300
agtctggcca acacagcagc cattcaagca atcctataca accgtatcgg cgatatcggt     360
ttcatcctcg ccttagcatg atttatccta cactccaact catgagaccc acaacaaata     420
gcccttctaa acgctaatcc aagcctcacc ccactactag gcctcctcct agcagcagca     480
ggcaaatcag cccaattagg tctccacccc tgactcccct cagccataga aggccccacc     540
ccagtctcag ccctactcca ctcaagcact atagttgtag caggaatctt cttactcatc     600
cgcttccacc ccctagcaga aaatagccca ctaatccaaa ctctaacact atgcttaggc     660
gctatcacca ctctgttcgc agcagtctgc gcccttacac aaaatgacat caaaaaaatc     720
gtagccttct ccacttcaag tcaactagga ctcataatag ttacaatcgg catcaaccaa     780
ccacacctag cattcctgca catctgtacc cacgccttct tcaaagccat actatttatg     840
tgctccgggt ccatcatcca caaccttaac aatgaacaag atattcgaaa aataggagga     900
ctactcaaaa ccatacctct cacttcaacc tccctcacca ttggcagcct agcattagca     960
ggaatacctt tcctcacagg tttctactcc aaagaccaca tcatcgaaac cgcaaacata    1020
tcatacacaa acgcctgagc cctatctatt actctcatcg ctacctccct gacaagcgcc    1080
tatagcactc gaataattct tctcacccta acaggtcaac ctcgcttccc cacccttact    1140
```

```
aacattaacg aaaataaccc caccctacta aaccccatta aacgcctggc agccggaagc   1200

ctattcgcag gatttctcat tactaacaac atttccccg catcccccctt ccaaacaaca   1260

atccccctct acctaaaact cacagccctc gctgtcactt tcctaggact tctaacagcc   1320

ctagacctca actacctaac caacaaactt aaaataaaat ccccactatg cacattttat   1380

ttctccaaca tactcggatt ctaccctagc atcacacacc gcacaatccc ctatctaggc   1440

cttcttacga gccaaaacct gcccctactc ctcctagacc taacctgact agaaaagcta   1500

ttacctaaaa caatttcaca gcaccaaatc tccacctcca tcatcacctc aacccaaaaa   1560

ggcataatta aactttactt cctctctttc ttcttcccac tcatcctaac cctactccta   1620

atcacataa                                                           1629
```

```
<210> SEQ ID NO 17
<211> LENGTH: 129
<212> TYPE: DNA
<213> ORGANISM: Artificial
<220> FEATURE:
<223> OTHER INFORMATION: cDNA

<400> SEQUENCE: 17

atgccccaac taaatactac cgtatggccc accataatta cccccatact ccttacacta     60

ttcctcatca cccaactaaa aatattaaac acaaactacc acctacctcc ctcaccattg    120

gcagcctag                                                            129
```

```
<210> SEQ ID NO 18
<211> LENGTH: 783
<212> TYPE: RNA
<213> ORGANISM: Human

<400> SEQUENCE: 18

auggcccacc auaauuaccc ccauacuccu uacacuauuc cucaucaccc aacuaaaaau     60

auuaaacaca aacuaccacc uaccucccuc accauuggca gccuagcauu agcaggaaua    120

ccuuuccuca cagguuucua cuccaaagac cacaucaucg aaaccgcaaa cauaucauac    180

acaaacgccu gagcccuauc uauuacucuc aucgcuaccu cccugacaag cgccuauagc    240

acucgaauaa uucuucucac ccuaacaggu caaccucgcu uccccacccu uacuaacauu    300

aacgaaaaua accccacccu acuaaacccc auuaaacgcc uggcagccgg aagccuauuc    360

gcaggauuuc ucauuacuaa caacauuucc cccgcauccc ccuuccaaac aacaaucccc    420

cucuaccuaa aacucacagc ccucgcuguc acuuuccuag gacuucuaac agcccuagac    480

cucaacuacc uaaccaacaa acuuaaaaua aaauccccac uaugcacauu uuauuucucc    540

aacauacucg gauucuaccc uagcaucaca caccgcacaa uccccuaucu aggccuucuu    600

acgagccaaa accugccccu acuccuccua gaccuaaccu gacuagaaaa gcuauuaccu    660

aaaacaauuu cacagcacca aaucuccacc uccaucauca ccucaaccca aaaaggcaua    720

auuaaacuuu acuuccucuc uuucuucuuc ccacucaucc uaacccuacu ccuaaucaca    780

uaa                                                                  783
```

```
<210> SEQ ID NO 19
<211> LENGTH: 300
<212> TYPE: RNA
<213> ORGANISM: Human

<400> SEQUENCE: 19
```

-continued augccccuca uuuacauaaa uauuauacua gcauuuacca ucucacuucu aggaauacua 60
guauaucgcu cacaccucau auccucccua cuaugccuag aaggaauaau acuaucgcug 120
uucauuauag cuacucucau aacccucaac acccacuccc ucuuagccaa uauugugccu 180
auugccauac uagucuuugc cgccugcgaa gcagcggugg gccuagcccu acuagucuca 240
aucuccaaca cauauggccu agacuacgua cauaaccuaa cccuacuccu aaucacauaa 300

<210> SEQ ID NO 20
<211> LENGTH: 781
<212> TYPE: RNA
<213> ORGANISM: Human

<400> SEQUENCE: 20
auggcacaug cagcgcaagu aggucuacaa gacgcuacuu ccccuaucau agaagagcuu 60
aucaccuuuc augaucacgc ccucauaauc auuuuccuua ucugcuuccu aguccuguau 120
gcccuuuucc uaacacucac aacaaaacua acuaauacua acaucucaga cgcucaggaa 180
auagaaaccg ucugaacuau ccugcccgcc aucauccuag uccucaucgc ccucccaucc 240
cuacgcaucc uuuacauaac agacgagguc aacgaucccu cccuuaccau caaaucaauu 300
ggccaccaau gguacugaac cuacgaguac accgacuacg gcggacuaau cuucaacucc 360
uacauacuuc ccccauuauu ccuagaacca ggcgacccag acaauuauac ccuagccaac 420
cccuuaaaca ccccuucccca caucaagccc gaaugauauu uccuauucgc cuacacaauu 480
cuccgauccg ucccuaacaa acuaggaggc guccuugccc uauuacuauc cauccucauc 540
cuagcaauaa uccccauccu ccauauaucc aaacaacaaa gcauaauauu ucgcccacua 600
agccaaucac uuuauugacu ccuagccgca gaccuccuca uucuaaccug aaucggagga 660
caaccaguaa gcuacccuuu uaccaucauu ggacaaguag cauccguacu auacuucaca 720
acaauccuaa uccuaauacc aacuaucucc cuaauugaaa acaaaauacu caaaugggcc 780
u 781

<210> SEQ ID NO 21
<211> LENGTH: 565
<212> TYPE: RNA
<213> ORGANISM: Human

<400> SEQUENCE: 21
auggcacaug cagcgcaagu aggucuacaa gacgcuacuu ccccuaucau agaagagcuu 60
aucaccuuuc augaucacgc ccucauaauc auuuuccuua ucugcuuccu aguccuguau 120
gcccuuuucc uaacacucac aacaaaacua acuaauacua acaucucaga cgcucaggaa 180
auagaaaccg ucugaacuau ccugcccgcc aucauccuag uccucaucgc ccucccaucc 240
cuacgcaucc uuuacauaac agacgagguc aacgaucccu cccuuaccau caaaucaauu 300
ggccaccaau gguacugaac cuacgaguac accgacuacg gcggacuaau cuucaacucc 360
uacauacuuc ccccauuauu ccuagaacca ggcgaccugc gacuccuagc cgcagaccuc 420
cucauucuaa ccugaaucgg aggacaacca guaagcuacc cuuuuaccau cauuggacaa 480
guagcauccg uacuauacuu cacaacaauc cuaauccuaa uaccaacuau cucccuaauu 540
gaaaacaaaa uacucaaaug ggccu 565

<210> SEQ ID NO 22
<211> LENGTH: 1174
<212> TYPE: RNA
<213> ORGANISM: Human

<400> SEQUENCE: 22
auggcacaug cagcgcaagu aggucuacaa gacgcuacuu ccccuaucau agaagagcuu 60
aucaccuuuc augaucacgc ccucauaauc auuuuccuua ucugcuuccu aguccuguau 120
gcccuuuucc uaacacucac aacaaaacua acuaauacua acaucucaga cgcucaggaa 180
auagaaaccg ucugaacuau ccugcccgcc aucauccuag ucccucaucgc ccucccaucc 240
cuacgcaucc uuuacauaac agacgagguc aacgaucccu cccuuaccau caaaucaauu 300
ggccaccaau gguacugaac cuacgaguac accgacuacg gcggacuaau cuucaacucc 360
uacauacuuc ccccauuauu ccuagaacca ggcgaccugc gacuccuuga cguugacaau 420
cgaguaguac ucccgauuga agcccccauu cguauaauaa uuacaucaca agacgucuug 480
cacucaugag cuguccccac auuaggcuua aaaacagaug caauucccgg acgucuaaac 540
caaaccacuu ucaccgcuac acgaccgggg guauacuacg gucaaugcuc ugaaaucugu 600
ggagcaaacc acaguuucau gcccauauuc uugcacgaaa cgggaucaaa caaccccua 660
ggaaucaccu cccauuccga uaaaaucacc uuccacccuu acuacacaau caaagacgcc 720
cucggcuuac uucucuuccu ucucuccuua augacauuaa cacuauucuc accagaccuc 780
cuaggcgacc cagacaauua uacccuagcc aaccccuuaa acaccccucc ccacaucaag 840
cccgaaugau auuuccuauu cgccuacaca auucuccgau ccgucccuaa caaacuagga 900
ggcguccuug cccuauuacu auccauccuc auccuagcaa uaaucccau ccuccauaua 960
uccaaacaac aaagcauaau auuucgccca cuaagccaau cacuuuauug acuccuagcc 1020
gcagaccucc ucauucuaac cugaaucgga ggacaaccag uaagcuaccc uuuuaccauc 1080
auuggacaag uagcauccgu acuauacuuc acaacaaucc uaauccuaau accaacuauc 1140
ucccuaauug aaaacaaaau acucaaaugg gccu 1174

<210> SEQ ID NO 23
<211> LENGTH: 1294
<212> TYPE: RNA
<213> ORGANISM: Human

<400> SEQUENCE: 23
augaacgaaa aucuguucgc uucauucauu gcccccacaa uccuaggccu acccgccgca 60
guacugauca uucuauuucc cccucuauug auccccaccu ccaaauaucu caucaacaac 120
cgacuaauca ccacccaaca augacuaauc aaacuaaccu caaaacaaau gauaaccaua 180
cacaacacua aaggacgaac cugaucucuu auacuaguau ccuuaaucau uuuuauugcc 240
acaacuaacc uccucggacu ccugccucac ucauuuacac caaccaccca acuaucuaua 300
aaccuagcca ugcacuacuc accagacgcc ucaaccgccu uuucaucaau cgcccacauc 360
acucgagacg uaaauuaugg cugaaucauc cgcuaccuuc acgccaaugg cgccucaaua 420
uucuuuaucu gccucuuccu acacaucggg cgaggccuau auuacggauc auuucucuac 480
ucagaaaccu gaaacaucgg cauuauccuc cugcuugcaa cuauagcaac agccuucaua 540
ggcuaugucc ucccgugagg ccaaauauca uucugagggg ccacaguaau uacaaacuua 600
cuauccgcca ucccauacau ugggacagac cuaguucaau gaaucugagg aggcuacuca 660
guagacaguc ccacccucac acgauucuuu accuuucacu ucaucuugcc cuucauuauu 720
gcagcccuag caacacucca ccuccuauuc uugcacgaaa cgggaucaaa caaccccua 780
ggaaucaccu cccauuccga uaaaaucacc uuccacccuu acuacacaau caaagacgcc 840

-continued cucggcuuac uucucuuccu ucucuccuua augacauuaa cacuauucuc accagaccuc 900
cuaggcgacc cagacaauua uacccuagcc aaccccuuaa acaccccucc ccacaucaag 960
cccgaaugau auuuccuauu cgccuacaca auucuccgau ccgucccuaa caaacuagga 1020
ggcguccuug cccuauuacu auccauccuc auccuagcaa uaaucccau ccuccauaua 1080 uccaaacaac aaagcauaau auuucgccca cuaagccaau cacuuuauug acuccuagcc 1140
gcagaccucc ucauucuaac cugaaucgga ggacaaccag uaagcuaccc uuuuaccauc 1200
auuggacaag uagcauccgu acuauacuuc acaacaaucc uaauccuaau accaacuauc 1260
ucccuaauug aaaacaaaau acucaaaugg gccu 1294

<210> SEQ ID NO 24
<211> LENGTH: 1228
<212> TYPE: RNA
<213> ORGANISM: Human

<400> SEQUENCE: 24
augccccuca uuuacauaaa uauuauacua gcauuuacca ucucacuucu aggaauacua 60
guauaucgcu cacaccucau auccucccua cuaugccuag aaggaauaau acuaucgcug 120
uucauuauag cuacucucau aacccucaac acccacuccc ucuuagccaa uauugugccu 180
auugccauac uagucuuugg cgccugccug auccuccaaa ucaccacagg acuauuccua 240
gccaugcacu acucaccaga cgcccucaacc gccuuuucau caaucgccca caucacucga 300
gacguaaauu auggcugaau cauccgcuac cuucacgcca auggcgccuc aauauucuuu 360
aucugccucu uccuacacau cgggcgaggc cuauauuacg gaucauuucu cuacucagaa 420
accugaaaca ucggcauuau ccuccugcuu gcaacuauag caacagccuu cauaggcuau 480
guccucccgu gaggccaaau aucauucuga ggggccacag uaauuacaaa cuuacuaucc 540
gccaucccau acauugggac agaccuaguu caaugaaucu gaggaggcua cucaguagac 600
agucccaccc ucacacgauu cuuuaccuuu cacuucaucu ugcccuucau uauugcagcc 660
cuagcaacac uccaccuccu auucuugcac gaaacgggau caaacaaccc ccuaggaauc 720
accucccauu ccgauaaaau caccuuccac ccuuacuaca caaucaaaga cgcccucggc 780
uuacuucucu uccuucucuc cuuaaugaca uuaacacuau ucucaccaga ccuccuaggc 840
gacccagaca auuauacccu agccaacccc uuaaacaccc cuccccacau caagcccgaa 900
ugauauuucc uauucgccua cacaauucuc cgauccgucc cuaacaaacu aggaggcguc 960
cuugcccuau uacuauccau ccucauccua gcaauaaucc ccauccucca uauauccaaa 1020
caacaaagca uaauauuucg cccacuaagc caaucacuuu auugacuccu agccgcagac 1080
cuccucauuc uaaccugaau cggaggacaa ccaguaagcu acccuuuuac caucauugga 1140
caaguagcau ccguacuaua cuucacaaca auccuaaucc uaauaccaac uaucucccua 1200
auugaaaaca aaauacucaa augggccu 1228

<210> SEQ ID NO 25
<211> LENGTH: 522
<212> TYPE: RNA
<213> ORGANISM: Human

<400> SEQUENCE: 25
auguucgccg accguugacu auucucuaca aaccacaaag acauuggaac acuauaccua 60
uuauucggcg caugagcugg aguccuaggc acagcucuaa gccuccuuau ucgagccgag 120
cugggccagc caggcaaccu ucuagguaac gaccacaucu acaacguuau cgucacagcc 180
cucgcuguca cuuuccuagg acuucuaaca gcccuagacc ucaacuaccu aaccaacaaa 240
cuuaaaauaa aauccccacu augcacauuu uauuucucca acauacucgg auucuacccu 300
agcaucacac accgcacaau ccccuaucua ggccuucuua cgagccaaaa ccugccccua 360
cuccuccuag accuaaccug acuagaaaag cuauuaccua aaacaauuuc acagcaccaa 420
aucuccaccu ccaucaucac cucaacccaa aaaggcauaa uuaaacuuua cuuccucucu 480
uucuucuucc cacucauccu aacccuacuc cuaaucacau aa 522

<210> SEQ ID NO 26
<211> LENGTH: 582
<212> TYPE: RNA
<213> ORGANISM: Human

<400> SEQUENCE: 26
auguucgccg accguugacu auucucuaca aaccacaaag acauuggaac acuauaccua 60
uuauucggcg caugagcugg aguccuaggc acagcucuaa gccuccuuau ucgagccgag 120
cugggccagc caggcaaccu ucuagguaac gaccacaucu acaacguuau cgucacagcc 180
caugcauuug uaauaaucuu cuucauagua auacccauca uaaucggagg cuuuggcaac 240
ugacuaguuc cccuaauaau cggugccccc gauauggcgu uuccccgcau aaacaacaua 300
agcuucugac ucuuaccucc cucucuccua cuccugcucg caucugcuau aguggaggcc 360
ggagcaggaa cagguugaac agucuacccu cccuuagcag ggaacuacuc ccacccugga 420
gcccuccuag accuaaccug acuagaaaag cuauuaccua aaacaauuuc acagcaccaa 480
aucuccaccu ccaucaucac cucaacccaa aaaggcauaa uuaaacuuua cuuccucucu 540
uucuucuucc cacucauccu aacccuacuc cuaaucacau aa 582

<210> SEQ ID NO 27
<211> LENGTH: 2208
<212> TYPE: RNA
<213> ORGANISM: Human

<400> SEQUENCE: 27
auguucgccg accguugacu auucucuaca aaccacaaag acauuggaac acuauaccua 60
uuauucggcg caugagcugg aguccuaggc acagcucuaa gccuccuuau ucgagccgag 120
cugggccagc caggcaaccu ucuagguaac gaccacaucu acaacguuau cgucacagcc 180
caugcauuug uaauaaucuu cuucauagua auacccauca uaaucggagg cuuuggcaac 240
ugacuaguuc cccuaauaau cggugccccc gauauggcgu uuccccgcau aaacaacaua 300
agcuucugac ucuuaccucc cucucuccua cuccugcucg caucugcuau aguggaggcc 360
ggagcaggaa cagguugaac agucuacccu cccuuagcag ggaacuacuc ccacccugga 420
gccuccguag accuaaccau cuucuccuua caccuagcag gugucuccuc uaucuuaggg 480
gccaucaauu ucaucacaac aauuaucaau auaaaacccc cugccauaac ccaauaccaa 540
acgccccucu ucgucugauc cguccuaauc acagcagucc uacuucuccu aucucuccca 600
guccuagcug cuggcaucac uauacuacua acagaccgca accucaacac caccuucuuc 660
gaccccgccg gaggaggaga ccccauucua uaccaacacc uauucugauu uuucggucac 720
ccugaaguuu auauucuuau ccuaccaggc uucggaauaa ucucccauau uguaacuuac 780
uacuccggaa aaaaagaacc auuuggauac auagguaugg ucugagcuau gauaucaauu 840
ggcuuccuag gguuuaucgu gugagcacac cauauauuua caguaggaau agacguagac 900

```
acacgagcau auuucaccuc cgcuaccaua aucaucgcua uccccaccgg cgucaaagua     960
uuuagcugac ucgccacacu ccacggaagc aauaugaaau gaucugcugc agugcucuga    1020
gcccuaggau ucaucuuucu uuucaccgua gguggccuga cuggcauugu auuagcaaac    1080
ucaucacuag acaucguacu acacgacacg uacuacguug uagcccacuu ccacuauguc    1140
cuaucaauag gagcuguauu ugccaucaua ggaggcuuca uucacugauu uccccuauuc    1200
ucaggcuaca cccuagacca aaccuacgcc aaaauccauu ucacuaucau auucaucggc    1260
guaaaucuaa cuuucuuccc acaacacuuu cucggccuau ccggaaugcc ccgacguuac    1320
ucggacuacc ccgaugcaua caccacauga aacauccuau caucuguagg cucauucauu    1380
ucucuaacag caguaauauu aauaauuuuc augauuugag aagccuucgc uucgaagcga    1440
aaaguccuaa uaguagaaga acccuccaua aaccuggagu gacuauaugg augcccccca    1500
cccuaccaca cauucgaaga acccguauac auaaaagcag gaauaccuuu ccucacaggu    1560
uucuacucca aagaccacau caucgaaacc gcaaacauau cauacacaaa cgccugagcc    1620
cuaucuauua cucucaucgc uaccucccug acaagcgccu auagcacucg aauaauucuu    1680
cucacccuaa caggucaacc ucgcuucccc acccuuacua acauuaacga aaauaacccc    1740
acccuacuaa accccauuaa acgccuggca gccggaagcc uauucgcagg auuucucauu    1800
acuaacaaca uuucccccgc auccccccuuc caaacaacaa ucccccucua ccuaaaacuc    1860
acagcccucg cugucacuuu ccuaggacuu cuaacagccc uagaccucaa cuaccuaacc    1920
aacaaacuua aaauaaaauc cccacuaugc acauuuuauu ucuccaacau acucggauuc    1980
uacccuagca ucacacaccg cacaaucccc uaucuaggcc uucuuacgag ccaaaaccug    2040
ccccuacucc uccuagaccu aaccugacua gaaaagcuau uaccuaaaac aauuucacag    2100
caccaaaucu ccaccuccau caucaccuca acccaaaaag gcauaauuaa acuuuacuuc    2160
cucucuuucu ucuucccacu cauccuaacc cuacuccuaa ucacauaa                 2208
```

<210> SEQ ID NO 28
<211> LENGTH: 807
<212> TYPE: RNA
<213> ORGANISM: Human

<400> SEQUENCE: 28

```
auggcacaug cagcgcaagu aggucuacaa gacgcuacuu ccccuaucau agaagagcuu      60
aucaccuuuc augaucacgc ccucauaauc auuuuccuua ucugcuuccu aguccuguau     120
gcccuuuucc uaacacucac aacaaaacua acuaauacua acaucucaga cgcucaggaa     180
auagaaaccg caaacauauc auacacaaac gccugagccc uaucuauuac ucucaucgcu     240
accucccuga caagcgccua uagcacucga auaauucuuc ucacccuaac aggucaaccu     300
cgcuucccca cccuuacuaa cauuaacgaa aauaacccca cccuacuaaa ccccauuaaa     360
cgccuggcag ccggaagccu auucgcagga uuucucauua cuaacaacau uucccccgca     420
ucccccuucc aaacaacaau cccccucuac cuaaaacuca cagcccucgc ugucacuuuc     480
cuaggacuuc uaacagcccu agaccucaac uaccuaacca acaaacuuaa aauaaaaucc     540
ccacuaugca cauuuuauuu cuccaacaua cucggauucu acccuagcau cacacaccgc     600
acaaucccccu aucuaggccu ucuuacgagc caaaaccugc cccuacuccu ccuagaccua     660
accugacuag aaaagcuauu accuaaaaca auuucacagc accaaaucuc caccuccauc     720
aucaccucaa cccaaaaagg cauaauuaaa cuuuacuucc ucucuuucuu cuucccacuc     780
auccuaaccc uacuccuaau cacauaa                                         807
```

<210> SEQ ID NO 29
<211> LENGTH: 786
<212> TYPE: RNA
<213> ORGANISM: Human

<400> SEQUENCE: 29
auggcacaug cagcgcaagu aggucuacaa gacgcuacuu ccccuaucau agaagagcuu 60
aucaccuuuc augaucacgc ccucauaauc auuuuccuua ucugcuuccu aguccuguau 120
gcccuuuucc uaacacucac aacaaaacua acuaauacua acaucucaga cgcucaggaa 180
auagaaaccg ucugaacuau ccugcccgcc aucauccuag uccucaucgc ccucccaucc 240
cuacgcaucc uuuacauaac agacgagguc aacgaucccu cccuuaccau caaaucaauu 300
ggccaccaau gguacugaac cuacgaguac accgacuacg gcggacuaau cuucaacucc 360
uacauacuuc ccccauuauu ccuagaacca ggcgaccugc gacuccuuga cguugacaau 420
cgaguaguac ucccgauuga agcccccauu cguauaauaa uuacaucaca agacgucuug 480
cacucaugag cuguccccac auuaggcuua aaaacagaug caauucccgg acgucuaaac 540
caaaccacuu ucaccgcuac acgaccgggg guauacuacg gucaaugcuc ugaaaucugu 600
ggagcaaacc acaguuucau gcccaucguc cuagaccuaa ccugacuaga aaagcuauua 660
ccuaaaacaa uuucacagca ccaaaucucc accuccauca ucaccucaac ccaaaaaggc 720
auaauuaaac uuuacuuccu cucuuucuuc uucccacuca uccuaacccu acuccuaauc 780
acauaa 786

<210> SEQ ID NO 30
<211> LENGTH: 1905
<212> TYPE: RNA
<213> ORGANISM: Human

<400> SEQUENCE: 30
augaacgaaa aucuguucgc uucauucauu gcccccacaa uccuaggccu acccgccgca 60
guacugauca uucuauuucc ccccucuauug aucccccaccu ccaaauaucu caucaacaac 120
cgacuaauca ccacccaaca augacuaauc aaacuaaccu caaaacaaau gauaaccaua 180
cacaacacua aaggacgaac cugaucucuu auacuaguau ccuuaaucau uuuuauugcc 240
acaacuaacc uccucggacu ccugccucac ucauuuacac caaccaccca acuaucuaua 300
aaccuagcca uggccauccc cuuaugagcg ggcacaguga uuauaggcuu ucgcucuaag 360
auuaaaaaug cccuagccca cuucuuacca caaggcacac cuacaccccu uauccccaua 420
cuaguuauua ucgaaaccau cagccuacuc auucaaccaa uagcccuggc cguacgccua 480
accgcuaaca uuacugcagg ccaccuacuc augcaccuaa uuggaagcgc caccuagca 540 auaucaacca uuaaccuucc cucuacacuu aucaucuuca caauucuaau ucuacugacu 600
auccuagaaa ucgcugucgc cuuaauccaa gccuacguuu ucacacuucu aguaagccuc 660
uaccuacacu ccaacucaug agacccacaa caaauagccc uucuaaacgc uaauccaagc 720
cucaccccac uacuaggccu ccuccuagca gcagcaggca aaucagccca auuaggucuc 780
caccccugac uccccucagc cauagaaggc cccaccccag ucucagcccu acuccacuca 840
agcacuauag uuguagcagg aaucuucuua cucauccgcu uccacccccu agcagaaaau 900
agcccacuaa uccaaacucu aacacuaugc uuaggcgcua ucaccacucu guucgcagca 960
gucugcgccc uuacacaaaa ugacaucaaa aaaaucguag ccuucuccac uucaagucaa 1020

```
cuaggacuca uaauaguuac aaucggcauc aaccaaccac accuagcauu ccugcacauc   1080
uguacccacg ccuucuucaa agccauacua uuuaugugcu ccggguccau cauccacaac   1140
cuuaacaaug aacaagauau ucgaaaaaua ggaggacuac ucaaaaccau accucucacu   1200
ucaaccuccc ucaccauugg cagccuagca uuagcaggaa uaccuuuccu cacagguuuc   1260
uacuccaaag accacaucau cgaaaccgca aacauaucau acacaaacgc cugagcccua   1320
ucuauuacuc ucaucgcuac cucccugaca agcgccuaua gcacucgaau aauucuucuc   1380
acccuaacag gucaaccucg cuuccccacc cuuacuaaca uuaacgaaaa uaaccccacc   1440
cuacuaaacc ccauuaaacg ccuggcagcc ggaagccuau ucgcaggauu ucucauuacu   1500
aacaacauuu cccccgcauc ccccuuccaa acaacaaucc cccucuaccu aaaacucaca   1560
gcccucgcug ucacuuuccu aggacuucua acagcccuag accucaacua ccuaaccaac   1620
aaacuuaaaa uaaaaucccc acuaugcaca uuuuauuucu ccaacauacu cggauucuac   1680
ccuagcauca cacaccgcac aauccccuau cuaggccuuc uuacgagcca aaaccugccc   1740
cuacuccucc uagaccuaac cugacuagaa aagcuauuac cuaaaacaau uucacagcac   1800
caaaucucca ccuccaucau caccucaacc caaaaaggca uaauuaaacu uuacuuccuc   1860
ucuuucuucu ucccacucau ccuaacccua cuccuaauca cauaa                   1905
```

<210> SEQ ID NO 31
<211> LENGTH: 1545
<212> TYPE: RNA
<213> ORGANISM: Human

<400> SEQUENCE: 31

```
augacccacc aaucacaugc cuaucauaua guaaaaccca gcccaugacc ccuaacaggg     60
gcccucucag cccuccuaau gaccuccggc cuagccaugu gauuucacuu ccacuccaua    120
acgcuccuca uacuaggccu acuaaccaac acacuaacca uauaccaaug auggcgcgau    180
guaacacgag aaagcacaua ccaaggccac cacacaccac cuguccaaaa aggccuucga    240
uacgggauaa uccuauuuau uaccucagaa guuuuuuucu ucgcaggauu uuucugagcc    300
uuuuaccacu ccagccuagc cccuaccccc caauuaggag ggcacuggcc cccaacaggc    360
aucaccccac uacuaggccu ccuccuagca gcagcaggca aaucagccca auuaggucuc    420
caccccugac ucccucagc cauagaaggc cccaccccag ucucagcccu acuccacuca     480
agcacuauag uuguagcagg aaucuucuua cucauccgcu uccacccccu agcagaaaau    540
agcccacuaa uccaaacucu aacacuaugc uuaggcgcua ucaccacucu guucgcagca    600
gucugcgccc uuacacaaaa ugacaucaaa aaaaucguag ccuucuccac uucaagucaa    660
cuaggacuca uaauaguuac aaucggcauc aaccaaccac accuagcauu ccugcacauc    720
uguacccacg ccuucuucaa agccauacua uuuaugugcu ccggguccau cauccacaac    780
cuuaacaaug aacaagauau ucgaaaaaua ggaggacuac ucaaaaccau accucucacu    840
ucaaccuccc ucaccauugg cagccuagca uuagcaggaa uaccuuuccu cacagguuuc    900
uacuccaaag accacaucau cgaaaccgca aacauaucau acacaaacgc cugagcccua    960
ucuauuacuc ucaucgcuac cucccugaca agcgccuaua gcacucgaau aauucuucuc   1020
acccuaacag gucaaccucg cuuccccacc cuuacuaaca uuaacgaaaa uaaccccacc   1080
cuacuaaacc ccauuaaacg ccuggcagcc ggaagccuau ucgcaggauu ucucauuacu   1140
aacaacauuu cccccgcauc ccccuuccaa acaacaaucc cccucuaccu aaaacucaca   1200
gcccucgcug ucacuuuccu aggacuucua acagcccuag accucaacua ccuaaccaac   1260
```

-continued aaacuuaaaa uaaaaucccc acuaugcaca uuuuauuucu ccaacauacu cggauucuac 1320
ccuagcauca cacaccgcac aaucccccuau cuaggccuuc uuacgagcca aaaccugccc 1380
cuacuccucc uagaccuaac cugacuagaa aagcuauuac cuaaaacaau uucacagcac 1440
caaaucucca ccuccaucau caccucaacc caaaaaggca uaauuaaacu uuacuuccuc 1500
ucuuucuucu ucccacucau ccuaacccua cuccuaauca cauaa 1545

<210> SEQ ID NO 32
<211> LENGTH: 1629
<212> TYPE: RNA
<213> ORGANISM: Human

<400> SEQUENCE: 32
auaaacuucg ccuuaauuuu aauaaucaac acccuccuag ccuuacuacu aauaauuauu 60
acauuuugac uaccacaacu caacggcuac auagaaaaau ccacccccuua cgagugcggc 120 uucgacccua uauccccccgc ccgcgucccu uucuccauaa aauucuucuu aguagcuauu 180
accuucuuau uauuugaucu agaaauugcc cuccuuuuac cccuaccaug agcccuacaa 240
acaacuaacc ugccacuaau aguuauguca ucccucuuau uaaucaucau ccuagcccua 300
agucuggcca acacagcagc cauucaagca auccuauaca accguaucgg cgauaucggu 360
uucauccucg ccuuagcaug auuuauccua cacuccaacu caugagaccc acaacaaaua 420
gcccuucuaa acgcuaaucc aagccucacc ccacuacuag gccuccuccu agcagcagca 480
ggcaaaucag cccaauuagg ucuccacccc ugacuccccu cagccauaga aggcccccacc 540 ccagucucag cccuacucca cucaagcacu auaguuguag caggaaucuu cuuacucauc 600
cgcuuccacc cccuagcaga aaauagccca cuaauccaaa cucuaacacu augcuuaggc 660
gcuaucacca cucuguucgc agcagucugc gcccuuacac aaaaugacau caaaaaaauc 720
guagccuucu ccacuucaag ucaacuagga cucauaauag uuacaaucgg caucaaccaa 780
ccacaccuag cauuccugca caucuguacc cacgccuucu ucaaagccau acuauuuaug 840
ugcuccgggu ccaucaucca caaccuuaac aaugaacaag auauucgaaa aauaggagga 900
cuacucaaaa ccauaccucu cacuucaacc ucccucacca uuggcagccu agcauuagca 960
ggaauaccuu ucccucacagg uuucuacucc aaagaccaca ucaucgaaac cgcaaacaua 1020
ucauacacaa acgccugagc ccuaucuauu acucucaucg cuaccucccu gacaagcgcc 1080
uauagcacuc gaauaauucu ucucacccua acaggucaac cucgcuuccc cacccuuacu 1140
aacauuaacg aaaauaaccc cacccuacua aaccccauua aacgccuggc agccggaagc 1200
cuauucgcag gauuucucau uacuaacaac auuuccccccg cauccccccuu ccaaacaaca 1260 aucccccucu accuaaaacu cacagcccuc gcugucacuu ucccuaggacu ucuaacagcc 1320 cuagaccuca acuaccuaac caacaaacuu aaaauaaaau ccccacuaug cacauuuuau 1380
uucuccaaca uacucggauu cuacccuagc aucacacacc gcacaauccc cuaucuaggc 1440
cuucuuacga gccaaaaccu gccccuacuc cuccuagacc uaaccugacu agaaaagcua 1500
uuaccuaaaa caauuucaca gcaccaaauc uccaccucca ucaucaccuc aacccaaaaa 1560
ggcauaauua aacuuuacuu ccucucuuuc uucuucccac ucauccuaac ccuacuccua 1620
aucacauaa 1629

<210> SEQ ID NO 33
<211> LENGTH: 129
<212> TYPE: RNA

<213> ORGANISM: Human

<400> SEQUENCE: 33

```
augccccaac uaaauacuac cguauggccc accauaauua cccccauacu ccuuacacua     60

uuccucauca cccaacuaaa aauauuaaac acaaacuacc accuaccucc cucaccauug    120

gcagccuag                                                            129
```

<210> SEQ ID NO 34
<211> LENGTH: 261
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (261)..(261)
<223> OTHER INFORMATION: Xaa can be any naturally occurring amino acid

<400> SEQUENCE: 34

```
Met Ala His His Asn Tyr Pro His Thr Pro Tyr Thr Ile Pro His His
1               5                   10                  15

Pro Thr Lys Asn Ile Lys His Lys Leu Pro Pro Thr Ser Leu Thr Ile
            20                  25                  30

Gly Ser Leu Ala Leu Ala Gly Met Pro Phe Leu Thr Gly Phe Tyr Ser
        35                  40                  45

Lys Asp His Ile Ile Glu Thr Ala Asn Met Ser Tyr Thr Asn Ala Trp
    50                  55                  60

Ala Leu Ser Ile Thr Leu Ile Ala Thr Ser Leu Thr Ser Ala Tyr Ser
65                  70                  75                  80

Thr Arg Met Ile Leu Leu Thr Leu Thr Gly Gln Pro Arg Phe Pro Thr
                85                  90                  95

Leu Thr Asn Ile Asn Glu Asn Asn Pro Thr Leu Leu Asn Pro Ile Lys
            100                 105                 110

Arg Leu Ala Ala Gly Ser Leu Phe Ala Gly Phe Leu Ile Thr Asn Asn
        115                 120                 125

Ile Ser Pro Ala Ser Pro Phe Gln Thr Thr Ile Pro Leu Tyr Leu Lys
    130                 135                 140

Leu Thr Ala Leu Ala Val Thr Phe Leu Gly Leu Leu Thr Ala Leu Asp
145                 150                 155                 160

Leu Asn Tyr Leu Thr Asn Lys Leu Lys Met Lys Ser Pro Leu Cys Thr
                165                 170                 175

Phe Tyr Phe Ser Asn Met Leu Gly Phe Tyr Pro Ser Ile Thr His Arg
            180                 185                 190

Thr Ile Pro Tyr Leu Gly Leu Leu Thr Ser Gln Asn Leu Pro Leu Leu
        195                 200                 205

Leu Leu Asp Leu Thr Trp Leu Glu Lys Leu Leu Pro Lys Thr Ile Ser
    210                 215                 220

Gln His Gln Ile Ser Thr Ser Ile Ile Thr Ser Thr Gln Lys Gly Met
225                 230                 235                 240

Ile Lys Leu Tyr Phe Leu Ser Phe Phe Phe Pro Leu Ile Leu Thr Leu
                245                 250                 255

Leu Leu Ile Thr Xaa
            260
```

<210> SEQ ID NO 35
<211> LENGTH: 100
<212> TYPE: PRT

<213> ORGANISM: Artificial
<220> FEATURE:
<223> OTHER INFORMATION: putative protein sequence
<220> FEATURE:
<221> NAME/KEY: misc_feature
<222> LOCATION: (100)..(100)
<223> OTHER INFORMATION: Xaa can be any naturally occurring amino acid

<400> SEQUENCE: 35

```
Met Pro Leu Ile Tyr Met Asn Ile Met Leu Ala Phe Thr Ile Ser Leu
1               5                   10                  15

Leu Gly Met Leu Val Tyr Arg Ser His Leu Met Ser Ser Leu Leu Cys
            20                  25                  30

Leu Glu Gly Met Met Leu Ser Leu Phe Ile Met Ala Thr Leu Met Thr
        35                  40                  45

Leu Asn Thr His Ser Leu Leu Ala Asn Ile Val Pro Ile Ala Met Leu
    50                  55                  60

Val Phe Ala Ala Cys Glu Ala Ala Val Gly Leu Ala Leu Leu Val Ser
65                  70                  75                  80

Ile Ser Asn Thr Tyr Gly Leu Asp Tyr Val His Asn Leu Thr Leu Leu
                85                  90                  95

Leu Ile Thr Xaa
            100
```

<210> SEQ ID NO 36
<211> LENGTH: 261
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (261)..(261)
<223> OTHER INFORMATION: Xaa can be any naturally occurring amino acid

<400> SEQUENCE: 36

```
Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Pro Asp Asn Tyr Thr Leu Ala Asn Pro Leu Asn Thr
    130                 135                 140

Pro Pro His Ile Lys Pro Glu Trp Tyr Phe Leu Phe Ala Tyr Thr Ile
145                 150                 155                 160

Leu Arg Ser Val Pro Asn Lys Leu Gly Gly Val Leu Ala Leu Leu Leu
                165                 170                 175

Ser Ile Leu Ile Leu Ala Met Ile Pro Ile Leu His Met Ser Lys Gln
```

```
            180                 185                 190

Gln Ser Met Met Phe Arg Pro Leu Ser Gln Ser Leu Tyr Trp Leu Leu
        195                 200                 205

Ala Ala Asp Leu Leu Ile Leu Thr Trp Ile Gly Gly Gln Pro Val Ser
    210                 215                 220

Tyr Pro Phe Thr Ile Ile Gly Gln Val Ala Ser Val Leu Tyr Phe Thr
225                 230                 235                 240

Thr Ile Leu Ile Leu Met Pro Thr Ile Ser Leu Ile Glu Asn Lys Met
                245                 250                 255

Leu Lys Trp Ala Xaa
            260


<210> SEQ ID NO 37
<211> LENGTH: 189
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (189)..(189)
<223> OTHER INFORMATION: Xaa can be any naturally occurring amino acid

<400> SEQUENCE: 37

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Ala Ala Asp Leu Leu Ile Leu Thr
    130                 135                 140

Trp Ile Gly Gly Gln Pro Val Ser Tyr Pro Phe Thr Ile Ile Gly Gln
145                 150                 155                 160

Val Ala Ser Val Leu Tyr Phe Thr Thr Ile Leu Ile Leu Met Pro Thr
                165                 170                 175

Ile Ser Leu Ile Glu Asn Lys Met Leu Lys Trp Ala Xaa
            180                 185


<210> SEQ ID NO 38
<211> LENGTH: 392
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (392)..(392)
<223> OTHER INFORMATION: Xaa can be any naturally occurring amino acid
```

-continued

<400> SEQUENCE: 38

```
Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
    130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205

Met Phe Leu His Glu Thr Gly Ser Asn Asn Pro Leu Gly Ile Thr Ser
    210                 215                 220

His Ser Asp Lys Ile Thr Phe His Pro Tyr Tyr Thr Ile Lys Asp Ala
225                 230                 235                 240

Leu Gly Leu Leu Leu Phe Leu Leu Ser Leu Met Thr Leu Thr Leu Phe
                245                 250                 255

Ser Pro Asp Leu Leu Gly Asp Pro Asp Asn Tyr Thr Leu Ala Asn Pro
            260                 265                 270

Leu Asn Thr Pro Pro His Ile Lys Pro Glu Trp Tyr Phe Leu Phe Ala
        275                 280                 285

Tyr Thr Ile Leu Arg Ser Val Pro Asn Lys Leu Gly Gly Val Leu Ala
    290                 295                 300

Leu Leu Leu Ser Ile Leu Ile Leu Ala Met Ile Pro Ile Leu His Met
305                 310                 315                 320

Ser Lys Gln Gln Ser Met Met Phe Arg Pro Leu Ser Gln Ser Leu Tyr
                325                 330                 335

Trp Leu Leu Ala Ala Asp Leu Leu Ile Leu Thr Trp Ile Gly Gly Gln
            340                 345                 350

Pro Val Ser Tyr Pro Phe Thr Ile Ile Gly Gln Val Ala Ser Val Leu
        355                 360                 365

Tyr Phe Thr Thr Ile Leu Ile Leu Met Pro Thr Ile Ser Leu Ile Glu
    370                 375                 380

Asn Lys Met Leu Lys Trp Ala Xaa
385                 390
```

<210> SEQ ID NO 39

```
<211> LENGTH: 432
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (432)..(432)
<223> OTHER INFORMATION: Xaa can be any naturally occurring amino acid

<400> SEQUENCE: 39

Met Asn Glu Asn Leu Phe Ala Ser Phe Ile Ala Pro Thr Ile Leu Gly
1               5                   10                  15

Leu Pro Ala Ala Val Leu Ile Ile Leu Phe Pro Pro Leu Leu Ile Pro
            20                  25                  30

Thr Ser Lys Tyr Leu Ile Asn Asn Arg Leu Ile Thr Thr Gln Gln Trp
        35                  40                  45

Leu Ile Lys Leu Thr Ser Lys Gln Met Met Thr Met His Asn Thr Lys
    50                  55                  60

Gly Arg Thr Trp Ser Leu Met Leu Val Ser Leu Ile Ile Phe Ile Ala
65                  70                  75                  80

Thr Thr Asn Leu Leu Gly Leu Leu Pro His Ser Phe Thr Pro Thr Thr
                85                  90                  95

Gln Leu Ser Met Asn Leu Ala Met His Tyr Ser Pro Asp Ala Ser Thr
            100                 105                 110

Ala Phe Ser Ser Ile Ala His Ile Thr Arg Asp Val Asn Tyr Gly Trp
        115                 120                 125

Ile Ile Arg Tyr Leu His Ala Asn Gly Ala Ser Met Phe Phe Ile Cys
    130                 135                 140

Leu Phe Leu His Ile Gly Arg Gly Leu Tyr Tyr Gly Ser Phe Leu Tyr
145                 150                 155                 160

Ser Glu Thr Trp Asn Ile Gly Ile Ile Leu Leu Leu Ala Thr Met Ala
                165                 170                 175

Thr Ala Phe Met Gly Tyr Val Leu Pro Trp Gly Gln Met Ser Phe Trp
            180                 185                 190

Gly Ala Thr Val Ile Thr Asn Leu Leu Ser Ala Ile Pro Tyr Ile Gly
        195                 200                 205

Thr Asp Leu Val Gln Trp Ile Trp Gly Gly Tyr Ser Val Asp Ser Pro
    210                 215                 220

Thr Leu Thr Arg Phe Phe Thr Phe His Phe Ile Leu Pro Phe Ile Ile
225                 230                 235                 240

Ala Ala Leu Ala Thr Leu His Leu Leu Phe Leu His Glu Thr Gly Ser
                245                 250                 255

Asn Asn Pro Leu Gly Ile Thr Ser His Ser Asp Lys Ile Thr Phe His
            260                 265                 270

Pro Tyr Tyr Thr Ile Lys Asp Ala Leu Gly Leu Leu Leu Phe Leu Leu
        275                 280                 285

Ser Leu Met Thr Leu Thr Leu Phe Ser Pro Asp Leu Leu Gly Asp Pro
    290                 295                 300

Asp Asn Tyr Thr Leu Ala Asn Pro Leu Asn Thr Pro Pro His Ile Lys
305                 310                 315                 320

Pro Glu Trp Tyr Phe Leu Phe Ala Tyr Thr Ile Leu Arg Ser Val Pro
                325                 330                 335

Asn Lys Leu Gly Gly Val Leu Ala Leu Leu Leu Ser Ile Leu Ile Leu
            340                 345                 350

Ala Met Ile Pro Ile Leu His Met Ser Lys Gln Gln Ser Met Met Phe
```

```
        355                 360                 365

Arg Pro Leu Ser Gln Ser Leu Tyr Trp Leu Leu Ala Ala Asp Leu Leu
    370                 375                 380

Ile Leu Thr Trp Ile Gly Gly Gln Pro Val Ser Tyr Pro Phe Thr Ile
385                 390                 395                 400

Ile Gly Gln Val Ala Ser Val Leu Tyr Phe Thr Thr Ile Leu Ile Leu
                405                 410                 415

Met Pro Thr Ile Ser Leu Ile Glu Asn Lys Met Leu Lys Trp Ala Xaa
            420                 425                 430
```

<210> SEQ ID NO 40
<211> LENGTH: 410
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (410)..(410)
<223> OTHER INFORMATION: Xaa can be any naturally occurring amino acid

<400> SEQUENCE: 40

```
Met Pro Leu Ile Tyr Met Asn Ile Met Leu Ala Phe Thr Ile Ser Leu
1               5                   10                  15

Leu Gly Met Leu Val Tyr Arg Ser His Leu Met Ser Ser Leu Leu Cys
            20                  25                  30

Leu Glu Gly Met Met Leu Ser Leu Phe Ile Met Ala Thr Leu Met Thr
        35                  40                  45

Leu Asn Thr His Ser Leu Leu Ala Asn Ile Val Pro Ile Ala Met Leu
    50                  55                  60

Val Phe Gly Ala Cys Leu Ile Leu Gln Ile Thr Thr Gly Leu Phe Leu
65                  70                  75                  80

Ala Met His Tyr Ser Pro Asp Ala Ser Thr Ala Phe Ser Ser Ile Ala
                85                  90                  95

His Ile Thr Arg Asp Val Asn Tyr Gly Trp Ile Ile Arg Tyr Leu His
            100                 105                 110

Ala Asn Gly Ala Ser Met Phe Phe Ile Cys Leu Phe Leu His Ile Gly
        115                 120                 125

Arg Gly Leu Tyr Tyr Gly Ser Phe Leu Tyr Ser Glu Thr Trp Asn Ile
    130                 135                 140

Gly Ile Ile Leu Leu Leu Ala Thr Met Ala Thr Ala Phe Met Gly Tyr
145                 150                 155                 160

Val Leu Pro Trp Gly Gln Met Ser Phe Trp Gly Ala Thr Val Ile Thr
                165                 170                 175

Asn Leu Leu Ser Ala Ile Pro Tyr Ile Gly Thr Asp Leu Val Gln Trp
            180                 185                 190

Ile Trp Gly Gly Tyr Ser Val Asp Ser Pro Thr Leu Thr Arg Phe Phe
        195                 200                 205

Thr Phe His Phe Ile Leu Pro Phe Ile Ile Ala Ala Leu Ala Thr Leu
    210                 215                 220

His Leu Leu Phe Leu His Glu Thr Gly Ser Asn Asn Pro Leu Gly Ile
225                 230                 235                 240

Thr Ser His Ser Asp Lys Ile Thr Phe His Pro Tyr Tyr Thr Ile Lys
                245                 250                 255

Asp Ala Leu Gly Leu Leu Leu Phe Leu Leu Ser Leu Met Thr Leu Thr
            260                 265                 270
```

```
Leu Phe Ser Pro Asp Leu Leu Gly Asp Pro Asp Asn Tyr Thr Leu Ala
        275                 280                 285

Asn Pro Leu Asn Thr Pro Pro His Ile Lys Pro Glu Trp Tyr Phe Leu
    290                 295                 300

Phe Ala Tyr Thr Ile Leu Arg Ser Val Pro Asn Lys Leu Gly Gly Val
305                 310                 315                 320

Leu Ala Leu Leu Leu Ser Ile Leu Ile Leu Ala Met Ile Pro Ile Leu
                325                 330                 335

His Met Ser Lys Gln Gln Ser Met Met Phe Arg Pro Leu Ser Gln Ser
            340                 345                 350

Leu Tyr Trp Leu Leu Ala Ala Asp Leu Leu Ile Leu Thr Trp Ile Gly
        355                 360                 365

Gly Gln Pro Val Ser Tyr Pro Phe Thr Ile Ile Gly Gln Val Ala Ser
    370                 375                 380

Val Leu Tyr Phe Thr Thr Ile Leu Ile Leu Met Pro Thr Ile Ser Leu
385                 390                 395                 400

Ile Glu Asn Lys Met Leu Lys Trp Ala Xaa
                405                 410
```

<210> SEQ ID NO 41
<211> LENGTH: 174
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (174)..(174)
<223> OTHER INFORMATION: Xaa can be any naturally occurring amino acid

<400> SEQUENCE: 41

```
Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala Leu Ala Val Thr
    50                  55                  60

Phe Leu Gly Leu Leu Thr Ala Leu Asp Leu Asn Tyr Leu Thr Asn Lys
65                  70                  75                  80

Leu Lys Met Lys Ser Pro Leu Cys Thr Phe Tyr Phe Ser Asn Met Leu
                85                  90                  95

Gly Phe Tyr Pro Ser Ile Thr His Arg Thr Ile Pro Tyr Leu Gly Leu
            100                 105                 110

Leu Thr Ser Gln Asn Leu Pro Leu Leu Leu Asp Leu Thr Trp Leu
        115                 120                 125

Glu Lys Leu Leu Pro Lys Thr Ile Ser Gln His Gln Ile Ser Thr Ser
    130                 135                 140

Ile Ile Thr Ser Thr Gln Lys Gly Met Ile Lys Leu Tyr Phe Leu Ser
145                 150                 155                 160

Phe Phe Phe Pro Leu Ile Leu Thr Leu Leu Leu Ile Thr Xaa
                165                 170
```

<210> SEQ ID NO 42
<211> LENGTH: 194
<212> TYPE: PRT
<213> ORGANISM: Artificial

<220> FEATURE:
<223> OTHER INFORMATION: putative protein sequence
<220> FEATURE:
<221> NAME/KEY: misc_feature
<222> LOCATION: (194)..(194)
<223> OTHER INFORMATION: Xaa can be any naturally occurring amino acid

<400> SEQUENCE: 42

```
Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Leu Leu Leu Leu
            100                 105                 110

Leu Ala Ser Ala Met Val Glu Ala Gly Ala Gly Thr Gly Trp Thr Val
        115                 120                 125

Tyr Pro Pro Leu Ala Gly Asn Tyr Ser His Pro Gly Ala Leu Leu Asp
    130                 135                 140

Leu Thr Trp Leu Glu Lys Leu Leu Pro Lys Thr Ile Ser Gln His Gln
145                 150                 155                 160

Ile Ser Thr Ser Ile Ile Thr Ser Thr Gln Lys Gly Met Ile Lys Leu
                165                 170                 175

Tyr Phe Leu Ser Phe Phe Phe Pro Leu Ile Leu Thr Leu Leu Leu Ile
            180                 185                 190

Thr Xaa
```

<210> SEQ ID NO 43
<211> LENGTH: 736
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (736)..(736)
<223> OTHER INFORMATION: Xaa can be any naturally occurring amino acid

<400> SEQUENCE: 43

```
Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95
```

-continued

```
Met Asn Asn Met Ser Phe Trp Leu Leu Pro Pro Ser Leu Leu Leu Leu
            100                 105                 110

Leu Ala Ser Ala Met Val Glu Ala Gly Ala Gly Thr Gly Trp Thr Val
        115                 120                 125

Tyr Pro Pro Leu Ala Gly Asn Tyr Ser His Pro Gly Ala Ser Val Asp
    130                 135                 140

Leu Thr Ile Phe Ser Leu His Leu Ala Gly Val Ser Ser Ile Leu Gly
145                 150                 155                 160

Ala Ile Asn Phe Ile Thr Thr Ile Ile Asn Met Lys Pro Pro Ala Met
                165                 170                 175

Thr Gln Tyr Gln Thr Pro Leu Phe Val Trp Ser Val Leu Ile Thr Ala
            180                 185                 190

Val Leu Leu Leu Leu Ser Leu Pro Val Leu Ala Ala Gly Ile Thr Met
        195                 200                 205

Leu Leu Thr Asp Arg Asn Leu Asn Thr Thr Phe Phe Asp Pro Ala Gly
    210                 215                 220

Gly Gly Asp Pro Ile Leu Tyr Gln His Leu Phe Trp Phe Phe Gly His
225                 230                 235                 240

Pro Glu Val Tyr Ile Leu Ile Leu Pro Gly Phe Gly Met Ile Ser His
                245                 250                 255

Ile Val Thr Tyr Tyr Ser Gly Lys Lys Glu Pro Phe Gly Tyr Met Gly
            260                 265                 270

Met Val Trp Ala Met Met Ser Ile Gly Phe Leu Gly Phe Ile Val Trp
        275                 280                 285

Ala His His Met Phe Thr Val Gly Met Asp Val Asp Thr Arg Ala Tyr
    290                 295                 300

Phe Thr Ser Ala Thr Met Ile Ile Ala Ile Pro Thr Gly Val Lys Val
305                 310                 315                 320

Phe Ser Trp Leu Ala Thr Leu His Gly Ser Asn Met Lys Trp Ser Ala
                325                 330                 335

Ala Val Leu Trp Ala Leu Gly Phe Ile Phe Leu Phe Thr Val Gly Gly
            340                 345                 350

Leu Thr Gly Ile Val Leu Ala Asn Ser Ser Leu Asp Ile Val Leu His
        355                 360                 365

Asp Thr Tyr Tyr Val Val Ala His Phe His Tyr Val Leu Ser Met Gly
    370                 375                 380

Ala Val Phe Ala Ile Met Gly Gly Phe Ile His Trp Phe Pro Leu Phe
385                 390                 395                 400

Ser Gly Tyr Thr Leu Asp Gln Thr Tyr Ala Lys Ile His Phe Thr Ile
                405                 410                 415

Met Phe Ile Gly Val Asn Leu Thr Phe Phe Pro Gln His Phe Leu Gly
            420                 425                 430

Leu Ser Gly Met Pro Arg Arg Tyr Ser Asp Tyr Pro Asp Ala Tyr Thr
        435                 440                 445

Thr Trp Asn Ile Leu Ser Ser Val Gly Ser Phe Ile Ser Leu Thr Ala
    450                 455                 460

Val Met Leu Met Ile Phe Met Ile Trp Glu Ala Phe Ala Ser Lys Arg
465                 470                 475                 480

Lys Val Leu Met Val Glu Glu Pro Ser Met Asn Leu Glu Trp Leu Tyr
                485                 490                 495

Gly Cys Pro Pro Pro Tyr His Thr Phe Glu Glu Pro Val Tyr Met Lys
            500                 505                 510

Ala Gly Met Pro Phe Leu Thr Gly Phe Tyr Ser Lys Asp His Ile Ile
```

```
        515                 520                 525

Glu Thr Ala Asn Met Ser Tyr Thr Asn Ala Trp Ala Leu Ser Ile Thr
    530                 535                 540

Leu Ile Ala Thr Ser Leu Thr Ser Ala Tyr Ser Thr Arg Met Ile Leu
545                 550                 555                 560

Leu Thr Leu Thr Gly Gln Pro Arg Phe Pro Thr Leu Thr Asn Ile Asn
                565                 570                 575

Glu Asn Asn Pro Thr Leu Leu Asn Pro Ile Lys Arg Leu Ala Ala Gly
            580                 585                 590

Ser Leu Phe Ala Gly Phe Leu Ile Thr Asn Asn Ile Ser Pro Ala Ser
        595                 600                 605

Pro Phe Gln Thr Thr Ile Pro Leu Tyr Leu Lys Leu Thr Ala Leu Ala
    610                 615                 620

Val Thr Phe Leu Gly Leu Leu Thr Ala Leu Asp Leu Asn Tyr Leu Thr
625                 630                 635                 640

Asn Lys Leu Lys Met Lys Ser Pro Leu Cys Thr Phe Tyr Phe Ser Asn
                645                 650                 655

Met Leu Gly Phe Tyr Pro Ser Ile Thr His Arg Thr Ile Pro Tyr Leu
            660                 665                 670

Gly Leu Leu Thr Ser Gln Asn Leu Pro Leu Leu Leu Leu Asp Leu Thr
        675                 680                 685

Trp Leu Glu Lys Leu Leu Pro Lys Thr Ile Ser Gln His Gln Ile Ser
    690                 695                 700

Thr Ser Ile Ile Thr Ser Thr Gln Lys Gly Met Ile Lys Leu Tyr Phe
705                 710                 715                 720

Leu Ser Phe Phe Phe Pro Leu Ile Leu Thr Leu Leu Leu Ile Thr Xaa
                725                 730                 735


<210> SEQ ID NO 44
<211> LENGTH: 269
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (269)..(269)
<223> OTHER INFORMATION: Xaa can be any naturally occurring amino acid

<400> SEQUENCE: 44

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Ala
    50                  55                  60

Asn Met Ser Tyr Thr Asn Ala Trp Ala Leu Ser Ile Thr Leu Ile Ala
65                  70                  75                  80

Thr Ser Leu Thr Ser Ala Tyr Ser Thr Arg Met Ile Leu Leu Thr Leu
                85                  90                  95

Thr Gly Gln Pro Arg Phe Pro Thr Leu Thr Asn Ile Asn Glu Asn Asn
            100                 105                 110

Pro Thr Leu Leu Asn Pro Ile Lys Arg Leu Ala Ala Gly Ser Leu Phe
        115                 120                 125
```

```
Ala Gly Phe Leu Ile Thr Asn Asn Ile Ser Pro Ala Ser Pro Phe Gln
    130                 135                 140

Thr Thr Ile Pro Leu Tyr Leu Lys Leu Thr Ala Leu Ala Val Thr Phe
145                 150                 155                 160

Leu Gly Leu Leu Thr Ala Leu Asp Leu Asn Tyr Leu Thr Asn Lys Leu
                165                 170                 175

Lys Met Lys Ser Pro Leu Cys Thr Phe Tyr Phe Ser Asn Met Leu Gly
            180                 185                 190

Phe Tyr Pro Ser Ile Thr His Arg Thr Ile Pro Tyr Leu Gly Leu Leu
        195                 200                 205

Thr Ser Gln Asn Leu Pro Leu Leu Leu Leu Asp Leu Thr Trp Leu Glu
    210                 215                 220

Lys Leu Leu Pro Lys Thr Ile Ser Gln His Gln Ile Ser Thr Ser Ile
225                 230                 235                 240

Ile Thr Ser Thr Gln Lys Gly Met Ile Lys Leu Tyr Phe Leu Ser Phe
                245                 250                 255

Phe Phe Pro Leu Ile Leu Thr Leu Leu Leu Ile Thr Xaa
            260                 265


<210> SEQ ID NO 45
<211> LENGTH: 262
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (262)..(262)
<223> OTHER INFORMATION: Xaa can be any naturally occurring amino acid

<400> SEQUENCE: 45

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
            20                  25                  30

Leu Ile Cys Phe Leu Val Leu Tyr Ala Leu Phe Leu Thr Leu Thr Thr
        35                  40                  45

Lys Leu Thr Asn Thr Asn Ile Ser Asp Ala Gln Glu Met Glu Thr Val
    50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
    130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205
```

```
Ile Val Leu Asp Leu Thr Trp Leu Glu Lys Leu Leu Pro Lys Thr Ile
    210                 215                 220

Ser Gln His Gln Ile Ser Thr Ser Ile Ile Thr Ser Thr Gln Lys Gly
225                 230                 235                 240

Met Ile Lys Leu Tyr Phe Leu Ser Phe Phe Phe Pro Leu Ile Leu Thr
                245                 250                 255

Leu Leu Leu Ile Thr Xaa
            260


<210> SEQ ID NO 46
<211> LENGTH: 635
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (635)..(635)
<223> OTHER INFORMATION: Xaa can be any naturally occurring amino acid

<400> SEQUENCE: 46

Met Asn Glu Asn Leu Phe Ala Ser Phe Ile Ala Pro Thr Ile Leu Gly
1               5                   10                  15

Leu Pro Ala Ala Val Leu Ile Ile Leu Phe Pro Pro Leu Leu Ile Pro
            20                  25                  30

Thr Ser Lys Tyr Leu Ile Asn Asn Arg Leu Ile Thr Thr Gln Gln Trp
        35                  40                  45

Leu Ile Lys Leu Thr Ser Lys Gln Met Met Thr Met His Asn Thr Lys
    50                  55                  60

Gly Arg Thr Trp Ser Leu Met Leu Val Ser Leu Ile Ile Phe Ile Ala
65                  70                  75                  80

Thr Thr Asn Leu Leu Gly Leu Leu Pro His Ser Phe Thr Pro Thr Thr
                85                  90                  95

Gln Leu Ser Met Asn Leu Ala Met Ala Ile Pro Leu Trp Ala Gly Thr
            100                 105                 110

Val Ile Met Gly Phe Arg Ser Lys Ile Lys Asn Ala Leu Ala His Phe
        115                 120                 125

Leu Pro Gln Gly Thr Pro Thr Pro Leu Ile Pro Met Leu Val Ile Ile
    130                 135                 140

Glu Thr Ile Ser Leu Leu Ile Gln Pro Met Ala Leu Ala Val Arg Leu
145                 150                 155                 160

Thr Ala Asn Ile Thr Ala Gly His Leu Leu Met His Leu Ile Gly Ser
                165                 170                 175

Ala Thr Leu Ala Met Ser Thr Ile Asn Leu Pro Ser Thr Leu Ile Ile
            180                 185                 190

Phe Thr Ile Leu Ile Leu Leu Thr Ile Leu Glu Ile Ala Val Ala Leu
        195                 200                 205

Ile Gln Ala Tyr Val Phe Thr Leu Leu Val Ser Leu Tyr Leu His Ser
    210                 215                 220

Asn Ser Trp Asp Pro Gln Gln Met Ala Leu Leu Asn Ala Asn Pro Ser
225                 230                 235                 240

Leu Thr Pro Leu Leu Gly Leu Leu Leu Ala Ala Ala Gly Lys Ser Ala
                245                 250                 255

Gln Leu Gly Leu His Pro Trp Leu Pro Ser Ala Met Glu Gly Pro Thr
            260                 265                 270

Pro Val Ser Ala Leu Leu His Ser Ser Thr Met Val Val Ala Gly Ile
```

```
        275                 280                 285

Phe Leu Leu Ile Arg Phe His Pro Leu Ala Glu Asn Ser Pro Leu Ile
    290                 295                 300

Gln Thr Leu Thr Leu Cys Leu Gly Ala Ile Thr Thr Leu Phe Ala Ala
305                 310                 315                 320

Val Cys Ala Leu Thr Gln Asn Asp Ile Lys Lys Ile Val Ala Phe Ser
                325                 330                 335

Thr Ser Ser Gln Leu Gly Leu Met Met Val Thr Ile Gly Ile Asn Gln
            340                 345                 350

Pro His Leu Ala Phe Leu His Ile Cys Thr His Ala Phe Phe Lys Ala
        355                 360                 365

Met Leu Phe Met Cys Ser Gly Ser Ile Ile His Asn Leu Asn Asn Glu
    370                 375                 380

Gln Asp Ile Arg Lys Met Gly Gly Leu Leu Lys Thr Met Pro Leu Thr
385                 390                 395                 400

Ser Thr Ser Leu Thr Ile Gly Ser Leu Ala Leu Ala Gly Met Pro Phe
                405                 410                 415

Leu Thr Gly Phe Tyr Ser Lys Asp His Ile Ile Glu Thr Ala Asn Met
            420                 425                 430

Ser Tyr Thr Asn Ala Trp Ala Leu Ser Ile Thr Leu Ile Ala Thr Ser
        435                 440                 445

Leu Thr Ser Ala Tyr Ser Thr Arg Met Ile Leu Leu Thr Leu Thr Gly
    450                 455                 460

Gln Pro Arg Phe Pro Thr Leu Thr Asn Ile Asn Glu Asn Asn Pro Thr
465                 470                 475                 480

Leu Leu Asn Pro Ile Lys Arg Leu Ala Ala Gly Ser Leu Phe Ala Gly
                485                 490                 495

Phe Leu Ile Thr Asn Asn Ile Ser Pro Ala Ser Pro Phe Gln Thr Thr
            500                 505                 510

Ile Pro Leu Tyr Leu Lys Leu Thr Ala Leu Ala Val Thr Phe Leu Gly
        515                 520                 525

Leu Leu Thr Ala Leu Asp Leu Asn Tyr Leu Thr Asn Lys Leu Lys Met
    530                 535                 540

Lys Ser Pro Leu Cys Thr Phe Tyr Phe Ser Asn Met Leu Gly Phe Tyr
545                 550                 555                 560

Pro Ser Ile Thr His Arg Thr Ile Pro Tyr Leu Gly Leu Leu Thr Ser
                565                 570                 575

Gln Asn Leu Pro Leu Leu Leu Leu Asp Leu Thr Trp Leu Glu Lys Leu
            580                 585                 590

Leu Pro Lys Thr Ile Ser Gln His Gln Ile Ser Thr Ser Ile Ile Thr
        595                 600                 605

Ser Thr Gln Lys Gly Met Ile Lys Leu Tyr Phe Leu Ser Phe Phe Phe
    610                 615                 620

Pro Leu Ile Leu Thr Leu Leu Leu Ile Thr Xaa
625                 630                 635
```

```
<210> SEQ ID NO 47
<211> LENGTH: 515
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (515)..(515)
<223> OTHER INFORMATION: Xaa can be any naturally occurring amino acid
```

<400> SEQUENCE: 47

Met Thr His Gln Ser His Ala Tyr His Met Val Lys Pro Ser Pro Trp
1 5 10 15

Pro Leu Thr Gly Ala Leu Ser Ala Leu Leu Met Thr Ser Gly Leu Ala
20 25 30

Met Trp Phe His Phe His Ser Met Thr Leu Leu Met Leu Gly Leu Leu
35 40 45

Thr Asn Thr Leu Thr Met Tyr Gln Trp Trp Arg Asp Val Thr Arg Glu
50 55 60

Ser Thr Tyr Gln Gly His His Thr Pro Pro Val Gln Lys Gly Leu Arg
65 70 75 80

Tyr Gly Met Ile Leu Phe Ile Thr Ser Glu Val Phe Phe Phe Ala Gly
85 90 95

Phe Phe Trp Ala Phe Tyr His Ser Ser Leu Ala Pro Thr Pro Gln Leu
100 105 110

Gly Gly His Trp Pro Pro Thr Gly Ile Thr Pro Leu Leu Gly Leu Leu
115 120 125

Leu Ala Ala Ala Gly Lys Ser Ala Gln Leu Gly Leu His Pro Trp Leu
130 135 140

Pro Ser Ala Met Glu Gly Pro Thr Pro Val Ser Ala Leu Leu His Ser
145 150 155 160

Ser Thr Met Val Val Ala Gly Ile Phe Leu Leu Ile Arg Phe His Pro
165 170 175

Leu Ala Glu Asn Ser Pro Leu Ile Gln Thr Leu Thr Leu Cys Leu Gly
180 185 190

Ala Ile Thr Thr Leu Phe Ala Ala Val Cys Ala Leu Thr Gln Asn Asp
195 200 205

Ile Lys Lys Ile Val Ala Phe Ser Thr Ser Ser Gln Leu Gly Leu Met
210 215 220

Met Val Thr Ile Gly Ile Asn Gln Pro His Leu Ala Phe Leu His Ile
225 230 235 240

Cys Thr His Ala Phe Phe Lys Ala Met Leu Phe Met Cys Ser Gly Ser
245 250 255

Ile Ile His Asn Leu Asn Asn Glu Gln Asp Ile Arg Lys Met Gly Gly
260 265 270

Leu Leu Lys Thr Met Pro Leu Thr Ser Thr Ser Leu Thr Ile Gly Ser
275 280 285

Leu Ala Leu Ala Gly Met Pro Phe Leu Thr Gly Phe Tyr Ser Lys Asp
290 295 300

His Ile Ile Glu Thr Ala Asn Met Ser Tyr Thr Asn Ala Trp Ala Leu
305 310 315 320

Ser Ile Thr Leu Ile Ala Thr Ser Leu Thr Ser Ala Tyr Ser Thr Arg
325 330 335

Met Ile Leu Leu Thr Leu Thr Gly Gln Pro Arg Phe Pro Thr Leu Thr
340 345 350

Asn Ile Asn Glu Asn Asn Pro Thr Leu Leu Asn Pro Ile Lys Arg Leu
355 360 365

Ala Ala Gly Ser Leu Phe Ala Gly Phe Leu Ile Thr Asn Asn Ile Ser
370 375 380

Pro Ala Ser Pro Phe Gln Thr Thr Ile Pro Leu Tyr Leu Lys Leu Thr
385 390 395 400

Ala Leu Ala Val Thr Phe Leu Gly Leu Leu Thr Ala Leu Asp Leu Asn

```
                405                 410                 415

Tyr Leu Thr Asn Lys Leu Lys Met Lys Ser Pro Leu Cys Thr Phe Tyr
            420                 425                 430

Phe Ser Asn Met Leu Gly Phe Tyr Pro Ser Ile Thr His Arg Thr Ile
        435                 440                 445

Pro Tyr Leu Gly Leu Leu Thr Ser Gln Asn Leu Pro Leu Leu Leu Leu
    450                 455                 460

Asp Leu Thr Trp Leu Glu Lys Leu Leu Pro Lys Thr Ile Ser Gln His
465                 470                 475                 480

Gln Ile Ser Thr Ser Ile Ile Thr Ser Thr Gln Lys Gly Met Ile Lys
                485                 490                 495

Leu Tyr Phe Leu Ser Phe Phe Phe Pro Leu Ile Leu Thr Leu Leu Leu
            500                 505                 510

Ile Thr Xaa
        515


<210> SEQ ID NO 48
<211> LENGTH: 543
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (543)..(543)
<223> OTHER INFORMATION: Xaa can be any naturally occurring amino acid

<400> SEQUENCE: 48

Met Asn Phe Ala Leu Ile Leu Met Ile Asn Thr Leu Leu Ala Leu Leu
1               5                   10                  15

Leu Met Ile Ile Thr Phe Trp Leu Pro Gln Leu Asn Gly Tyr Met Glu
            20                  25                  30

Lys Ser Thr Pro Tyr Glu Cys Gly Phe Asp Pro Met Ser Pro Ala Arg
        35                  40                  45

Val Pro Phe Ser Met Lys Phe Phe Leu Val Ala Ile Thr Phe Leu Leu
    50                  55                  60

Phe Asp Leu Glu Ile Ala Leu Leu Leu Pro Leu Pro Trp Ala Leu Gln
65                  70                  75                  80

Thr Thr Asn Leu Pro Leu Met Val Met Ser Ser Leu Leu Leu Ile Ile
                85                  90                  95

Ile Leu Ala Leu Ser Leu Ala Asn Thr Ala Ala Ile Gln Ala Ile Leu
            100                 105                 110

Tyr Asn Arg Ile Gly Asp Ile Gly Phe Ile Leu Ala Leu Ala Trp Phe
        115                 120                 125

Ile Leu His Ser Asn Ser Trp Asp Pro Gln Gln Met Ala Leu Leu Asn
    130                 135                 140

Ala Asn Pro Ser Leu Thr Pro Leu Leu Gly Leu Leu Leu Ala Ala Ala
145                 150                 155                 160

Gly Lys Ser Ala Gln Leu Gly Leu His Pro Trp Leu Pro Ser Ala Met
                165                 170                 175

Glu Gly Pro Thr Pro Val Ser Ala Leu Leu His Ser Ser Thr Met Val
            180                 185                 190

Val Ala Gly Ile Phe Leu Leu Ile Arg Phe His Pro Leu Ala Glu Asn
        195                 200                 205

Ser Pro Leu Ile Gln Thr Leu Thr Leu Cys Leu Gly Ala Ile Thr Thr
    210                 215                 220
```

```
Leu Phe Ala Ala Val Cys Ala Leu Thr Gln Asn Asp Ile Lys Lys Ile
225                 230                 235                 240

Val Ala Phe Ser Thr Ser Ser Gln Leu Gly Leu Met Met Val Thr Ile
                245                 250                 255

Gly Ile Asn Gln Pro His Leu Ala Phe Leu His Ile Cys Thr His Ala
            260                 265                 270

Phe Phe Lys Ala Met Leu Phe Met Cys Ser Gly Ser Ile Ile His Asn
        275                 280                 285

Leu Asn Asn Glu Gln Asp Ile Arg Lys Met Gly Gly Leu Leu Lys Thr
    290                 295                 300

Met Pro Leu Thr Ser Thr Ser Leu Thr Ile Gly Ser Leu Ala Leu Ala
305                 310                 315                 320

Gly Met Pro Phe Leu Thr Gly Phe Tyr Ser Lys Asp His Ile Ile Glu
                325                 330                 335

Thr Ala Asn Met Ser Tyr Thr Asn Ala Trp Ala Leu Ser Ile Thr Leu
            340                 345                 350

Ile Ala Thr Ser Leu Thr Ser Ala Tyr Ser Thr Arg Met Ile Leu Leu
        355                 360                 365

Thr Leu Thr Gly Gln Pro Arg Phe Pro Thr Leu Thr Asn Ile Asn Glu
    370                 375                 380

Asn Asn Pro Thr Leu Leu Asn Pro Ile Lys Arg Leu Ala Ala Gly Ser
385                 390                 395                 400

Leu Phe Ala Gly Phe Leu Ile Thr Asn Asn Ile Ser Pro Ala Ser Pro
                405                 410                 415

Phe Gln Thr Thr Ile Pro Leu Tyr Leu Lys Leu Thr Ala Leu Ala Val
            420                 425                 430

Thr Phe Leu Gly Leu Leu Thr Ala Leu Asp Leu Asn Tyr Leu Thr Asn
        435                 440                 445

Lys Leu Lys Met Lys Ser Pro Leu Cys Thr Phe Tyr Phe Ser Asn Met
    450                 455                 460

Leu Gly Phe Tyr Pro Ser Ile Thr His Arg Thr Ile Pro Tyr Leu Gly
465                 470                 475                 480

Leu Leu Thr Ser Gln Asn Leu Pro Leu Leu Leu Leu Asp Leu Thr Trp
                485                 490                 495

Leu Glu Lys Leu Leu Pro Lys Thr Ile Ser Gln His Gln Ile Ser Thr
            500                 505                 510

Ser Ile Ile Thr Ser Thr Gln Lys Gly Met Ile Lys Leu Tyr Phe Leu
        515                 520                 525

Ser Phe Phe Phe Pro Leu Ile Leu Thr Leu Leu Leu Ile Thr Xaa
    530                 535                 540
```

<210> SEQ ID NO 49
<211> LENGTH: 43
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (43)..(43)
<223> OTHER INFORMATION: Xaa can be any naturally occurring amino acid

<400> SEQUENCE: 49

```
Met Pro Gln Leu Asn Thr Thr Val Trp Pro Thr Met Ile Thr Pro Met
1               5                   10                  15

Leu Leu Thr Leu Phe Leu Ile Thr Gln Leu Lys Met Leu Asn Thr Asn
            20                  25                  30
```

```
Tyr His Leu Pro Pro Ser Pro Leu Ala Ala Xaa
        35                  40

<210> SEQ ID NO 50
<211> LENGTH: 951
<212> TYPE: RNA
<213> ORGANISM: Human

<400> SEQUENCE: 50

augaacgaaa aucuguucgc uucauucauu gcccccacaa uccuaggccu acccgccgca     60

guacugauca uucuauuucc cccucuauug auccccaccu ccaaauaucu caucaacaac    120

cgacuaauca ccacccaaca augacuaauc aaacuaaccu caaaacaaau gauaaccaua    180

cacaacacua aaggacgaac cugaucucuu auacuaguau ccuuaaucau uuuuauugcc    240

acaacuaacc uccucggacu ccugccucac ucauuuacac caaccaccca acuaucuaua    300

aaccuagcca uggccauccc cuuaugagcg ggcacaguga uuauaggcuu ucgcucuaag    360

auuaaaaaug cccuagccca cuucuuacca caaggcacac cuacaccccu uauccccaua    420

cuaguuauua ucgaaaccau cagccuacuc auucaaccaa uagcccuggc cguacgccua    480

accgcuaaca uuacugcagg ccaccuacuc augcaccuaa uuggaagcgc cacccuagca    540

auaucaacca uuaaccuucc cucuacacuu aucaucuuca caauucuaau ucuacugacu    600

auccuagaaa ucgcugucac uuuccuagga cuucuaacag cccuagaccu caacuaccua    660

accaacaaac uuaaaauaaa auccccacua ugcacauuuu auuucuccaa cauacucgga    720

uucuacccua gcaucacaca ccgcacaauc cccuaucuag gccuucuuac gagccaaaac    780

cugccccuac uccuccuaga ccuaaccuga cuagaaaagc uauuaccuaa aacaauuuca    840

cagcaccaaa ucuccaccuc caucaucacc ucaacccaaa aaggcauaau uaaacuuuac    900

uuccucucuu ucuucuuccc acucauccua acccuacucc uaaucacaua a             951

<210> SEQ ID NO 51
<211> LENGTH: 951
<212> TYPE: DNA
<213> ORGANISM: Artificial
<220> FEATURE:
<223> OTHER INFORMATION: cDNA

<400> SEQUENCE: 51

atgaacgaaa atctgttcgc ttcattcatt gcccccacaa tcctaggcct acccgccgca     60

gtactgatca ttctatttcc ccctctattg atccccacct ccaaatatct catcaacaac    120

cgactaatca ccacccaaca atgactaatc aaactaacct caaaacaaat gataaccata    180

cacaacacta aaggacgaac ctgatctctt atactagtat ccttaatcat ttttattgcc    240

acaactaacc tcctcggact cctgcctcac tcatttacac caaccaccca actatctata    300

aacctagcca tggccatccc cttatgagcg ggcacagtga ttataggctt tcgctctaag    360

attaaaaatg ccctagccca cttcttacca caaggcacac ctacacccct tatccccata    420

ctagttatta tcgaaaccat cagcctactc attcaaccaa tagccctggc cgtacgccta    480

accgctaaca ttactgcagg ccacctactc atgcacctaa ttggaagcgc caccctagca    540

atatcaacca ttaaccttcc ctctacactt atcatcttca caattctaat tctactgact    600

atcctagaaa tcgctgtcac tttcctagga cttctaacag ccctagacct caactaccta    660

accaacaaac ttaaaataaa atccccacta tgcacatttt atttctccaa catactcgga    720

ttctacccta gcatcacaca ccgcacaatc ccctatctag gccttcttac gagccaaaac    780
```

ctgcccctac tcctcctaga cctaacctga ctagaaaagc tattacctaa aacaatttca 840
cagcaccaaa tctccacctc catcatcacc tcaacccaaa aaggcataat taaactttac 900
ttcctctctt tcttcttccc actcatccta accctactcc taatcacata a 951

<210> SEQ ID NO 52
<211> LENGTH: 317
<212> TYPE: PRT
<213> ORGANISM: Artificial
<220> FEATURE:
<223> OTHER INFORMATION: putative protein sequence
<220> FEATURE:
<221> NAME/KEY: misc_feature
<222> LOCATION: (317)..(317)
<223> OTHER INFORMATION: Xaa can be any naturally occurring amino acid

<400> SEQUENCE: 52

Met Asn Glu Asn Leu Phe Ala Ser Phe Ile Ala Pro Thr Ile Leu Gly
1 5 10 15

Leu Pro Ala Ala Val Leu Ile Ile Leu Phe Pro Pro Leu Leu Ile Pro
20 25 30

Thr Ser Lys Tyr Leu Ile Asn Asn Arg Leu Ile Thr Thr Gln Gln Trp
35 40 45

Leu Ile Lys Leu Thr Ser Lys Gln Met Met Thr Met His Asn Thr Lys
50 55 60

Gly Arg Thr Trp Ser Leu Met Leu Val Ser Leu Ile Ile Phe Ile Ala
65 70 75 80

Thr Thr Asn Leu Leu Gly Leu Leu Pro His Ser Phe Thr Pro Thr Thr
85 90 95

Gln Leu Ser Met Asn Leu Ala Met Ala Ile Pro Leu Trp Ala Gly Thr
100 105 110

Val Ile Met Gly Phe Arg Ser Lys Ile Lys Asn Ala Leu Ala His Phe
115 120 125

Leu Pro Gln Gly Thr Pro Thr Pro Leu Ile Pro Met Leu Val Ile Ile
130 135 140

Glu Thr Ile Ser Leu Leu Ile Gln Pro Met Ala Leu Ala Val Arg Leu
145 150 155 160

Thr Ala Asn Ile Thr Ala Gly His Leu Leu Met His Leu Ile Gly Ser
165 170 175

Ala Thr Leu Ala Met Ser Thr Ile Asn Leu Pro Ser Thr Leu Ile Ile
180 185 190

Phe Thr Ile Leu Ile Leu Leu Thr Ile Leu Glu Ile Ala Val Thr Phe
195 200 205

Leu Gly Leu Leu Thr Ala Leu Asp Leu Asn Tyr Leu Thr Asn Lys Leu
210 215 220

Lys Met Lys Ser Pro Leu Cys Thr Phe Tyr Phe Ser Asn Met Leu Gly
225 230 235 240

Phe Tyr Pro Ser Ile Thr His Arg Thr Ile Pro Tyr Leu Gly Leu Leu
245 250 255

Thr Ser Gln Asn Leu Pro Leu Leu Leu Leu Asp Leu Thr Trp Leu Glu
260 265 270

Lys Leu Leu Pro Lys Thr Ile Ser Gln His Gln Ile Ser Thr Ser Ile
275 280 285

Ile Thr Ser Thr Gln Lys Gly Met Ile Lys Leu Tyr Phe Leu Ser Phe
290 295 300

Phe Phe Pro Leu Ile Leu Thr Leu Leu Leu Ile Thr Xaa

-continued

```
305                 310                 315


<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53

ccttacacta ttcctcatca c                                               21


<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54

tgacctgtta gggtgagaag                                                 20


<210> SEQ ID NO 55
<211> LENGTH: 21
<212> TYPE: DNA
<213> ORGANISM: Artificial Sequence
<220> FEATURE:
<223> OTHER INFORMATION: primer

<400> SEQUENCE: 55

tcgctcacac ctcatatcct c                                               21


<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56

tgtgattagg agtagggtta gg                                              22
```

ABERRANT MITOCHONDRIAL DNA, ASSOCIATED FUSION TRANSCRIPTS AND HYBRIDIZATION PROBES THEREFOR

CROSS REFERENCE TO RELATED APPLICATIONS

This application is a Continuation of U.S. patent application Ser. No. 12/935,181, filed Jan. 17, 2011, which is a national entry of PCT Patent Application Number PCT/CA2009/000351, filed Mar. 27, 2009, which claims the benefit of priority under 35 U.S.C. § 119(e) of U.S. Provisional Patent Application No. 61/040,616, filed Mar. 28, 2008. Each of the aforementioned applications is incorporated by reference herein as if set forth in its entirety.

FIELD OF THE INVENTION

The present invention relates to the field of mitochondrial genomics. In one aspect, the invention relates to the identification and use of mitochondrial genome fusion transcripts and probes that hybridize thereto.

BACKGROUND OF THE INVENTION

Mitochondrial Genome

The mitochondrial genome is a compact yet critical sequence of nucleic acids. Mitochondrial DNA, or "mtDNA", comprises a small genome of 16,569 nucleic acid base pairs (bp) (Anderson et al., 1981; Andrews et al., 1999) in contrast to the immense nuclear genome of 3.3 billion bp (haploid). Its genetic complement is substantially smaller than that of its nuclear cell mate (0.0005%). However, individual cells carry anywhere from $10^3$ to $10^4$ mitochondria depending on specific cellular functions (Singh and Modica-Napolitano 2002). Communication or chemical signalling routinely occurs between the nuclear and mitochondrial genomes (Sherratt et al., 1997). Moreover, specific nuclear components are responsible for the maintenance and integrity of mitochondrial sequences (Croteau et al., 1999). All mtDNA genomes in a given individual are identical due to the clonal expansion of mitochondria within the ovum, once fertilization has occurred. However mutagenic events can induce sequence diversity reflected as somatic mutations. These mutations may accumulate in different tissues throughout the body in a condition known as heteroplasmy.

Mitochondrial Proteome

About 3,000 nuclear genes are required to construct, operate and maintain mitochondria, with only thirty-seven of these coded by the mitochondrial genome, indicating heavy mitochondrial dependence on nuclear loci. The mitochondrial genome codes for a complement of 24 genes, including 2 rRNAs and 22 tRNAs that ensure correct translation of the remaining 13 genes which are vital to electron transport (see FIG. 1). The mitochondrial genome is dependent on seventy nuclear encoded proteins to accomplish the oxidation and reduction reactions necessary for this vital function, in addition to the thirteen polypeptides supplied by the mitochondrial genome. Both nuclear and mitochondrial proteins form complexes spanning the inner mitochondrial membrane and collectively generate 80-90% of the chemical fuel adenosine triphosphate, or ATP, required for cellular metabolism. In addition to energy production, mitochondria play a central role in other metabolic pathways as well. A critical function of the mitochondria is mediation of cell death, or apoptosis (see Green and Kroemer, 2005). Essentially, there are signal pathways which permeabilize the outer mitochondrial membrane, or in addition, the inner mitochondrial membrane as well. When particular mitochondrial proteins are released into the cytosol, non-reversible cell death is set in motion. This process highlights the multi-functional role that some mitochondrial proteins have. These multi-tasking proteins suggest that there are other mitochondrial proteins as well which may have alternate functions.

Mitochondrial Fusion Transcriptome

The mitochondrial genome is unusual in that it is a circular, intron-less DNA molecule. The genome is interspersed with repeat motifs which flank specific lengths of sequences. Sequences between these repeats are prone to deletion under circumstances which are not well understood. Given the number of repeats in the mitochondrial genome, there are many possible deletions. The best known example is the 4977 "common deletion." This deletion has been associated with several purported conditions and diseases and is thought to increase in frequency with aging (Dai et al., 2004; Ro et al., 2003; Barron et al., 2001; Lewis et al., 2000; Muller-Hocker, 1998; Porteous et al., 1998) (FIG. 4). The current thinking in the field of mitochondrial genomics is that mitochondrial deletions are merely deleterious by-products of damage to the mitochondrial genome by such agents as reactive oxygen species and UVR. (Krishnan et al 2008, Nature Genetics). Further, though it is recognized that high levels of mtDNA deletions can have severe consequences on the cell's ability to produce energy in the form of ATP as a result of missing gene sequences necessary for cellular respiration, it is not anticipated that these deleted mitochondrial molecules may be a component of downstream pathways, have an intended functional role, and possibly may be more aptly viewed as alternate natural forms of the recognized genes of the mitochondria as has been anticipated by the Applicant.

The sequence dynamics of mtDNA are important diagnostic tools. Mutations in mtDNA are often preliminary indicators of developing disease. For example, it has been demonstrated that point mutations in the mitochondrial genome are characteristic of tumour foci in the prostate. This trend also extends to normal appearing tissue both adjacent to and distant from tumour tissue (Parr et al. 2006). This suggests that mitochondrial mutations occur early in the malignant transformation pathway.

For example, the frequency of a 3.4 kb mitochondrial deletion has excellent utility in discriminating between benign and malignant prostate tissues (Maki et al. 2008).

Mitochondrial fusion transcripts have been reported previously in the literature, first in soybeans (Morgens et al. 1984) and then later in two patients with Kearns-Sayre Syndrome, a rare neuromuscular disorder (Nakase et al 1990). Importantly, these transcripts were not found to have (or investigated regarding) association with any human cancers.

SUMMARY OF THE INVENTION

An object of the present invention to provide aberrant mitochondrial DNA, associated fusion transcripts and hybridization probes therefor.

In accordance with an aspect of the invention, there is provided an isolated mitochondrial fusion transcript associated with cancer.

In accordance with an aspect of the invention, there is provided a mitochondrial fusion protein corresponding to the above fusion transcript, having a sequence as set forth in any one of SEQ ID NOs: 34 to 49 and 52.

In accordance with another aspect of the invention, there is provided an isolated mtDNA encoding a fusion transcript of the invention.

In accordance with another aspect of the invention, there is provided a hybridization probe having a nucleic acid sequence complementary to at least a portion of a mitochondrial fusion transcript or an mtDNA of the invention.

In accordance with another aspect of the invention, there is provided a method of detecting a cancer in a mammal, the method comprising assaying a tissue sample from the mammal for the presence of at least one mitochondrial fusion transcript associated with cancer by hybridizing the sample with at least one hybridization probe having a nucleic acid sequence complementary to at least a portion of a mitochondrial fusion transcript according to the invention.

In accordance with another aspect of the invention, there is provided a method of detecting a cancer in a mammal, the method comprising assaying a tissue sample from the mammal for the presence of at least one aberrant mtDNA associated with cancer by hybridizing the sample with at least one hybridization probe having a nucleic acid sequence complementary to at least a portion of an mtDNA according to the invention.

In accordance with another aspect of the invention, there is provided a kit for conducting an assay for detecting the presence of a cancer in a mammal, said kit comprising at least one hybridization probe complementary to at least a portion of a fusion transcript or an mtDNA of the invention.

In accordance with another aspect of the invention, there is provided a screening tool comprised of a microarray having 10's, 100's, or 1000's of mitochondrial fusion transcripts for identification of those associated with cancer.

In accordance with another aspect of the invention, there is provided a screening tool comprised of a microarray having 10's, 100's, or 1000's of mitochondrial DNAs corresponding to mitochondrial fusion transcripts for identification of those associated with cancer.

In accordance with another aspect of the invention, there is provided a screening tool comprised of a multiplexed branched DNA assay having 10's, 100's, or 1000's of mitochondrial fusion transcripts for identification of those associated with cancer.

In accordance with another aspect of the invention, there is provided a screening tool comprised of a multiplexed branched DNA assay having 10's, 100's, or 1000's of mitochondrial DNAs corresponding to mitochondrial fusion transcripts for identification of those associated with cancer.

BRIEF DESCRIPTION OF THE DRAWINGS

The embodiments of the invention will now be described by way of example only with reference to the appended drawings wherein:

FIGS. 10A to 10K illustrate the results for transcripts 2, 3, 4, 11, 12, 13, 15, 16 and 20 of the invention in the identification of testicular cancer.

FIGS. 11A to 11I illustrate the results for transcripts 2, 3, 4, 11, 12, 13, 15, 16 and 20 of the invention in the identification of testicular cancer.

FIGS. 12A to 12E illustrate the results for transcripts 2, 3, 4, 11, 12, 13, 15, 16 and 20 of the invention in the identification of testicular cancer.

FIGS. 13A to 13I illustrate the results for transcripts 2, 3, 4, 11, 12, 13, 15, 16 and 20 of the invention in the identification of testicular cancer.

FIGS. 14A to 14I illustrate the results for transcripts 2, 3, 4, 11, 12, 13, 15, 16 and 20 of the invention in the identification of testicular cancer.

FIGS. 16A to 16E illustrate the results for transcripts 2, 3, 4, 11, 12, 13, 15, 16 and 20 of the invention in the identification of testicular cancer.

FIGS. 17A to 17J illustrate the results for transcripts 2, 3, 4, 11, 12, 13, 15, 16 and 20 of the invention in the identification of testicular cancer.

FIGS. 18A to 18I illustrate the results for transcripts 2, 3, 4, 11, 12, 13, 15, 16 and 20 of the invention in the identification of testicular cancer.

DETAILED DESCRIPTION OF THE INVENTION

Figure 1:
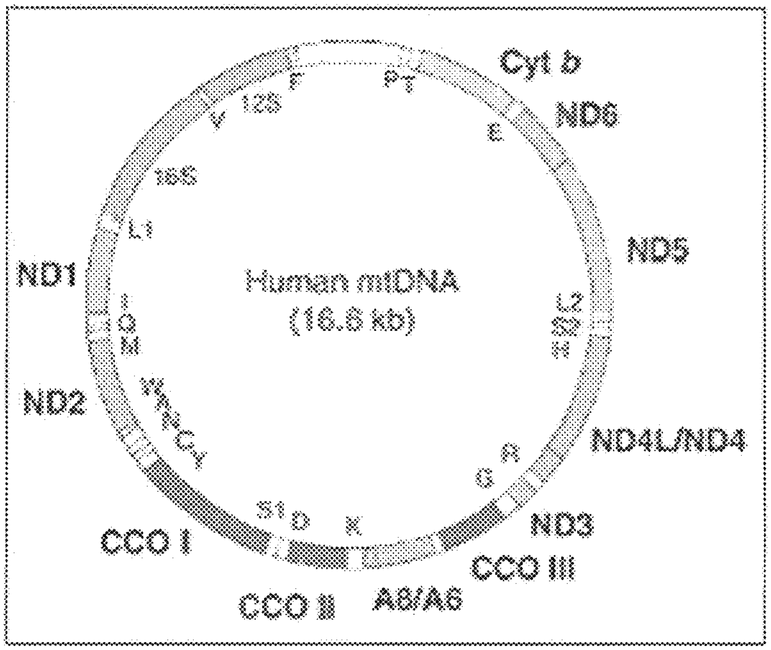
FIG. 1 is an illustration showing mitochondrial coding genes.

The present invention provides novel mitochondrial fusion transcripts and the parent mutated mtDNA molecules that are useful for predicting, diagnosing and/or monitoring cancer. The invention further provides hybridization probes for the detection of fusion transcripts and associated mtDNA molecules and the use of such probes.

Definitions

Unless defined otherwise, all technical and scientific terms used herein have the same meaning as commonly understood by one of ordinary skill in the art to which this invention belongs.

As used herein, "aberration" or "mutation" encompasses any modification in the wild type mitochondrial DNA sequence that results in a fusion transcript and includes, without limitation, insertions, translocations, deletions, duplications, recombinations, rearrangements or combinations thereof.

As defined herein, "biological sample" refers to a tissue or bodily fluid containing cells from which a molecule of interest can be obtained. For example, the biological sample can be derived from tissue such as prostate, breast, colorectal, lung and skin, or from blood, saliva, cerebral spinal fluid, sputa, urine, mucous, synovial fluid, peritoneal fluid, amniotic fluid and the like. The biological sample may be a surgical specimen or a biopsy specimen. The biological sample can be used either directly as obtained from the source or following a pre-treatment to modify the character of the sample. Thus, the biological sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, and the like.

A "continuous" transcript is a fusion transcript that keeps the reading frame from the beginning to the end of both spliced genes. An "end" transcript is a fusion transcript that results in a premature termination codon before the original termination codon of a second spliced gene.

As used herein, "mitochondrial DNA" or "mtDNA" is DNA present in mitochondria.

As used herein, the expression "mitochondrial fusion transcript" or "fusion transcript" refers to an RNA transcription product produced as a result of the transcription of a mutated mitochondrial DNA sequence wherein such mutations may comprise mitochondrial deletions and other large-scale mitochondrial DNA rearrangements.

Computer Analysis and Sequence Targeting

As discussed above, mitochondrial fusion transcripts have been reported in soybeans (Morgens et al. 1984) and in humans suffering from a rare neuromuscular disorder (Nakase et al 1990). Fusion transcripts associated with human cancer have not, however, been described.

Using the knowledge gained from mapping the large-scale deletions of the human mitochondrial genome associated with cancer, the observation of high frequencies of these deletions, and the evidence in another organism and another disease type of trancriptionally active mutated mtDNA molecules, Applicant hypothesized that such deletions may have importance beyond the DNA molecule and the damage and repair processes as it relates to cancer. To test this hypothesis computer analysis of the mitochondrial genome was conducted, specific for repeat elements, which suggested many potential deletion sites. Following this initial step identifying unique repeats in the mitochondrial sequence having non-adjacent or non-tandem locations, a filter was then applied to identify those repeats that upon initiating a deletion event in the DNA molecule would then likely reclose or religate to produce a fused DNA sequence having an open reading frame (ORF). A subset of 18 molecules were then selected for targeting to investigate whether: 1) they existed in the natural biological state of humans and 2) they had relevance to malignancy. Results from these investigations are described hereinafter.

Genomic Mutations

Mitochondrial DNA (mtDNA) dynamics are an important diagnostic tool. Mutations in mtDNA are often preliminary indicators of developing disease and behave as biomarkers indicative of risk factors associated with disease onset. According to the present invention, large-scale rearrangement mutations in the mitochondrial genome result in the generation of fusion transcripts associated with cancer. Thus, the use of mtDNA encoding such transcripts and probes directed thereto for the detection, diagnosis and monitoring of cancer is provided.

One of skill in the art will appreciate that the mtDNA molecules for use in the methods of the present invention may be derived through the isolation of naturally-occurring mutants or may be based on the complementary sequence of any of the fusion transcripts described herein. Exemplary mtDNA sequences and fusion transcripts are disclosed in Applicant's U.S. priority application no. 61/040,616, herein incorporated in its entirety by reference.

Detection of Mutant Genomic Sequences

Mutant mtDNA sequences according to the present invention may comprise any modification that results in the generation of a fusion transcript. Non-limiting examples of such modifications include insertions, translocations, deletions, duplications, recombinations, rearrangements or combinations thereof. While the modification or change can vary greatly in size from only a few bases to several kilobases, preferably the modification results in a substantive deletion or other large-scale genomic aberration.

Extraction of DNA to detect the presence of such mutations may take place using art-recognized methods, followed by amplification of all or a region of the mitochondrial genome, and may include sequencing of the mitochondrial genome, as described in Current Protocols in Molecular Biology. Alternatively, crude tissue homogenates may be used as well as techniques not requiring amplification of specific fragments of interest.

The step of detecting the mutations can be selected from any technique as is known to those skilled in the art. For example, analyzing mtDNA can comprise selection of targets by branching DNA, sequencing the mtDNA, amplifying mtDNA by PCR, Southern, Northern, Western South-Western blot hybridizations, denaturing HPLC, hybridization to microarrays, biochips or gene chips, molecular marker analysis, biosensors, melting temperature profiling or a combination of any of the above.

Any suitable means to sequence mitochondrial DNA may be used. Preferably, mtDNA is amplified by PCR prior to sequencing. The method of PCR is well known in the art and may be performed as described in Mullis and Faloona, 1987, Methods Enzymol., 155: 335. PCR products can be sequenced directly or cloned into a vector which is then placed into a bacterial host. Examples of DNA sequencing methods are found in Brumley, R. L. Jr. and Smith, L. M., 1991, Rapid DNA sequencing by horizontal ultrathin gel electrophoresis, Nucleic Acids Res. 19:4121-4126 and Luckey, J. A., et al, 1993, High speed DNA sequencing by capillary gel electrophoresis, Methods Enzymol. 218: 154-172. The combined use of PCR and sequencing of mtDNA is described in Hopgood, R., et al, 1992, Strategies for automated sequencing of human mtDNA directly from PCR products, Biotechniques 13:82-92 and Tanaka, M. et al, 1996, Automated sequencing of mtDNA, Methods Enzymol. 264: 407-421.

Methods of selecting appropriate sequences for preparing various primers are also known in the art. For example, the primer can be prepared using conventional solid-phase synthesis using commercially available equipment, such as that available from Applied Biosystems USA Inc. (Foster City, Calif.), DuPont, (Wilmington, Del.), or Milligen (Bedford, Mass.).

According to an aspect of the invention, to determine candidate genomic sequences, a junction point of a sequence deletion is first identified. Sequence deletions are primarily identified by direct and indirect repetitive elements which flank the sequence to be deleted at the 5' and 3' end. The removal of a section of the nucleotides from the genome followed by the ligation of the genome results in the creation of a novel junction point.

Upon identification of the junction point, the nucleotides of the genes flanking the junction point are determined in order to identify a spliced gene. Typically the spliced gene comprises the initiation codon from the first gene and the termination codon of the second gene, and may be expressed as a continuous transcript, i.e. one that keeps the reading frame from the beginning to the end of both spliced genes. It is also possible that alternate initiation or termination codons contained within the gene sequences may be used as is evidenced by SEQ ID No:2 and SEQ ID No: 17 disclosed herein. Some known mitochondrial deletions discovered to have an open reading frame (ORF) when the rearranged sequences are rejoined at the splice site are provided in Table 1.

Exemplary mtDNA molecules for use in the methods of the present invention, which have been verified to exist in the lab, are provided below. These mtDNAs are based on modifications of the known mitochondrial genome (SEQ ID NO: 1) and have been assigned a fusion or "FUS" designation, wherein A:B represents the junction point between the last mitochondrial nucleotide of the first spliced gene and the first mitochondrial nucleotide of the second spliced gene. The identification of the spliced genes is provided in parentheses followed by the corresponding sequence identifier. Where provided below, (AltMet) and (OrigMet) refer to alternate and original translation start sites, respectively.

FUS 8469:13447 (AltMet) (ATP synthase F0 subunit 8 to NADH dehydrogenase subunit) (SEQ ID No: 2)
FUS 10744:14124 (NADH dehydrogenase subunit 4L (ND4L) to NADH dehydrogenase subunit 5 (ND5)) (SEQ ID No: 3)
FUS 7974:15496 (Cytochrome c oxidase subunit II (COII) to Cytochrome b (Cytb)) (SEQ ID No: 4)
FUS 7992:15730 (Cytochrome c oxidase subunit II (COII) to Cytochrome b (Cytb)) (SEQ ID No: 5)
FUS 8210:15339 (Cytochrome c oxidase subunit II (COII) to Cytochrome b (Cytb)) (SEQ ID No: 6)
FUS 8828:14896 (ATP synthase F0 subunit 6 (ATPase6) to Cytochrome b (Cytb)) (SEQ ID No: 7)
FUS 10665:14856 (NADH dehydrogenase subunit 4L (ND4L) to Cytochrome b (Cytb)) (SEQ ID No: 8)
FUS 6075:13799 (Cytochrome c oxidase subunit I (COI) to NADH de hydrogenase subunit 5 (ND5)) (SEQ ID No: 9)
FUS 6325:13989 (Cytochrome c oxidase subunit I (COI) to NADH dehydrogenase subunit 5 (ND5)) (SEQ ID No: 10)
FUS 7438:13476 (Cytochrome c oxidase subunit I (COI) to NADH dehydrogenase subunit 5 (ND5)) (SEQ ID No: 11)
FUS 7775:13532 (Cytochrome c oxidase subunit II (COII) to NADH dehydrogenase subunit 5 (ND5)) (SEQ ID No: 12)
FUS 8213:13991 (Cytochrome c oxidase subunit II (COII) to NADH dehydrogenase subunit 5 (ND5)) (SEQ ID No: 13)
FUS 9191:12909 (ATP synthase F0 subunit 6 (ATPase6) to NADH dehydrogenase subunit 5 (ND5)) (SEQ ID No: 14)
FUS 9574:12972 (Cytochrome c oxidase subunit III (COIII) to NADH dehydrogenase subunit 5 (ND5)) (SEQ ID No: 15)
FUS 10367:12829 (NADH dehydrogenase subunit 3 (ND3) to NADH dehydrogenase subunit 5 (ND5)) (SEQ ID No: 16)
FUS 8469:13447 (OrigMet) (ATP synthase F0 subunit 8 to NADH dehydrogenase subunit) (SEQ ID No: 17)
FUS 9144:13816 ((ATP synthase F0 subunit 6 (ATPase6) to NADH dehydrogenase subunit 5 (ND5)) (SEQ ID No: 51)

The present invention also provides the use of variants or fragments of these sequences for predicting, diagnosing and/or monitoring cancer.

"Variant", as used herein, refers to a nucleic acid differing from a mtDNA sequence of the present invention, but retaining essential properties thereof. Generally, variants are overall closely similar, and, in many regions, identical to a select mtDNA sequence. Specifically, the variants of the present invention comprise at least one of the nucleotides of the junction point of the spliced genes, and may further comprise one or more nucleotides adjacent thereto. In one embodiment of the invention, the variant sequence is at least 80%, 85%, 90%, 95%, 96%, 97%, 98% or 99% identical to any one of the mtDNA sequences of the invention, or the complementary strand thereto.

In the present invention, "fragment" refers to a short nucleic acid sequence which is a portion of that contained in the disclosed genomic sequences, or the complementary strand thereto. This portion includes at least one of the nucleotides comprising the junction point of the spliced genes, and may further comprise one or more nucleotides adjacent thereto. The fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases of any one of the mtDNA sequences listed above. In this context "about" includes the particularly recited value, a value larger or smaller by several (5, 4, 3, 2, or 1) nucleotides, at either terminus or at both termini. These fragments have uses that include, but are not limited to, as diagnostic probes and primers as discussed herein. Of course, larger fragments (e.g., 50, 150, 500, 600, 2000 nucleotides) are also contemplated.

Thus, in specific embodiments of the invention, the mtDNA sequences are selected from the group consisting of:

SEQ ID NO: 2 (FUS 8469:13447; AltMet)
SEQ ID NO: 3 (FUS 10744:14124)
SEQ ID NO: 4 (FUS 7974:15496)
SEQ ID NO: 5 (FUS 7992:15730)
SEQ ID NO: 6 (FUS 8210:15339)
SEQ ID NO: 7 (FUS 8828:14896)
SEQ ID NO: 8 (FUS 10665:14856)
SEQ ID NO: 9 (FUS 6075:13799)
SEQ ID NO: 10 (FUS 6325:13989)
SEQ ID NO: 11 (FUS 7438:13476)
SEQ ID NO: 12 (FUS 7775:13532)
SEQ ID NO: 13 (FUS 8213:13991)
SEQ ID NO: 14 (FUS 9191:12909)
SEQ ID NO: 15 (FUS 9574:12972)
SEQ ID NO: 16 (FUS 10367:12829)
SEQ ID NO: 17(FUS 8469:13447; OrigMet)
SEQ ID NO: 51 (FUS 9144:13816), and fragments or variants thereof.

Probes

Another aspect of the invention is to provide a hybridization probe capable of recognizing an aberrant mtDNA sequence of the invention. As used herein, the term "probe" refers to an oligonucleotide which forms a duplex structure with a sequence in the target nucleic acid, due to complementarity of at least one sequence in the probe with a sequence in the target region. The probe may be labeled, according to methods known in the art.

Once aberrant mtDNA associated with a particular disease is identified, hybridization of mtDNA to, for example, an array of oligonucleotides can be used to identify particular mutations, however, any known method of hybridization may be used.

As with the primers of the present invention, probes may be generated directly against exemplary mtDNA fusion molecules of the invention, or to a fragment or variant thereof. For instance, the sequences set forth in SEQ ID NOs: 2-17 and 51 and those disclosed in Table 1 can be used to design primers or probes that will detect a nucleic acid sequence comprising a fusion sequence of interest. As would be understood by those of skill in the art, primers or probes which hybridize to these nucleic acid molecules may do so under highly stringent hybridization conditions or lower stringency conditions, such conditions known to those skilled in the art and found, for example, in Current Protocols in Molecular Biology (John Wiley & Sons, New York (1989)), 6.3.1-6.3.6.

In specific embodiments of the invention, the probes of the invention contain a sequence complementary to at least a portion of the aberrant mtDNA comprising the junction point of the spliced genes. This portion includes at least one of the nucleotides involved in the junction point A:B, and may further comprise one or more nucleotides adjacent thereto. In this regard, the present invention encompasses any suitable targeting mechanism that will select an mtDNA molecule using the nucleotides involved and/or adjacent to the junction point A:B.

Various types of probes known in the art are contemplated by the present invention. For example, the probe may be a hybridization probe, the binding of which to a target nucleotide sequence can be detected using a general DNA binding dye such as ethidium bromide, SYBR® Green, SYBR® Gold and the like. Alternatively, the probe can incorporate one or more detectable labels. Detectable labels are molecules or moieties a property or characteristic of which can be detected directly or indirectly and are chosen such that the ability of the probe to hybridize with its target sequence is not affected. Methods of labelling nucleic acid sequences are well-known in the art (see, for example, Ausubel et al., (1997 & updates) *Current Protocols in Molecular Biology*, Wiley & Sons, New York).

Labels suitable for use with the probes of the present invention include those that can be directly detected, such as radioisotopes, fluorophores, chemiluminophores, enzymes, colloidal particles, fluorescent microparticles, and the like. One skilled in the art will understand that directly detectable labels may require additional components, such as substrates, triggering reagents, light, and the like to enable detection of the label. The present invention also contemplates the use of labels that are detected indirectly.

The probes of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A probe of "at least 20 nt in length," for example, is intended to include 20 or more contiguous bases that are complementary to an mtDNA sequence of the invention. Of course, larger probes (e.g., 50, 150, 500, 600, 2000 nucleotides) may be preferable.

The probes of the invention will also hybridize to nucleic acid molecules in biological samples, thereby enabling the methods of the invention. Accordingly, in one aspect of the invention, there is provided a hybridization probe for use in the detection of cancer, wherein the probe is complementary to at least a portion of an aberrant mtDNA molecule. In another aspect the present invention provides probes and a use of (or a method of using) such probes for the detection of colorectal cancer, lung cancer, breast cancer, ovarian cancer, testicular, cancer, prostate cancer and/or melanoma skin cancer.

Assays

Measuring the level of aberrant mtDNA in a biological sample can determine the presence of one or more cancers in a subject. The present invention, therefore, encompasses methods for predicting, diagnosing or monitoring cancer, comprising obtaining one or more biological samples, extracting mtDNA from the samples, and assaying the samples for aberrant mtDNA by: quantifying the amount of one or more aberrant mtDNA sequences in the sample and comparing the quantity detected with a reference value. As would be understood by those of skill in the art, the reference value is based on whether the method seeks to predict, diagnose or monitor cancer. Accordingly, the reference value may relate to mtDNA data collected from one or more known non-cancerous biological samples, from one or more known cancerous biological samples, and/or from one or more biological samples taken over time.

In one aspect, the invention provides a method of detecting cancer in a mammal, the method comprising assaying a tissue sample from the mammal for the presence of an aberrant mitochondrial DNA described above. The present invention also provides for methods comprising assaying a tissue sample from the mammal by hybridizing the sample with at least one hybridization probe. The probe may be generated against a mutant mitochondrial DNA sequence of the invention as described herein.

In another aspect, the invention provides a method as above, wherein the assay comprises:

a) conducting a hybridization reaction using at least one of the probes to allow the at least one probe to hybridize to a complementary aberrant mitochondrial DNA sequence;

b) quantifying the amount of the at least one aberrant mitochondrial DNA sequence in the sample by quantifying the amount of the mitochondrial DNA hybridized to the at least one probe; and, c) comparing the amount of the mitochondrial DNA in the sample to at least one known reference value.

Also included in the present invention are methods for predicting, diagnosing or monitoring cancer comprising diagnostic imaging assays as described below. The diagnostic assays of the invention can be readily adapted for high-throughput. High-throughput assays provide the advantage of processing many samples simultaneously and significantly decrease the time required to screen a large number of samples. The present invention, therefore, contemplates the use of the nucleotides of the present invention in high-throughput screening or assays to detect and/or quantitate target nucleotide sequences in a plurality of test samples.

Fusion Transcripts

The present invention further provides the identification of fusion transcripts and associated hybridization probes useful in methods for predicting, diagnosing and/or monitoring cancer. One of skill in the art will appreciate that such molecules may be derived through the isolation of naturally-occurring transcripts or, alternatively, by the recombinant expression of mtDNAs isolated according to the methods of the invention. As discussed, such mtDNAs typically comprise a spliced gene having the initiation codon from the first gene and the termination codon of the second gene. Accordingly, fusion transcripts derived therefrom comprise a junction point associated with the spliced genes.

Detection of Fusion Transcripts

Naturally occurring fusion transcripts can be extracted from a biological sample and identified according to any suitable method known in the art, or may be conducted according to the methods described in the examples. In one embodiment of the invention, stable polyadenylated fusion transcripts are identified using Oligo(dT) primers that target transcripts with poly-A tails, followed by RT-PCR using primer pairs designed against the target transcript.

The following exemplary fusion transcripts were detected using such methods and found useful in predicting, diagnosing and/or monitoring cancer as indicated in the examples. Likewise, fusion transcripts derived from the ORF sequences identified in Table 1 may be useful in predicting, diagnosing and/or monitoring cancer according to the assays and methods of the present invention.

SEQ ID NO: 18 (Transcripts 1; 8469:13447; AltMet)
SEQ ID NO: 19 (Transcript 2; 10744:14124)
SEQ ID NO: 20 (Transcript 3; 7974:15496)
SEQ ID NO: 21 (Transcript 4; 7992:15730)
SEQ ID NO: 22 (Transcript 5; 8210:15339)
SEQ ID NO: 23 (Transcript 6; 8828:14896)
SEQ ID NO: 24 (Transcript 7; 10665:14856)
SEQ ID NO: 25 (Transcript 8; 6075:13799)
SEQ ID NO: 26 (Transcript 9; 6325:13989)
SEQ ID NO: 27 (Transcript 10; 7438:13476)
SEQ ID NO: 28 (Transcript 11; 7775:13532)
SEQ ID NO: 29 (Transcript 12; 8213:13991)
SEQ ID NO: 30 (Transcript 14; 9191:12909)
SEQ ID NO: 31 (Transcript 15; 9574:12972)
SEQ ID NO: 32 (Transcript 16; 10367:12829)
SEQ ID NO: 33 (Transcript 20; 8469:13447; OrigMet)
SEQ ID NO: 50 (Transcript 13; 9144:13816)

Further, fusion transcripts of like character to those described herein are contemplated for use in the field of clinical oncology.

Fusion transcripts can also be produced by recombinant techniques known in the art. Typically this involves transformation (including transfection, transduction, or infection) of a suitable host cell with an expression vector comprising an mtDNA sequence of interest.

Variants or fragments of the fusion transcripts identified herein are also provided. Such sequences may adhere to the size limitations and percent identities described above with respect to genomic variants and fragments, or as determined suitable by a skilled technician.

In addition, putative protein sequences corresponding to transcripts 1-16 and 20 are listed below. These sequences, which encode hypothetical fusion proteins, are provided as a further embodiment of the present invention.

SEQ ID NO: 34 (Transcripts 1)
SEQ ID NO: 35 (Transcript 2)
SEQ ID NO: 36 (Transcript 3)
SEQ ID NO: 37 (Transcript 4)
SEQ ID NO: 38 (Transcript 5)
SEQ ID NO: 39 (Transcript 6)
SEQ ID NO: 40 (Transcript 7)
SEQ ID NO: 41 (Transcript 8)
SEQ ID NO: 42 (Transcript 9)
SEQ ID NO: 43 (Transcript 10)
SEQ ID NO: 44 (Transcript 11)
SEQ ID NO: 45 (Transcript 12)
SEQ ID NO: 46 (Transcript 14)
SEQ ID NO: 47 (Transcript 15)
SEQ ID NO: 48 (Transcript 16)
SEQ ID NO: 49 (Transcripts 20)
SEQ ID NO: 52 (Transcript 13)

Probes

Once a fusion transcript has been characterized, primers or probes can be developed to target the transcript in a biological sample. Such primers and probes may be prepared using any known method (as described above) or as set out in the examples provided below. A probe may, for example, be generated for the fusion transcript, and detection technologies, such as QuantiGene 2.0™ by Panomics™, used to detect the presence of the transcript in a sample. Primers and probes may be generated directly against exemplary fusion transcripts of the invention, or to a fragment or variant thereof. For instance, the sequences set forth in SEQ ID NOs: 18-33 and 50 as well as those disclosed in Table 1 can be used to design probes that will detect a nucleic acid sequence comprising a fusion sequence of interest.

As would be understood by those skilled in the art, probes designed to hybridize to the fusion transcripts of the invention contain a sequence complementary to at least a portion of the transcript expressing the junction point of the spliced genes. This portion includes at least one of the nucleotides complementary to the expressed junction point, and may further comprise one or more complementary nucleotides adjacent thereto. In this regard, the present invention encompasses any suitable targeting mechanism that will select a fusion transcript that uses the nucleotides involved and adjacent to the junction point of the spliced genes.

Various types of probes and methods of labelling known in the art are contemplated for the preparation of transcript probes. Such types and methods have been described above with respect to the detection of genomic sequences. The transcript probes of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A probe of "at least 20 nt in length," for example, is intended to include 20 or more contiguous bases that are complementary to an mtDNA sequence of the invention. Of course, larger probes (e.g., 50, 150, 500, 600, 2000 nucleotides) may be preferable.

In one aspect, the invention provides a hybridization probe for use in the detection of cancer, wherein the probe is complementary to at least a portion of a mitochondrial fusion transcript provided above.

In another aspect, the present invention provides probes and a use of (or a method of using) such probes for the detection of colorectal cancer, lung cancer, breast cancer, ovarian cancer, testicular cancer, prostate cancer or melanoma skin cancer.

Assays

Measuring the level of mitochondrial fusion transcripts in a biological sample can determine the presence of one or more cancers in a subject. The present invention, therefore, provides methods for predicting, diagnosing or monitoring cancer, comprising obtaining one or more biological samples, extracting mitochondrial RNA from the samples, and assaying the samples for fusion transcripts by: quantifying the amount of one or more fusion transcripts in the sample and comparing the quantity detected with a reference value. As would be understood by those of skill in the art, the reference value is based on whether the method seeks to predict, diagnose or monitor cancer. Accordingly, the reference value may relate to transcript data collected from one or more known non-cancerous biological samples, from one or more known cancerous biological samples, and/or from one or more biological samples taken over time.

In one aspect, the invention provides a method of detecting a cancer in a mammal, the method comprising assaying a tissue sample from said mammal for the presence of at least one fusion transcript of the invention by hybridizing said sample with at least one hybridization probe having a nucleic acid sequence complementary to at least a portion of the mitochondrial fusion transcript.

In another aspect, the invention provides a method as above, wherein the assay comprises:

a) conducting a hybridization reaction using at least one of the above-noted probes to allow the at least one probe to hybridize to a complementary mitochondrial fusion transcript;

b) quantifying the amount of the at least one mitochondrial fusion transcript in the sample by quantifying the amount of the transcript hybridized to the at least one probe; and, c) comparing the amount of the mitochondrial fusion transcript in the sample to at least one known reference value.

As discussed above, the diagnostic assays of the invention may also comprise diagnostic methods and screening tools as described herein and can be readily adapted for high-throughput. The present invention, therefore, contemplates the use of the fusion transcripts and associated probes of the present invention in high-throughput screening or assays to detect and/or quantitate target nucleotide sequences in a plurality of test samples.

Diagnostic Methods and Screening Tools

Methods and screening tools for diagnosing specific diseases or identifying specific mitochondrial mutations are also herein contemplated. Any known method of hybridization may be used to carry out such methods including, without limitation, probe/primer based technologies such as branched DNA and qPCR, both single-plex and multi-plex. Array technology, which has oligonucleotide probes matching the wild type or mutated region, and a control probe, may also be used. Commercially available arrays such as microarrays or gene chips are suitable. These arrays contain thousands of matched and control pairs of probes on a slide or microchip, and are capable of sequencing the entire genome very quickly. Review articles describing the use of microarrays in genome and DNA sequence analysis are available on-line.

Screening tools designed to identify targets which are relevant to a given biological condition may include specific arrangements of nucleic acids associated with a particular disease or disorder. Thus, in accordance with one embodiment of the invention, there is provided a screening tool comprised of a microarray having 10's, 100's, or 1000's of mitochondrial fusion transcripts for identification of those associated with one or more cancers. In accordance with another embodiment, there is provided a screening tool comprised of a microarray having 10's, 100's, or 1000's of mitochondrial DNAs corresponding to mitochondrial fusion transcripts for identification of those associated with one or more cancers. In a further embodiment, there is provided a screening tool comprised of a multiplexed branched DNA assay having 10's, 100's, or 1000's of mitochondrial fusion transcripts for identification of those associated with one or more cancers. In yet another embodiment of the invention, there is provided a screening tool comprised of a multiplexed branched DNA assay having 10's, 100's, or 1000's of mitochondrial DNAs corresponding to mitochondrial fusion transcripts for identification of those associated with one or more cancers.

Approaches useful in the field of clinical oncology are also herein contemplated and may include such diagnostic imaging techniques as Positron Emission Tomography (PET), contrast Magnetic Resonance Imaging (MRI) or the like. These diagnostic methods are well known to those of skill in the art and are useful in the diagnosis and prognosis of cancer.

Diagnostic Monitoring

The methods of the present invention may further comprise the step of recommending a monitoring regime or course of therapy based on the outcome of one or more assays. This allows clinicians to practice personalized medicine; e.g. cancer therapy, by monitoring the progression of the patients cancer (such as by recognizing when an initial or subsequent mutation occurs) or treatment (such as by recognizing when a mutation is stabilized).

With knowledge of the boundaries of the sequence variation in hand, the information can be used to diagnose a pre-cancerous condition or existing cancer condition. Further, by quantitating the amount of aberrant mtDNA in successive samples over time, the progression of a cancer condition can be monitored. For example, data provided by assaying the patient's tissues at one point in time to detect a first set of mutations from wild-type could be compared against data provided from a subsequent assay, to determine if changes in the aberration have occurred.

Where a mutation is found in an individual who has not yet developed symptoms of cancer, the mutation may be indicative of a genetic susceptibility to develop a cancer condition. A determination of susceptibility to disease or diagnosis of its presence can further be evaluated on a qualitative basis based on information concerning the prevalence, if any, of the cancer condition in the patient's family history and the presence of other risk factors, such as exposure to environmental factors and whether the patient's cells also carry a mutation of another sort.

Biological Sample

The present invention provides for diagnostic tests which involve obtaining or collecting one or more biological samples. In the context of the present invention, "biological sample" refers to a tissue or bodily fluid containing cells from which mtDNA and mtRNA can be obtained. For example, the biological sample can be derived from tissue including, but not limited to, skin, lung, breast, prostate, nervous, muscle, heart, stomach, colon, rectal tissue and the like; or from blood, saliva, cerebral spinal fluid, sputa, urine, mucous, synovial fluid, peritoneal fluid, amniotic fluid and the like. The biological sample may be obtained from a cancerous or non-cancerous tissue and may be, but is not limited to, a surgical specimen or a biopsy specimen.

The biological sample can be used either directly as obtained from the source or following a pre-treatment to modify the character of the sample. Thus, the biological sample can be pre-treated prior to use by, for example, preparing plasma or serum from blood, disrupting cells, preparing liquids from solid materials, diluting viscous fluids, filtering liquids, distilling liquids, concentrating liquids, inactivating interfering components, adding reagents, and the like.

One skilled in the art will understand that more than one sample type may be assayed at a single time (i.e. for the detection of more than one cancer). Furthermore, where a course of collections are required, for example, for the monitoring of cancer over time, a given sample may be diagnosed alone or together with other samples taken throughout a test period. In this regard, biological samples may be taken once only, or at regular intervals such as biweekly, monthly, semi-annually or annually.

Kits

The present invention provides diagnostic/screening kits for detecting cancer in a clinical environment. Such kits may include one or more sampling means, in combination with one or more probes according to the present invention.

The kits can optionally include reagents required to conduct a diagnostic assay, such as buffers, salts, detection reagents, and the like. Other components, such as buffers and solutions for the isolation and/or treatment of a biological sample, may also be included in the kit. One or more of the components of the kit may be lyophilised and the kit may further comprise reagents suitable for the reconstitution of the lyophilised components.

Where appropriate, the kit may also contain reaction vessels, mixing vessels and other components that facilitate the preparation of the test sample. The kit may also optionally include instructions for use, which may be provided in paper form or in computer-readable form, such as a disc, CD, DVD or the like.

In one embodiment of the invention there is provided a kit for diagnosing cancer comprising sampling means and a hybridization probe of the invention.

Various aspects of the invention will be described by illustration using the following examples. The examples provided herein serve only to illustrate certain specific embodiments of the invention and are not intended to limit the scope of the invention in any way.

EXAMPLES

Example 1: Detection of Mitochondrial Fusion Transcripts

Figure 2:
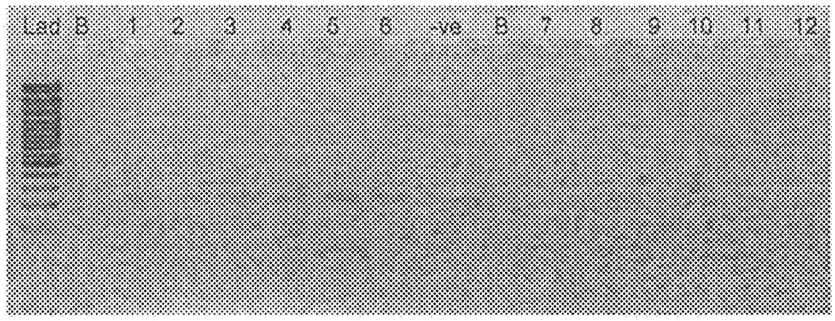
FIG. 2 shows polyadenalated fusion transcripts in prostate samples invoked by the loss of the 3.4 kb deletion.
Figure 3:
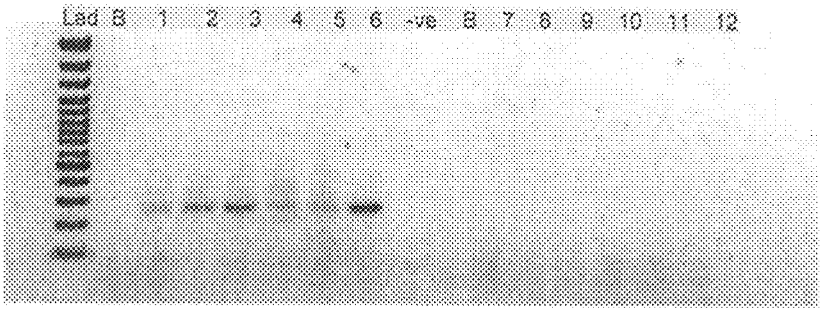
FIG. 3 shows polyadenalated fusion transcripts in prostate samples invoked by the loss of the 4977 kb common deletion.
Figure 4:
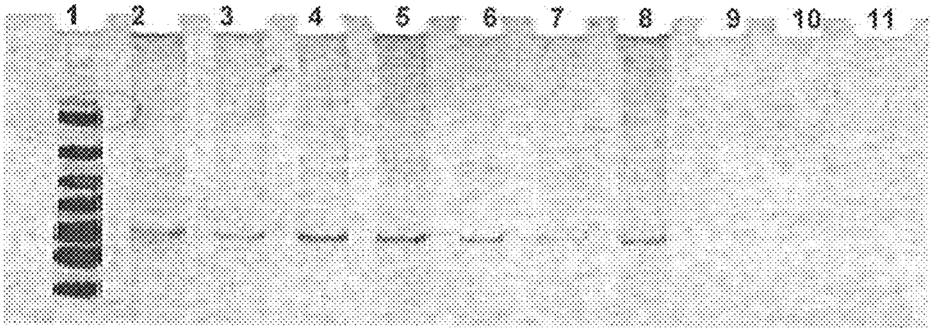
FIG. 4 shows polyadenalated fusion transcripts in breast samples invoked by the loss of the 3.4 kb segment from the mtgenome.

The mitochondrial 4977 "common deletion" and a 3.4kb deletion previously identified by the present Applicant in PCT application no. PCT/CA2007/001711 (the entire contents of which are incorporated by reference) result in unique open reading frames having active transcripts as identified by oligo-dT selection in prostate tissue (FIGS. 2 and 3). Examination of breast tissue samples also reveals the presence of a stable polyadenylated fusion transcript resulting from the 3.4 kb deletion (FIG. 4).

Reverse Transcriptase-PCR Protocol for Deletion Transcript Detection

RNA Isolation cDNA Synthesis

Total RNA was isolated from snap frozen prostate and breast tissue samples (both malignant and normal samples adjacent to tumours) using the Aurum™ Total RNA Fatty and Fibrous Tissue kit (Bio-Rad, Hercules, Calif.) following the manufacturer's instructions. Since in this experiment, genomic DNA contamination was to be avoided, a DNase I treatment step was included, using methods as commonly known in the art. RNA quantity and quality were determined with an ND-1000 spectrophotometer (NanoDrop® technologies). From a starting material of about 100 g, total RNA concentrations varied from 100-1000 ng/ul with a 260/280 ratio between 1.89-2.10. RNA concentrations were adjusted to 100 ng/ul and 2 ul of each template were used for first strand DNA synthesis with SuperScript™ First-Strand Synthesis System for RT-PCR (Invitrogen) following the manufacturer's instructions. In order to identify stable polyadenylated fusion transcripts, Oligo(dT) primers that target transcripts with poly-A tails were used.

PCR

Real time PCR was performed using 5 ul of each cDNA template with the iQ™ SYBR® Green Supermix (Bio-Rad, Hercules, Calif.) on DNA Engine Opticon® 2 Continuous Fluorescence Detection System (Bio-Rad, Hercules, Calif.). The primer pairs targeting the 4977 bp deletion are; 8416F 5'-CCTTACACTATTCCTCATCAC-3' (SEQ ID NO: 53), 13637R 5'-TGACCTGTTAGGGTGAGAAG-3' (SEQ ID NO: 54), and those for the 3.4 kb deletion are; ND4LF 5'-TCGCTCACACCTCATATCCTC-3' (SEQ ID NO: 55), ND5R 5'-TGTGATTAGGAGTAGGGTTAGG-3' (SEQ ID NO: 56). The reaction cocktail included: 2×SYBR® Green Supermix (100 mM KCL, 40 mM Tris-HCl, pH 8.4, 0.4 mM of each dNTP [dATP, dCTP, dGTP, and dTTP], iTaq™ DNA polymerase, 50 units/ml, 6 mM $MgCl_2$, SYBR® Green 1, 20 nM flourescein, and stabilizers), 250 nM each of primers, and $ddH_2O$. PCR cycling parameters were as follows; (1) 95° C. for 2 min, (2) 95° C. for 30 sec, (3) 55° C. (for the 4977 bp deletion) and 63° C. (for the 3.4 kb deletion) for 30 sec, (4) 72° C. for 45 sec, (5) plate read, followed by 39 cycles of steps 3 to 5, and final incubation at 4° C. Apart from cycling threshold and melting curve analysis, samples were run on agarose gels for specific visualization of amplification products (see FIGS. 2 to 4).

FIG. 2 is an agarose gel showing polyadenalated fusion transcripts in prostate samples invoked by the loss of 3.4 kb from the mitochondrial genome. Legend for FIG. 2: B-blank, Lanes 1-6 transcripts detected in cDNA; lanes 7-12 no reverse transcriptase (RT) controls for samples in lanes 1-6.

FIG. 3 shows polyadenalated fusion transcripts in prostate samples invoked by the loss of the 4977 kb common deletion. Legend for FIG. 3: B-blank, Lanes 1-6 transcripts detected in cDNA; lanes 7-12 no RT controls for samples in lanes 1-6.

FIG. 4 shows polyadenalated fusion transcripts in breast samples invoked by the loss of 3.4 kb from the mtgenome. Legend for FIG. 4: Lanes 2-8 transcripts from breast cDNAs; lane 9 negative (water) control; lanes 10 and 11, negative, no RT, controls for samples in lanes 2 and 3.

These results demonstrate the existence of stable mitochondrial fusion transcripts.

Example 2: Identification and Targeting of Fusion Products

Various hybridization probes were designed to detect, and further demonstrate the presence of novel transcripts resulting from mutated mitochondrial genomes, such as the 3.4 kb deletion. For this purpose, a single-plex branched DNA platform for quantitative gene expression analysis (QuantiGene 2.0™, Panomics™) was utilized. The specific deletions and sequences listed in this example are based on their relative positions with the entire mtDNA genome, which is recited in SEQ ID NO: 1. The nucleic acid sequences of the four transcript to which the probes were designed in this example are identified herein as follows: Transcript 1 (SEQ ID NO: 18), Transcript 2 (SEQ ID NO: 19), Transcript 3 (SEQ ID NO: 20) and Transcript 4 (SEQ ID NO: 21).

An example of a continuous transcript from the 3.4 kb mitochondrial genome deletion occurs with the genes ND4L (NADH dehydrogenase subunit 4L) and ND5 (NADH dehydrogenase subunit 5). A probe having a complementary sequence to SEQ ID NO: 19, was used to detect transcript 2. The repetitive elements occur at positions 10745-10754 in ND4L and 14124-14133 in ND5.

Figure 5A:
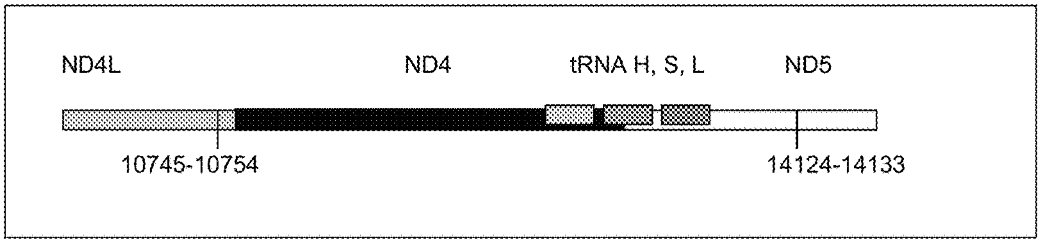
FIGS. 5A and 5B show an example of a mitochondrial DNA region before and after splicing of genes.
Figure 5B:
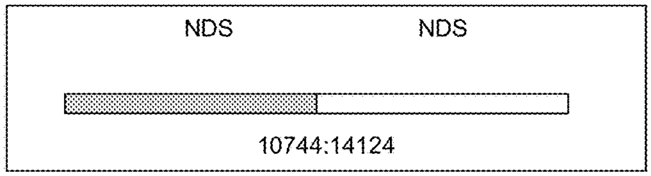
Figure 6A:
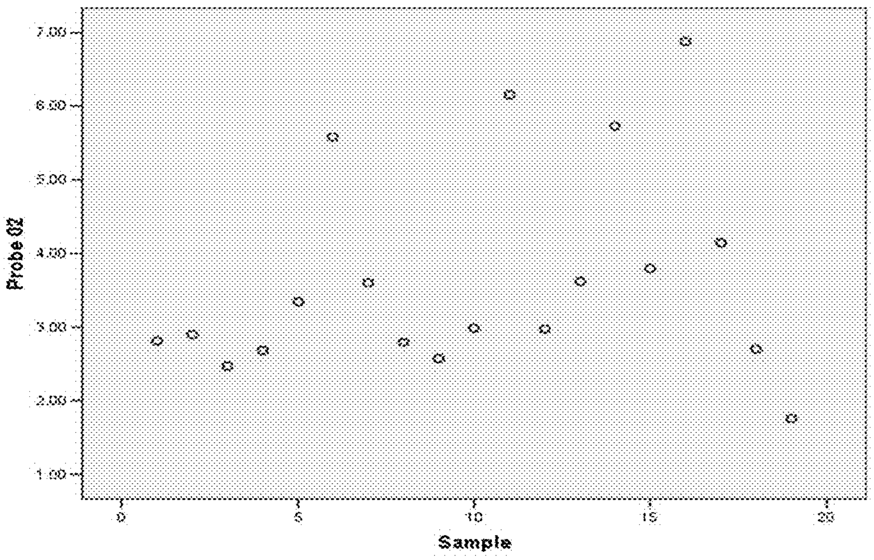
FIGS. 6A to 6BB illustrate the results for transcripts 2, 3, 8, 9, 10, 11 and 12 of the invention in the identification of colorectal cancer tumours.
Figure 6B:
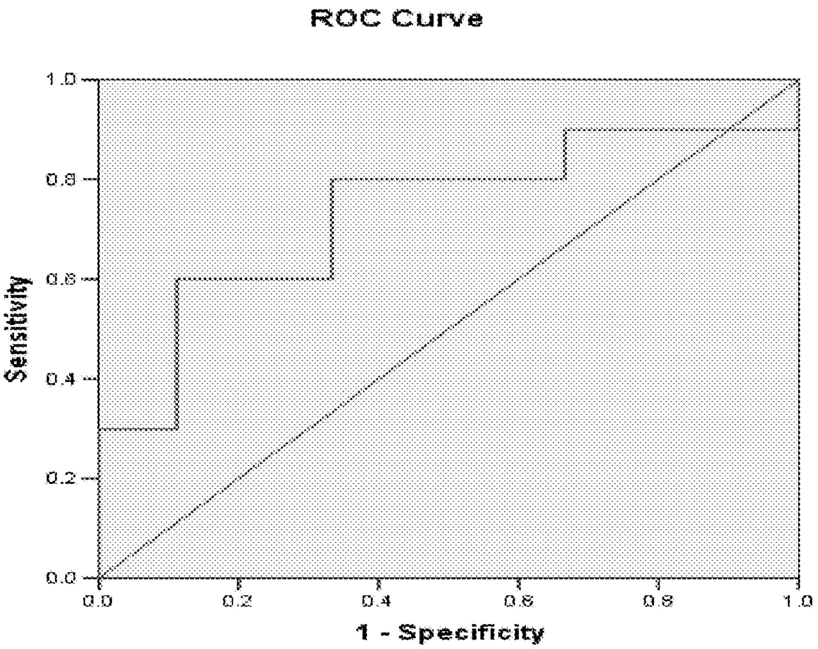
Figures 6D, 6E:
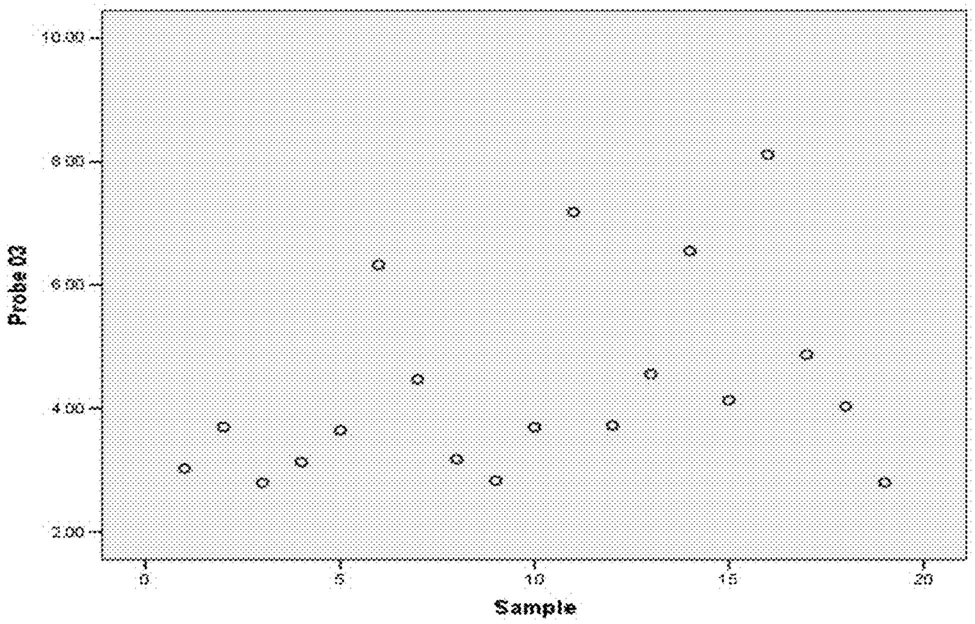
Figure 6F:
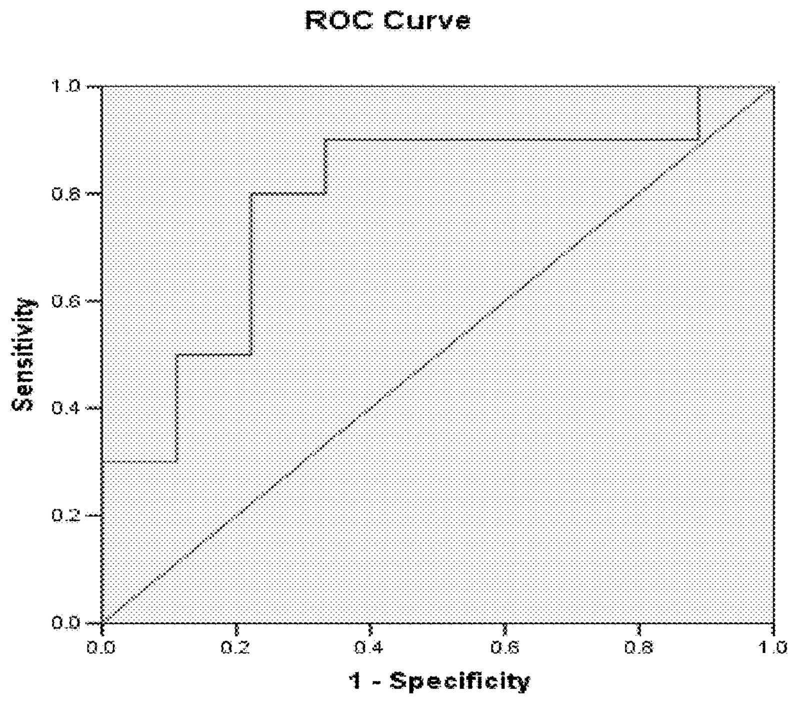
Figures 6H, 6I:
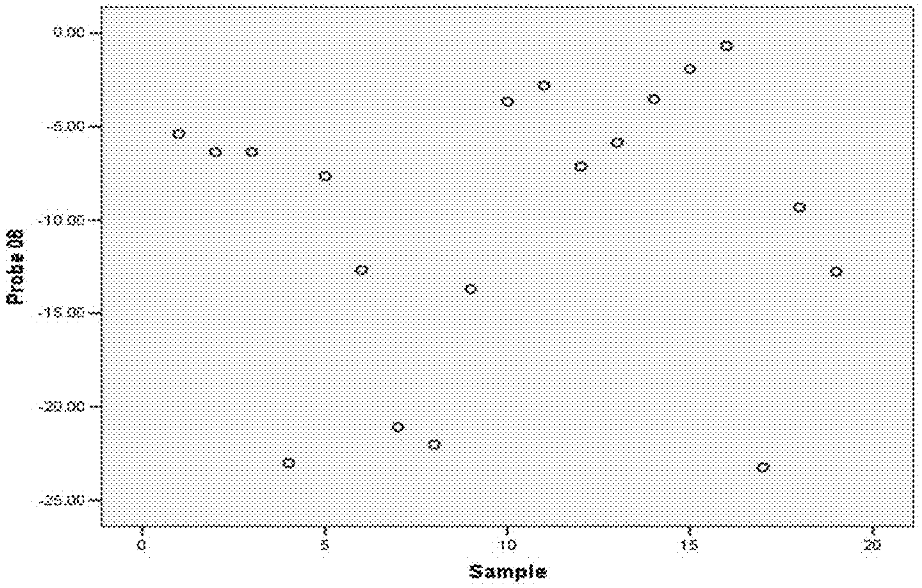
Figure 6J:
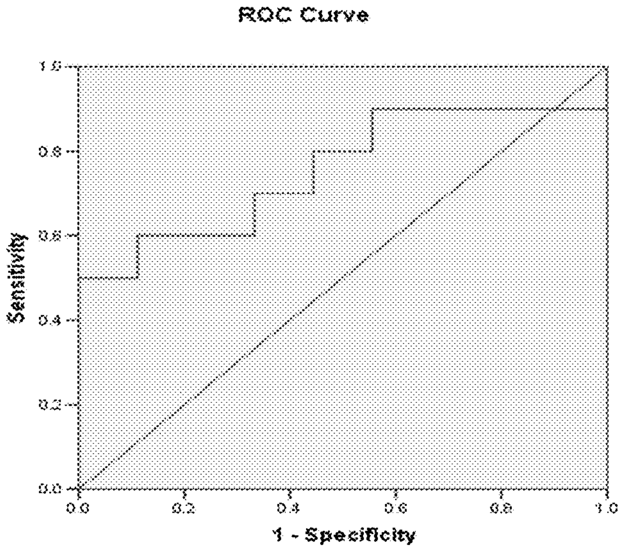
Figures 6L, 6M:
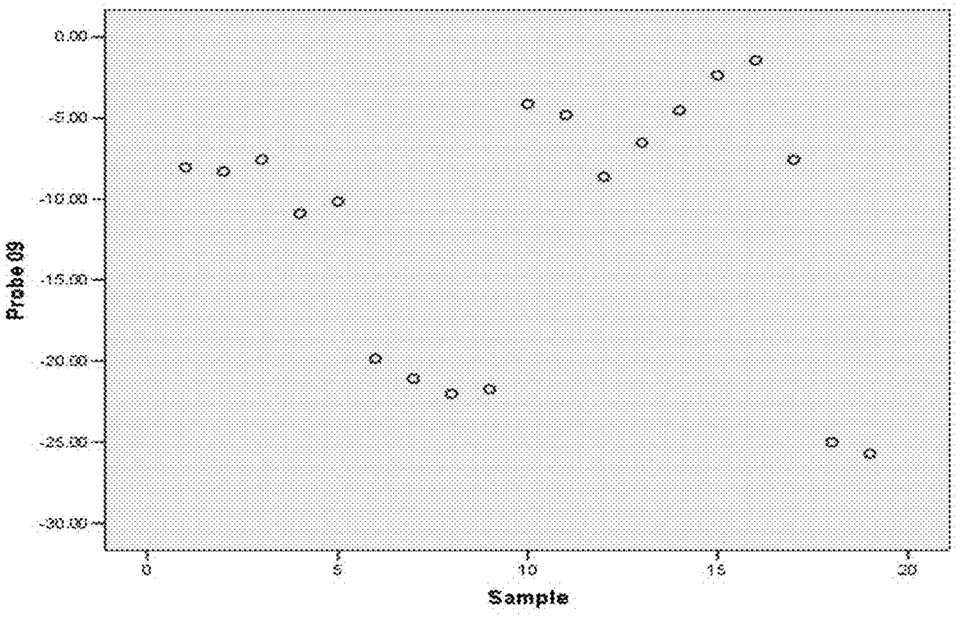
Figure 6N:
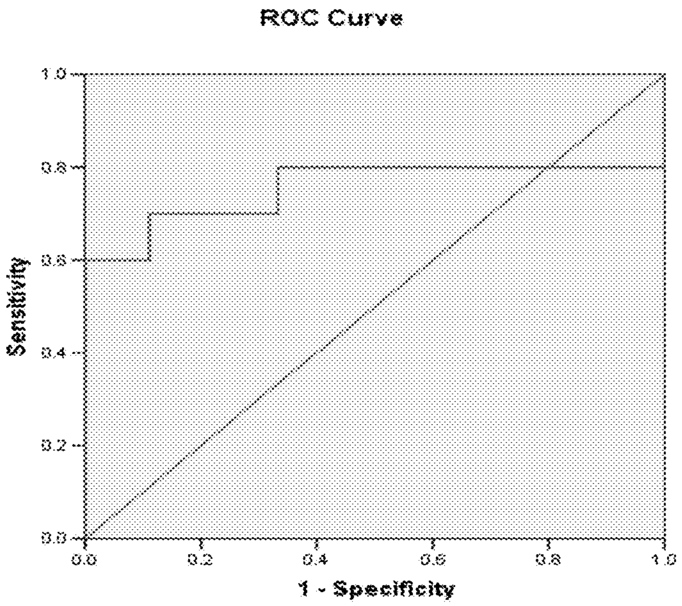
Figures 6P, 6Q:
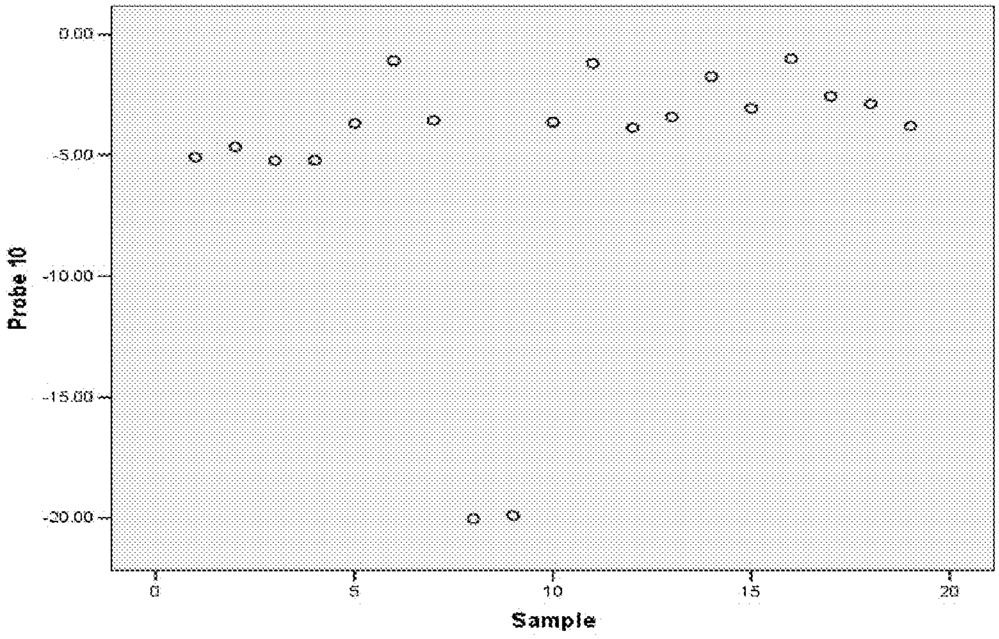
Figure 6R:
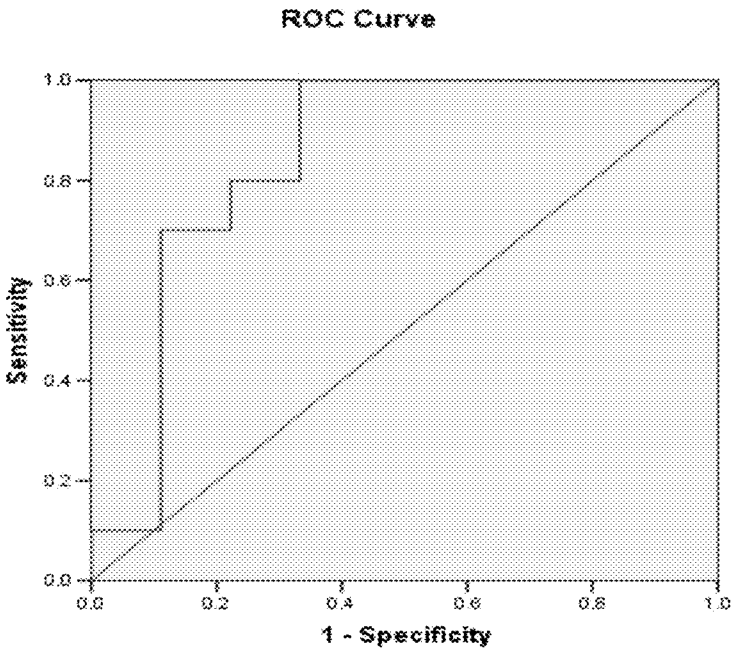
Figures 6T, 6U:
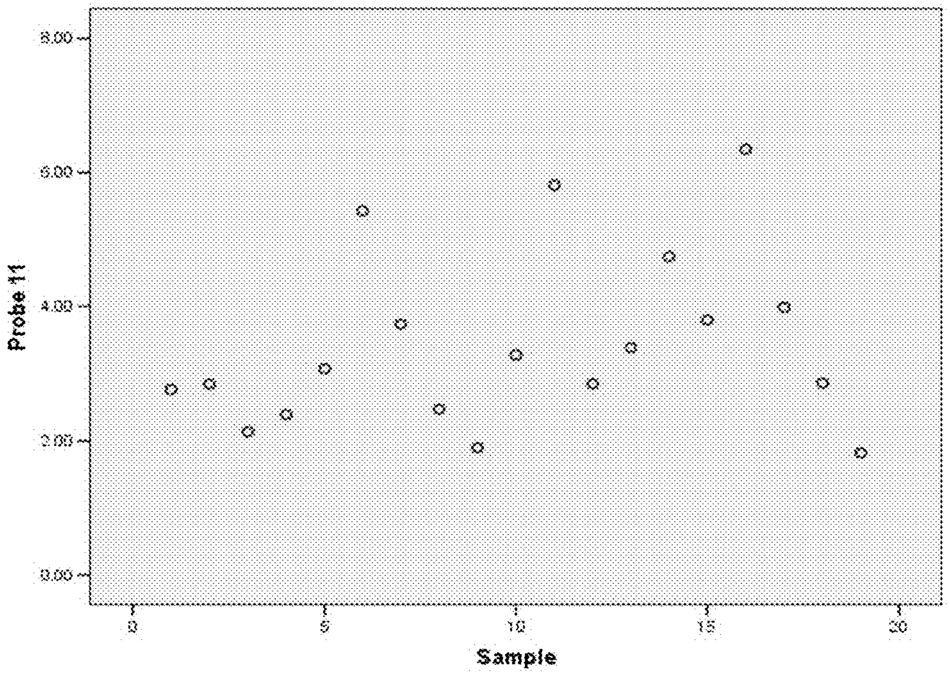
Figure 6V:
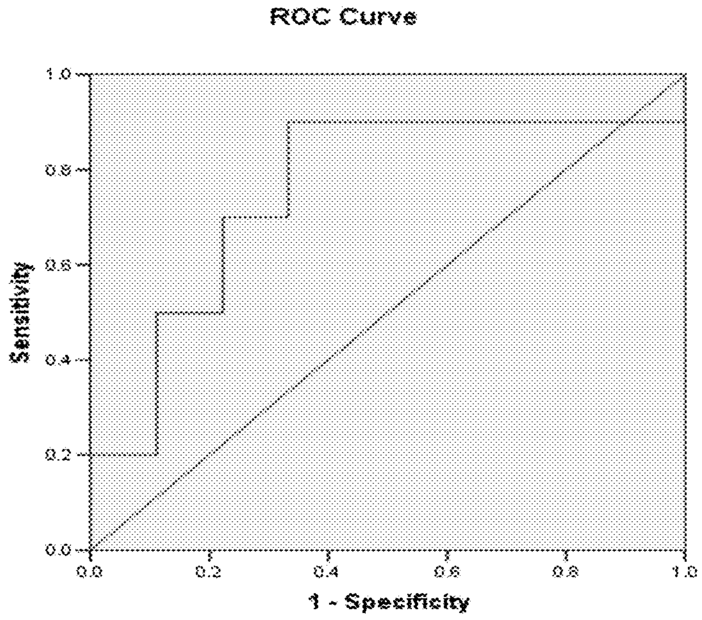
Figures 6X, 6Y:
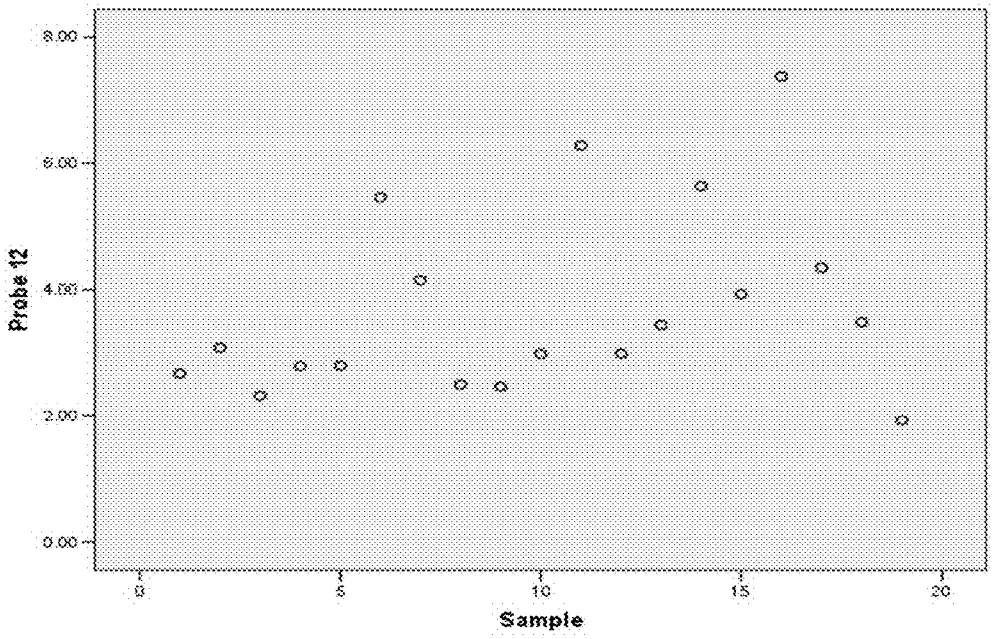
Figure 6Z:
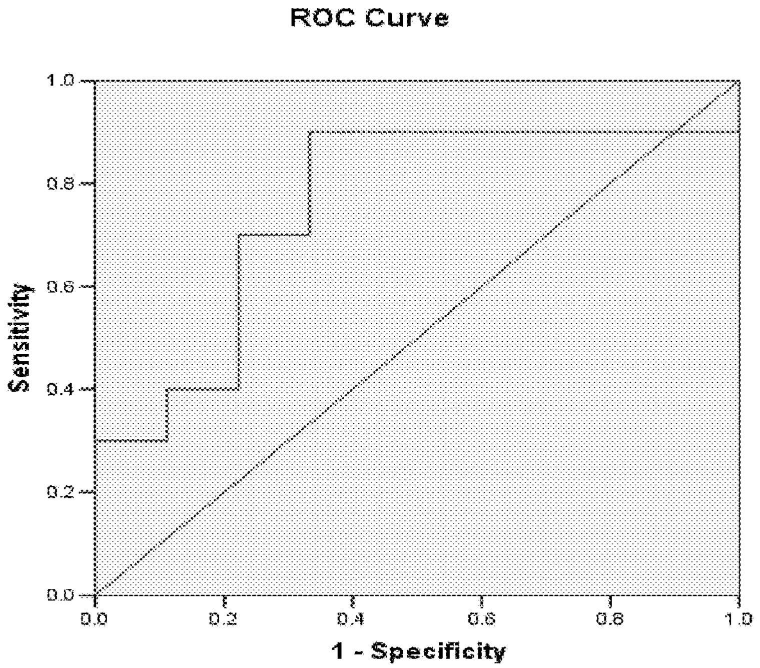
Figure 7A:
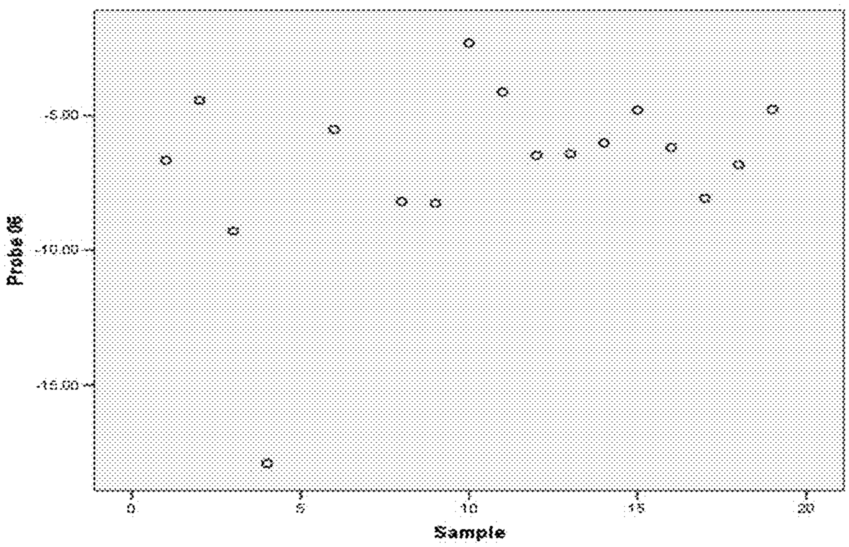
FIGS. 7A to 7P illustrate the results for transcripts 6, 8, 10 and 20 of the invention in the identification of lung cancer tumours.
Figure 7B:
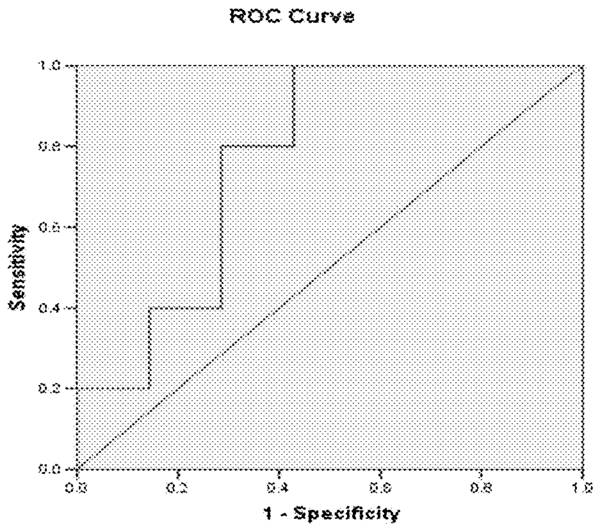
Figures 7D, 7E:
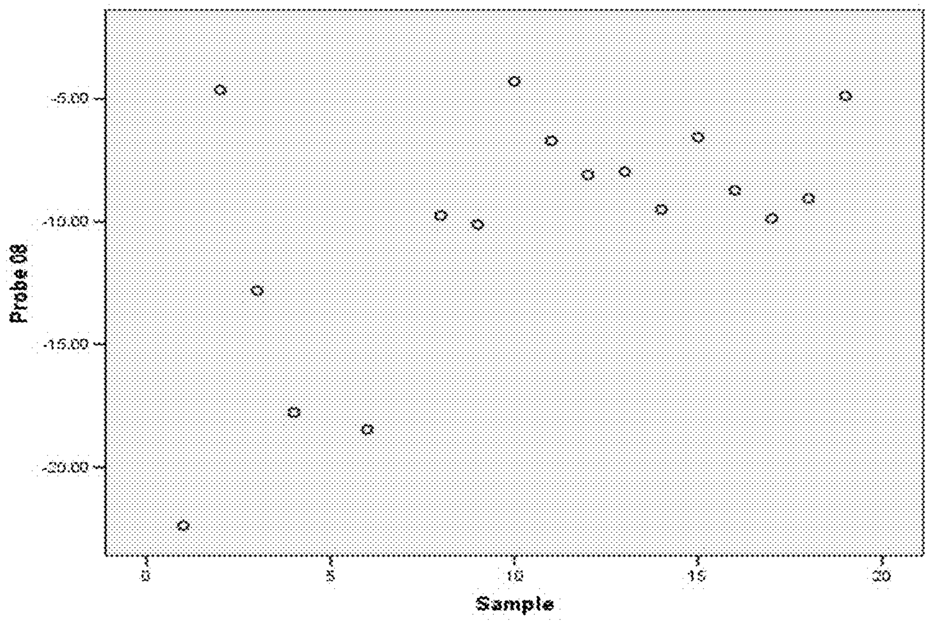
Figure 7F:
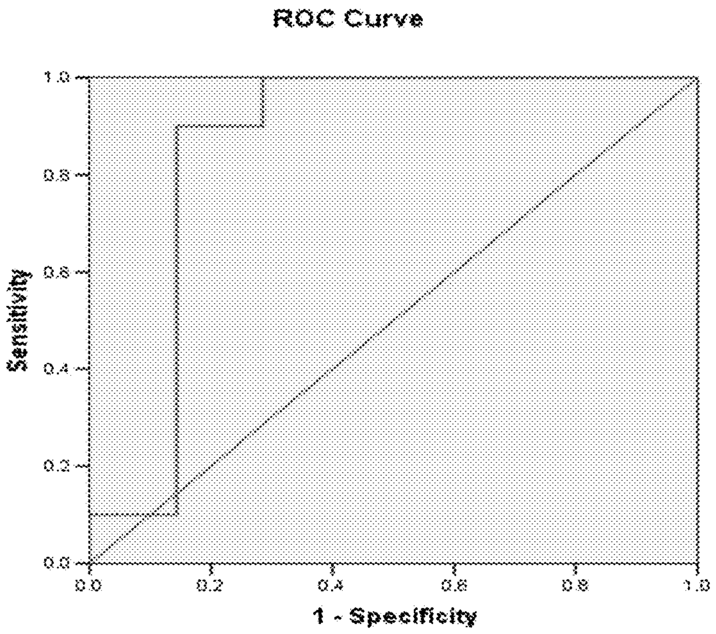
Figures 7H, 7I:
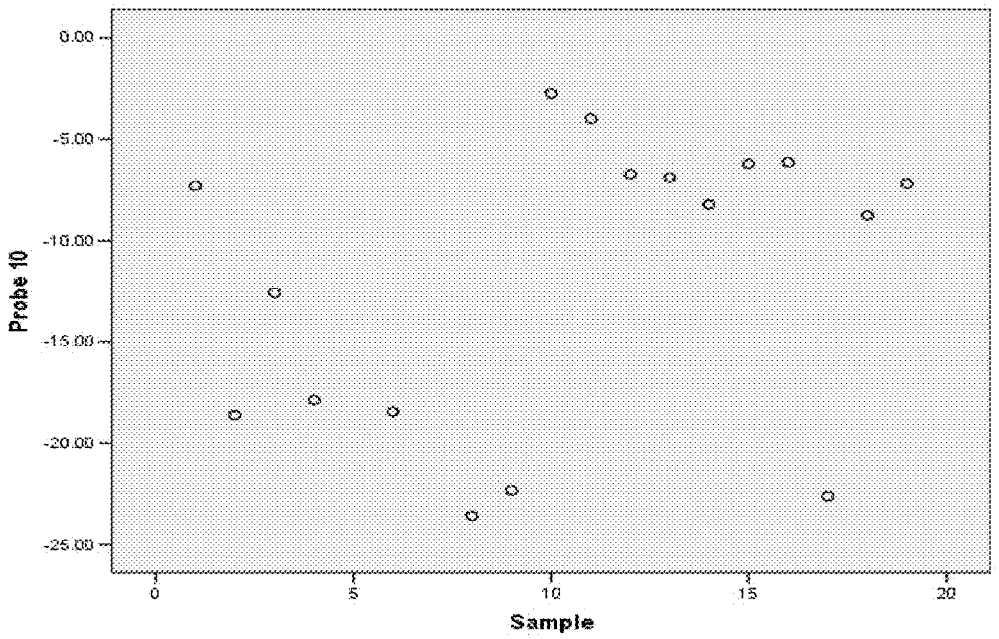
Figure 7J:
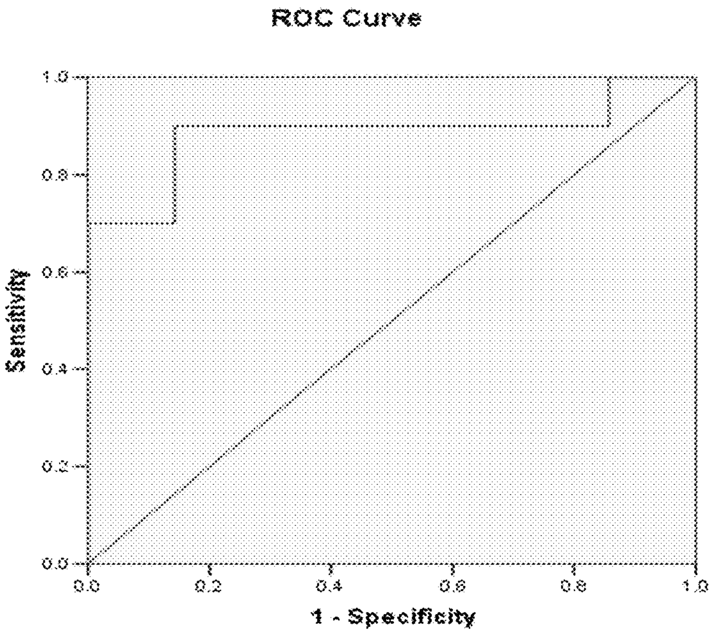
Figures 7L, 7M:
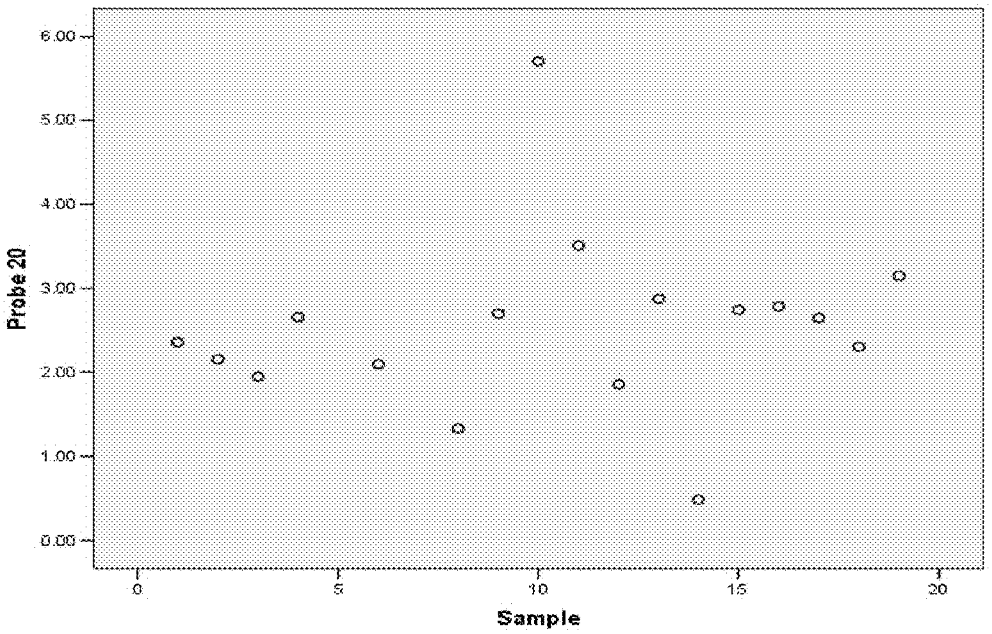
Figure 7N:
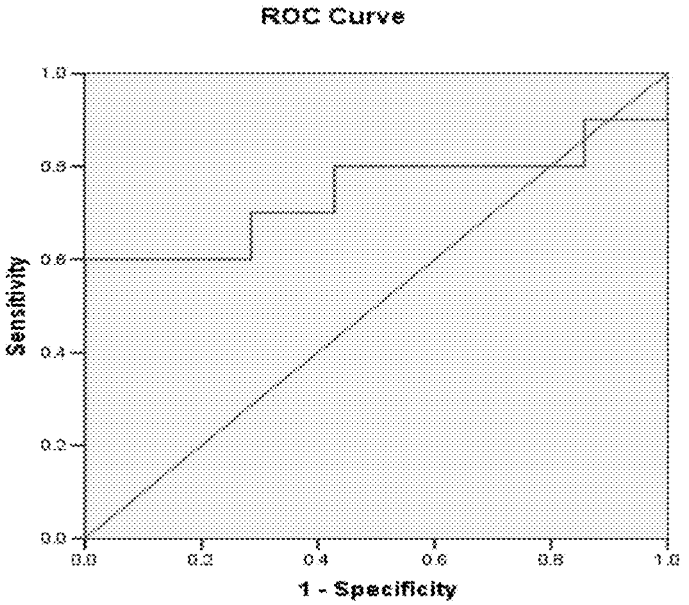
Figures 7P, 8A:
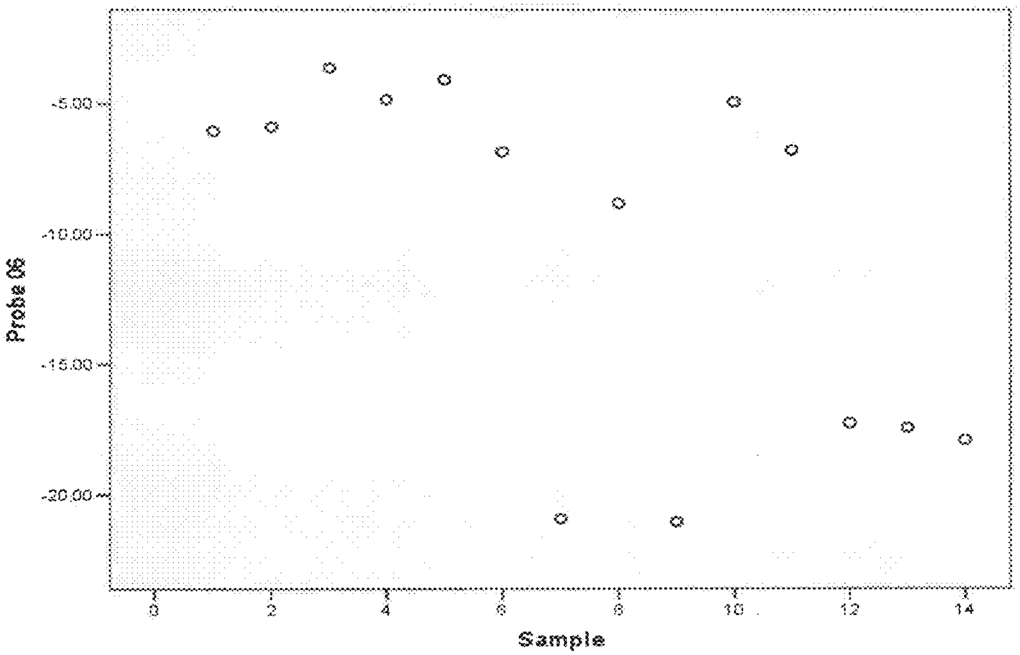
FIGS. 8A to 8BB illustrate the results for transcripts 6, 10, 11, 14, 15, 16 and 20 of the invention in the identification of melanomas.
Figure 8B:
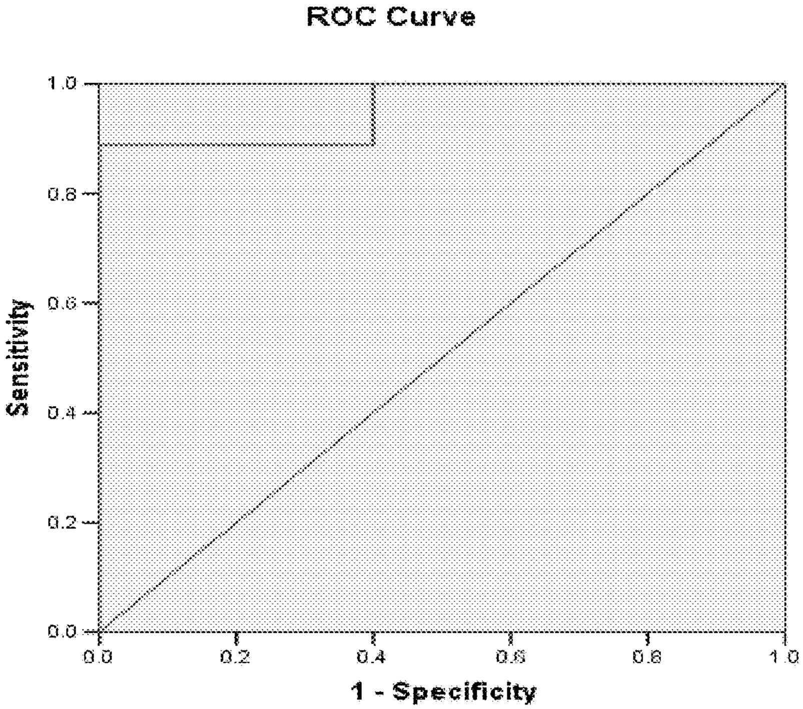
Figures 8D, 8E:
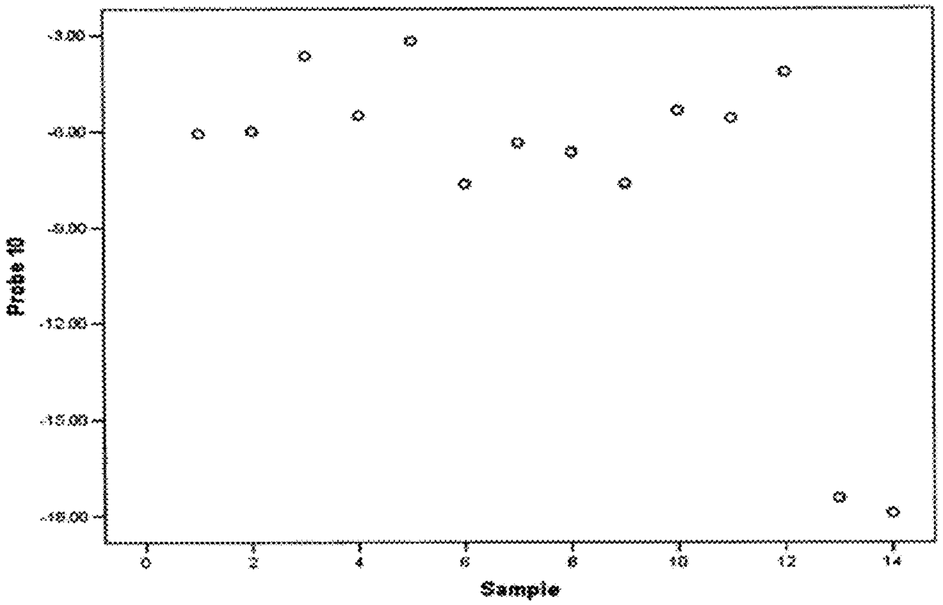
Figure 8F:
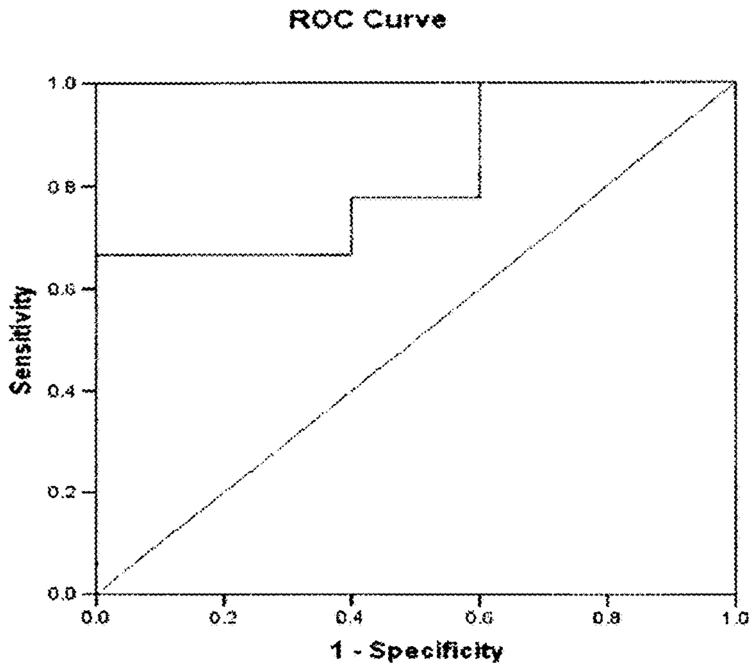
Figures 8H, 8I:
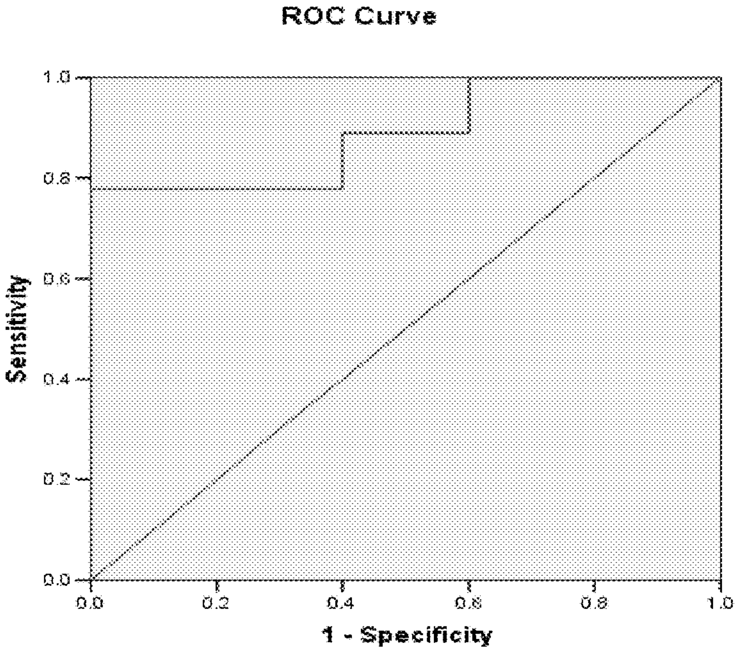
Figure 8J:
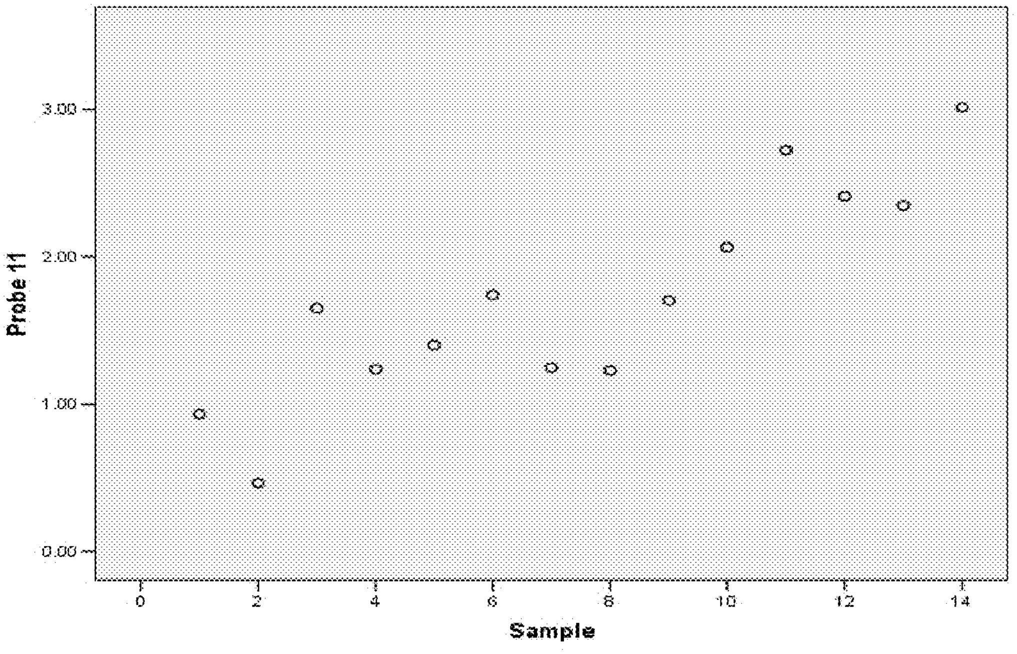
Figure 8K:
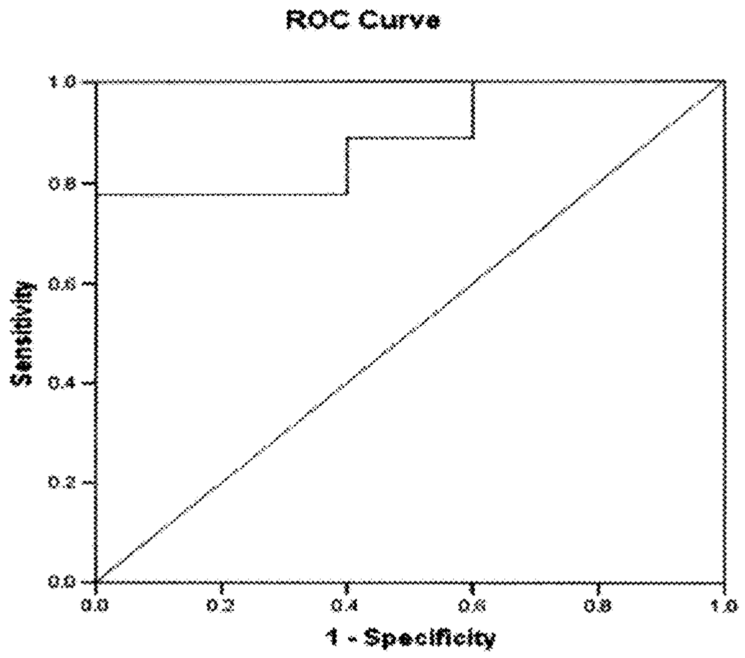
Figure 8N:
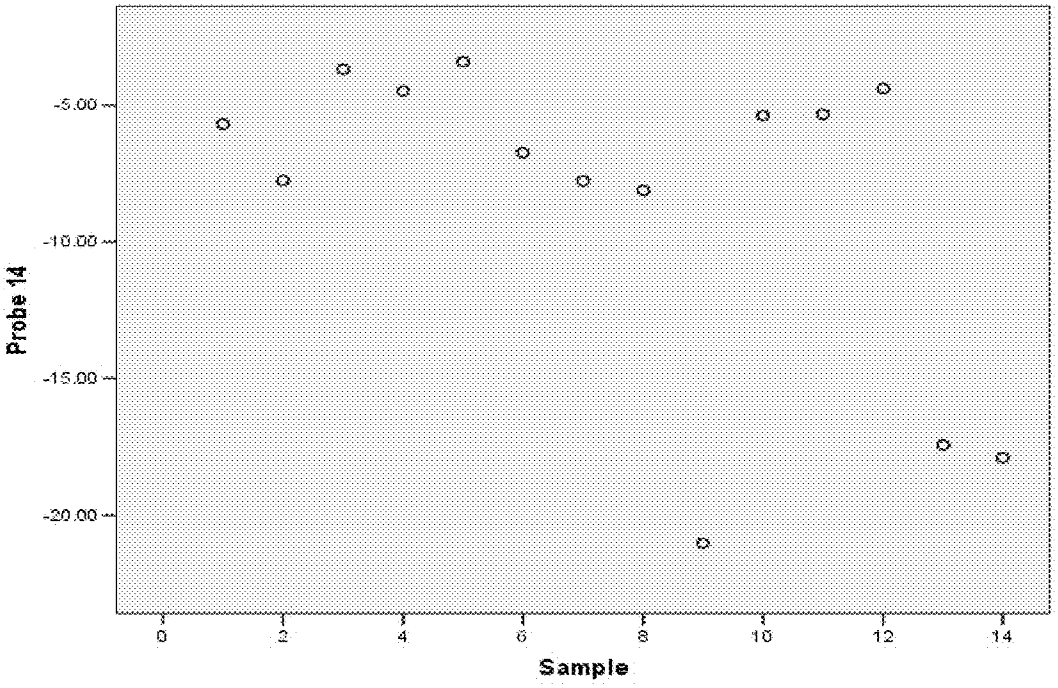
Figure 8O:
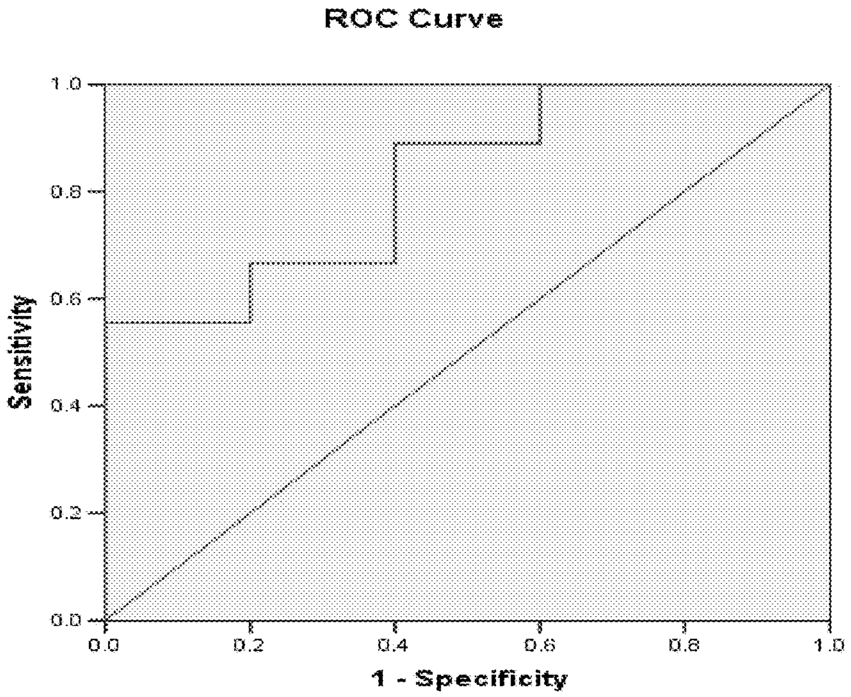
Figure 8R:
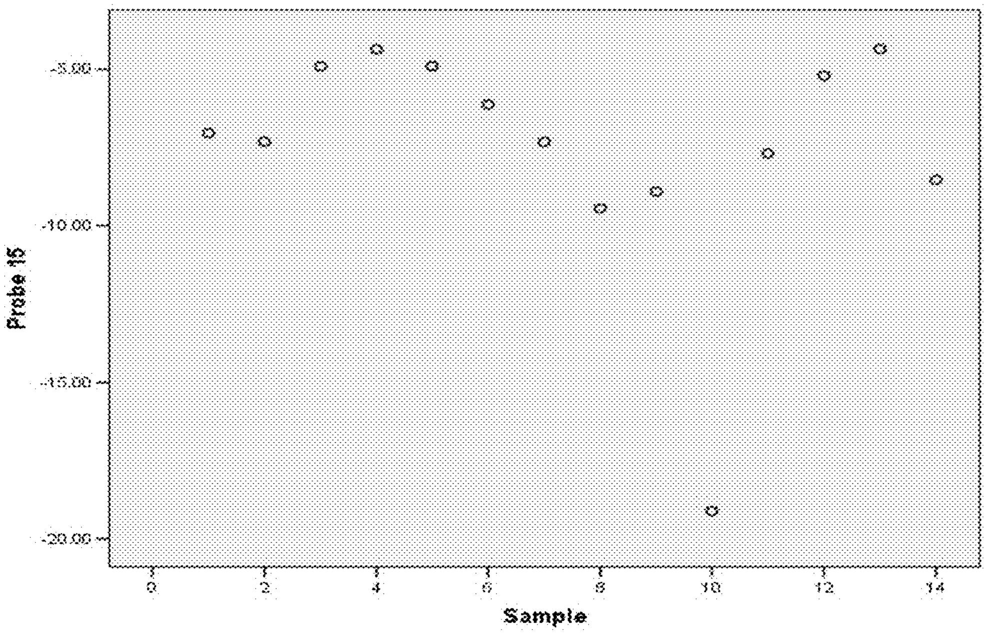
Figure 8S:
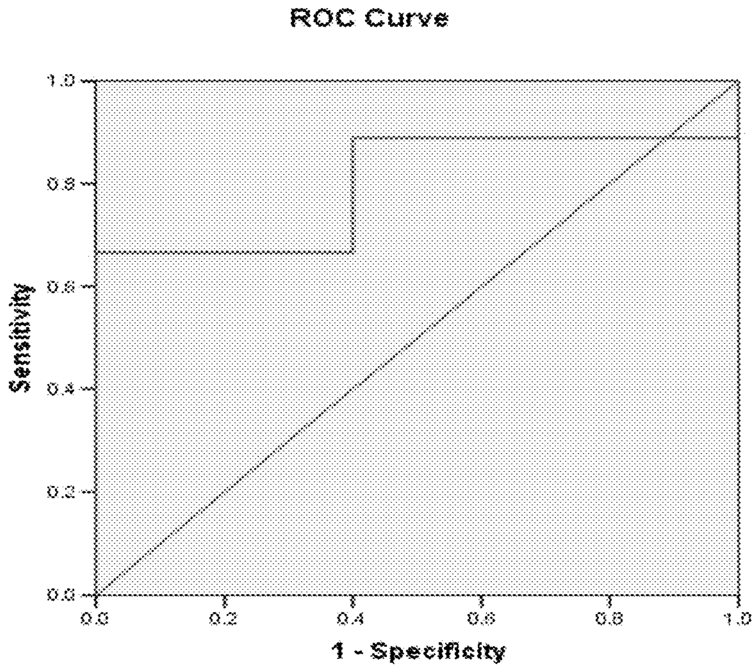
Figure 8V:
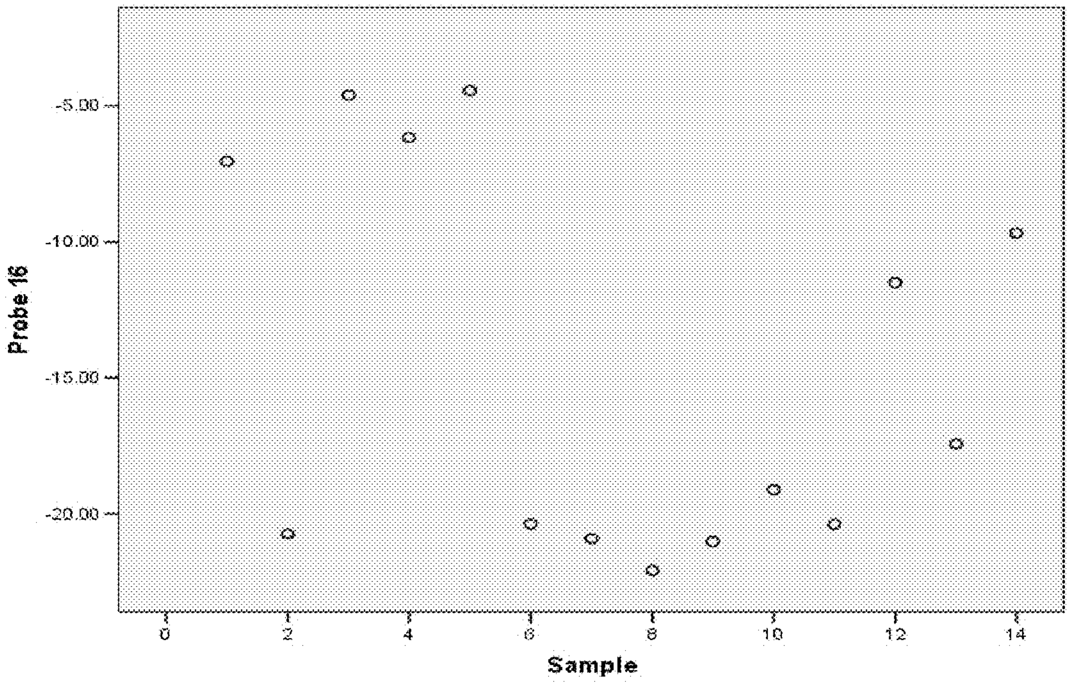
Figures 8X, 8Y:
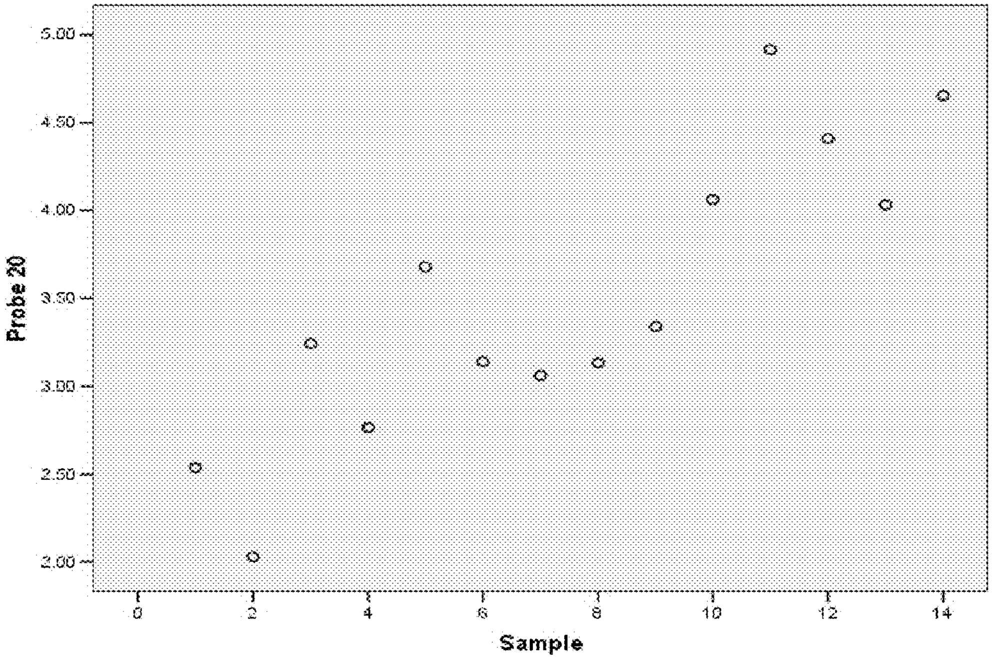
Figure 8Z:
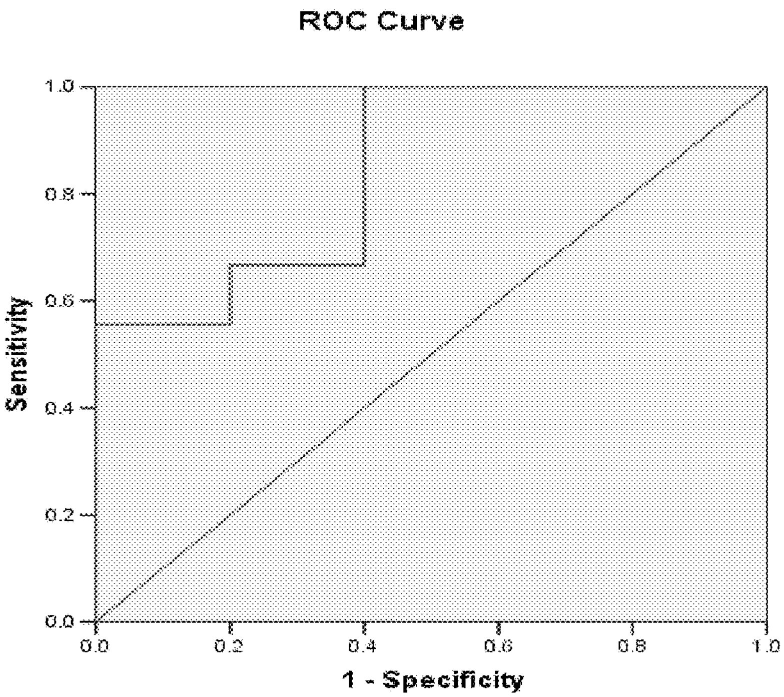
Figure 9A:
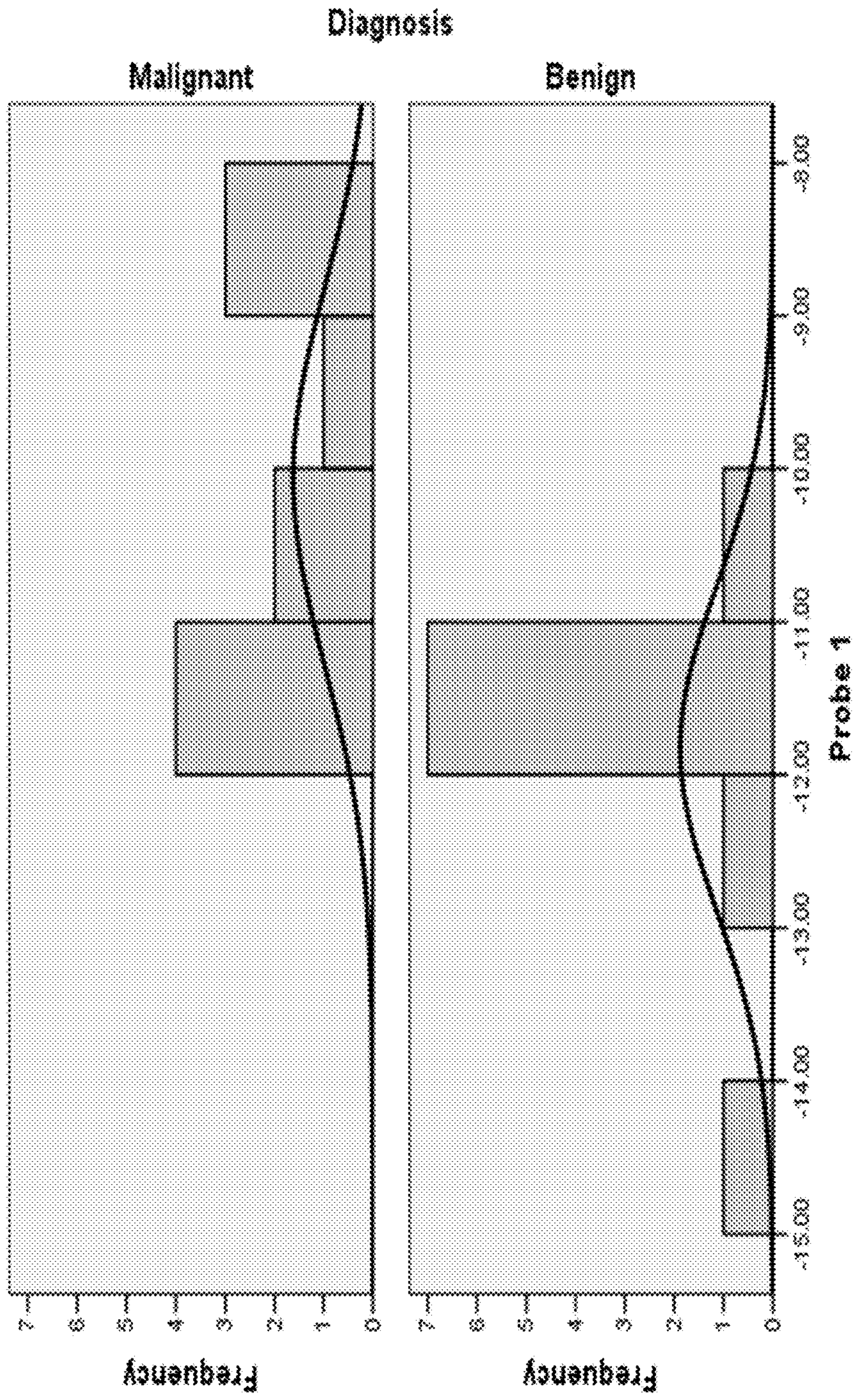
FIGS. 9A to 9NN illustrate the results for transcripts 1, 2, 3, 6, 11, 12, 15 and 20 of the invention in the identification of ovarian cancer.
Figure 9C:
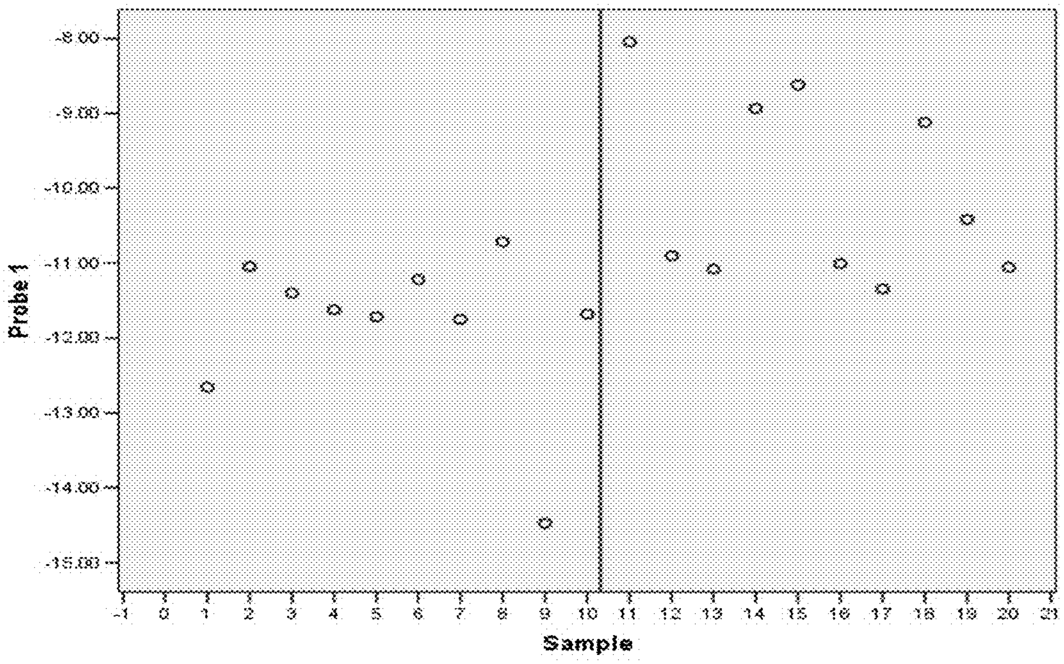
Figure 9D:
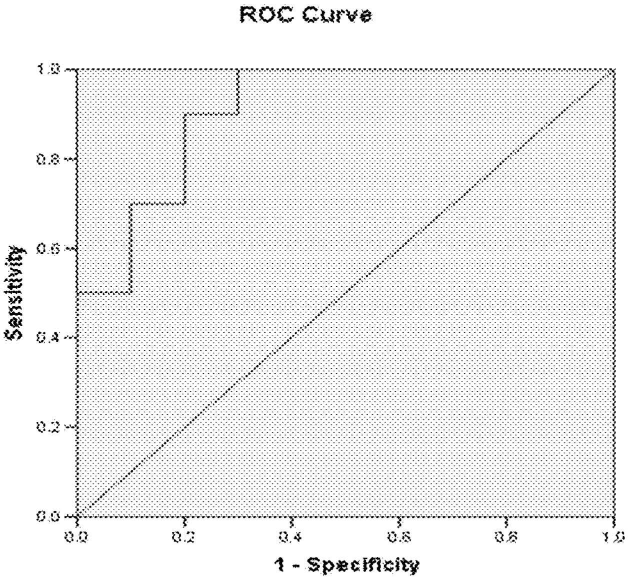
Figure 9F:
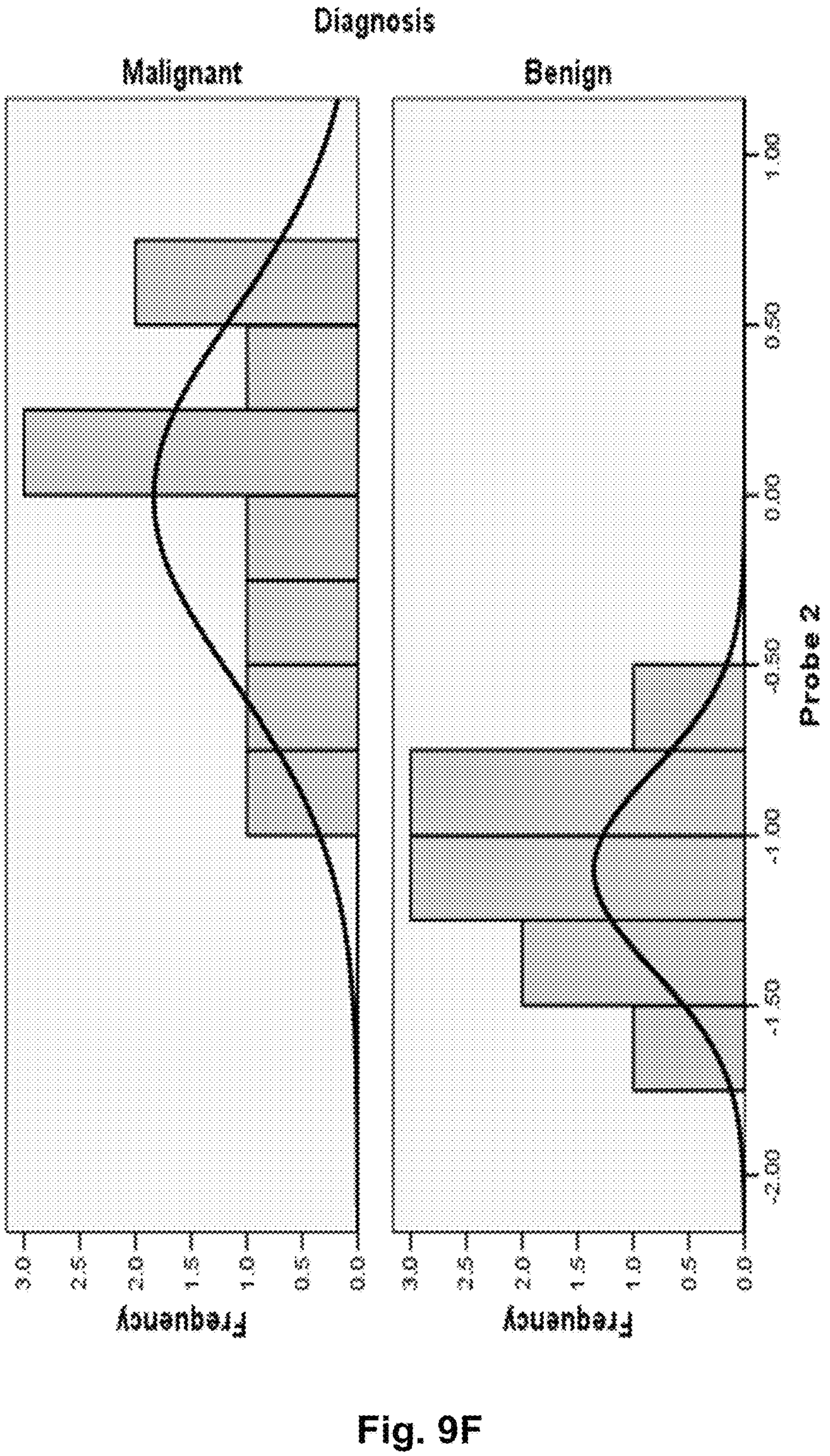
Figure 9H:
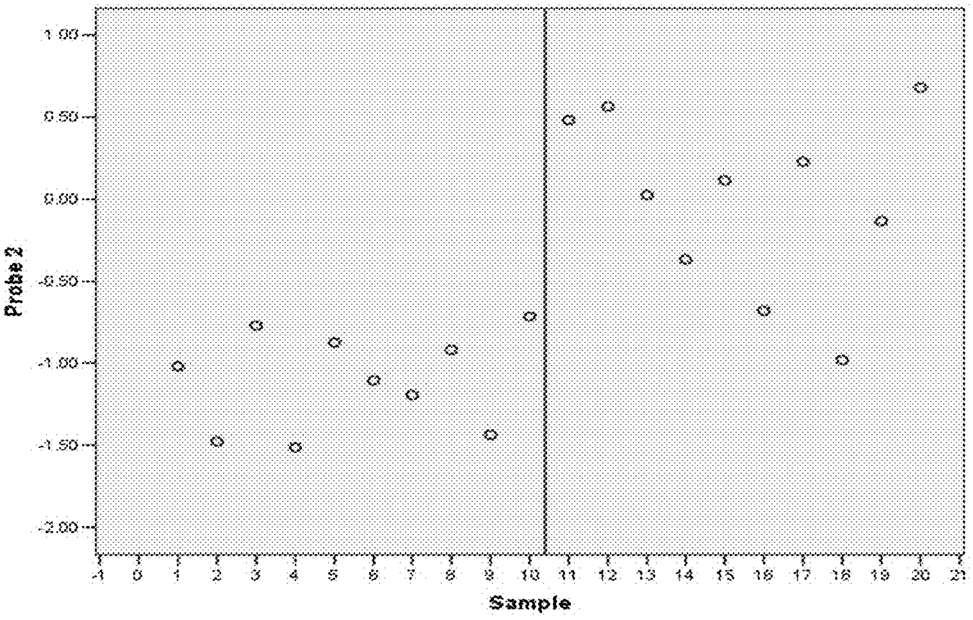
Figures 9I, 9J:
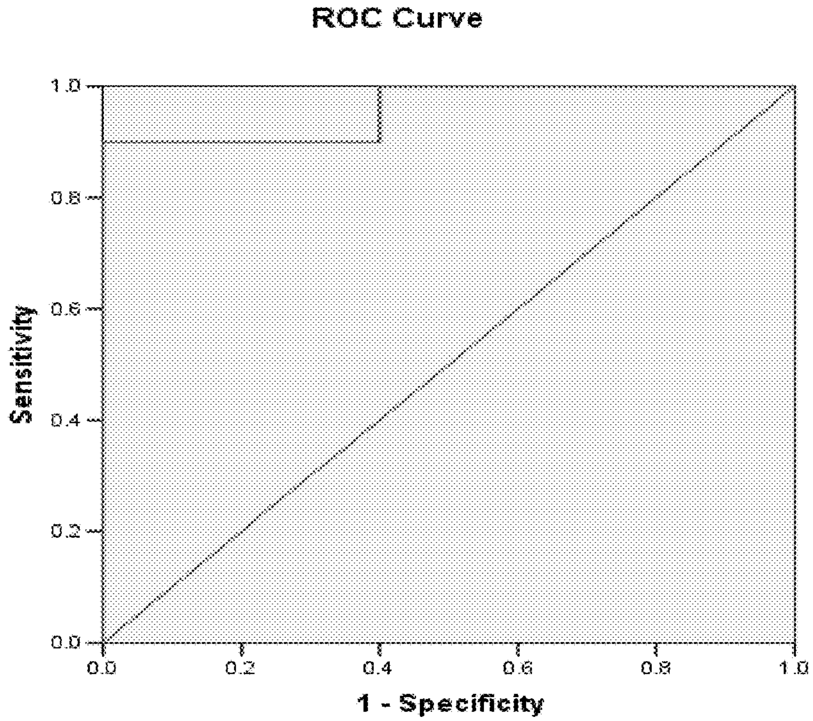
Figure 9K:
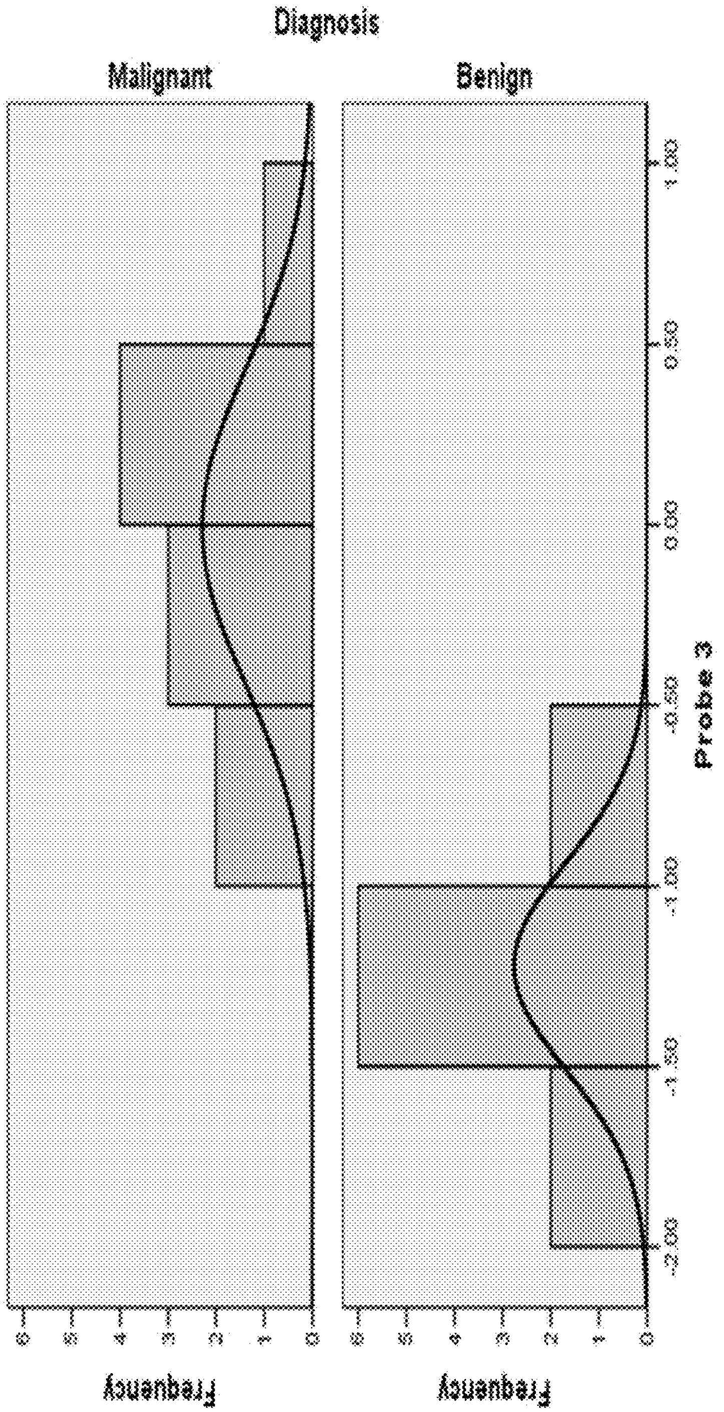
Figure 9M:
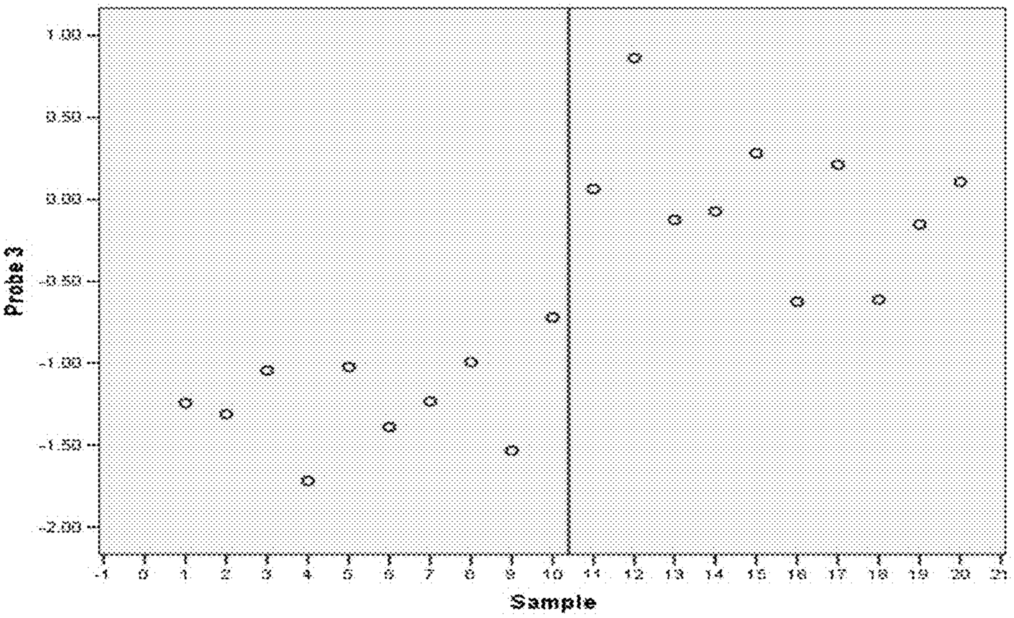
Figure 9N:
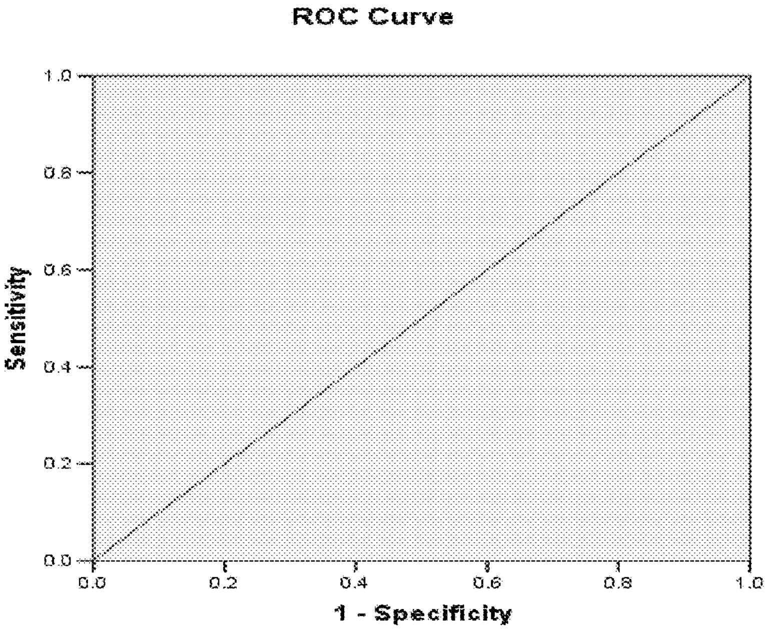
Figure 9P:
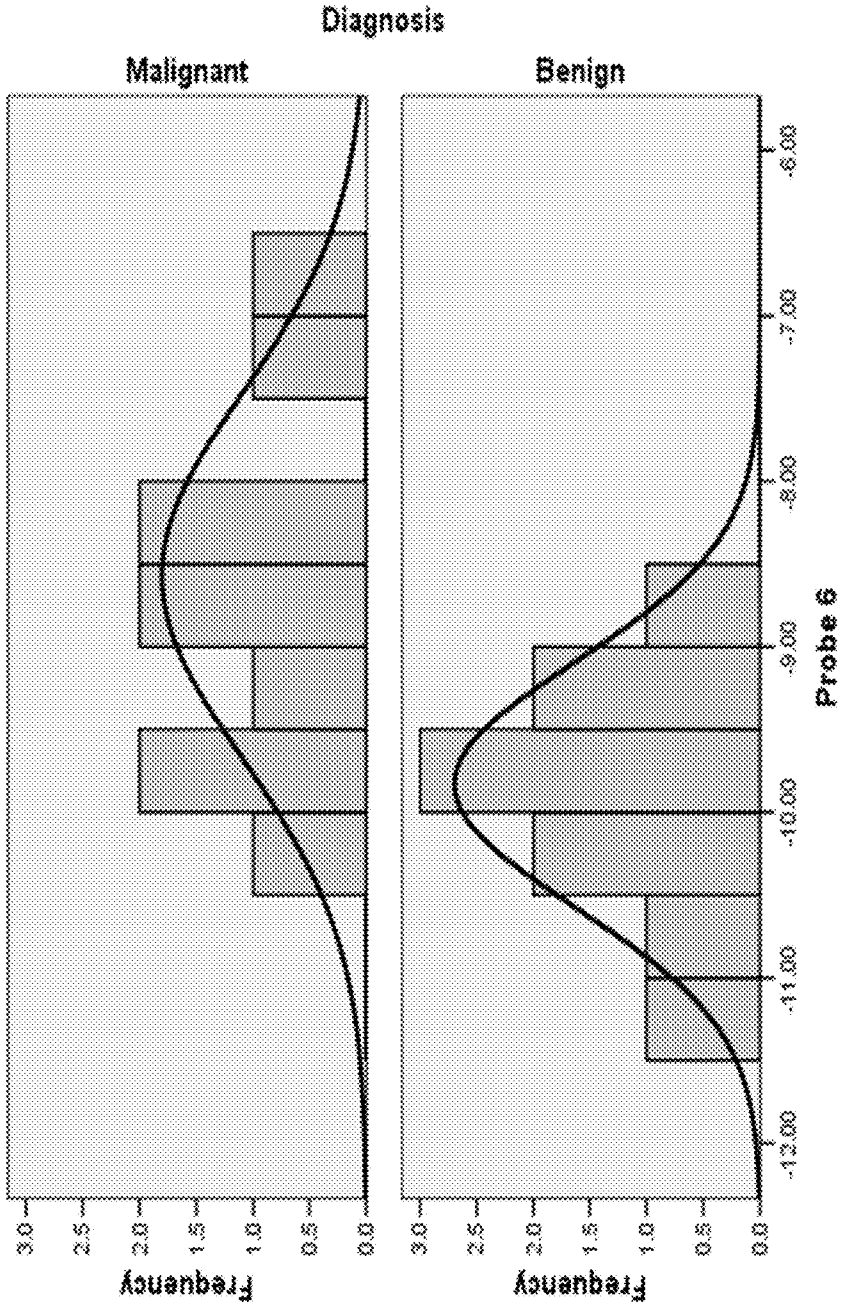
Figure 9R:
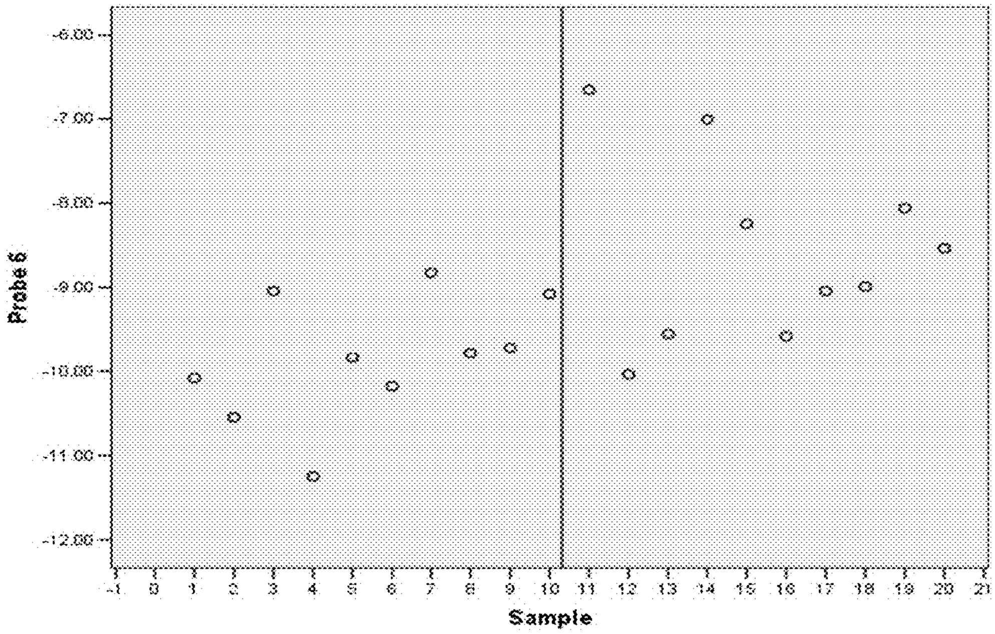
Figures 9S, 9T:
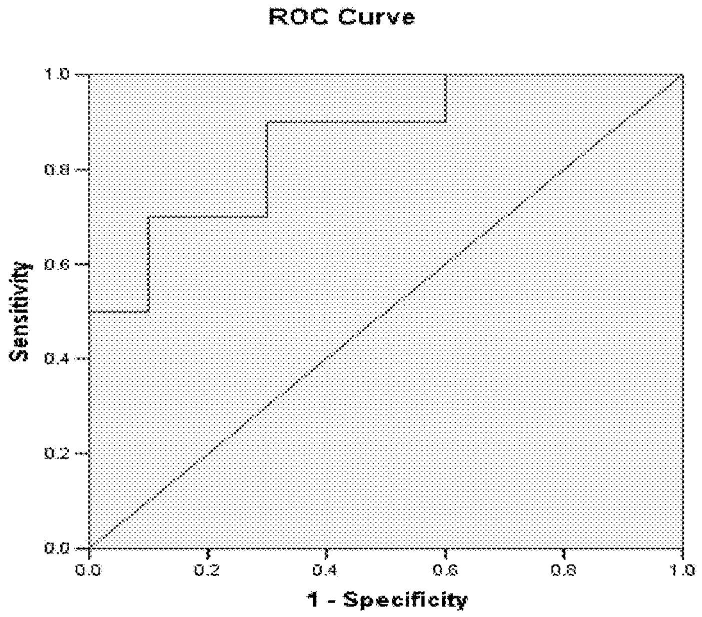
Figure 9U:
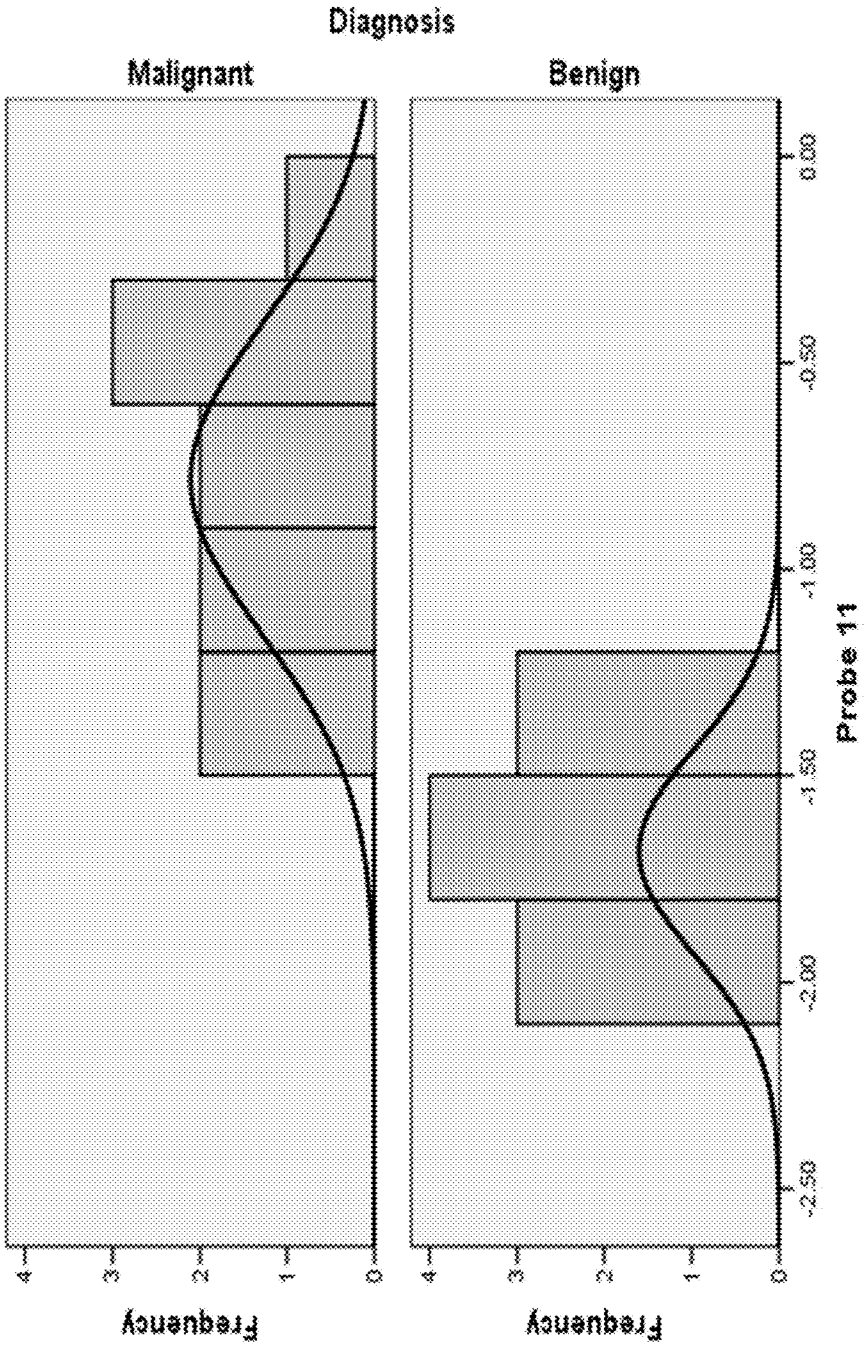
Figure 9W:
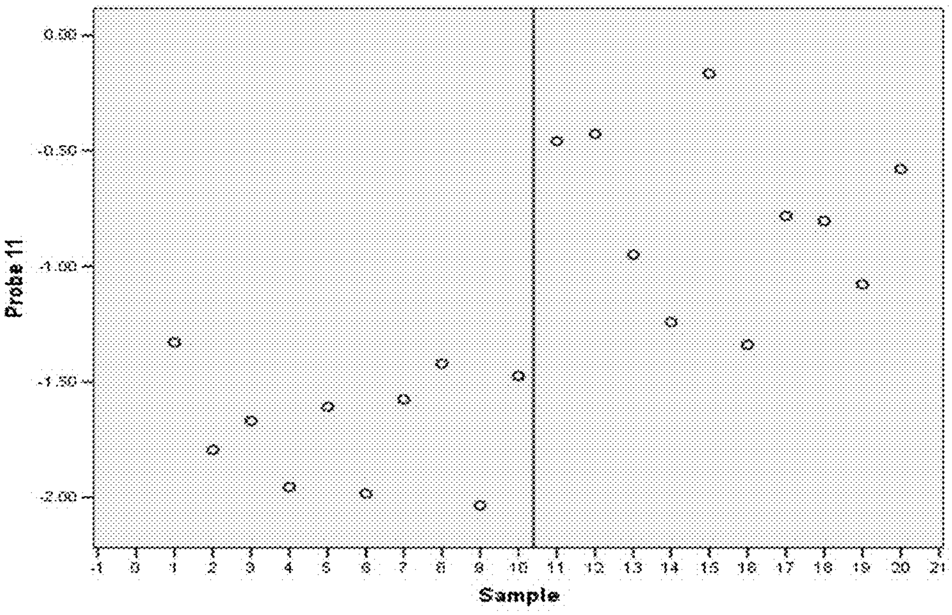
Figure 9X:
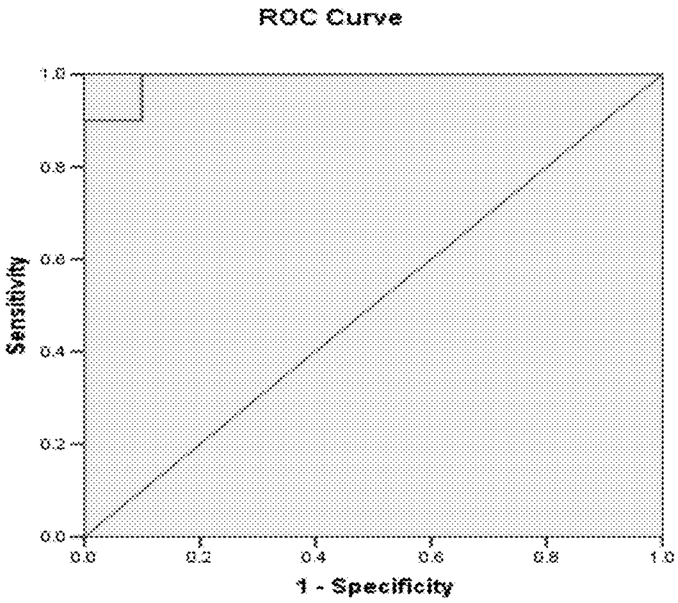
Figure 9Z:
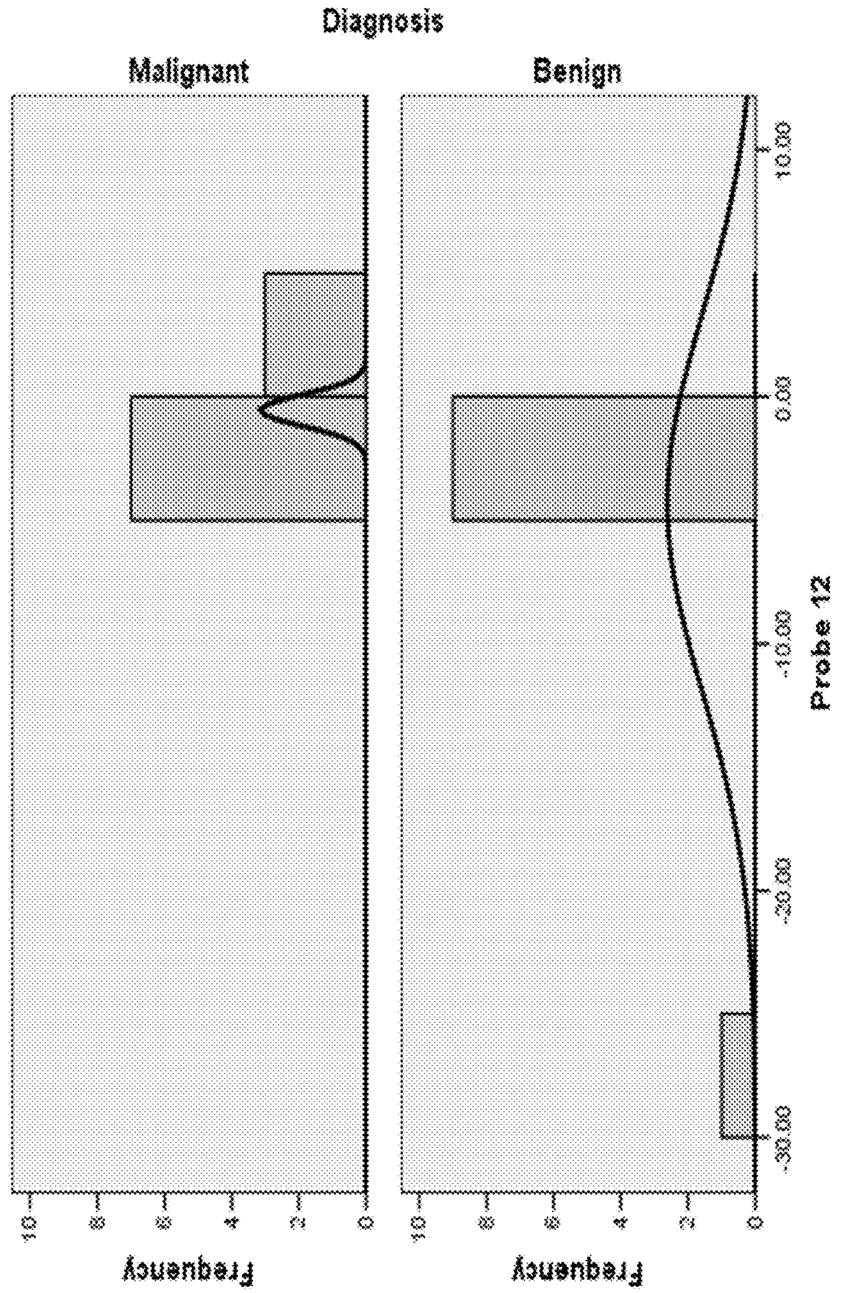
Figure 9B:
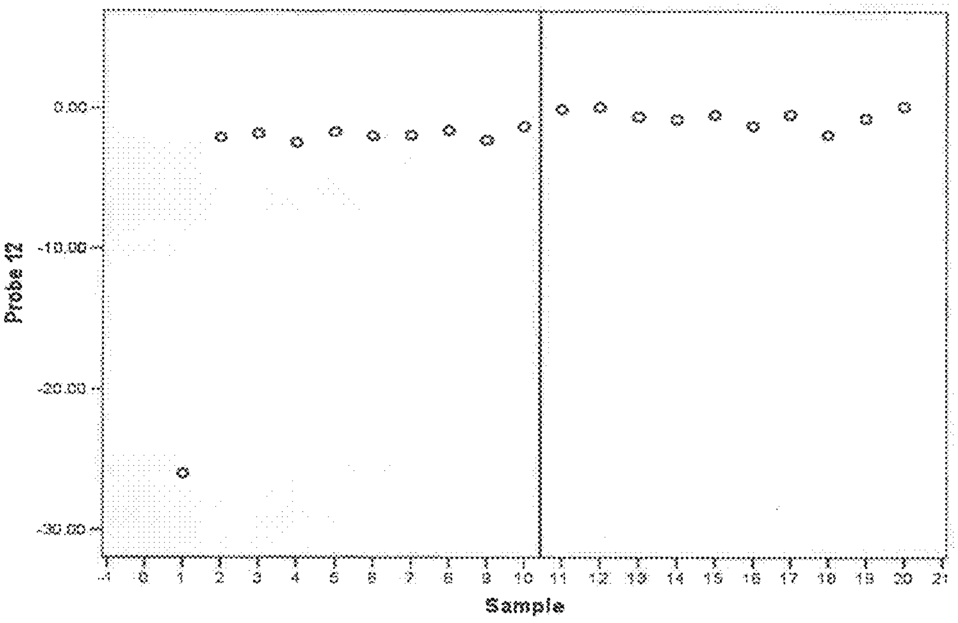
Figure 9C:
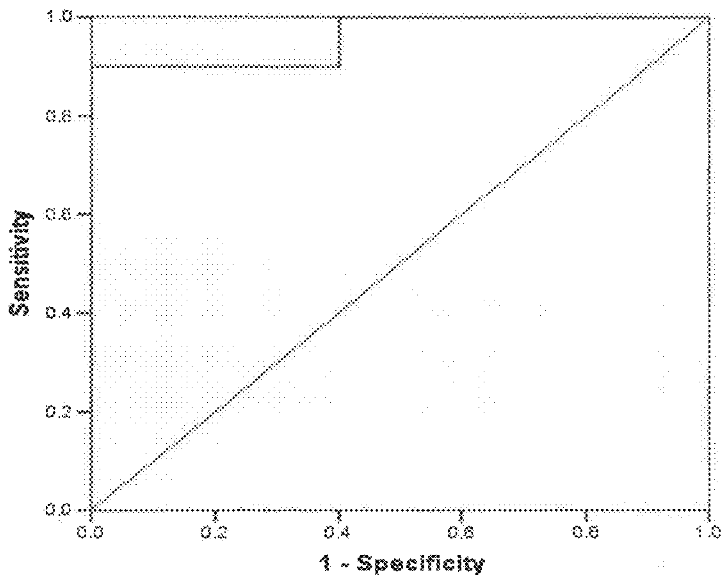
Figure 9E:
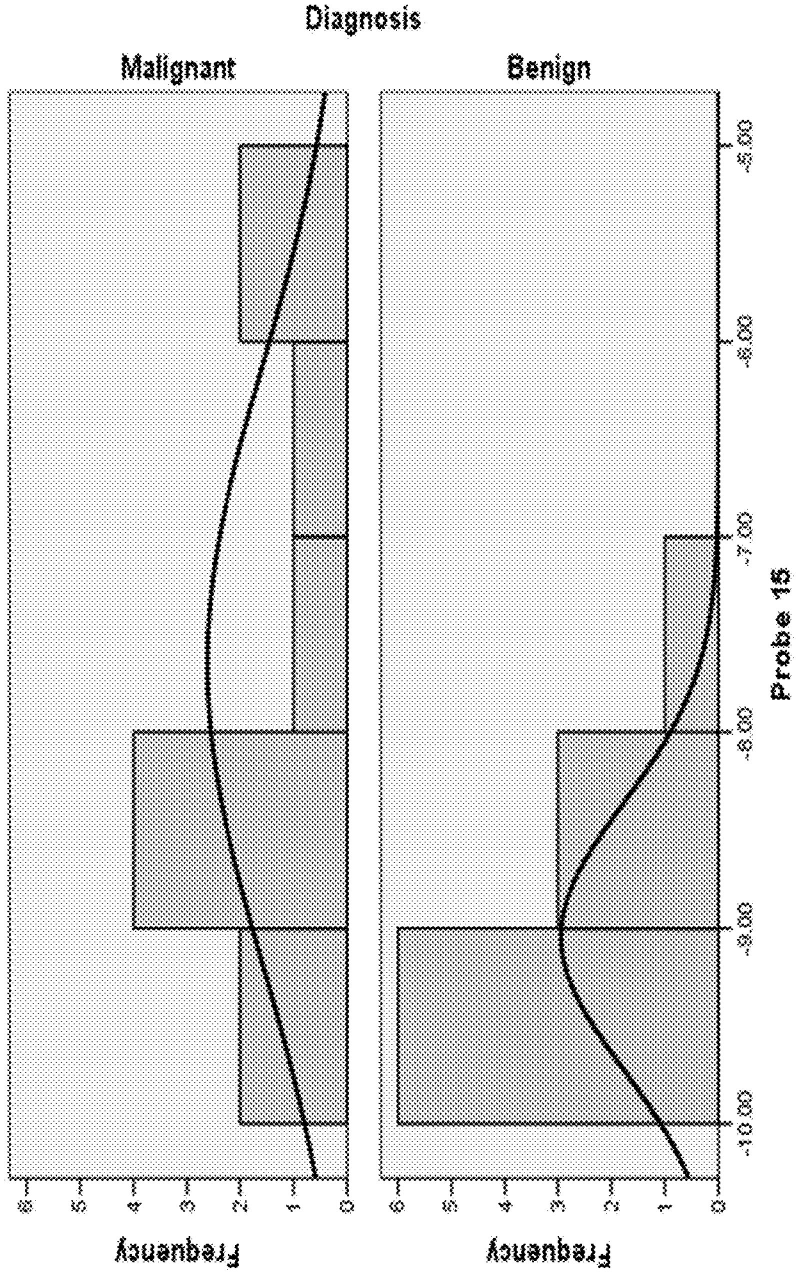
Figure 9G:
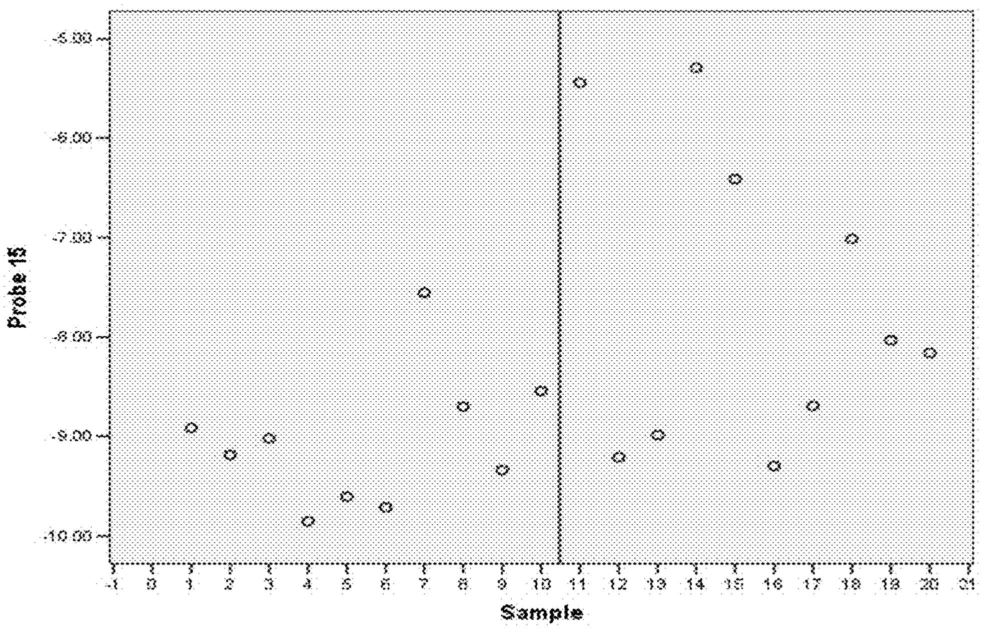
Figure 9H:
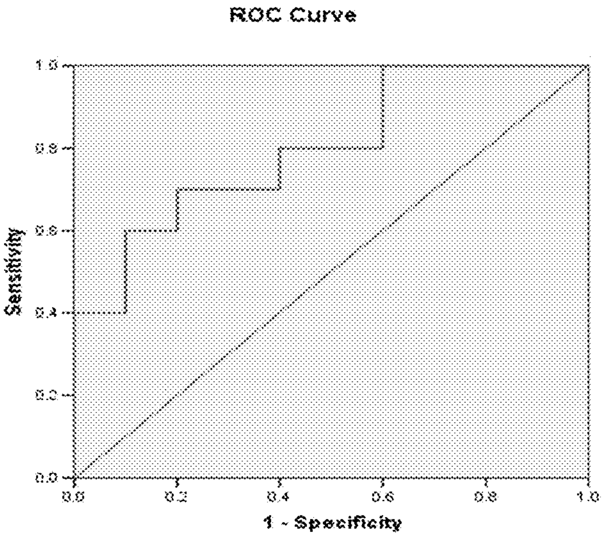
Figure 9J:
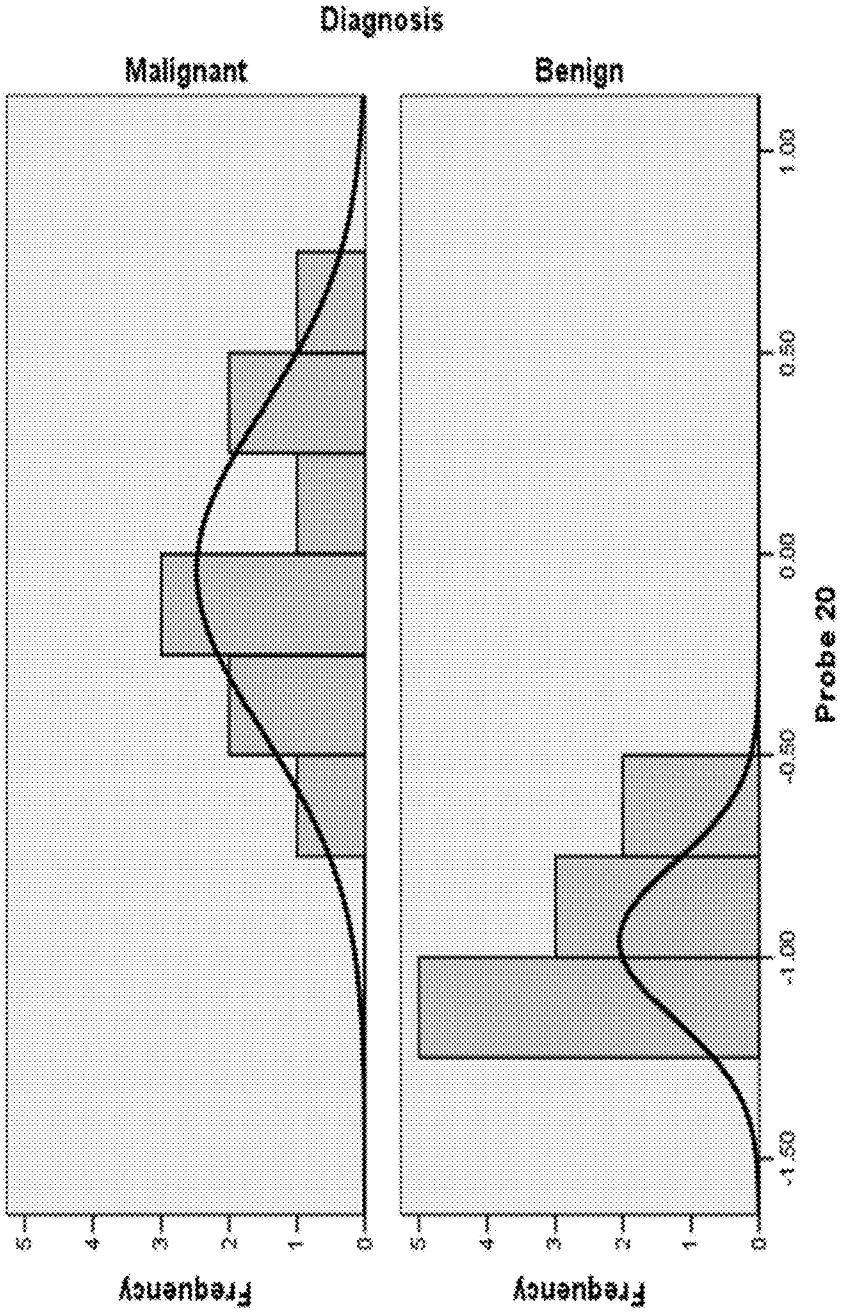
Figure 9L:
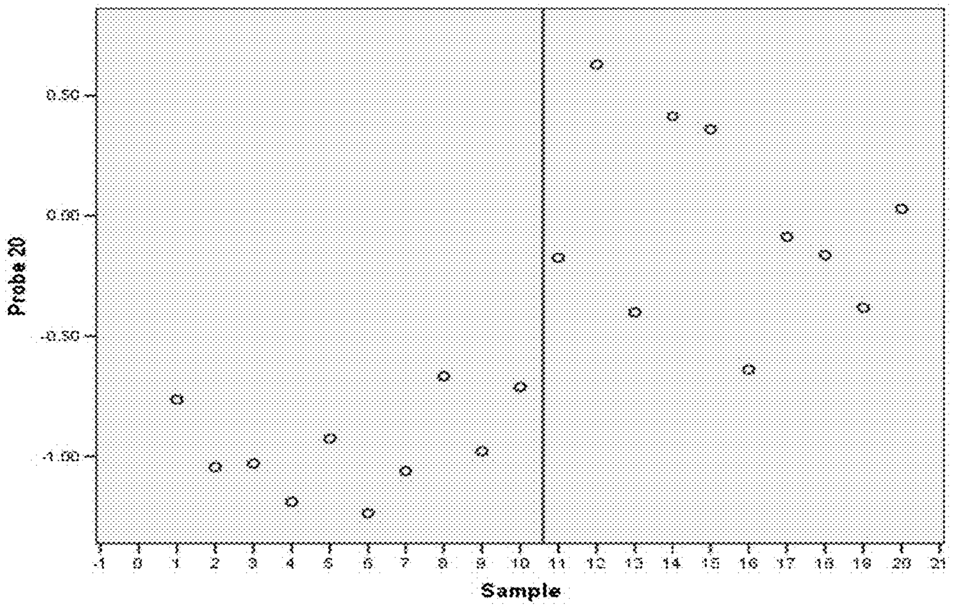
Figure 9M:
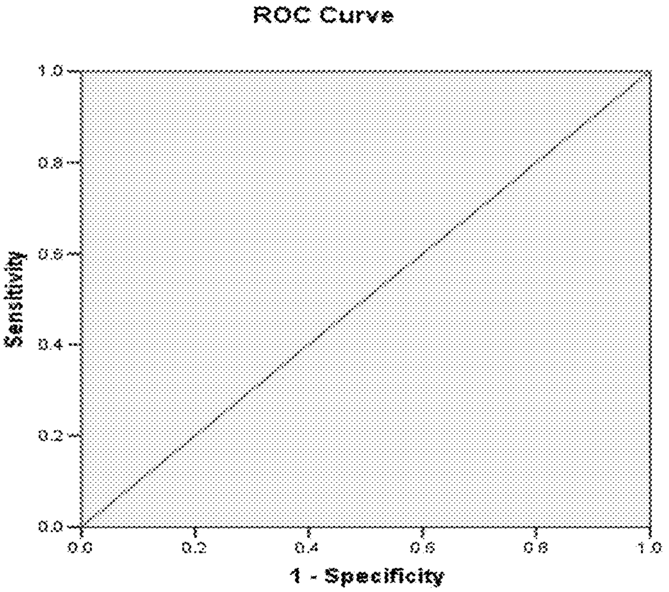
Figure 10A:
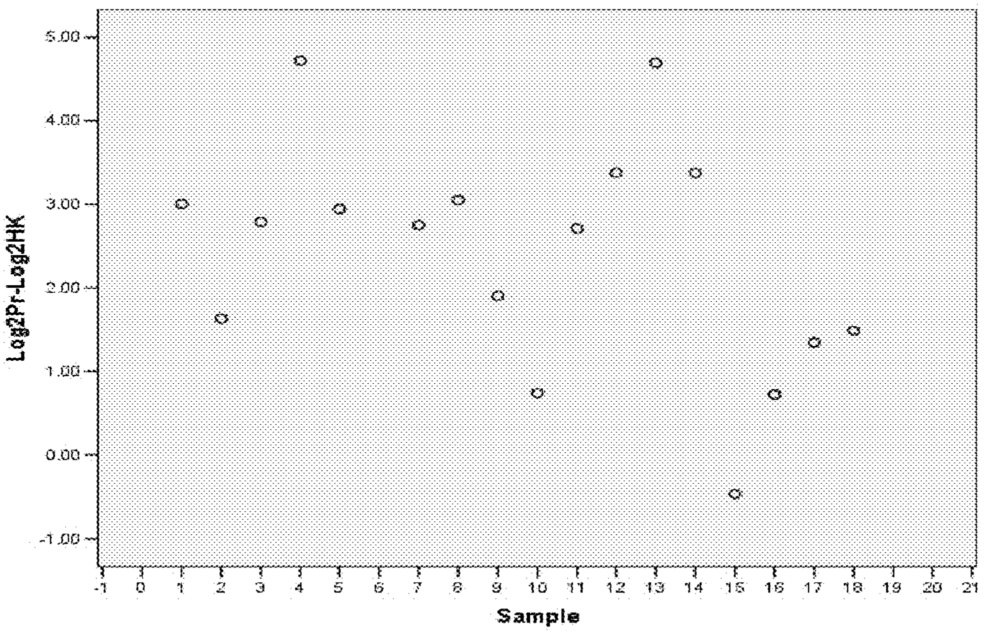
Figure 10D:
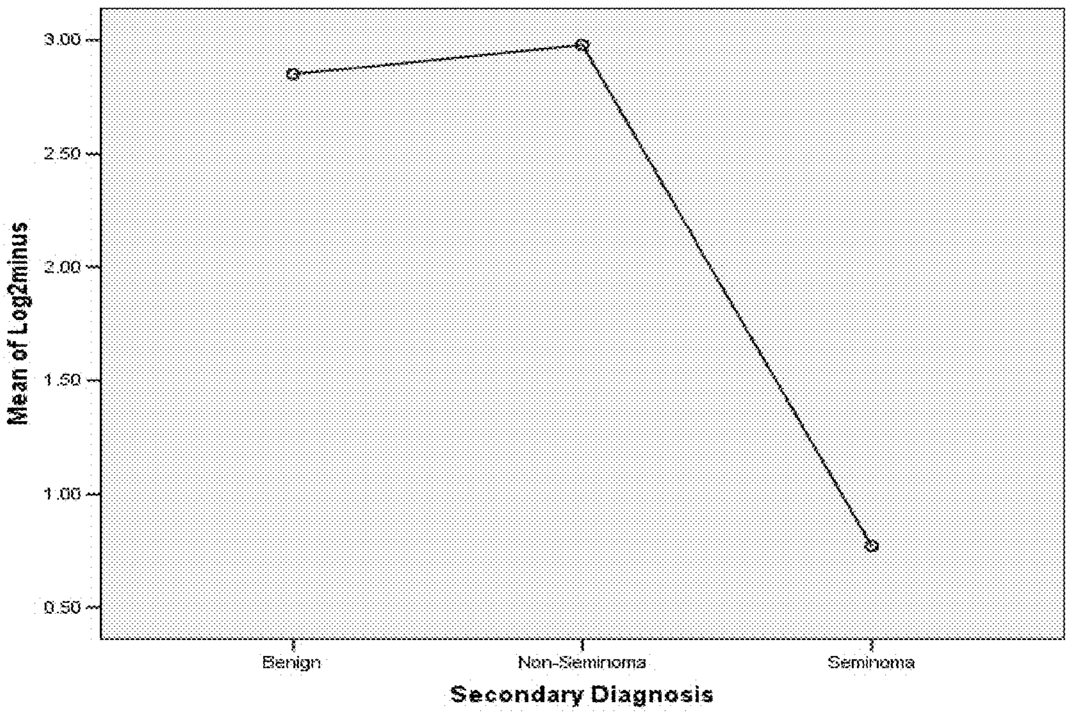
Figure 10E:
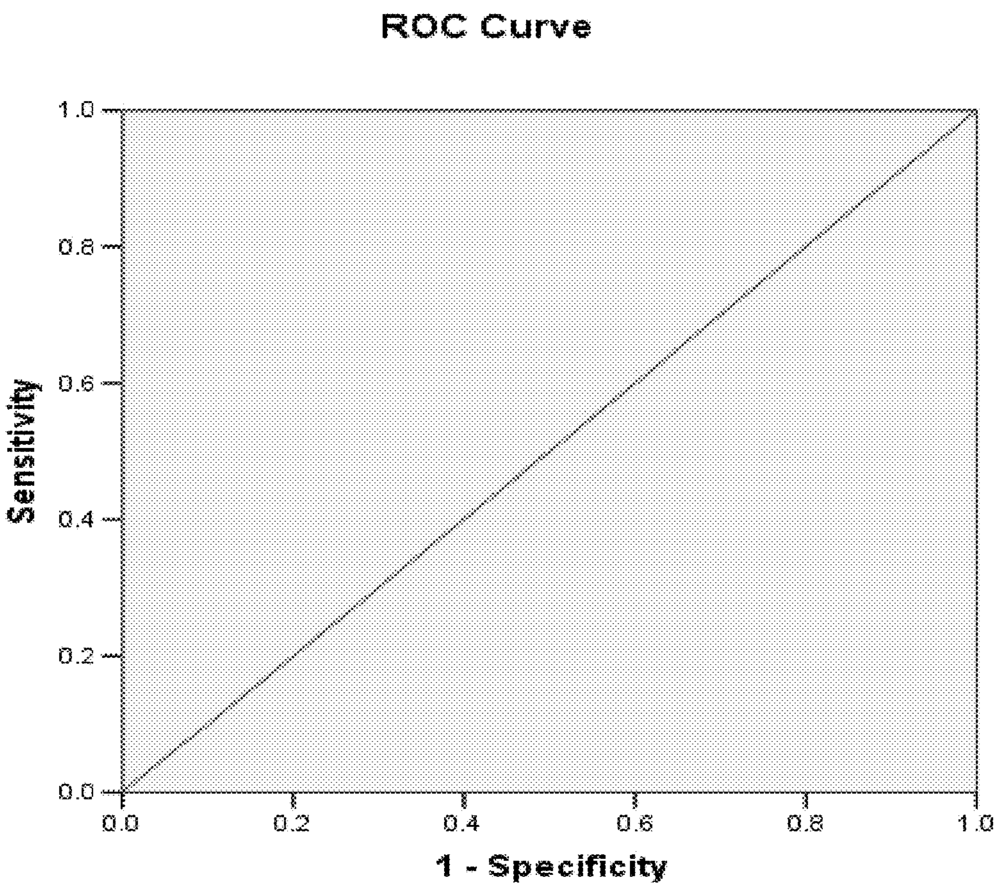
Figure 10H:
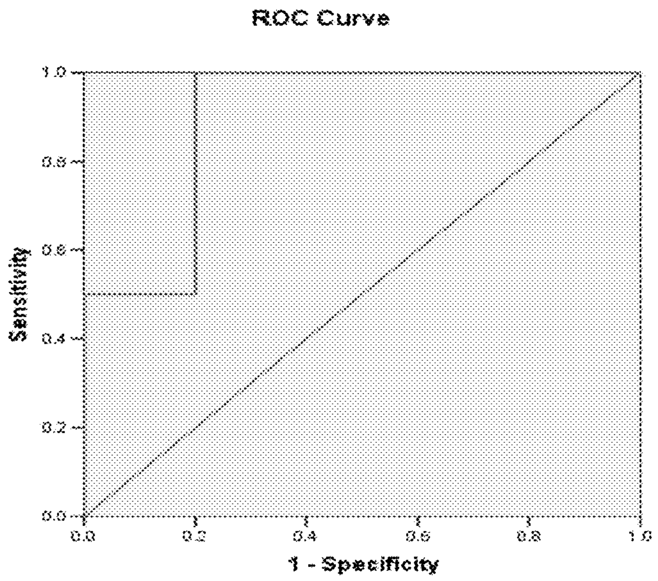
Figure 10I:
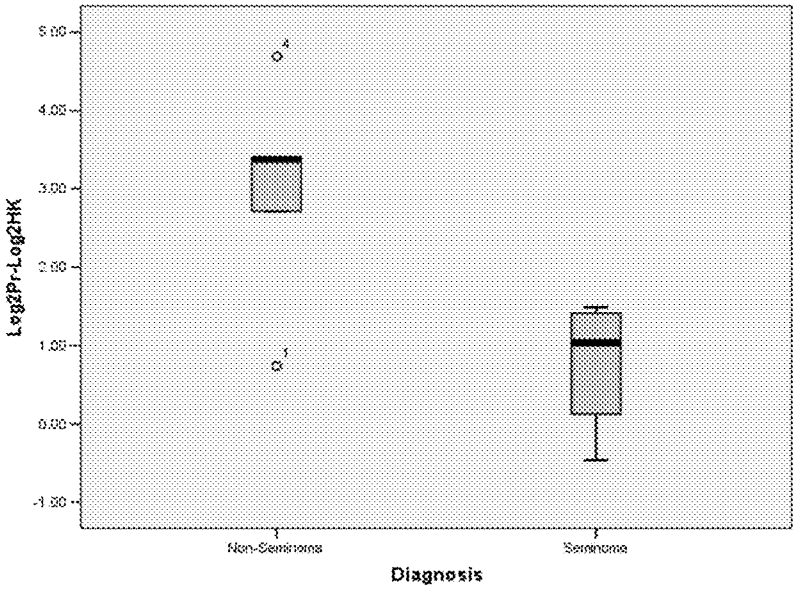
Figure 11A:
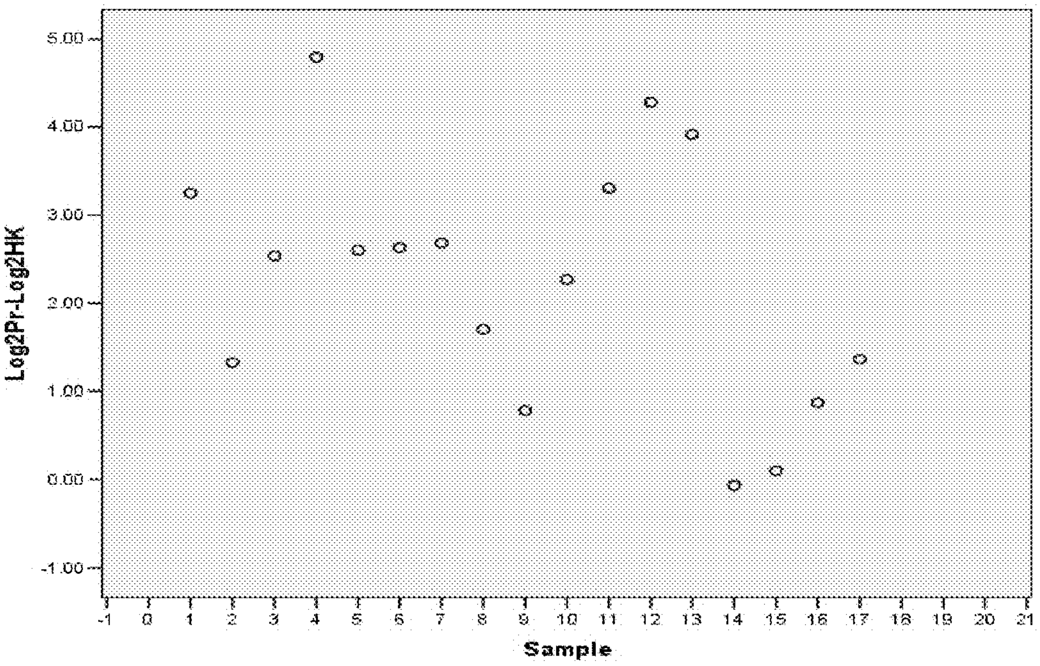
Figure 11C:
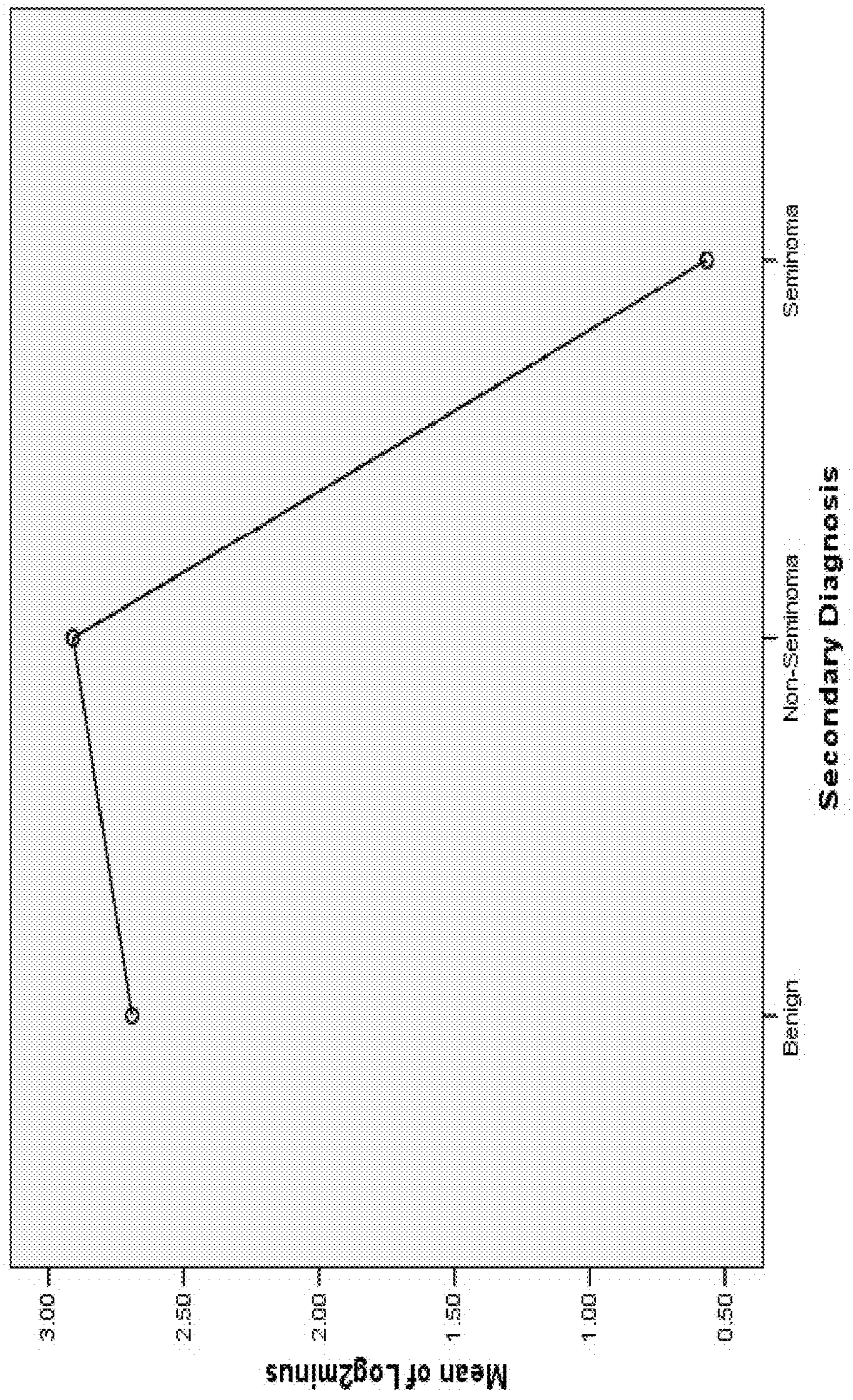
Figure 12A:
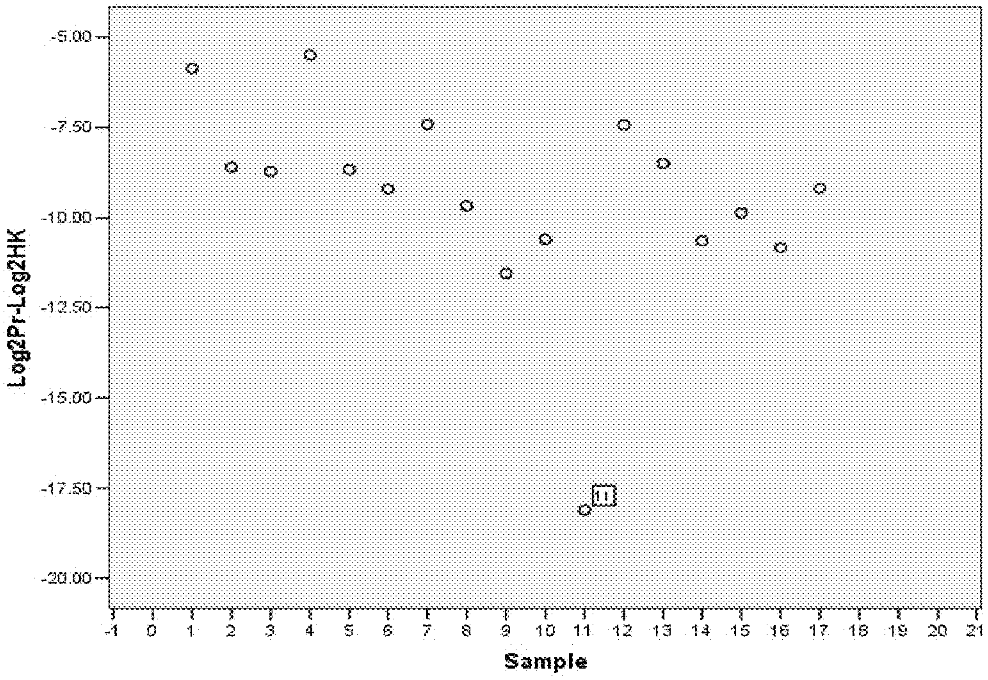
Figure 12C:
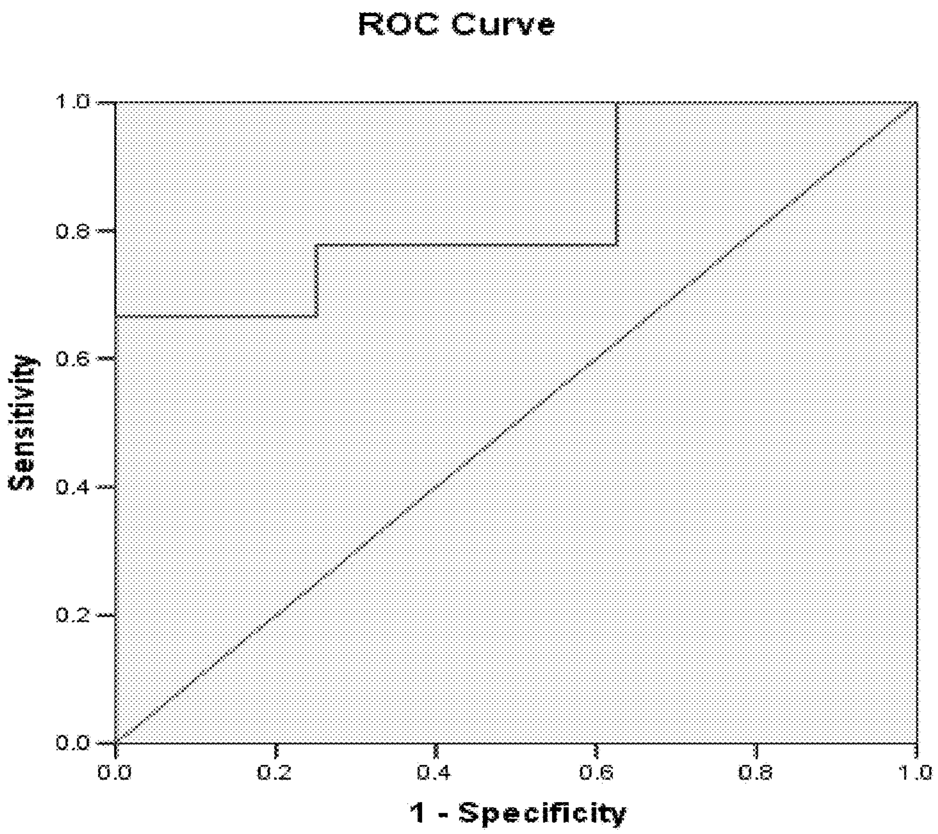
Figure 13A:
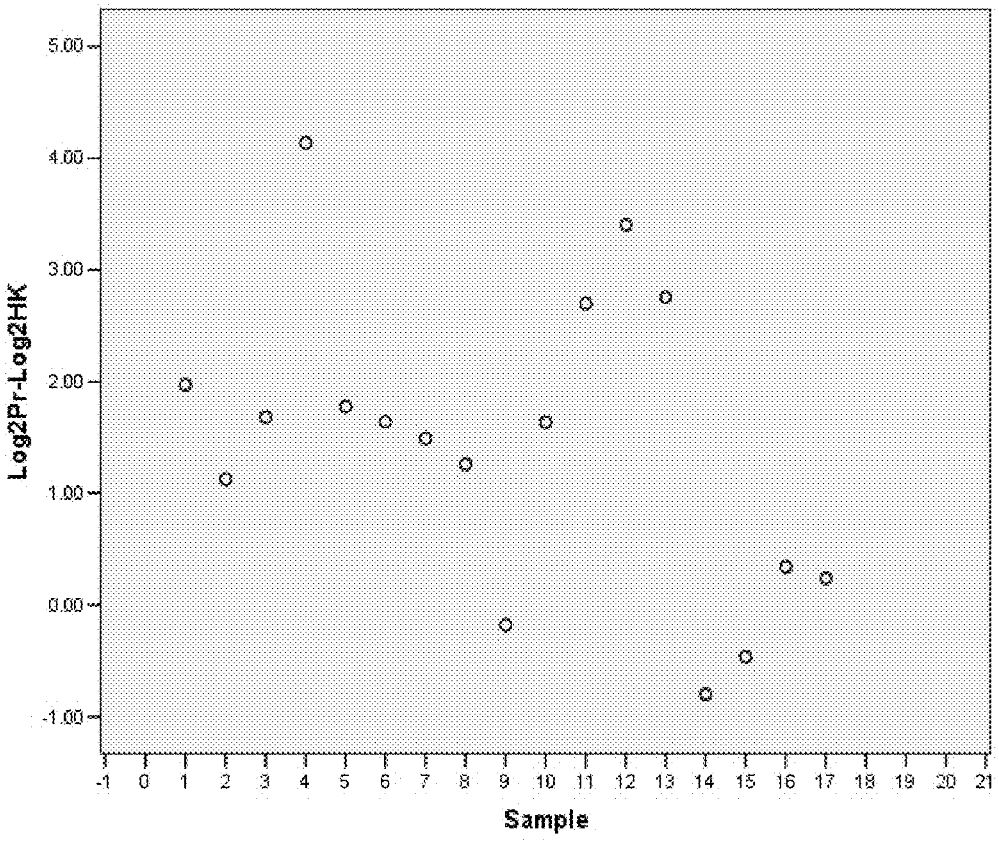
Figure 13C:
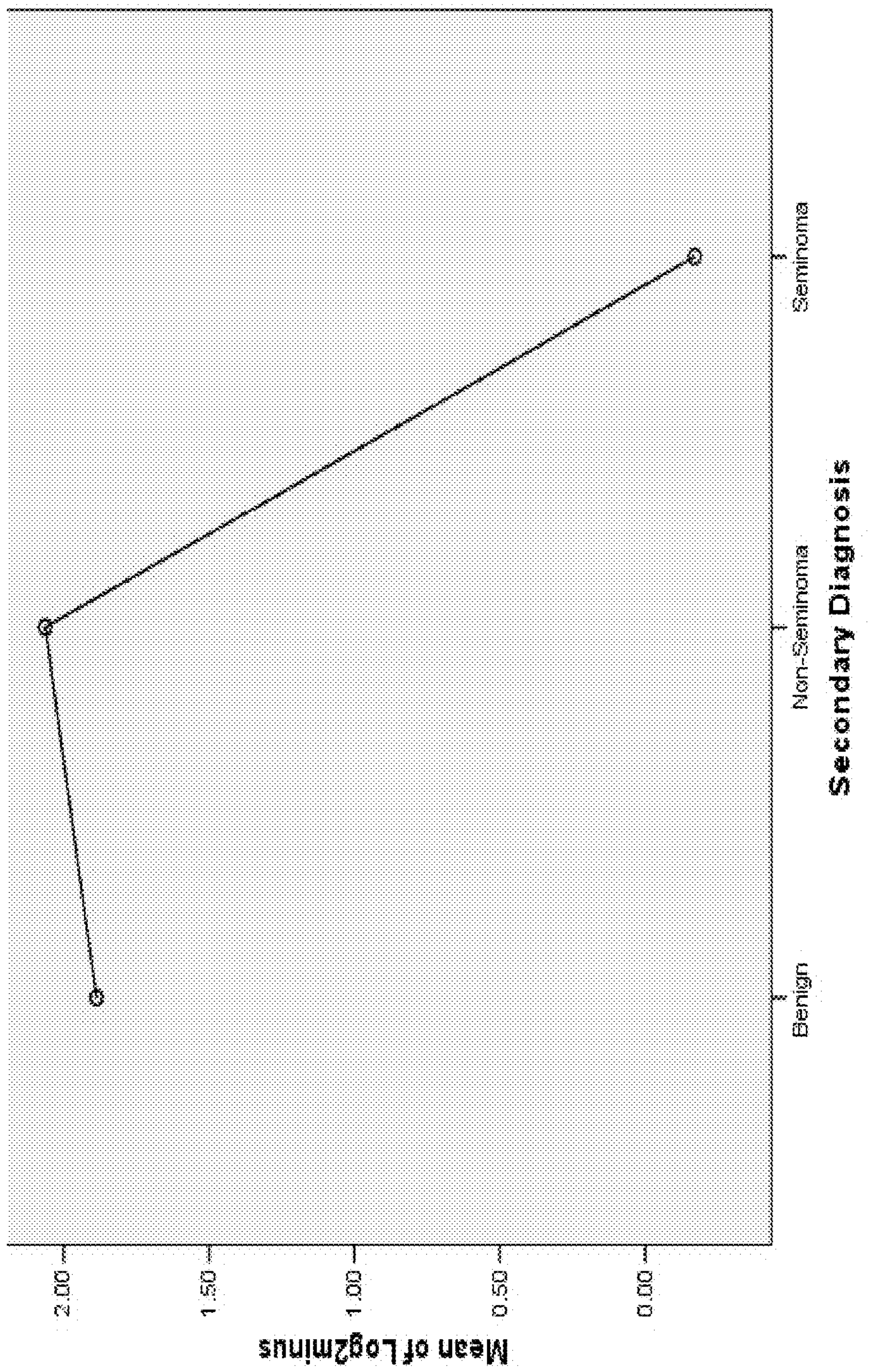
Figure 13D:
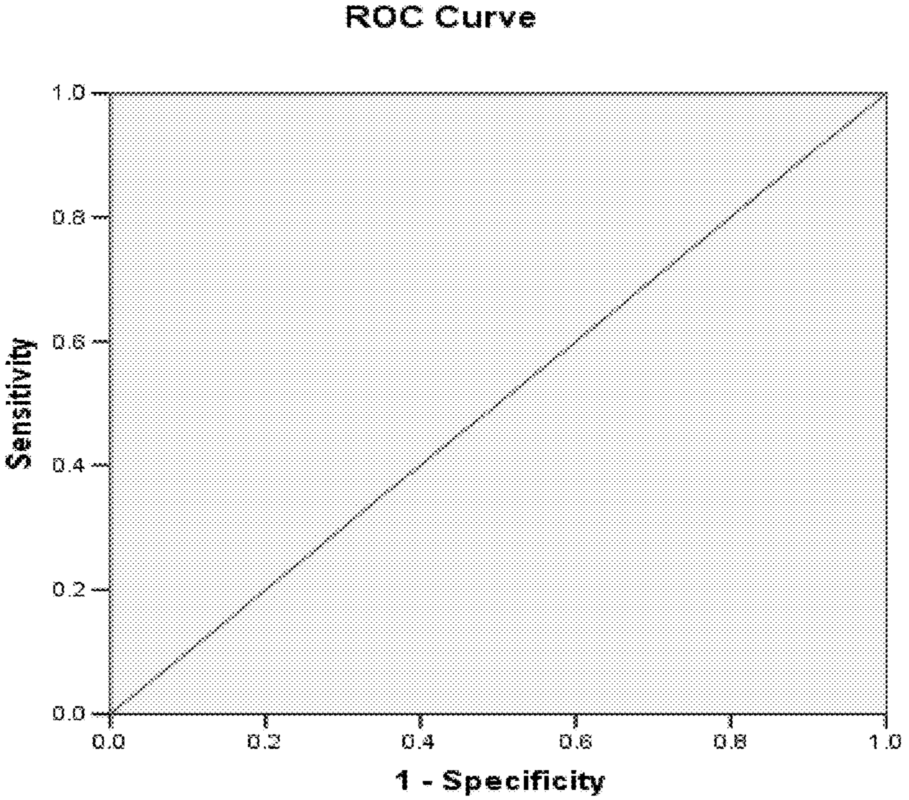
Figure 13G:
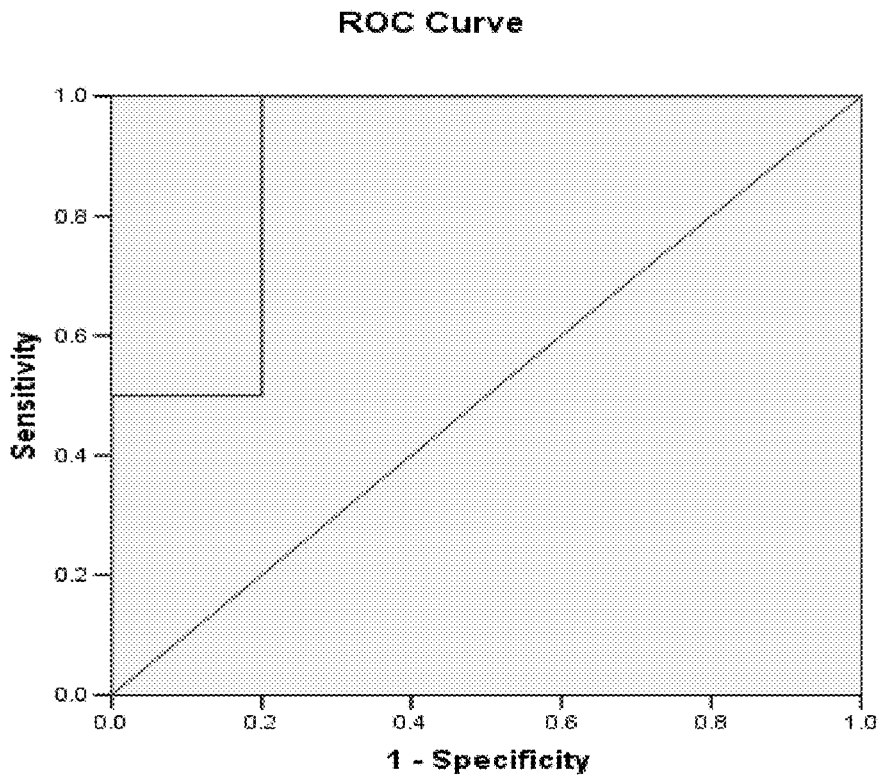
Figure 14A:
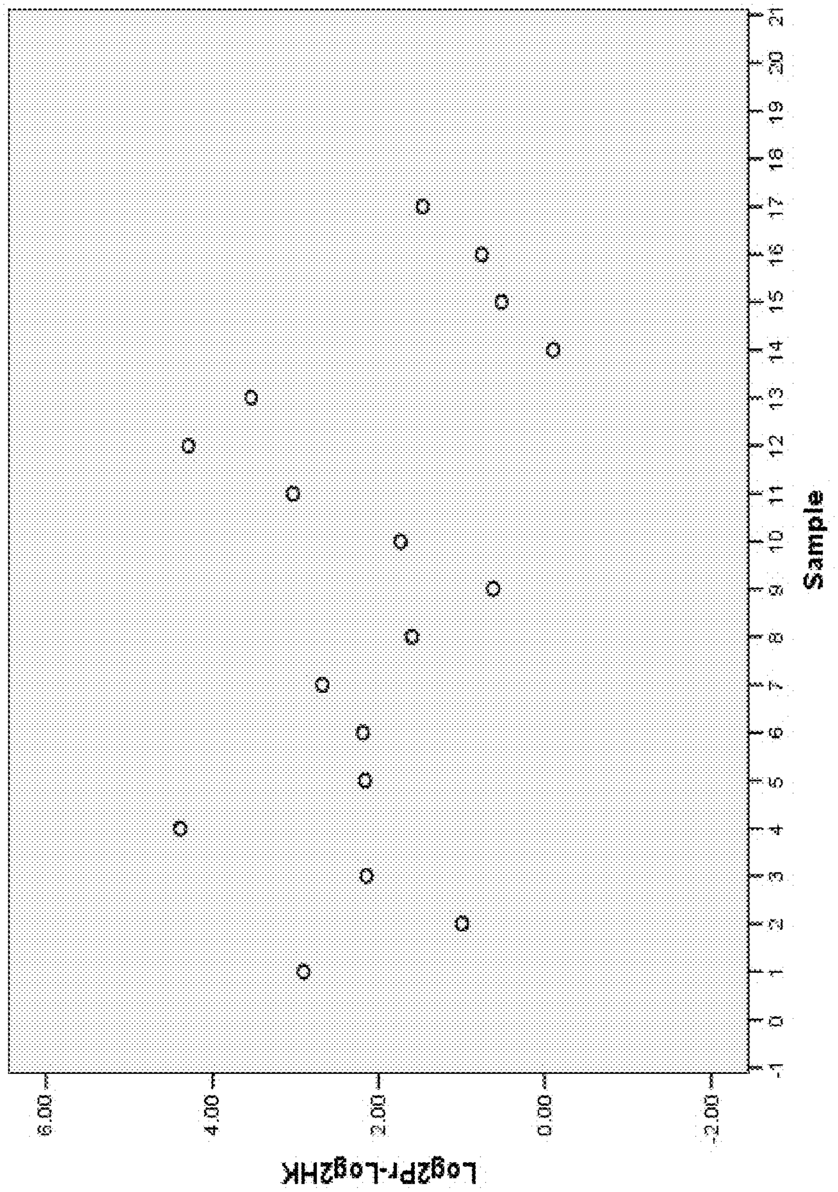
Figure 14C:
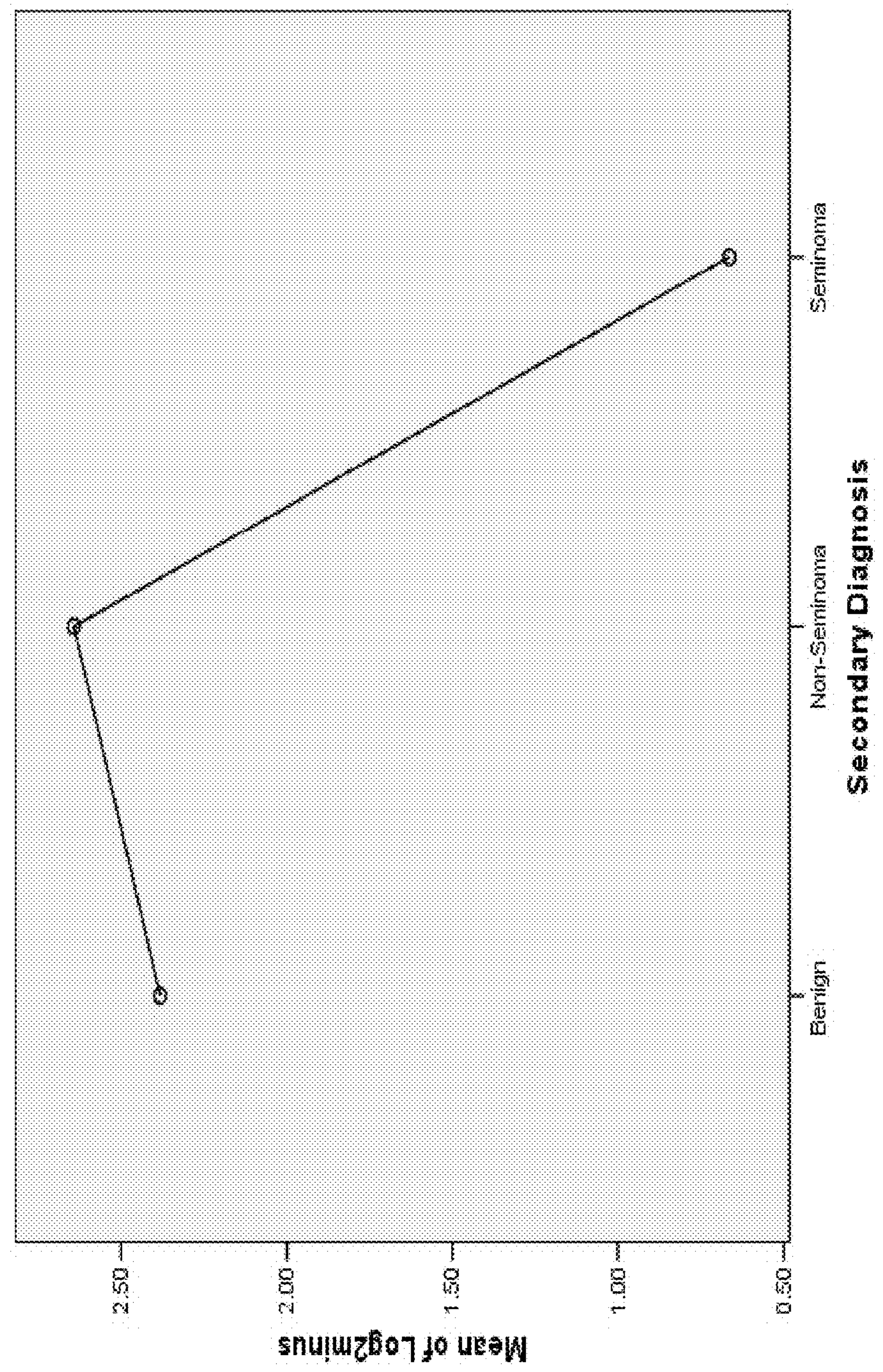
Figure 14D:
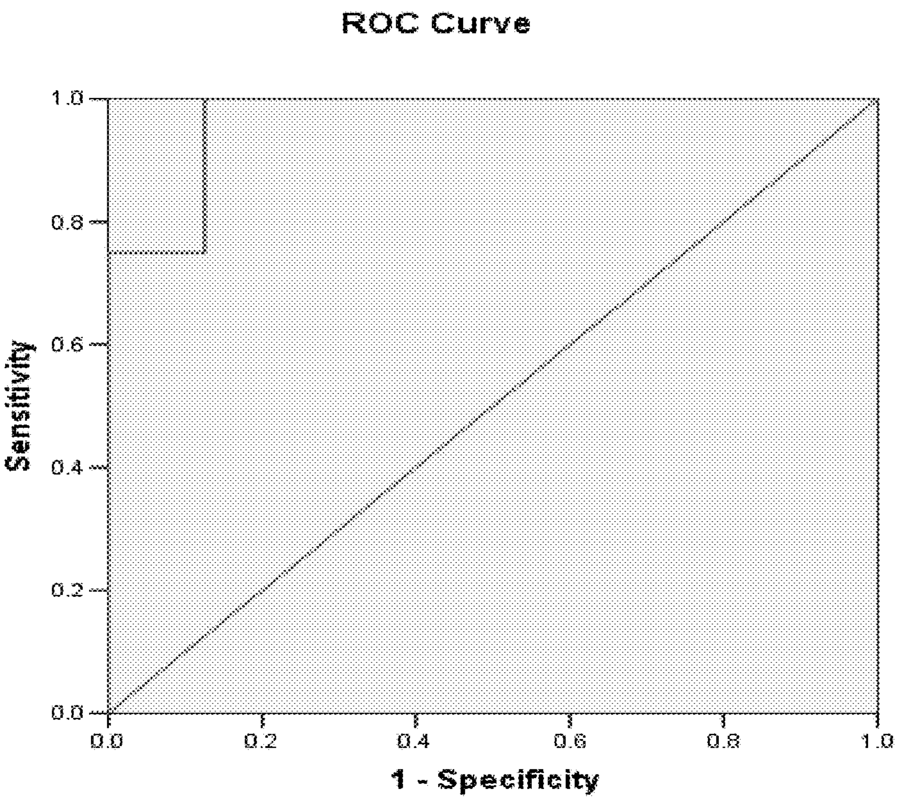
Figure 14G:
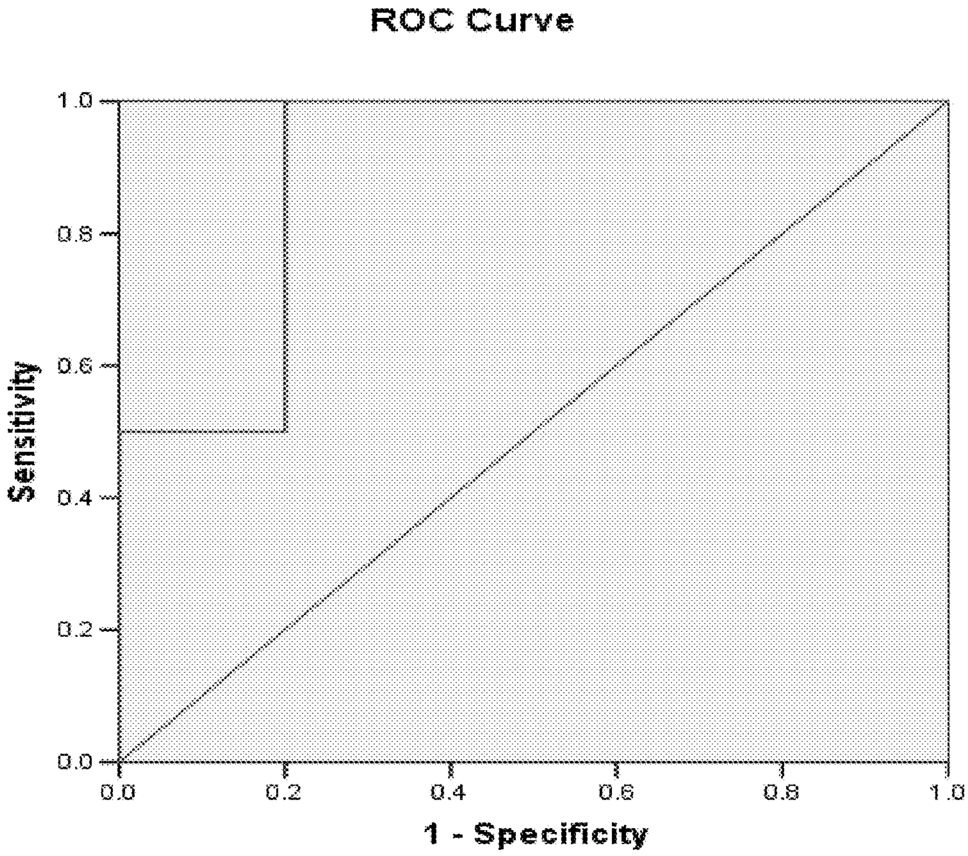
Figure 15A:
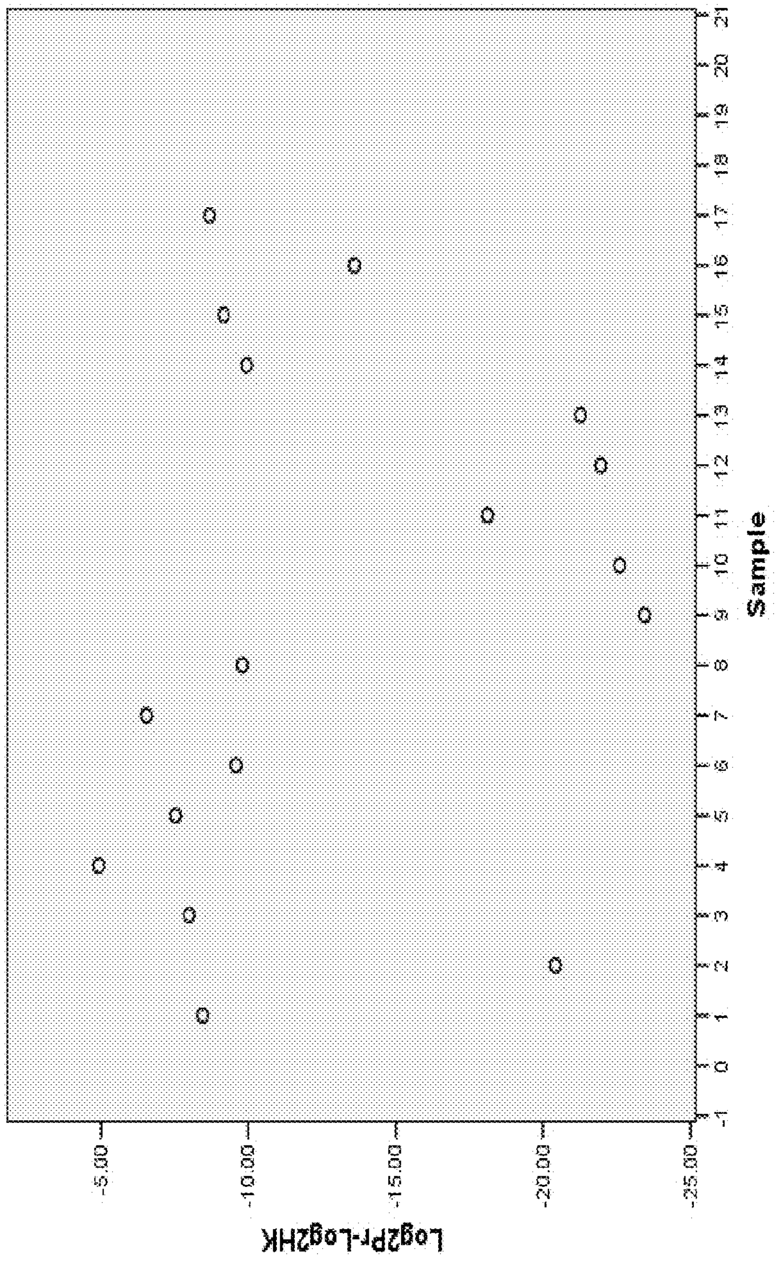
FIGS. 15A to 15N illustrate the results for transcripts 2, 3, 4, 11, 12, 13, 15, 16 and 20 of the invention in the identification of testicular cancer.
Figures 15D, 15E:
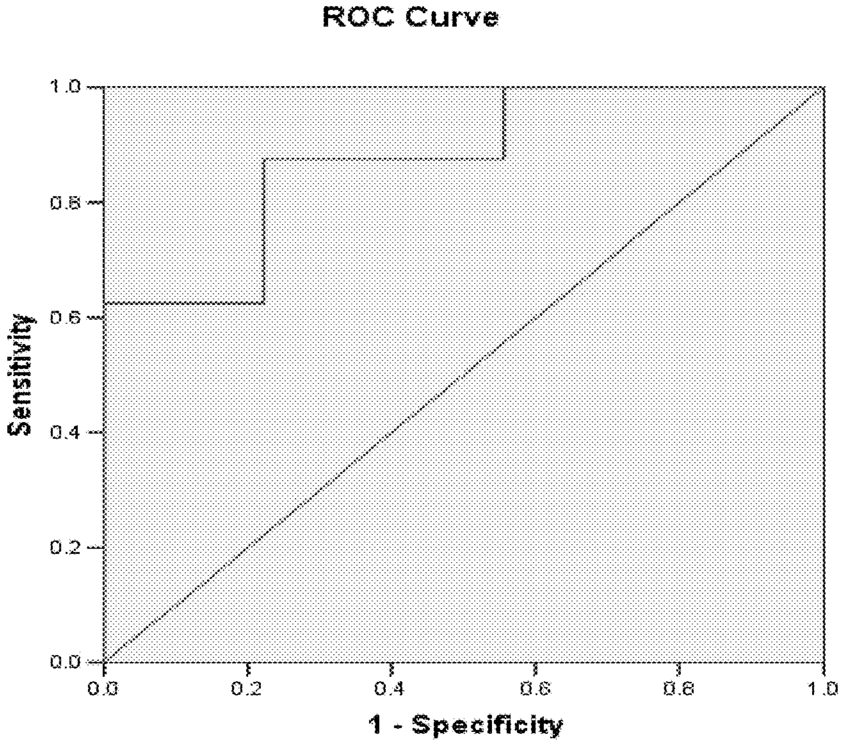
Figure 15F:
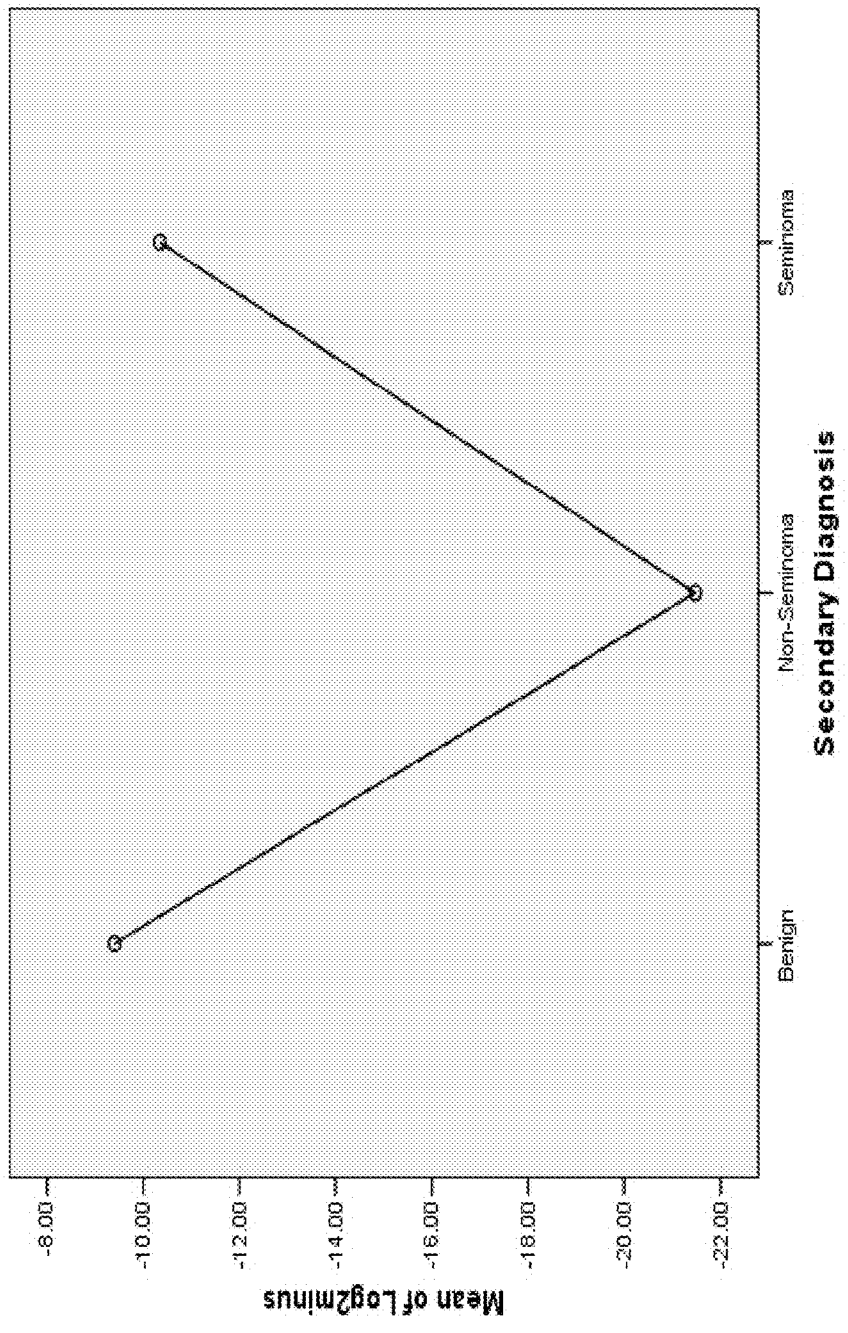
Figure 15H:
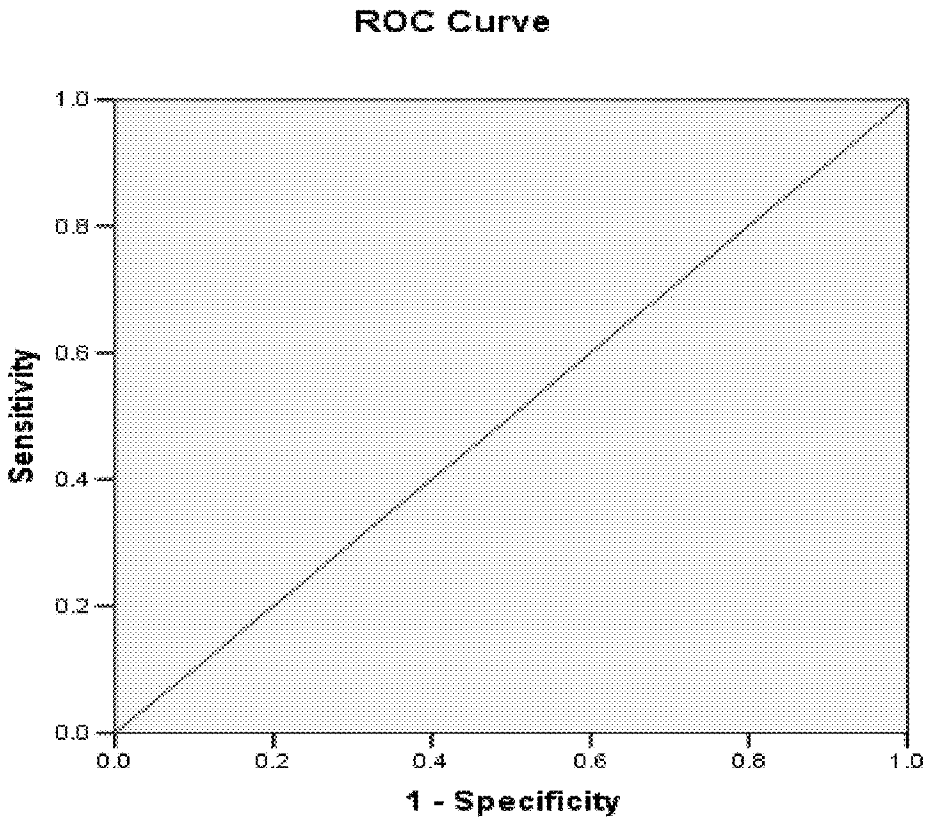
Figure 15K:
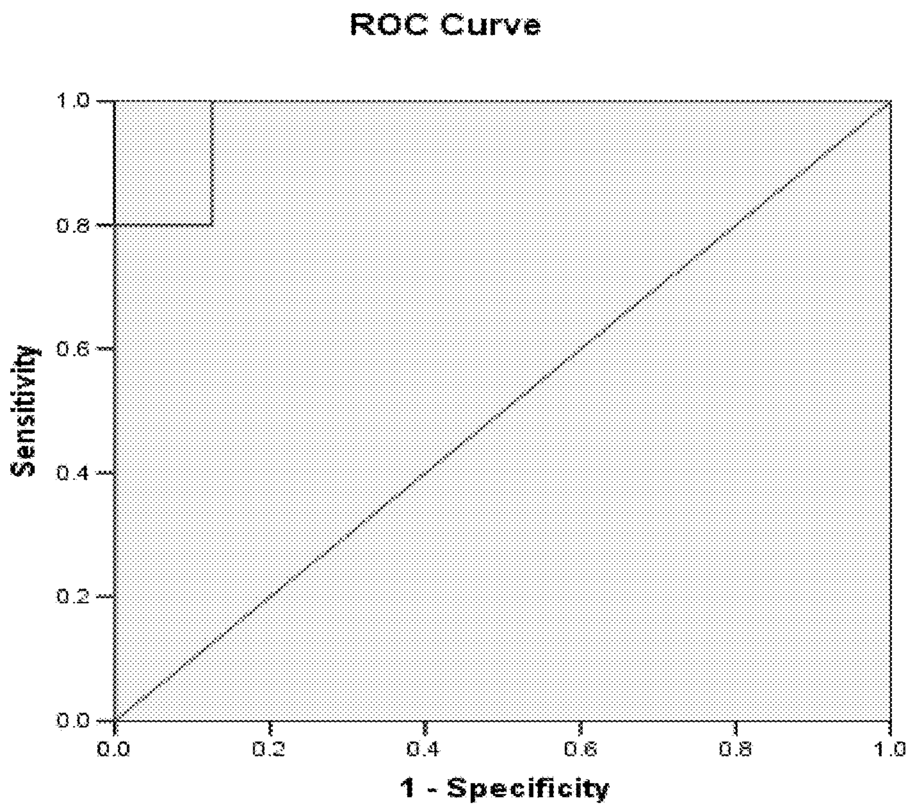
Figure 16A:
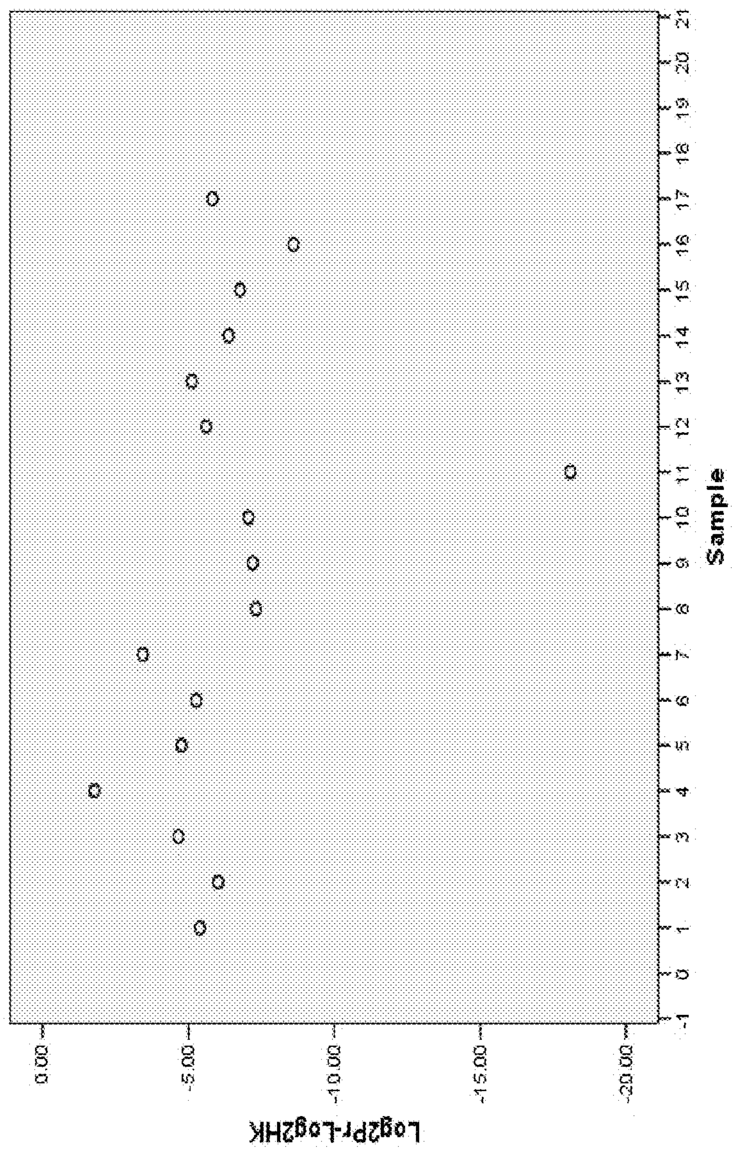
Figure 16C:
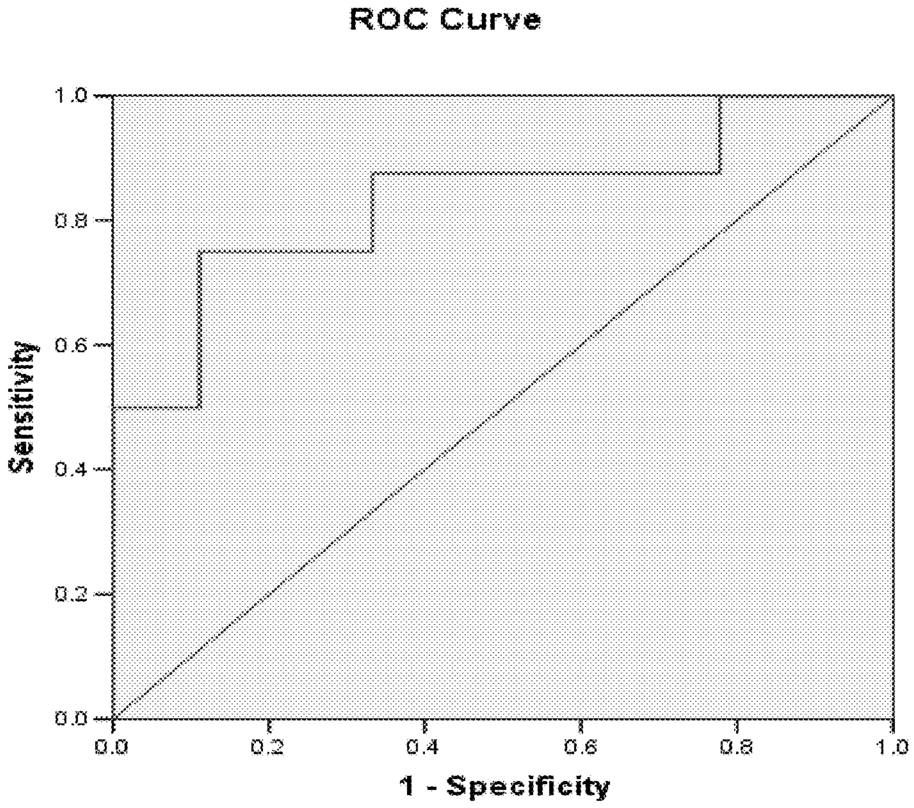
Figure 17A:
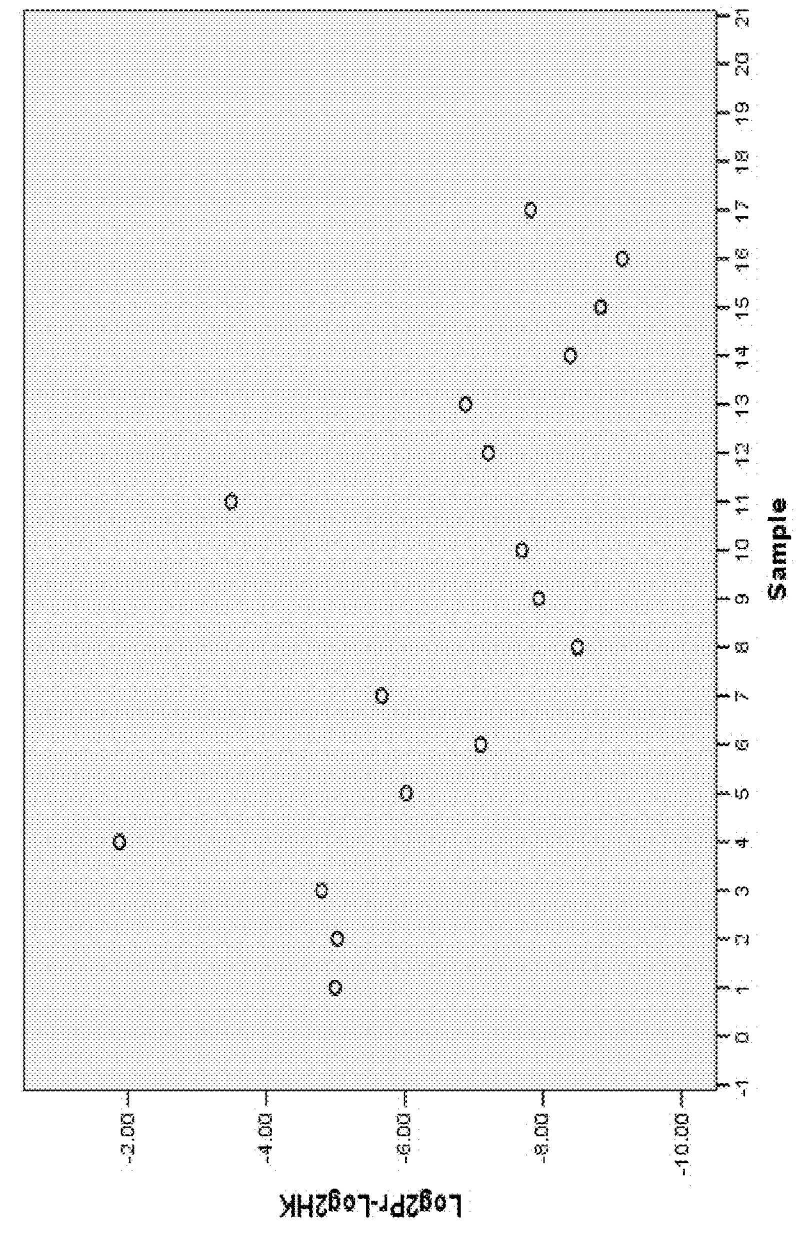
Figure 17C:
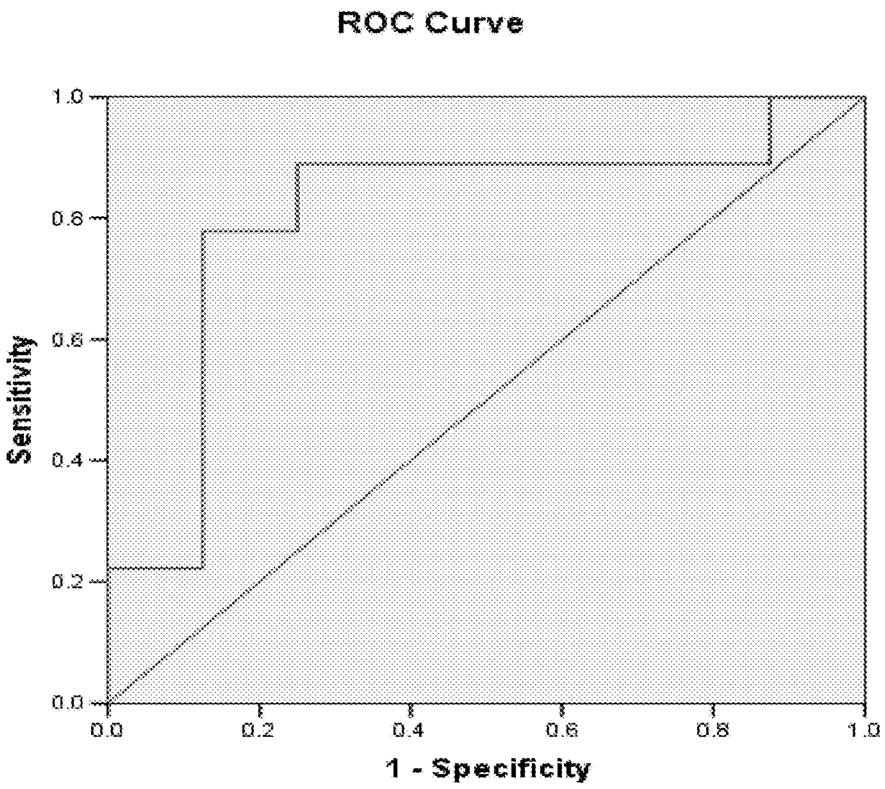
Figure 17G:
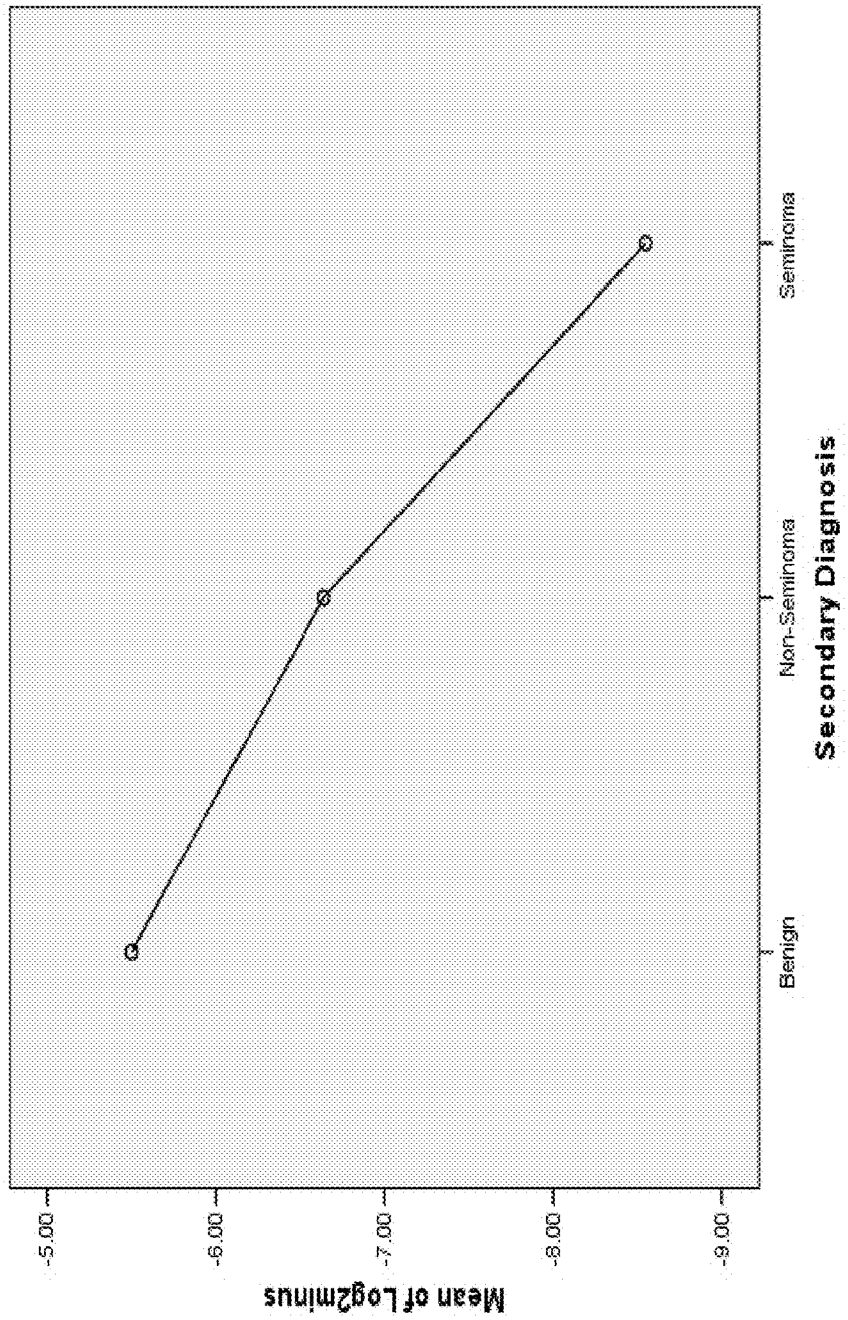
Figure 17H:
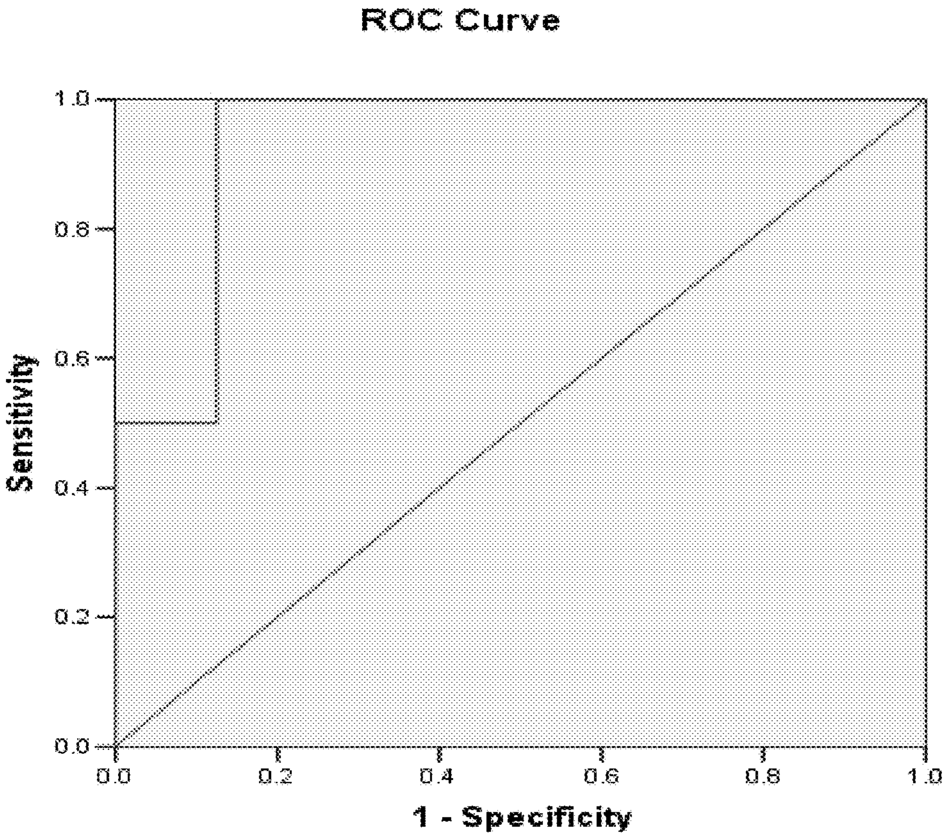
Figure 18A:
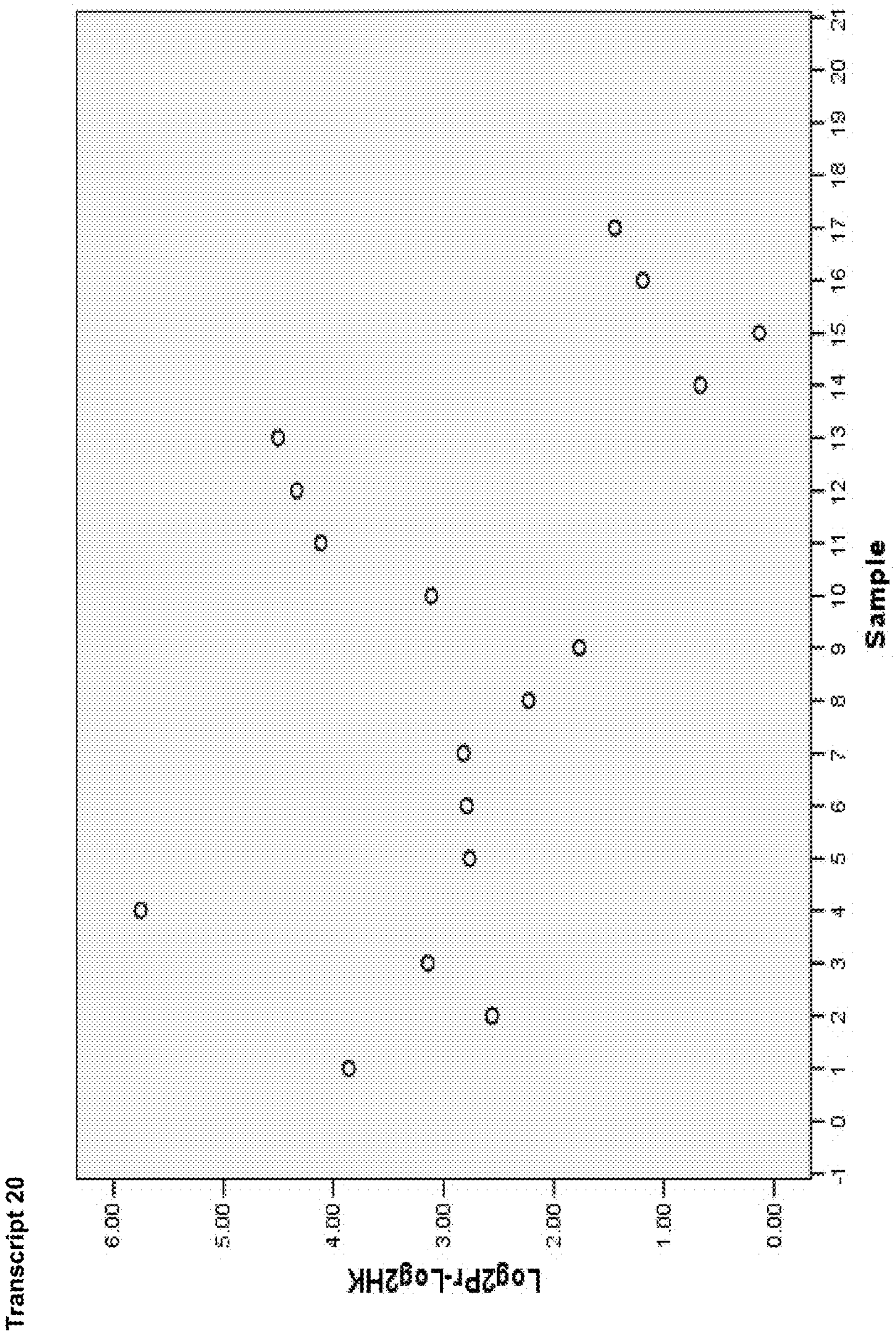
Figure 18C:
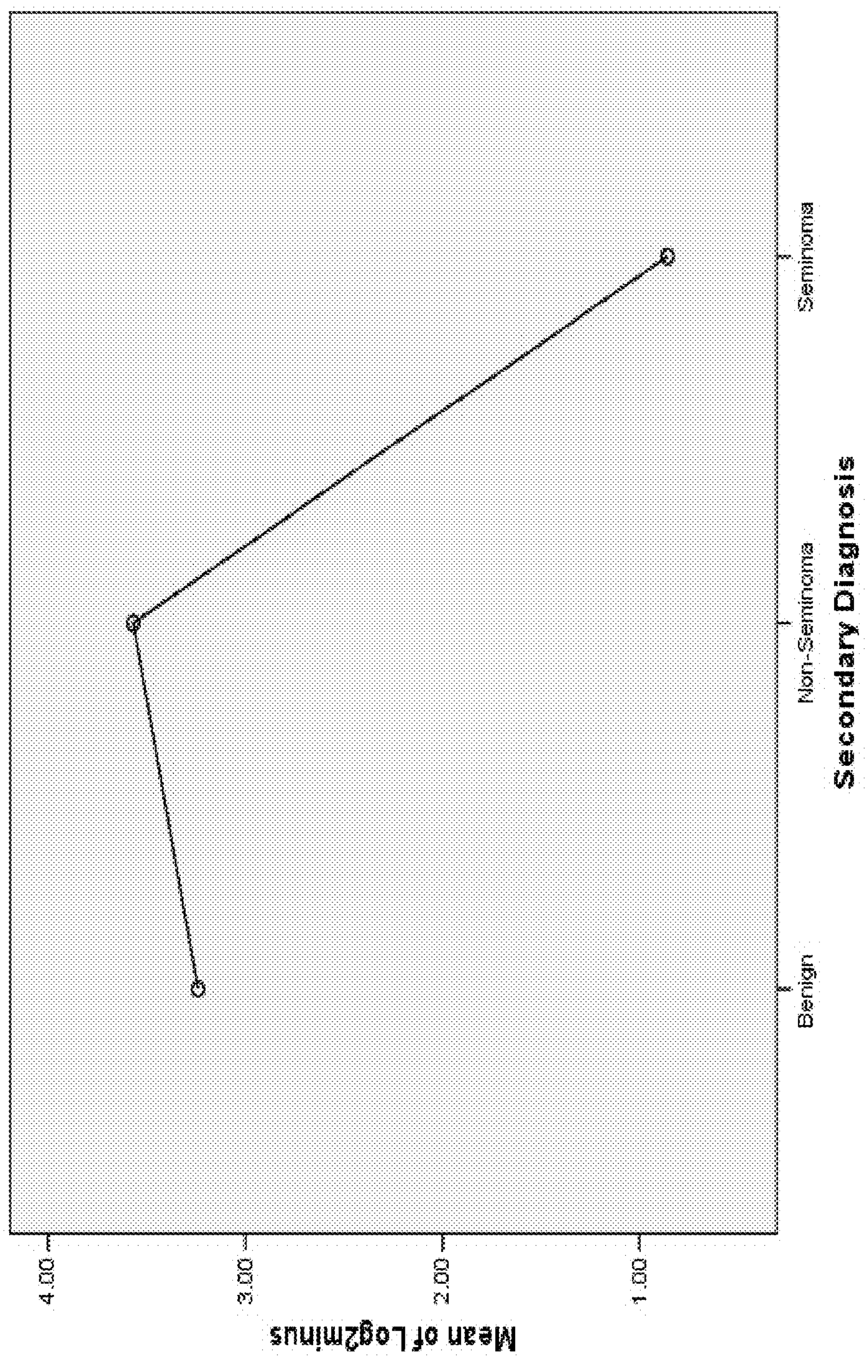
Figure 18D:
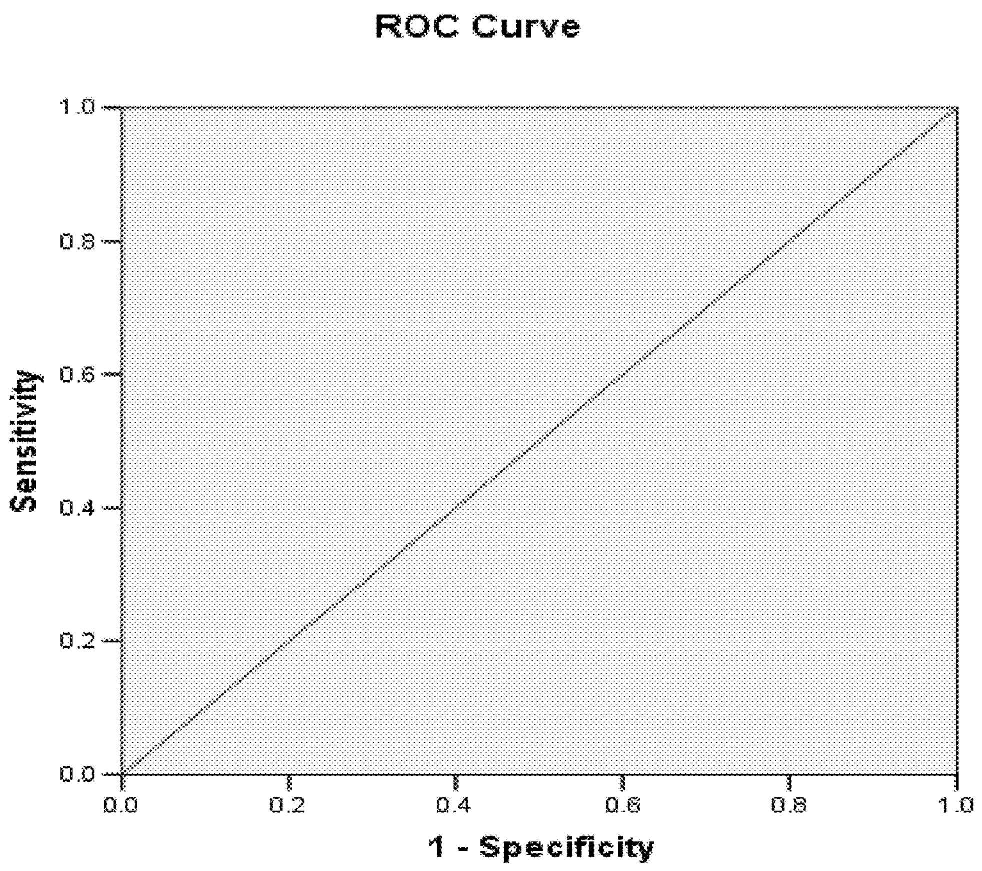
Figure 18G:
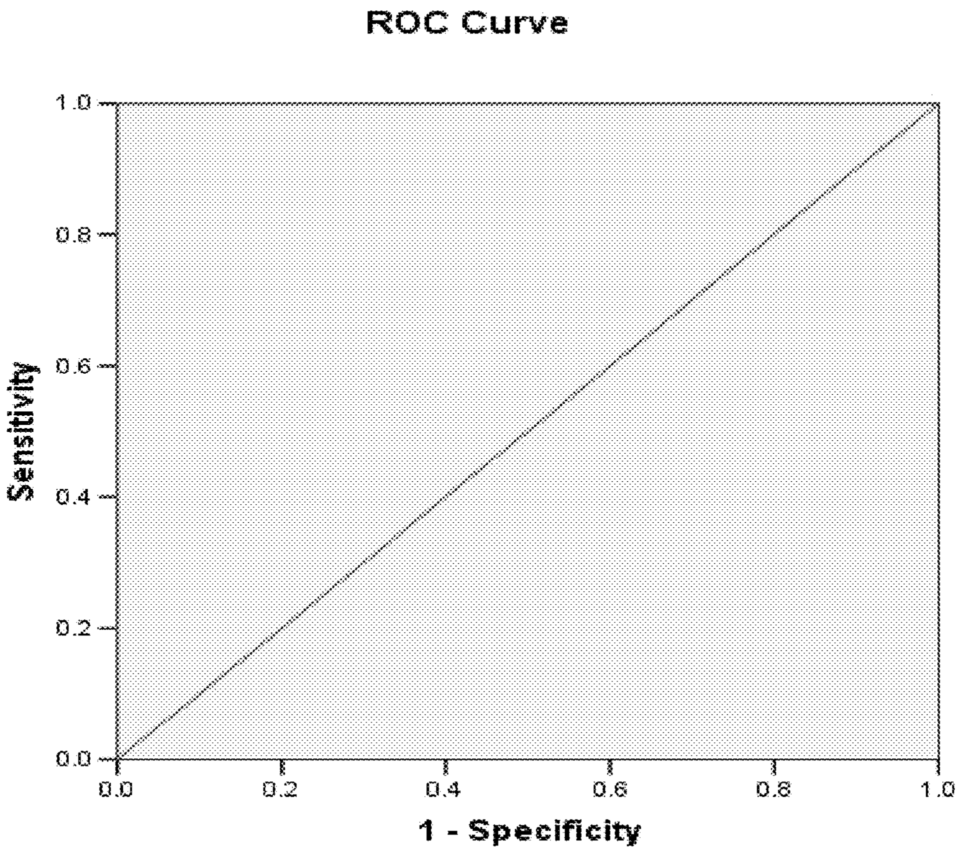

The 3.4 kb deletion results in the removal of the 3' end of ND4L, the full ND4 gene, tRNA histidine, tRNA serine2, tRNA leucine2, and the majority of the 5' end of ND5 (see FIG. 5*a*), resulting in a gene splice of ND4L and ND5 with a junction point of 10744(ND4L):14124(ND5) (FIG. 5*b*). SEQ ID NO: 3 is the complementary DNA sequence to the RNA transcript (SEQ ID NO: 19) detected in the manner described above.

Similarly, transcript 1 is a fusion transcript between ATPase 8 and ND5 associated with positions 8469:13447 (SEQ ID NO: 18). Transcripts 3 and 4 (SEQ ID NO: 20 and SEQ ID NO: 21, respectively) are fusion transcripts between COII and Cytb associated with nucleotide positions 7974: 15496 and 7992:15730 respectively. Table 3 provides a summary of the relationships between the various sequences used in this example. Table 3 includes the detected fusion transcript and the DNA sequence complementary to the fusion transcript detected.

Example 3: Application to Prostate Cancer

Using the four fusion transcripts, i.e. transcripts 1 to 4, discussed above, two prostate tissue samples from one patient were analyzed to assess the quantitative difference of the novel predicted fusion transcripts. The results of the experiment are provided in Table 2 below, wherein "Homog 1" refers to the homogenate of frozen prostate tumour tissue from a patient and "Homog 2" refers to the homogenate of frozen normal prostate tissue adjacent to the tumour of the patient. These samples were processed according to the manufacturer's protocol (*QuantiGene® Sample Processing Kit for Fresh or Frozen Animal Tissues; and QuantiGene®* 2.0 *Reagent System User Manual*) starting with 25.8 mg of Homog 1 and 28.9 mg of Homog 2 (the assay setup is shown in Tables 5a and 5b).

Clearly demonstrated is an increased presence of mitochondrial fusion transcripts in prostate cancer tissue compared to normal adjacent prostate tissue. The fusion transcript is present in the normal tissue, although at much lower levels. The relative luminescence units (RLU) generated by hybridization of a probe to a target transcript are directly proportional to the abundance of each transcript. Table 2 also indicates the coefficients of variation, CV, expressed as a percentage, of the readings taken for the samples. The CV comprises the Standard deviation divided by the average of the values. The significance of such stably transcribed mitochondrial gene products in cancer tissue has implications in disease evolution and progression.

Example 4: Application to Breast Cancer

Using the same protocol from Example 3 but focusing only on Transcript 2, the novel fusion transcript associated with the 3.4 kb mtgenome deletion, analyses were conducted on two samples of breast tumour tissue and two samples of tumour-free tissues adjacent to those tumours, as well as three samples of prostate tumour tissue, one sample comprising adjacent tumour-free tissue. Results for this example are provided in Table 4. The prostate tumour tissue sample having a corresponding normal tissue section demonstrated a similar pattern to the prostate sample analyzed in Example 3 in that the tumour tissue had approximately 2 times the amount of the fusion transcript than did the normal adjacent tissue. The breast tumour samples demonstrated a marked increase in the fusion transcript levels when compared to the adjacent non-tumour tissues. A 1:100 dilution of the homogenate was used for this analysis as it performed most reproducibly in the experiment cited in Example 3.

Thus, the above discussed results illustrate the application of the transcripts of the invention in the detection of tumours of both prostate and breast tissue.

Example 5: Application to Colorectal Cancer

This study sought to determine the effectiveness of several transcripts of the invention in detecting colorectal cancer. A total of 19 samples were prepared comprising nine control (benign) tissue samples (samples 1 to 9) and ten tumour (malignant) tissue samples (samples 10 to 19). The samples were homogenized according to the manufacturer's recommendations (Quantigene® Sample Processing Kit for Fresh or Frozen Animal Tissues; and Quantigene 2.0 Reagent System User Manual). Seven target transcripts and one housekeeper transcript were prepared in the manner as outlined above in previous examples. The characteristics of the transcripts are summarized as follows:

TABLE 7

Characteristics of Breast Cancer Transcripts

| Transcript ID | Junction Site | Gene Junction |
|---|---|---|
| 2 | 10744:14124 | ND4L:ND5 |
| 3 | 7974:15496 | COII:Cytb |
| 10 | 7438:13476 | COI:ND5 |
| 11 | 7775:13532 | COII:ND5 |
| 12 | 8213:13991 | COII:ND5 |
| Peptidylpropyl isomerase B (PPIB) ("housekeeper") | N/A | N/A |

It is noted that transcripts 2 and 3 are the same as those discussed above with respect to Examples 3 and 4.

Homogenates were prepared using approximately 25 mg of tissue from OCT blocks and diluted 1:1 for transcripts 2 and 4, and 1:8 for transcripts 10 and 11. The quantity of the transcripts was measured in Relative Luminenscence Units RLU on a Glomax™ Multi Detection System (Promega). All samples were assayed in triplicate for each transcript. Background measurements (no template) were done in triplicate as well. The analysis accounted for background by subtracting the lower limit from the RLU values for the samples. Input RNA was accounted for by using the formula $\log_2$ a RLU−$\log_2$ h RLU where a is the target fusion transcript and h is the housekeeper transcript.

The analysis of the data comprised the following steps:

a) Establish CV's (coefficients of variation) for triplicate assays; acceptable if ≤15%.

b) Establish average RLU value for triplicate assays of target fusion transcript (a) and housekeeper transcript (h).

c) Establish lower limit from triplicate value of background RLU (I).

d) Subtract lower limit (I) from (a).

e) Calculate $\log_2$ a RLU−$\log_2$ h RLU.

Summary of Results:

The results of the above analysis are illustrated in FIGS. 6*a* to 6*g*, which comprise plots of the $\log_2$ a RLU−$\log_2$ h RLU against sample number. Also illustrated are the respective ROC (Receiver Operating Characteristic) curves determined from the results for each transcript.

Transcript 2:

There exists a statistically significant difference between the means ($p<0.10$) of the normal and malignant groups ($p>0.09$), using a cutoff value of 3.6129 as demonstrated by the ROC curve results in a sensitivity of 60% and specificity of 89% and the area under the curve is 0.73 indicating fair test accuracy. The threshold value chosen may be adjusted to increase either the specificity or sensitivity of the test for a particular application.

Transcript 3:

There exists a statistically significant difference between the means ($p<0.05$) of the normal and malignant groups ($p=0.03$), using a cutoff value of 4.0813 as demonstrated by the ROC curve results in a sensitivity of 60% and specificity of 78% and the area under the curve is 0.79 indicating fair to good test accuracy. The threshold value chosen may be adjusted to increase either the specificity or sensitivity of the test for a particular application.

Transcript 8:

There exists a statistically significant difference between the means ($p<0.1$) of the normal and malignant groups ($p=0.06$). Using a cutoff value of −6.0975 as demonstrated by the ROC curve results in a sensitivity of 60% and specificity of 89% and the area under the curve is 0.76 indicating fair test accuracy. The threshold value chosen may be adjusted to increase either the specificity or sensitivity of the test for a particular application.

Transcript 9:

There exists a statistically significant difference between the means ($p<0.1$) of the normal and malignant groups ($p=0.06$). Using a cutoff value of −7.5555 as demonstrated by the ROC curve results in a sensitivity of 60% and specificity of 89% and the area under the curve is 0.76 indicating fair to good test accuracy. The threshold value chosen may be adjusted to increase either the specificity or sensitivity of the test for a particular application.

Transcript 10:

There is a statistically significant difference between the means ($p\leq0.01$) of the normal and malignant groups ($p=0.01$). Using a cutoff value of −3.8272 as demonstrated by the ROC curve results in a sensitivity of 90% and specificity of 67% and the area under the curve is 0.84, indicating good test accuracy. The threshold value chosen may be adjusted to increase either the specificity or sensitivity of the test for a particular application.

Transcript 11:

There exists a statistically significant difference between the means ($p<0.1$) of the normal and malignant groups ($p=0.06$), using a cutoff value of 3.1753 as demonstrated by the ROC curve results in a sensitivity of 70% and specificity of 78% and the area under the curve is 0.76 indicating fair to good test accuracy. The threshold value chosen may be adjusted to increase either the specificity or sensitivity of the test for a particular application.

Transcript 12:

There exists a statistically significant difference between the means ($p<0.1$) of the normal and malignant groups ($p=0.06$), using a cut-off value of 3.2626 as demonstrated by the ROC curve results in a sensitivity of 70% and specificity of 78% and the area under the curve is 0.76 indicating fair to good test accuracy. The threshold value chosen may be adjusted to increase either the specificity or sensitivity of the test for a particular application.

Conclusions:

The above results illustrate the utility of transcripts 2, 3, 8, 9, 10, 11, and 12 in the detection of colorectal cancer and in distinguishing malignant from normal colorectal tissue. As indicated above, transcripts 2 and 3 were also found to have utility in the detection of prostate cancer. Transcript 2 was also found to have utility in the detection of breast cancer. Transcript 11 was also found to have utility in the detection of melanoma skin cancer. Transcript 10 was also found to have utility in the detection of lung cancer and melanoma. Transcript 8 was also found to have utility in the detection of lung cancer. Any of the 7 transcripts listed may be used individually or in combination as a tool for the detection of characterization of colorectal cancer in a clinical setting.

Example 6: Application to Lung Cancer

This study sought to determine the effectiveness of several transcripts of the invention in the detection of lung cancer. As in Example 5, nine control (benign) tissue samples (samples 1 to 9) and ten tumour (malignant) tissue samples (samples 10 to 19) were homogenized according to the manufacturer's recommendations (Quantigene® Sample Processing Kit for Fresh or Frozen Animal Tissues; and Quantigene 2.0 Reagent System User Manual). Homogenates were diluted 1:8 and the quantity of 4 target transcripts and 1 housekeeper transcript was measured in Relative Luminenscence Units RLU on a Glomax™ Multi Detection System (Promega). All samples were assayed in triplicate for each transcript. Background measurements (no template) were done in triplicate as well.

The following transcripts were prepared for this example:

TABLE 8

Characteristics of Lung Cancer Transcripts

| Transcript ID | Junction Site | Gene Junction |
|---|---|---|
| 6 | 8828:14896 | ATPase6:Cytb |
| 8 | 6075:13799 | COI:ND5 |
| 10 | 7438:13476 | COI:ND5 |
| 20 | 8469:13447 | ATPase8:ND5 |
| Peptidylpropyl isomerase B (PPIB) ("housekeeper") | N/A | N/A |

The tissue samples used in this example had the following characteristics:

TABLE 9

Characteristics of Lung Cancer Samples

| Sample | Malignant | Comments (source of tissue) |
|---|---|---|
| 1 | NO | interstitial lung disease |
| 2 | NO | emphysema |
| 3 | NO | aneurysm |
| 4 | NO | bronchopneumonia, COPD |
| 5 | NO | malignant neoplasm in liver, origin unknown, calcified granulomas in lung |
| 6 | NO | 12 hours post mortem, mild emphysema |
| 7 | NO | 12 hours post mortem, large B cell lymphoma, pulmonary edema, pneumonia |
| 8 | NO | pneumonia, edema, alveolar damage |
| 9 | NO | congestion and edema |
| 10 | YES | adenocarcinoma, non-small cell |
| 11 | YES | small cell |
| 12 | YES | squamous cell carcinoma, NSC, emphysema |
| 13 | YES | adenocarcinoma, lung cancer, nsc, metastatic |
| 14 | YES | squamous cell carcinoma, non-small cell |
| 15 | YES | mixed squamous and adenocarcinoma |
| 16 | YES | non-small cell carcinoma, squamous |
| 17 | YES | small cell carcinoma |
| 18 | YES | adenocarcinoma, lung cancer, nsc |
| 19 | YES | adenocarcinoma, lung cancer, nsc, metastatic |

The analysis of data was performed according to the method described in Example 5. The results are illustrated in FIGS. 7*a*, 7*b*, 7*c* and 7*d*.

Summary of Results:

Transcript 6:

There exists a statistically significant difference between the means ($p<0.1$) of the normal (benign) and malignant groups ($p=0.06$), using a cutoff value of −6.5691 as demonstrated by the ROC curve results in a sensitivity of 80% and specificity of 71% and the area under the curve is 0.77, indicating fair test accuracy. The threshold value chosen may be adjusted to increase either the specificity or sensitivity of the test for a particular application.

Transcript 8:

The difference between the means of the normal and malignant groups is statistically significant, $p<0.05$ ($p=0.02$). Using a cutoff value of −9.6166 as demonstrated by the ROC curve results in a sensitivity of 90% and specificity of 86% and the area under the curve is 0.86 indicating good test accuracy. The threshold value chosen may be adjusted to increase either the specificity or sensitivity of the test for a particular application.

Transcript 10:

The difference between the means of the normal and malignant groups is statistically significant, $p\leq0.01$ ($p=0.01$). Using a cutoff value of −10.6717 as demonstrated by the ROC curve results in a sensitivity of 90% and specificity of 86% and the area under the curve is 0.89 indicating good test accuracy. The threshold value chosen may be adjusted to increase either the specificity or sensitivity of the test for a particular application.

Transcript 20:

The difference between the means of the normal and malignant groups is statistically significant, $p\leq0.1$ ($p=0.1$). Using a cutoff value of 2.5071 as demonstrated by the ROC curve results in a sensitivity of 70% and specificity of 71% and the area under the curve is 0.74 indicating fair test accuracy. The threshold value chosen may be adjusted to increase either the specificity or sensitivity of the test for a particular application.

Conclusions:

The results from example 6 illustrate the utility of transcripts 6, 8, 10, and 20 of the invention in the detection of lung cancer tumours and the distinction between malignant and normal lung tissues. Any of these three transcripts may be used for the detection or characterization of lung cancer in a clinical setting.

Example 7: Application to Melanoma

This study sought to determine the effectiveness of several transcripts of the invention in the detection of melanomas. In this study a total of 14 samples were used, comprising five control (benign) tissue samples and nine malignant tissue samples. All samples were formalin fixed, paraffin embedded (FFPE). The FFPE tissue samples were sectioned into tubes and homogenized according to the manufacturer's recommendations (Quantigene® 2.0 Sample Processing Kit for FFPE Samples; and Quantigene 2.0 Reagent System User Manual) such that each sample approximated 20 microns prior to homogenization. Homogenates were diluted 1:4 and the quantity of 7 target transcripts and 1 housekeeper transcript was measured in Relative Luminenscence Units RLU on a Glomax™ Multi Detection System (Promega). All samples were assayed in triplicate for each transcript. Background measurements (no template) were done in triplicate as well.

The 14 tissue samples used in this example had the following characteristics:

TABLE 10

Characteristics of Melanoma Cancer Samples

| Sample | Malignant | Comments (source of tissue) |
|---|---|---|
| 1 | NO | breast reduction tissue (skin) |
| 2 | NO | breast reduction tissue (skin) |
| 3 | NO | breast reduction tissue (skin) |
| 4 | NO | breast reduction tissue (skin) |
| 5 | NO | breast reduction tissue (skin) |
| 6 | YES | lentigo maligna, (melanoma in situ) invasive melanoma not present |
| 7 | YES | invasive malignant melanoma |
| 8 | YES | nodular melanoma, pT3b, associated features of lentigo maligna |
| 9 | YES | residual superficial spreading invasive malignant melanoma, Clark's level II |
| 10 | YES | superficial spreading malignant melanoma, Clark's Level II |
| 11 | YES | nodular malignant melanoma, Clark's level IV |
| 12 | YES | superficial spreading malignant melanoma in situ, no evidence of invasion |
| 13 | YES | superficial spreading malignant melanoma, Clark's level II, focally present vertical phase |
| 14 | YES | superficial spreading malignant melanoma in situ, Clark's level I |

The following transcripts were prepared for this example:

TABLE 11

Characteristics of Melanoma Cancer Transcripts

| Transcript ID | Junction Site | Gene Junction |
|---|---|---|
| 6 | 8828:4896 | ATPase6:Cytb |
| 10 | 7438:13476 | COI:ND5 |
| 11 | 7775:13532 | COII:ND5 |
| 14 | 9191:12909 | ATPase6:ND5 |
| 15 | 9574:12972 | COIII:ND5 |
| 16 | 10367:12829 | ND3:ND5 |
| 20 | 8469:13447 | ATPase8:ND5 |
| Peptidylpropyl isomerase B (PPIB) ("housekeeper") | N/A | N/A |

As indicated, transcripts 10 and 11 were also used in Example 5. The analysis of data was performed according to the method described in Example 5. The results are illustrated in FIGS. 8*a*-8*g*.

Summary of Results:

Transcript 6:

There exists a statistically significant difference between the means ($p\leq0.01$) of the normal and malignant groups ($p=0.01$). Further, using a cutoff value of −5.9531 as demonstrated by the ROC curve results in a sensitivity of 89% and specificity of 80% and the area under the curve is 0.96, indicating very good test accuracy. The threshold value chosen may be adjusted to increase either the specificity or sensitivity of the test for a particular application.

Transcript 10:

There exists a statistically significant difference between the means ($p\leq0.05$) of the normal and malignant groups ($p=0.05$), using a cutoff value of −4.7572 as demonstrated by the ROC curve results in a sensitivity of 89% and specificity of 40% and the area under the curve is 0.82, indicating good test accuracy. The threshold value chosen may be adjusted to increase either the specificity or sensitivity of the test for a particular application.

Transcript 11:

There exists a statistically significant difference between the means ($p<0.05$) of the normal and malignant groups ($p=0.02$). Further, using a cutoff value of 1.6762 as demonstrated by the ROC curve results in a sensitivity of 78% and specificity of 100% and the area under the curve is 0.89, indicating good test accuracy. The threshold value chosen may be adjusted to increase either the specificity or sensitivity of the test for a particular application.

Transcript 14:

There exists a statistically significant difference between the means ($p \leq 0.05$) of the normal and malignant groups ($p=0.05$). Further, using a cutoff value of −4.9118 as demonstrated by the ROC curve results in a sensitivity of 89% and specificity of 60% and the area under the curve is 0.82, indicating good test accuracy. The threshold value chosen may be adjusted to increase either the specificity or sensitivity of the test for a particular application.

Transcript 15:

There exists a statistically significant difference between the means ($p<0.1$) of the normal and malignant groups ($p=0.07$), using a cutoff value of −7.3107 as demonstrated by the ROC curve results in a sensitivity of 100% and specificity of 67% and the area under the curve is 0.80, indicating good test accuracy. The threshold value chosen may be adjusted to increase either the specificity or sensitivity of the test for a particular application.

Transcript 16:

There exists a statistically significant difference between the means ($p<0.05$) of the normal and malignant groups ($p=0.03$). Further, using a cutoff value of −10.5963 as demonstrated by the ROC curve results in a sensitivity of 89% and specificity of 80% and the area under the curve is 0.878, indicating good test accuracy. The threshold value chosen may be adjusted to increase either the specificity or sensitivity of the test for a particular application.

Transcript 20:

There exists a statistically significant difference between the means ($p<0.05$) of the normal and malignant groups ($p=0.04$). Further, using a cutoff value of −8.3543 as demonstrated by the ROC curve results in a sensitivity of 100% and specificity of 80% and the area under the curve is 0.89, indicating good test accuracy. The threshold value chosen may be adjusted to increase either the specificity or sensitivity of the test for a particular application.

Conclusions:

The results from example 7 illustrate the utility of transcripts 6, 10, 11, 14, 15, 16 and 20 of the invention in the detection of malignant melanomas. As indicated above, transcripts 10 and 11 were also found have utility in detecting colorectal cancer while transcript 6 has utility in the detection of lung cancer. A transcript summary by disease is provided at Table 6.

Example 8: Application to Ovarian Cancer

This study sought to determine the effectiveness of several transcripts of the invention in detecting ovarian cancer. A total of 20 samples were prepared comprising ten control (benign) tissue samples (samples 1 to 10) and ten tumour (malignant) tissue samples (samples 11 to 20). The samples were homogenized according to the manufacturer's recommendations (Quantigene® Sample Processing Kit for Fresh or Frozen Animal Tissues; and Quantigene 2.0 Reagent System User Manual). Eight target transcripts and one housekeeper transcript were prepared in the manner as outlined above in previous examples.

The 20 tissue samples used in this example had the following characteristics:

TABLE 12

Characteristics of Ovarian Cancer Samples

| Sample | Diagnosis | Comments |
|---|---|---|
| 1 | Normal | follicular cyst |
| 2 | Normal | fibroma |
| 3 | Normal | No pathological change in ovaries |
| 4 | Normal | follicular cysts |
| 5 | Normal | cellular fibroma |
| 6 | Normal | benign follicular and simple cysts |
| 7 | Normal | leiomyomata, corpora albicantia |
| 8 | Normal | copora albicantia and an epithelial inclusions cysts |
| 9 | Normal | corpora albicantia |
| 10 | Normal | corpora albicantia, surface inclusion cysts, follicullar cysts |
| 11 | Malignant | high grade poorly differentiated papillary serous carcinoma involving omentum |
| 12 | Malignant | endometrioid adenocarcinoma, well to moderately differentiated with focal serous differentiation |
| 13 | Malignant | papillary serous carcinoma |
| 14 | Malignant | mixed epithelial carcinoma predominantly papillary serous carcinoma |
| 15 | Malignant | High grade: serous carcinoma, papillary and solid growth patterns |
| 16 | Malignant | High Grade (3/3) Papillary serous carcinoma |
| 17 | Malignant | papillary serous carcinoma, high nuclear grade |
| 18 | Malignant | Papillary serous cystadenocarcinomas Grade:III |
| 19 | Malignant | poorly differentiated papillary serous carcinoma |
| 20 | Malignant | Well-differentiated adnocarcinoma, Endometrioid type, Grade 1 |

The characteristics of the transcripts are summarized as follows:

TABLE 13

Characteristics of Ovarian Cancer Transcripts

| Transcript ID | Junction Site | Gene Junction |
|---|---|---|
| 1 | 8469:13447 | ATPase8:ND5 |
| 2 | 10744:14124 | ND4L:ND5 |
| 3 | 7974:15496 | COII:Cytb |
| 6 | 8828:14896 | ATPase6:Cytb |
| 11 | 7775:13532 | COII:ND5 |
| 12 | 8213:13991 | COII:ND5 |
| 15 | 9574:12972 | COIII:ND5 |
| 20 | 8469:13447 | ATPase8:ND5 |
| Ribosomal Protein Large PO (LRP) Housekeeper | N/A | N/A |

It is noted that transcripts 1, 2, 3, 6, 11, 12, 15 and 20 are the same as those discussed above with respect to Examples 3-7.

Homogenates were prepared using approximately 25 mg of frozen tissue and diluted 1:4. The quantity of the transcripts was measured in Relative Luminenscence Units RLU on a Glomax™ Multi Detection System (Promega). All samples were assayed in triplicate for each transcript. Background measurements (no template) were done in triplicate as well. The analysis accounted for background by subtracting the lower limit from the RLU values for the samples. Input RNA was accounted for by using the formula $\log_2$ a RLU−$\log_2$ h RLU where a is the target fusion transcript and h is the housekeeper transcript.

The analysis of the data comprised the following steps:

a) Establish CV's (coefficients of variation) for triplicate assays; acceptable if ≤15%.

b) Establish average RLU value for triplicate assays of target fusion transcript (a) and housekeeper transcript (h).

c) Establish lower limit from triplicate value of background RLU (I).

d) Subtract lower limit (I) from (a).

e) Calculate $\log_2$ a RLU−$\log_2$ h RLU.

Summary of Results:

The results of the above analysis are illustrated in FIGS. 9*a* to 9*h*, which comprise plots of the $\log_2$ a RLU−$\log_2$ h RLU against sample number. Also illustrated are the respective ROC (Receiver Operating Characteristic) curves determined from the results for each transcript.

Transcript 1:

There exists a statistically significant difference between the means ($p<0.05$) of the normal and malignant groups ($p=0.002$). Using a cutoff value of −11.1503 as demonstrated by the ROC curve results in a sensitivity of 90% and specificity of 80% and the area under the curve is 0.91 indicating very good test accuracy. The threshold value chosen may be adjusted to increase either the specificity or sensitivity of the test for a particular application.

Transcript 2:

There exists a statistically significant difference between the means ($p<0.01$) of the normal and malignant groups ($p=0.001$). Using a cutoff value of 0.6962 as demonstrated by the ROC curve results in a sensitivity of 90% and specificity of 100% and the area under the curve is 0.96 indicating very good test accuracy. The threshold value chosen may be adjusted to increase either the specificity or sensitivity of the test for a particular application.

Transcript 3:

There exists a statistically significant difference between the means ($p<0.01$) of the normal and malignant groups ($p=0.000$). Using a cutoff value of 0.6754 as demonstrated by the ROC curve results in a sensitivity of 100% and specificity of 100% and the area under the curve is 1.00 indicating excellent test accuracy. The threshold value chosen may be adjusted to increase either the specificity or sensitivity of the test for a particular application.

Transcript 6:

There exists a statistically significant difference between the means ($p<0.01$) of the normal and malignant groups ($p=0.007$). Using a cutoff value of −9.6479 as demonstrated by the ROC curve results in a sensitivity of 90% and specificity of 70% and the area under the curve is 0.86 indicating good test accuracy. The threshold value chosen may be adjusted to increase either the specificity or sensitivity of the test for a particular application.

Transcript 11:

There is a statistically significant difference between the means ($p<0.01$) of the normal and malignant groups ($p=0.000$). Using a cutoff value of −1.3794 demonstrated by the ROC curve results in a sensitivity of 100% and specificity of 90% and the area under the curve is 0.99, indicating excellent test accuracy. The threshold value chosen may be adjusted to increase either the specificity or sensitivity of the test for a particular application.

Transcript 12:

There exists a statistically significant difference between the means ($p<0.01$) of the normal and malignant groups ($p=0.001$). Using a cutoff value of −1.2379 as demonstrated by the ROC curve results in a sensitivity of 90% and specificity of 100% and the area under the curve is 0.96 indicating excellent test accuracy. The threshold value chosen may be adjusted to increase either the specificity or sensitivity of the test for a particular application.

Transcript 15:

There exists a statistically significant difference between the means ($p<0.05$) of the normal and malignant groups ($p=0.023$). Using a cut-off value of −8.6926 as demonstrated by the ROC curve results in a sensitivity of 70% and specificity of 80% and the area under the curve is 0.80 indicating good test accuracy. The threshold value chosen may be adjusted to increase either the specificity or sensitivity of the test for a particular application.

Transcript 20:

There exists a statistically significant difference between the means ($p<0.01$) of the normal and malignant groups ($p=0.000$). Using a cut-off value of 0.6521 as demonstrated by the ROC curve results in a sensitivity of 100% and specificity of 100% and the area under the curve is 0.76 indicating fair to good test accuracy. The threshold value chosen may be adjusted to increase either the specificity or sensitivity of the test for a particular application.

Conclusions:

The above results illustrate the utility of transcripts 1, 2, 3, 6, 11, 12, 15, and 20 in the detection of ovarian cancer and in distinguishing malignant from normal ovarian tissue. Transcripts 1, 2 and 3 were also found to have utility in the detection of prostate cancer. Transcript 6 was also found to have utility in the detection of melanoma and lung cancer. Transcript 11 was also found to have utility in the detection of melanoma skin cancer, colorectal cancer and testicular cancer. Transcript 12 was also found to have utility in the detection of colorectal cancer and testicular cancer. Transcript 15 was also found to have utility in the detection of melanoma and testicular cancer. Transcript 20 was also found to have utility in the detection of colorectal cancer, melanoma, and testicular cancer. Any of the 8 transcripts listed may be used individually or in combination as a tool for the detection or characterization of ovarian cancer in a clinical setting.

Example 9: Application to Testicular Cancer

This study sought to determine the effectiveness of several transcripts of the invention in detecting testicular cancer. A total of 17 samples were prepared comprising eight control (benign) tissue samples (samples 1 to 8) and 9 tumour (malignant) tissue samples (samples 9 to 17), 5 of the malignant samples were non-seminomas (samples 9-13) and 4 were seminomas (samples 14-17). The samples were homogenized according to the manufacturer's recommendations (Quantigene® Sample Processing Kit for Fresh or Frozen Animal Tissues; and Quantigene 2.0 Reagent System User Manual). 10 target transcripts and one housekeeper transcript were prepared in the manner as outlined above in previous examples.

The 17 tissue samples used in this example had the following characteristics:

TABLE 14

Characteristics of Testicular Cancer Samples

| Sample | General Diagnosis | Stratified Malignant Diagnosis |
|---|---|---|
| 1 | Benign | Benign |
| 2 | Benign | Benign |
| 3 | Benign | Benign |
| 4 | Benign | Benign |
| 5 | Benign | Benign |
| 6 | Benign | Benign |
| 7 | Benign | Benign |
| 8 | Benign | Benign |
| 9 | Malignant | Non-Seminoma |
| 10 | Malignant | Non-Seminoma |

TABLE 14-continued

| Characteristics of Testicular Cancer Samples | | |
|---|---|---|
| Sample | General Diagnosis | Stratified Malignant Diagnosis |
| 11 | Malignant | Non-Seminoma |
| 12 | Malignant | Non-Seminoma |
| 13 | Malignant | Non-Seminoma |
| 14 | Malignant | Seminoma |
| 15 | Malignant | Seminoma |
| 16 | Malignant | Seminoma |
| 17 | Malignant | Seminoma |

The characteristics of the transcripts are summarized as follows:

TABLE 15

| Characteristics of Testicular Cancer Transcripts | | |
|---|---|---|
| Transcript ID | Junction Site | Gene Junction |
| 2 | 10744:14124 | ND4L:ND5 |
| 3 | 7974:15496 | COII:Cytb |
| 4 | 7992:15730 | COII:Cytb |
| 11 | 7775:13532 | COII:ND5 |
| 12 | 8213:13991 | COII:ND5 |
| 13 | 9144:13816 | ATPase6:ND5 |
| 15 | 9574:12972 | COIII:ND5 |
| 16 | 10367:12829 | ND3:ND5 |
| 20 | 8469:13447 | ATPase8:ND5 |
| Peptidylpropyl isomerase B (PPIB) | N/A | N/A |

It is noted that transcripts 2, 3, 4, 7, 11, 12, 15, 16 and 20 are the same as those discussed above with respect to Examples 3-8.

Homogenates were prepared using approximately 25 mg of frozen tissue and diluted 1:4. The quantity of the transcripts was measured in Relative Luminenscence Units RLU on a Glomax™ Multi Detection System (Promega). All samples were assayed in triplicate for each transcript. Background measurements (no template) were done in triplicate as well. The analysis accounted for background by subtracting the lower limit from the RLU values for the samples. Input RNA was accounted for by using the formula $\log_2$ a RLU−$\log_2$ h RLU where a is the target fusion transcript and h is the housekeeper transcript.

The analysis of the data comprised the following steps:

a) Establish CV's (coefficients of variation) for triplicate assays; acceptable if 15%.

b) Establish average RLU value for triplicate assays of target fusion transcript (a) and housekeeper transcript (h).

c) Establish lower limit from triplicate value of background RLU (I).

d) Subtract lower limit (I) from (a).

e) Calculate $\log_2$ a RLU−$\log_2$ h RLU.

Summary of Results:

The results of the above analysis are illustrated in FIGS. 10 to 18, which comprise plots of the $\log_2$ a RLU−$\log_2$ h RLU against sample number. Also illustrated are the respective ROC (Receiver Operating Characteristic) curves determined from the results for each transcript.

While some transcripts distinguish between benign and malignant testicular tissue, others demonstrate distinction between the tumour subtypes of seminoma and non-seminoma and/or benign testicular tissue. It is therefore anticipated that combining transcripts from each class will facilitate not only detection of testicular cancer but also classification into subtype of seminoma or non-seminomas.

Transcript 2:

There exists a statistically significant difference between the means ($p<0.05$) of the normal group and the malignant seminomas ($p=0.02$). Using a cutoff value of 1.5621 as demonstrated by the ROC curve results in a sensitivity of 100% and specificity of 100% and the area under the curve is 1.00 indicating excellent test accuracy. There also exists a statistically significant difference between the means ($p<0.05$) of the malignant seminomas and the malignant non-seminomas ($p=0.024$). Using a cutoff value of 2.1006 as demonstrated by the ROC curve results in a sensitivity of 100% and specificity of 80% and the area under the curve is 0.90 indicating excellent test accuracy. The threshold value chosen may be adjusted to increase either the specificity or sensitivity of the test for a particular application.

Transcript 3:

There exists a statistically significant difference between the means ($p<0.05$) of the normal group and the malignant seminomas ($p=0.018$). Using a cutoff value of 0.969 as demonstrated by the ROC curve results in a sensitivity of 100% and specificity of 87.5% and the area under the curve is 0.969 indicating excellent accuracy. There also exists a statistically significant difference between the means ($p<0.05$) of the malignant seminomas and the malignant non-seminomas ($p=0.017$). Using a cutoff value of 1.8181 as demonstrated by the ROC curve results in a sensitivity of 100% and specificity of 80% and the area under the curve is 0.9 indicating excellent test accuracy. The threshold value chosen may be adjusted to increase either the specificity or sensitivity of the test for a particular application.

Transcript 4:

There exists a statistically significant difference between the means ($p<0.05$) of the normal and malignant groups ($p=0.034$). Using a cutoff value of −9.7628 as demonstrated by the ROC curve results in a sensitivity of 67% and specificity of 100% and the area under the curve is 0.833 indicating good test accuracy. The threshold value chosen may be adjusted to increase either the specificity or sensitivity of the test for a particular application.

Transcript 11:

There exists a statistically significant difference between the means ($p<0.05$) of the normal group and the malignant seminomas ($p=0.016$). Using a cutoff value of 0.732 as demonstrated by the ROC curve results in a sensitivity of 100% and specificity of 100% and the area under the curve is 1.00 indicating excellent test accuracy. There also exists a statistically significant difference between the means ($p<0.05$) of the malignant seminomas and the malignant non-seminomas ($p=0.016$). Using a cutoff value of 0.9884 as demonstrated by the ROC curve results in a sensitivity of 100% and specificity of 80% and the area under the curve is 0.90 indicating excellent test accuracy. The threshold value chosen may be adjusted to increase either the specificity or sensitivity of the test for a particular application.

Transcript 12:

There exists a statistically significant difference between the means ($p<0.1$) of the normal group and the malignant seminomas ($p=0.056$). Using a cutoff value of 1.5361 as demonstrated by the ROC curve results in a sensitivity of 100% and specificity of 87.5% and the area under the curve is 0.969 indicating excellent test accuracy. There also exists a statistically significant difference between the means ($p<0.05$) of the malignant seminomas and the malignant non-seminomas (p=0.044). Using a cutoff value of 1.6039 as demonstrated by the ROC curve results in a sensitivity of 100% and specificity of 80% and the area under the curve is 0.9 indicating excellent test accuracy. The threshold value chosen may be adjusted to increase either the specificity or sensitivity of the test for a particular application.

Transcript 13:

There exists a statistically significant difference between the means (p<0.05) of the normal group and the malignant group (p=0.019). Using a cutoff value of −9.8751 as demonstrated by the ROC curve results in a sensitivity of 87.5% and specificity of 78% and the area under the curve is 0.875 indicating very good test accuracy. There also exists a statistically significant difference between the means (p<0.01) of the malignant non-seminomas and the benign group (p=0.000). Using a cutoff value of −13.9519 as demonstrated by the ROC curve results in a sensitivity of 100% and specificity of 87.5% and the area under the curve is 0.975 indicating excellent test accuracy. There also exists a statistically significant difference between the means (p<0.01) of the malignant seminomas and the malignant non-seminomas (p=0.001). Using a cutoff value of −15.8501 as demonstrated by the ROC curve results in a sensitivity of 100% and specificity of 100% and the area under the curve is 1.00 indicating excellent test accuracy. The threshold value chosen may be adjusted to increase either the specificity or sensitivity of the test for a particular application.

Transcript 15:

There exists a statistically significant difference between the means (p<0.1) of the normal and malignant groups (p=0.065). Using a cut-off value of −5.4916 as demonstrated by the ROC curve results in a sensitivity of 75% and specificity of 89% and the area under the curve is 0.833 indicating good test accuracy. The threshold value chosen may be adjusted to increase either the specificity or sensitivity of the test for a particular application.

Transcript 16:

There exists a statistically significant difference between the means (p<0.05) of the normal and malignant groups including both seminomas and non-seminomas (p=0.037). Using a cut-off value of −6.448 as demonstrated by the ROC curve results in a sensitivity of 89% and specificity of 75% and the area under the curve is 0.806 indicating good test accuracy. There also exists a statistically significant difference between the means (p<0.05) of the normal and malignant seminomas (p=0.037). Using a cut-off value of −7.4575 as demonstrated by the ROC curve results in a sensitivity of 100% and specificity of 87.5% and the area under the curve is 0.938 indicating excellent test accuracy. The threshold value chosen may be adjusted to increase either the specificity or sensitivity of the test for a particular application.

Transcript 20:

There exists a statistically significant difference between the means (p<0.01) of the normal group and the malignant seminomas (p=0.006). Using a cutoff value of 1.8364 as demonstrated by the ROC curve results in a sensitivity of 100% and specificity of 100% and the area under the curve is 1.00 indicating excellent test accuracy. There also exists a statistically significant difference between the means (p<0.01) of the malignant seminomas and the malignant non-seminomas (p=0.004). Using a cutoff value of 1.6065 as demonstrated by the ROC curve results in a sensitivity of 100% and specificity of 100% and the area under the curve is 1.00 indicating excellent test accuracy. The threshold value chosen may be adjusted to increase either the specificity or sensitivity of the test for a particular application.

Conclusions:

The above results illustrate the utility of transcripts 2, 3, 4, 11, 12, 13, 15, 16, and 20 in the detection of testicular cancer, and testicular cancer subtypes, and in distinguishing malignant from normal testicular tissue. Transcript 2 was also found to have utility in the detection of prostate, breast, colorectal and ovarian cancer. Transcript 3 was also found to have utility in the detection of prostate, breast, melanoma, colorectal, and ovarian cancers. Transcript 4 was also found to have utility in the detection of prostate and colorectal cancers. Transcript 11 was also found to have utility in the detection of colorectal, melanoma, and ovarian cancers. Transcript 12 was also found to have utility in the detection of colorectal and ovarian cancers. Transcript 15 was also found to have utility in the detection of melanoma and ovarian cancers. Transcript 16 was also found to have utility in the detection of melanoma skin cancer. Transcript 20 was also found to have utility in the detection of colorectal cancer, melanoma, and ovarian cancer. Any of the 9 transcripts listed may be used individually or in combination as a tool for the detection or characterization of testicular cancer in a clinical setting.

In one aspect, the invention provides a kit for conducting an assay for determining the presence of cancer in a tissue sample. The kit includes the required reagents for conducting the assay as described above. In particular, the kit includes one or more containers containing one or more hybridization probes corresponding to transcripts 1 to 17, and 20 described above. As will be understood, the reagents for conducting the assay may include any necessary buffers, salts, detection reagents etc. Further, the kit may include any necessary sample collection devices, containers etc. for obtaining the needed tissue samples, reagents or materials to prepare the tissue samples for example by homogenization or nucleic acid extraction, and for conducting the subject assay or assays. The kit may also include control tissues or samples to establish or validate acceptable values for diseased or non-diseased tissues.

Although the invention has been described with reference to certain specific embodiments, various modifications thereof will be apparent to those skilled in the art without departing from the spirit and scope of the invention as outlined in the claims appended hereto. All documents (articles, manuals, patent applications etc) referred to in the present application are incorporated herein in their entirety by reference.

BIBLIOGRAPHY

The following references, amongst others, were cited in the foregoing description. The entire contents of these references are incorporated herein by way of reference thereto.

| Author | Journal | Title | Volume | Date |
|---|---|---|---|---|
| Anderson et al | Nature | Sequence and Organization of the Human Mitochondrial Genome | 290(5806): 457-65 | 1981 |
| Andrews et al | Nat Genet | Reanalysis and revision of the Cambridge reference sequence for human mitochondrial DNA. | 23(2): 147 | 1999 |

-continued

| Author | Journal | Title | Volume | Date |
|---|---|---|---|---|
| Modica-Napolitano et al | Expert Rev Mol Med | Mitochondria as targets for detection and treatment of cancer | 4: 1-19 | 2002 |
| Sherratt et al | Clin Sci (Lond) | Mitochondrial DNA defects: a widening clinical spectrum of disorders. | 92(3): 225-35 | 1997 |
| Croteau et al | Mutat Res | Mitochondrial DNA repair pathways. | 434(3): 137-48 | 1999 |
| Green and Kroemer | J Clin Invest | Pharmacological manipulation of cell death: clinical applications in sight? | 115(10): 2610-2617 | 2005 |
| Dai et al | Acta Otolaryngol | Correlation of cochlear blood supply with mitochondrial DNA common deletion in presbyacusis. | 24(2): 130-6 | 2004 |
| Ro et al | Muscle Nerve | Deleted 4977-bp mitochondrial DNA mutation is associated with sporadic amyotrophic lateral sclerosis: a hospital-based case-control study. | 28(6): 737-43 | 2003 |
| Barron et al | Invest Ophthalmol Vis Sci | Mitochondrial abnormalities in ageing macular photoreceptors. | 42(12): 3016-22 | 2001 |
| Lewis et al | J Pathol | Detection of damage to the mitochondrial genome in the oncocytic cells of Warthin's tumour. | 191(3): 274-81 | 2000 |
| Muller-Hocker et al | Mod Pathol | The common 4977 base pair deletion of mitochondrial DNA preferentially accumulates in the cardiac conduction system of patients with Kearns-Sayre syndrome. | 11(3): 295-301. | 1998 |
| Porteous et al | Eur J Biochem | Bioenergetic consequences of accumulating the common 4977-bp mitochondrial DNA deletion. | 257(1): 192-201 | 1998 |
| Parr et al | J Mol Diagn | Somatic mitochondrial DNA mutations in prostate cancer and normal appearing adjacent glands in comparison to age-matched prostate samples without malignant histology. | 8(3): 312-9. | 2006 |
| Maki et al | Am J Clin Pathol | Mitochondrial genome deletion aids in the identification of false- and true-negative prostate needle core biopsy specimens. | 129(1): 57-66 | 2008 |
| Nakase et al | Am J Hum Genet | Transcription and translation of deleted mitochondrial genomes in Kearns-Sayre syndrome: implications for pathogenesis. | 46(3): 418-27. | 1990 |
| Libura et al | Blood | Therapy-related acute myeloid leukemia-like MLL rearrangements are induced by etoposide in primary human CD34+ cells and remain stable after clonal expansion. | 105(5): 2124-31 | 2005 |
| Meyer et al | Proc Natl Acad Sci USA | Diagnostic tool for the identification of MLL rearrangements including unknown partner genes. | 102(2): 449-54 | 2005 |
| Eguchi et al | Genes Chromosomes Cancer | MLL chimeric protein activation renders cells vulnerable to chromosomal damage: an explanation for the very short latency of infant leukemia. | 45(8): 754-60 | 2006 |
| Hayashi et al | Proc Natl Acad Sci USA | Introduction of disease-related mitochondrial DNA deletions into HeLa cells lacking mitochondrial DNA results in mitochondrial dysfunction | 88: 10614-10618 | 1991 |

TABLE 1

Known mitochondrial deletions having an ORF

| Deletion Junction (nt:nt) | Deletion Size (bp) | Repeat Location (nt/nt) | Number of Repeats | References |
|---|---|---|---|---|
| COXI-ND5 | | | | |
| 6075:13799 | −7723 | 6076-6084/13799-13807 | D, 9/9 | Mita, S., Rizzuto, R., Moraes, C. T., Shanske, S., Arnaudo, E., Fabrizi, G. M., Koga, Y., DiMauro, S., Schon, E. A. (1990) "Recombination via flanking direct repeats is a major cause of large-scale deletions of human mitochondrial DNA" Nucleic Acids Research 18(3): 561-567 |
| 6238:14103 | −7864 | 6235-6238/14099-14102 | D, 4/4 | Blok, R. B., Thorburn, D. R., Thompson, G. N., Dahl, H. H. (1995) "A topoisomerase II cleavage site is associated with a novel mitochondrial DNA deletion" Human Genetics 95 (1): 75-81 |
| 6325:13989 | −7663 | 6326-6341/13889-14004 | D, 16/17 | Larsson, N. G., Holme, E., Kristiansson, B., Oldfors, A., Tulinius, M. (1990) "Progressive increase of the mutated mitochondrial DNA fraction in Kearns-Sayre syndrome" Pediatric Research 28 (2): 131-136 |

TABLE 1-continued

| Known mitochondrial deletions having an ORF | | | | |
|---|---|---|---|---|
| Deletion Junction (nt:nt) | Deletion Size (bp) | Repeat Location (nt/nt) | Number of Repeats | References |
| 6330:13994 | −7663 | 6331-6341/13994-14004 | D, 11/11 | Larsson, N. G., Holme, E. (1992) "Multiple short direct repeats associated with single mtDNA deletions" Biochimica et Biophysica Acta 1139 (4): 311-314 Mita, S., Rizzuto, R., Moraes, C. T., Shanske, S., Arnaudo, E., Fabrizi, G. M., Koga, Y., DiMauro, S., Schon, E. A. (1990) "Recombination via flanking direct repeats is a major cause of large-scale deletions of human mitochondrial DNA" Nucleic Acids Research 18(3): 561-567 |
| COX II-ND5 | | | | |
| 7829:14135 | −6305 | 7824-7829/14129-14134 | D, 6/6 | Bet, L., Moggio, M., Comi, G. P., Mariani, C., Prelle, A., Checcarelli, N., Bordoni, A., Bresolin, N., Scarpini, E., Scarlato, G. (1994) "Multiple sclerosis and mitochondrial myopathy: an unusual combination of diseases" Journal of Neurology 241 (8): 511-516 |
| 8213:13991 | −5777 | 8214-8220/13991-13997 | D, 7/7 | Hinokio, Y., Suzuki, S., Komatu, K., Ohtomo, M., Onoda, M., Matsumoto, M., Hirai, S., Sato, Y., Akai, H., Abe, K., Toyota, T. (1995) "A new mitochondrial DNA deletion associated with diabetic amyotrophy, diabetic myoatrophy and diabetic fatty liver" Muscle and Nerve 3 (9): S142-149 |
| ATPase-ND5 | | | | |
| 8631:13513 | −4881 | 8625-8631/13506-13512 | D, 7/7 | Zhang, C., Baumer, A., Mackay, I. R., Linnane, A. W., Nagley, P. (1995) "Unusual pattern of mitochondrial DNA deletions in skeletal muscle of an adult human with chronic fatigue syndrome" Human Molecular Genetics 4 (4): 751-754 |
| 9144:13816 | −4671 | 9137-9144/13808-13815 | D, 8/8 | Ota, Y., Tanaka, M., Sato, W., Ohno, K., Yamamoto, T., Maehara, M., Negoro, T., Watanabe, K., Awaya, S., Ozawa, T. (1991) "Detection of platelet mitochondrial DNA deletions in Kearns-Sayre syndrome" Investigative Ophthalmology and Visual Science 32 (10): 2667-2675 |
| 9191:12909 | −3717 | 9189-9191/12906-12908 | D, 3/3 | Tanaka, M., Sato, W., Ohno, K., Yamamoto, T., Ozawa, T. (1989) "Direct sequencing of mitochondrial DNA in myopathic patients" Biochemical and Biophysical Research Communications 164 ( ): 156-163 |
| COX III-ND5 | | | | |
| 10190:13753 | −3562 | 10191-10198/13753-13760 | D, 8/8 | Rotig, A., Bourgeron, T., Chretien, D., Rustin, P., Munnich, A. (1995) "Spectrum of mitochondrial DNA rearrangements in the Pearson marrow-pancreas syndrome" Human Molecular Genetics 4 (8): 1327-1330 Rotig, A., Cormier, V., Koll, F., Mize, C. E., Saudubray, J.-M., Veerman, A., Pearson, H. A., Munnich, A. (1991) "Site-specific deletions of the mitochondrial genome in Pearson marrow-pancreas syndrome" Genomics 10 (2): 502-504 |
| 10367:12829 | −2461 | 10365-10367/12826-12828 | D, 3/3 | Kapsa, R., Thompson, G. N., Thorburn, D. R., Dahl, H. H., Marzuki, S., Byrne, E., Blok, R. B. (1994) "A novel mtDNA deletion in an infant with Pearson syndrome" Journal of Inherited Metabolic Disease 17 (5): 521-526 |
| ND4L-ND5 | | | | |
| 10744:14124 | −3379 | 10745-10754/14124-14133 | D, 9/10 | Cormier-Daire, V., Bonnefont, J. P., Rustin, P., Maurage, C., Ogler, H., Schmitz, J., Ricour, C. Saudubray, J. M., Munnich, A., Rotig, A. (1994) "Mitochondrial DNA rearrangements with onset as chronic diarrhea with villous atrophy" Journal of Pediatrics 124 (1): 63-70 |
| ND4-ND5 | | | | |
| 11232:13980 | −2747 | 11234-11242/13981-13989 | D, 9/9 | Rotig, A., Cormier, V., Koll, F., Mize, C. E., Saudubray, J.M., Veerman, A., Pearson, H. A., Munnich, A. (1991) "Site-specific deletions of the mitochondrial genome in Pearson marrow-pancreas syndrome" Genomics 10 (2): 502-504 Rotig, A., Cormier, V., Blanche, S., Bonnefont, J. P., Ledeist, F., Romero, N., Schmitz, J., Rustin, P., Fischer, A., Saudubray, J. M. (1990) "Pearson's marrow-pancreas syndrome. A multi-system mitochondrial disorder in infancy" Journal of Clinical Investigation 86 ( ): 1601-1608 Cormier, V., Rotig, A., Quartino, A. R., Forni, G. L., Cerone, R., Maier, M., Saudubray, J. M., Munnich, A. (1990) "Widespread multitissue deletions of the mitochondrial genome in Pearson marrow-pancreas syndrome" Journal of Pediatrics 117 (4): 599-602 Awata, T., Matsumoto, T., Iwamoto, Y., Matsuda, A., Kuzuya, T., Saito, T. (1993) "Japanese case of diabetes mellitus and deafness with mutations in mitochondrial tRNALeu(UUR) gene [letter]" Lancet 341 (8855): 1291-1292 |

| | | RNA | Homog 1 | Homog 2 | RNA | Homog 1 | Homog 2 | RNA | Homog 1 | Homog 2 | RNA | Homog 1 | Homog 2 |
|---|---|---|---|---|---|---|---|---|---|---|---|---|---|
| | | Transcript | | | | | | | | | | | |
| | | Transcript 1 1 | Transcript 1 2 | Transcript 1 3 | Transcript 2 4 | Transcript 2 5 | Transcript 2 6 | Transcript 3 7 | Transcript 3 8 | Transcript 3 9 | Transcript 4 10 | Transcript 4 11 | Transcript 4 12 |
| No dilution | A | 2957 | 353 | 233 | 144838 | 75374 | 17192 | 348424 | 333189 | 213844 | 509 | 565 | 207 |
| Replicate A | B | 3174 | 475 | 298 | 202793 | 100062 | 31750 | 320877 | 278137 | 210265 | 401 | 676 | 250 |
| 1:10 dilution | C | 1041 | 262 | 114 | 106195 | 98403 | 36191 | 238467 | 248677 | 123497 | 181 | 486 | 168 |
| Replicate C | D | 1040 | 272 | 176 | 120308 | 116930 | 50323 | 239231 | 262520 | 129778 | 153 | 467 | 149 |
| 1:100 dilution | E | 318 | 170 | 110 | 25155 | 64823 | 27725 | 100345 | 164606 | 85287 | 72 | 265 | 119 |
| Replicate E | F | 287 | 150 | 109 | 23500 | 50524 | 24629 | 100856 | 178527 | 84731 | 83 | 251 | 120 |
| 1:1000 dilution | G | 100 | 76 | 123 | 3002 | 12960 | 252 | 29203 | 102309 | 137 | 31 | 143 | 66 |
| Replicate G | H | 94 | 83 | 91 | 1263 | 5796 | 285 | 29092 | 97257 | 96 | 45 | 110 | 94 |
| % CV A | | 5.0 | 20.9 | 17.3 | 23.6 | 19.9 | 42.1 | 5.8 | 12.7 | 1.2 | 16.9 | 12.7 | 13.3 |
| % CV C | | 0.1 | 2.5 | 30.1 | 8.8 | 12.2 | 23.1 | 0.2 | 3.8 | 3.5 | 12.0 | 2.8 | 8.3 |
| % CV E | | 7.1 | 9.0 | 0.6 | 4.8 | 17.5 | 8.4 | 0.4 | 5.7 | 0.5 | 9.8 | 3.8 | 0.6 |
| % CV G | | 4.7 | 6.0 | 20.8 | 57.7 | 54.0 | 8.8 | 0.3 | 3.6 | 25.0 | 27.0 | 18.2 | 24.9 |

* unit results in table are RLU (relative luminescence units); Data read on Glorunner ™.

% CV = Coefficient of variation (as %).

Legend:

Homog = homogenate.

Homog 1: Prostate tumour tissue sample from patient;

Homog 2: Histologically normal tissue adjacent to tumour from patient.

RNA: Control: Total RNA from prostate tissue (Ambion p/n 7988).

TABLE 3

| Deletion/Transcript/DNA Complement | | | |
|---|---|---|---|
| Deletion | RNA transcript | DNA sequence with deletion complementary to RNA transcript | Transcript No. |
| ATP synthase F0 subunit 8 to NADH dehydrogenase subunit mitochondrial positions 8366-14148 (with reference to SEQ ID NO: 1). | SEQ ID NO: 18 | SEQ ID NO: 2 | 1 |
| NADH dehydrogenase subunit 4L (ND4L) to NADH dehydrogenase subunit 5 (ND5); Mitochondrial positions 10470-14148 (with reference to SEQ ID NO: 1) | SEQ ID NO: 19 | SEQ ID NO: 3 | 2 |
| Cytochrome c oxidase subunit II (COII) to Cytochrome b (Cytb); Mitochondrial positions 7586-15887 (with reference to SEQ ID NO: 1) | SEQ ID NO: 20 | SEQ ID NO: 4 | 3 |
| Cytochrome c oxidase subunit II (COII) to Cytochrome b (Cytb); Mitochondrial positions 7586-15887 (with reference to SEQ ID NO: 1) | SEQ ID NO: 21 | SEQ ID NO: 5 | 4 |

TABLE 4

| Breast and Prostate Cancer Detection | | | | | | | | | |
|---|---|---|---|---|---|---|---|---|---|
| | | Breast Tumour 1 1 | Normal adjacent Breast Tumour 1 2 | Breast Tumour 2 3 | Normal Adjacent to Breast Tumour 2 4 | Prostate Tumour 3 5 | Prostate Tumour 4 6 | Prostate Tumour 5 7 | Normal Adjacent to Prostate Tumour 5 8 |
| 1:100 dilution | E | 68920 | 2971 | 49108 | 1245 | 46723 | 56679 | 99836 | 35504 |

TABLE 4-continued

| Breast and Prostate Cancer Detection | | | | | | | | | |
|---|---|---|---|---|---|---|---|---|---|
| | | Breast Tumour 1<br>1 | Normal adjacent Breast Tumour 1<br>2 | Breast Tumour 2<br>3 | Normal Adjacent to Breast Tumour 2<br>4 | Prostate Tumour 3<br>5 | Prostate Tumour 4<br>6 | Prostate Tumour 5<br>7 | Normal Adjacent to Prostate Tumour 5<br>8 |
| 1:100 dilution replicate | F | 92409 | 3017 | 60637 | 1512 | 53940 | 56155 | 100582 | 44221 |
| | G | 420 | 3 | 31 | 6 | 26 | 25 | 44 | 23 |
| | H | 518 | 3 | 4 | 5 | 5 | 3 | 4 | 2 |
| | % CV | 20.6 | 1.1 | 14.9 | 13.7 | 10.1 | 0.7 | 0.5 | 15.5 |

unit results in table are RLU (relative luminescence units)
background G1, H1
empty well G2-G8, H2-H8

TABLE 5a

| Assay Conditions | | | | | | |
|---|---|---|---|---|---|---|
| | Template for the assay | | | | | |
| | RNA Transcript 1<br>1 | Homogen 1 Transcript 1<br>2 | Homogen 2 Transcript 1<br>3 | RNA Transcript 2<br>4 | Homogen 1 Transcript 2<br>5 | Homogen 2 Transcript 2<br>6 |
| A | RNA | Homog 1 | Homog 2 | RNA | Homog 1 | Homog 2 |
| B | Dil 1 | Dil 1 | Dil 1 | Dil 1 | Dil 1 | Dil 1 |
| C | RNA | Homog 1 | Homog 2 | RNA | Homog 1 | Homog 2 |
| D | Dil 2 | Dil 2 | Dil 2 | Dil 2 | Dil 2 | Dil 2 |
| E | RNA | Homog 1 | Homog 2 | RNA | Homog 1 | Homog 2 |
| F | Dil 3 | Dil 3 | Dil 3 | Dil 3 | Dil 3 | Dil 3 |
| G | RNA | Homog 1 | Transcript 1 | RNA | Homog 1 | Transcript 1 |
| H | Dil 4 | Dil 4 | Background | Dil 4 | Dil 4 | Background |
| | RNA Transcript 3<br>7 | Homogen 1 Transcript 3<br>8 | Homogen 2 Transcript 3<br>9 | RNA Transcript 4<br>10 | Homogen 1 Transcript 4<br>11 | Homogen 2 Transcript 4<br>12 |
| A | RNA | Homog 1 | Homog 2 | RNA | Homog 1 | Homog 2 |
| B | Dil 1 | Dil 1 | Dil 1 | Dil 1 | Dil 1 | Dil 1 |
| C | RNA | Homog 1 | Homog 2 | RNA | Homog 1 | Homog 2 |
| D | Dil 2 | Dil 2 | Dil 2 | Dil 2 | Dil 2 | Dil 2 |
| E | RNA | Homog 1 | Homog 2 | RNA | Homog 1 | Homog 2 |
| F | Dil 3 | Dil 3 | Dil 3 | Dil 3 | Dil 3 | Dil 3 |
| G | RNA | Homog 1 | Transcript 1 | RNA | Homog 1 | Transcript 1 |
| H | Dil 4 | Dil 4 | Background | Dil 4 | Dil 4 | Background |

Homogenate1 - Used 26 mg of tissue to homogenize in 700 ul H soln with Proteinase K (PK). Used Qiagen TissueRuptor. Used 40 ul homogenate supernatant, 20, 10 and 5 ul for dilution Homogenate1 = Tumour tissue from the tumorous Prostate
Homogenate2 - Used 29 mg of tissue to homogenize in 700 ul H soln with PK. Used Qiagen TissueRuptor. Used 40 ul homogenate supernatant, 20, 10 and 5 ul for dilution Homogenate2 = Normal tissue from the tumorous Prostate
RNA dilution was made as below. RNA was from Prostate Normal from Ambion.
Assay was done in duplicates.

TABLE 5b

| RNA dilution | | |
|---|---|---|
| RNA Dilution | | ng/ul |
| | Dil 1 | 3000 |
| 1:3 dil | Dil 2 | 1000 |
| Serial dil | Dil 3 | 333 |
| | Dil 4 | 111 |

TABLE 6

| Transcript Summary by Disease | | | | | | | |
|---|---|---|---|---|---|---|---|
| Probe | Prostate Cancer | Breast Cancer | Colo-rectal Cancer | Melanoma Skin Cancer | Lung Can-cer | Ovarian Cancer | Tes-ticular Cancer |
| 1 | • | | | | | • | |
| 2 | • | • | • | | | • | • |
| 3 | • | | • | | | • | • |
| 4 | • | | | | | | • |
| 5 | | | | | | | |
| 6 | | | | • | • | • | |
| 7 | | | | | | | |
| 8 | | | • | | • | | |

TABLE 6-continued

Transcript Summary by Disease

| Probe | Prostate Cancer | Breast Cancer | Colo-rectal Cancer | Melanoma Skin Cancer | Lung Can-cer | Ovarian Cancer | Tes-ticular Cancer |
|---|---|---|---|---|---|---|---|
| 9 | | | • | | | | |
| 10 | | | • | • | • | | |
| 11 | | | • | • | | • | • |
| 12 | | | • | | | • | • |
| 13 | | | | | | | • |
| 14 | | | | • | | | |
| 15 | | | | • | | • | • |
| 16 | | | | • | | | • |
| 17 | | | | | | | |
| 20 | | | | • | • | • | • |

The invention claimed is:

1. A method of detecting prostate or ovarian cancer in a mammal by assaying a tissue sample from the mammal for the presence of a mitochondrial fusion transcript associated with cancer, the method comprising hybridizing the sample with at least one hybridization probe having a nucleic acid sequence complementary to at least a portion of the mitochondrial fusion transcript, wherein:

the mitochondrial fusion transcript has the nucleic acid sequence as set forth in SEQ ID NO: 18 or SEQ ID NO: 33;

the portion of the mitochondrial fusion transcript to which the at least one hybridization probe is complementary comprises an expressed sequence of mtDNA including a junction point resulting from a deletion spanning nucleotides 8469 to 13447 of the human mtDNA genome; and the at least one hybridization probe comprises at least about 15 nucleotides.

2. The method of claim 1, further comprising:

a) quantifying the amount of the mitochondrial fusion transcript in said sample by quantifying the amount of said mitochondrial fusion transcript hybridized to said at least one hybridization probe; and b) comparing the amount of the mitochondrial fusion transcript in the sample to at least one known reference value.

3. The method of claim 1, wherein the assaying is carried out using diagnostic imaging technology, branched DNA technology, or PCR.

4. A method of detecting a mitochondrial fusion transcript in a mammal, the fusion transcript being associated with prostate or ovarian cancer, the method comprising hybridizing a tissue sample from the mammal with at least one hybridization probe having a nucleic acid sequence complementary to at least a portion of the mitochondrial fusion transcript, wherein:

the fusion transcript has the nucleic acid sequence as set forth in SEQ ID NO: 18 or SEQ ID NO: 33;

the portion of the mitochondrial fusion transcript to which the at least one hybridization probe is complementary comprises an expressed sequence of mtDNA including a junction point resulting from a deletion spanning nucleotides 8469 to 13447 of the human mtDNA genome; and the at least one hybridization probe comprises at least about 15 nucleotides.

* * * * *